US012781186B2

(12) United States Patent
Goldman et al.

(10) Patent No.: US 12,781,186 B2
(45) Date of Patent: Nov. 3, 2026

(54) METHOD FOR REJUVENATING GLIAL PROGENITOR CELLS AND REJUVENATED GLIAL PROGENITOR CELLS PER SE

(71) Applicant: UNIVERSITY OF ROCHESTER, Rochester, NY (US)

(72) Inventors: Steven A. Goldman, Webster, NY (US); John Mariani, Rochester, NY (US); Nguyen P.T. Huynh, Cambridge, MA (US)

(73) Assignee: University of Rochester, Rochester, NY (US)

( * ) Notice: Subject to any disclaimer, the term of this patent is extended or adjusted under 35 U.S.C. 154(b) by 975 days.

(21) Appl. No.: 18/046,930

(22) Filed: Oct. 16, 2022

(65) Prior Publication Data

US 2023/0226116 A1 Jul. 20, 2023

Related U.S. Application Data

(60) Provisional application No. 63/257,853, filed on Oct. 20, 2021.

(51) Int. Cl.

| | |
|---|---|
| ***C12N 5/079*** | (2010.01) |
| ***A61K 35/30*** | (2015.01) |
| ***A61P 25/28*** | (2006.01) |
| ***C12N 5/0797*** | (2010.01) |
| ***C12N 9/22*** | (2006.01) |
| ***C12N 15/11*** | (2006.01) |
| ***C12N 15/90*** | (2006.01) |

(52) U.S. Cl.

CPC ............ *C12N 5/0622* (2013.01); *A61K 35/30* (2013.01); *A61P 25/28* (2018.01); *C12N 5/0623* (2013.01); *C12N 9/22* (2013.01); *C12N 15/11* (2013.01); *C12N 15/907* (2013.01); *C12N 2310/20* (2017.05); *C12N 2506/02* (2013.01); *C12N 2510/00* (2013.01); *C12N 2800/80* (2013.01)

(58) Field of Classification Search

CPC .................................................... C12N 5/0622

See application file for complete search history.

(56) References Cited

U.S. PATENT DOCUMENTS 5,872,005 A 2/1999 Wang et al.
6,479,626 B1 11/2002 Kim et al.
6,607,882 B1 8/2003 Cox et al.
6,692,957 B2 2/2004 Goldman et al.
6,746,838 B1 6/2004 Choo et al.
6,794,136 B1 9/2004 Eisenberg et al.
6,824,978 B1 11/2004 Cox et al.
6,866,997 B1 3/2005 Choo et al.
6,903,185 B2 6/2005 Kim et al.
6,933,113 B2 8/2005 Case
6,979,539 B2 12/2005 Cox et al.
7,013,219 B2 3/2006 Case et al.
7,029,913 B2 4/2006 Thomson
7,030,215 B2 4/2006 Liu et al.
7,220,719 B2 5/2007 Case et al.
7,241,573 B2 7/2007 Choo et al.
7,241,574 B2 7/2007 Choo et al.
7,485,291 B2 2/2009 Fang et al.
7,585,849 B2 9/2009 Liu et al.
7,595,376 B2 9/2009 Kim et al.
7,745,592 B2 6/2010 Massie et al.
8,728,759 B2 5/2014 Xu et al.
10,279,051 B2 5/2019 Goldman
10,779,519 B2 9/2020 Goldman et al.
2003/0223972 A1 12/2003 Goldman et al.
2004/0029269 A1 2/2004 Goldman et al.
2007/0116691 A1* 5/2007 Cambier .............. C12N 5/0635 435/325
2008/0233610 A1 9/2008 Thomson et al.
2010/0156778 A1 6/2010 Yamagishi
2011/0200568 A1 8/2011 Ikeda et al.
2012/0276070 A1 11/2012 Musick (Continued)

FOREIGN PATENT DOCUMENTS

WO 2007/069666 6/2007
WO 2008/118820 10/2008
WO 2009/006930 1/2009

(Continued)

OTHER PUBLICATIONS

Brüstle et al. Embryonic Stem Cell-Derived Glial Precursors: A Source of Myelinating Transplants. Science 1999, 285:754-756. (Year: 1999).*

(Continued)

*Primary Examiner* — Christopher M Babic
*Assistant Examiner* — Jennifer S Spence
(74) *Attorney, Agent, or Firm* — Fox Rothschild LLP

(57) ABSTRACT

A method for rejuvenating glial progenitor cells and rejuvenated glial progenitor cells rejuvenated by such method are disclosed. The method comprises introducing a population of genetically modified glial progenitor cells into the brain and/or brain stem of a subject, wherein the genetically modified glial progenitor cells have increased expression of one or more genes compared to the same type of glial progenitor cells that have not been genetically modified, and wherein the one or more genes are selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195.

8 Claims, 81 Drawing Sheets
(75 of 81 Drawing Sheet(s) Filed in Color)
Specification includes a Sequence Listing.

(56) References Cited

U.S. PATENT DOCUMENTS

2012/0276636 A1 11/2012 Yamanaka et al.
2016/0187319 A1* 6/2016 Tanaka ................ A61K 31/711 435/7.23

FOREIGN PATENT DOCUMENTS

| | | |
|---|---|---|
| WO | 2009/006997 | 1/2009 |
| WO | 2009/007852 | 1/2009 |
| WO | 2014/124087 | 8/2014 |
| WO | 2019246262 A2 | 12/2019 |
| WO | 2020167822 | 8/2020 |

OTHER PUBLICATIONS

Fults et al. MYC Expression Promotes the Proliferation of Neural Progenitor Cells in Culture and In Vivo. Neoplasia Apr. 2002;1:32-39. (Year: 2002).*
Raschella et al. Requirement of B-myb Function for Survival and Differentiative Potential of Human Neuroblastoma Cells. Journal of Biological Chemistry 1995, 270;15:8540-8545. (Year: 1995).*
Martins, Filipa, et al. "The role of the integral type II transmembrane protein BRI2 in health and disease." Cellular and Molecular Life Sciences 78 (2021): pp. 6807-6822.
Vidal, Ruben, et al. "A stop-codon mutation in the BRI gene associated with familial British dementia." Nature 399.6738 (1999): pp. 776-781.
Del Campo, Marta, et al. "BRI2-BRICHOS is increased in human amyloid plaques in early stages of Alzheimer's disease." Neurobiology of aging 35.7 (2014): pp. 1596-1604.
Matsuda, Shuji, et al. "BRI2 inhibits amyloid 13-peptide precursor protein processing by interfering with the docking of secretases to the substrate." Journal of Neuroscience 28.35 (2008): pp. 8668-8676.
Matsuda, Shuji, and Takao Senda. "BRI2 as an anti-Alzheimer gene." Medical Molecular Morphology 52 (2019): pp. 1-7.
Choi, Seung-Il, et al. "Axonal transport of British and Danish amyloid peptides via secretory vesicles." The FAS EB journal 18.2 ( 2004): pp. 1-18.
Lepore, Angelo C., et al. "Human glial-restricted progenitor transplantation into cervical spinal cord of the SOD1 G93A mouse model of ALS." PloS one 6.10 (2011): e25968.
Matsuda, Shuji, et al. "The familial dementia BRI2 gene binds the Alzheimer gene amyloid-beta precursor protein and inhibits amyloid-beta production." Journal of Biological Chemistry 280.32 (2005): 28912-28916.
International Search Report and Written Opinion Issued in International Patent Application No. PCT/US/2022/078182, mail date Jan. 20, 2023.
International Search Report and Written Opinion Issued in International Patent Application No. PCT/US/2022/078181, mail date Mar. 21, 2023.
International Search Report and Written Opinion Issued in International Patent Application No. PCT/US/2022/077825, mail date Jan. 20, 2023.
Neumann Bjorn, et al., "Myc determines the functional age state of oligodendrocyte progenitor cell", vol. 1, No. 9, Sep. 14, 2021, pp. 826-837.
Lo L-C. et al., "V-myc immortialization of early rat neural crest cells yields a cional cell line which generates both glial and adrenergic proger or cells", Developmental Biology, Elsevier, Amsterdam, NL, vol. 145, No. 1, May 1, 1991.
Mariani, John, et al., "Age-Associated Induction of Senescent Transcriptional Programs in Human Glial Progenitor Cells", SSRN Electronic Journal, Sep. 25, 2021.
Albar et al. (2017). Nat Methods 14, 1083-1086.
Aird, et al. (2013). Cell Rep 3, 1252-1265.
Aleksovska, K, et al., "Systematic Review and Meta-Analysis of Circulating S100B Blood Levels in Schizophrenia," Plos One 9, e106342 (2014).
Alerasool et al., "An Efficient KRAB Domain for CRISPRi Applications in Human Cells," Nature Methods 17:1093-1096 (2020).
Ausubel et al., Current Protocols in Molecular Biology, John Wiley and Sons, Baltimore, Md, (1989).
Benraiss, A. et al. "Cell-intrinsic Glial Pathology is Conserved Across Human and Murine Models of Huntington's Disease," Cell Reports 36, 109308 (2021).
Benraiss, A. et al. Human glia can both induce and rescue aspects of disease phenotype in Huntington disease. Nature Communications 7, 11758 (2016).
Beurdeley et al., "Compact Designer TALENs for Efficient Genome Engineering," Nat. Commun. 4:1762 (2013).
Borgdorff, et al. (2010). Oncogene 29, 2262-2271.
Bouard et al., "Viral Vectors: From Virology to Transgene Expression," Br. J. Pharmacol. 157(2):153-165 (2009).
Bretones, et al. (2015). Biochim Biophys Acta 1849, 506-516.
Brezgin et al., "Dead Cas Systems: Types, Principles, and Applications," Int. J. Mol. Sci. 20:6041 (2019).
Budde, et al. (2010). Development 137, 2127.
Bulcha et al., "Viral Vector Platforms within the Gene Therapy Landscape," Nature 6:53 (2021).
Buning et al., "Recent Developments in Adeno-associated Virus Vector Technology," J. Gene Med. 10:717-733 (2008).
Bunt, et al. (2010). Mol Cancer Res 8, 1344-1357.
Butler et al. (2018). Nat Biotechnol 36, 411-420.
Cai et al., "Generation of Human Induced Pluripotent Stem Cells from Umbilical Cord Matrix and Amniotic Membrane Mesenchymal Cells," J. Biol. Chem. 285(15): 112227-11234 (2110).
Campos-Viguri, et al. (2020). Sci Rep 10, 3256.
Chang et al., Somatic Gene Therapy, CRC Press, Ann Arbor, Mich. (1995).
Chen, et al. (2016). J Exp Clin Cancer Res 35, 173.
Cho et al., "Induction of Pluripotent Stem Cells from Adult Somatic Cells by Protein-Based Reprogramming without Genetic Manipulation," Blood 116: 386-395 (2010).
Cho, et al. (2012). Cell Death Differ 19, 703-712.
Cowan et al., "Derivation of Embryonic Stem-Cell Lines from Human Blastocytes," N. Engl. J. Med. 350:1353-56 (2004).
Dang (1999). Molecular and Cellular Biology 19, 1.
Deneen, et al. (2006), Neuron 52, 953-968.
Diaz-Castro, B., et al., "Astrocyte Molecular Signatures in Huntington's Disease," Sci Transi Med 11, eaaw8646 (2019).
Diepenbruck, et al. (2014). Journal of cell science 127, 1523-1536.
Diril, et al. (2012). Proc Natl Acad Sci U S A 109, 3826-3831.
Du, et al. (2014a). Cellular Physiology and Biochemistry 34, 955-965.
Du, et al. (2014b). miR-17 extends mouse lifespan by inhibiting senescence signaling mediated by MKP7. Cell Death Dis 5, e1355.
Duke et al., "An Improved CRISPR/dCas9 Interference Tool for Neuronal Gene Suppression," Frontiers in Genome Editing 2:9 (2020).
Eckers, et al. (2016). Sci Rep 6, 19618.
Enright, et al. (2003). MicroRNA targets in *Drosophila*. Genome biology 5, R1.
Faideau, M. et al. "In Vivo Expression of Polyglutamine-Expanded Huntingtin by Mouse Striatal Astrocytes Impairs Glutamate Transport: A Correlation with Huntington's Disease Subjects," Hum Mol Genet 19: 3053-3067 (2010).
Feng et al., Nature Cell Biology 11: 197-203 (2009).
Franklin, R. J. M., et al., "Remyelination in the CNS: from Biology to Therapy," Nat Rev Neurosci 9, 839-855 (2008).
Freund, et al. (2012). Mol Biol Cell 23, 2066-2075.
Friedman, et al. (2009). Genome Res 19, 92-105.
Frietze, et al. (2010). PLoS One 5, e15082.
Fusaki et al., "Efficient Induction of Transgene-Free Human Pluripotent Stem Cells Using a Vector Based on Sendi Virus, an RNA Virus That Does Not Integrate into the Host Genome," Proc Jpn Acad. 85: 348-362 (2009).
Gaj et al., "Targeted Gene Knockout by Direct Delivery of Zinc-Finger Nuclease Proteins," Nat. Methods 9(8):805-807 (2012).
Aibar et al. (2017). Nat Methods 14, 1083-1086.
Diaz-Castro, B., et al., "Astrocyte Molecular Signatures in Huntington's Disease," Sci Transl Med 11, eaaw8546 (2019).

(56) References Cited

OTHER PUBLICATIONS

Du, et al. (2014a). Cellular Physiology and Biochemistry 34, 956-985.
Duke et al., "An Improved CRISPR/dCas Interference Tool for Neuronal Gene Suppression," Frontiers in Genome Editing 2:9 (2020).
Gilboa et al. Biotechniques 4 (6): 504-512, 1986.
Giorgetti et al., "Generation of Induced Pluripotent Stem Cells from Human Cord Blood Cells with only Two Factors: Oct4 and Sox2," Nature Protocols, 5(4):811-820 (2010).
Giorgio, F. P. D., et al., "Human Embryonic Stem Cell-Derived Motor Neurons Are Sensitive to the Toxic Effect of Glial Cells Carrying an ALS-Causing Mutation," Cell Stem Cell 3: 637-648 (2008).
Giorgio, F. P. D., et al., "Non-Cell Autonomous Effect of Glia on Motor Neurons in an Embryonic Are Sensitive to the Toxic Effect of Glial Cells Carrying an ALS-Causing Mutation," Cell Stem Cell 3: 637-648 (2008).
Giorgio, F. P. D., et al., "Non-Cell Autonomous Effect of Glia on Motor Neurons in an Embryonic Stem Cell-Based ALS Model," Nat Neurosci 10: 608-614 (2007).
Givogri, M. I. et al., "Oligodendroglial Progenitor Cell Therapy Limits Central Neurological Deficits in Mice with Metachromatic Leukodystrophy," J Neurosci 26, 3109-3119 (2006).
Goldman et al., (2015). Development 142, 3983-3995.
Goldman, S. A., "Stem and Progenitor Cell-Based Therapy of the Central Nervous System: Hopes, Hype, and Wishful Thinking," Cell Stem Cell 18, 174-188 (2016).
Grieger et al., "Adeno-associated Virus as a Gene Therapy Vector: Vector Development, Production and Clinical Applications," Adv. Biochem. Engin/Biotechnol. 99: 119-145 (2005).
Han, et al. (2020). Int J Oral Sci 12, 10.
Hanna et al., Cell 133(2): 250-264 (2008).
Harris, et al. (2021). Cell Stem Cell.
Hernandez-Segura, et al. (2017). Current biology : CB 27, 2652-2660 e2654.
Hollander, et al. (1999). Nat Genet 23, 176-184.
Hu et al., "Efficient Generation of Transgene-Free Induced Pluripotent Stem Cells from Normal land Neoplastic Bone Marrow and Cord Blood Mononuclear Cells," Blood doi: 10.1182/.
Hu et al., "Immunization Delivered by Lentiviral Vectors for Cancer and Infection Diseases," Immunol. Rev. 239: 45-61 (2011).
Huangfu et al., Nature Biotechnology 26: 1269-1275 (2008).
Jia et al., "A Nonviral Minicircle Vector for Deriving Hyman iPS Cells," Nat. Methods 7: 197-199 (2010).
Kaji et al., "Virus-Free Induction of Pluripotency and Subsequent Excision of Reprogramming Factors," Nature 458: 771-775 (2009).
Kallunki et al., "How to Choose the Right Inducible Gene Expression System for Mammalian Studies?" Cells 8(8):796 (2019).
Katsel, P. et al., "Astrocyte and Glutamate Markers in the Superficial, Deep, and White Matter Layers of the Anterior Cingulate Gyrus in Schizophrenia," Neuropsychopharmacol 3.
Kim et al., Cell 136(3 :411-419 (2009).
Kim et al., Nature 454: 646-650 (2008).
Kim, et al. (2012). EMBO J 31, 4289-4303.
Kojima, et al. (2013). IL-6-STAT3 signaling and premature senescence. JAKSTAT 2, e25763.
Krause et al., "Delivery of Antigens by Viral Vectors for Vaccination," Ther. Deliv. 2(1):51-70 (2011).
Lall, et al. (2006). Current biology : CB 16, 460-471.
Lau, et al. (2008). J Neurosci 28, 11720-11730.
Lau, P., et al. (2008). Identification of dynamically regulated microRNA and mRNA networks in developing oligodendrocytes. J Neurosci 28, 11720-11730.
Lee et al. (2016). Proceedings of the National Academy of Sciences 113, E3213-E3220.
Lee, Y. et al. "Oligodendroglia Metabolically Support Axons and Contribute to Neurodegeneration," Nature 487: 443-448 (2012).
Lengner et al., "Derivation of Pre-x inactivation Human Embryonic Stem Cell Line in Physiological Oxygen Conditions," Cell 141(5):872-83 (2010).
Li, et al. (2017). J Exp Clin Cancer Res 36, 59.
Liu et al., "CD44 Expression Identifies Astrocyte-Restricted Precursor Cells," Dev. Biol. 276(1):31-46 (2004).
Liu, et al. (2019). Journal of Experimental & Clinical Cancer Research 38, 369.
Ma, L. et al. (2010a). miR-9. a MYC/MYCN-activated microRNA, regulates ϵ-cadherin and cancer metastasis. Nat Cell Bio: 12, 247-256.
Maragkakis, et al. (2011). Nucleic Acids Res 39, W145-148.
Mason, et al. (2004). Oncogene 23, 9238-9246.
Meissner et al. Nat. Biotech. 25:1177-1181 (2007).
Meyer, K. et al. "Direct Conversion of Patient Fibroblasts Demonstrates Non-Cell Autonomous Toxicity of Astrocytes to Motor Neurons in Familial and Sporadic ALS," Proc Nation.
Meyer, K. et al. "Direct Conversion Of Patient Fibroblasts Demonstrates Non-Cell Autonomous Toxicity Of Astrocytes To Motor Neurons In Familial And Sporadic ALS." Proc Nationa.
Murakami-Tonami, et al. (2016). Scientific Reports 6, 31615.
Nakagawa et al., Nat. Biotechnol. 26:101-106 (2007).
Nakamura, et al. (2000). Mol Cell Biol 20, 3178-3186.
Neumann et al. (2021a). Nature Aging 1, 826-837.
Nunes et al., "Identification and Isolation of Multipotential Neural Progenitor Cells From the Subcortical White Matter of the Adult Human Brain.," Nat Med. 9(4):439-47 (2003).
Okita et al., "Generation of Mouse Induced Pluripotent Stem Cells without Viral Vectors," Science 322: 949-953 (2008).
Okita et al., Nature 448:313-317 (2007).
Osipovitch, M. et al., "Human ESC-Derived Chimeric Mouse Models of Huntington's Disease Reveal Cell-Intrinsic Defects in Glial Progenitor Cell Differentiation," Cell Stem Cell.
Park et al. Nature 451:141-146 (2008).
Piper, et al. (2002). Aging cell 1, 149-157.
Poudel, et al. (2020). Stem Cells.
Qi et al., "Repurposing CRISPR as an RNA-Guided Platform for Sequence-Specific Control of Gene Expression," Cell 152(5):1173-1183 (2013).
Reichardt, et al. (2006). Phys Rev E Stat Nonlin Soft Matter Phys 74, 016110.
Rohrberg, et al. (2020). Cell Rep 30, 3368-3382 e3367.
Sambrook et al., Molecular Cloning: A Laboratory Manual, Cold Springs Harbor Laboratory, New York (1989, 1992).
Scharenberg et al., "Genome Engineering with TAL-Effector Nucleases and Alternative Modular Nuclease Technologies," Curr. Gene Ther. 13(4):291-303 (2013).
Seki and Arai (1993). Neurosci Res 17, 265-290.
Shen, et al. (2015). A miR-130a—YAP positive feedback loop promotes organ size and tumorigenesis. Cell Res 25, 997-1012.
Shi et al., Cell Stem Cell 3(5): 568-574 (2008).
Shin, J.-Y. et al. "Expression of Mutant Huntingtin in Glial Cells Contributes to Neuronal Excitotoxicity," J Cell Biology 171: 1001-1012 (2005).
Sim et al. (2009). Neuron Glia Biol 5, 45-55.
Sim et al. (2011a). Nature Biotechnology 29, 934-941.
Sim, et al. (2006). Ann Neurol 59, 763-779.
Sim, F. J. et al., "CD140a Identifies a Population of Highly Myelinogenic, Migration-competent and Efficiently Engrafting Human Oligodendrocyte Progenitor cells," Nat Biotech.
Soldner et al., "Parkinson's Disease Patient-Derived Induced Pluripotent Stem Cells Free of Viral Reprogramming Factors," Cell 136:964-977 (2009).
Sommer and Mostoslavsky, "Experimental Approaches for the Generation of Induced Pluripotent Stem Cells." Stem Cell Res. Ther. 1:26 doi:10.1186/scrt26 (2010).
Sommer et al., "Generation of Human Induced Pluripotent Stem Cells from Peripheral Blood using the STEMCCA Lentiviral Vector," J. Vis. Exp. 68: e4327 doi:10.3791/4327 (2012).
Song, et al. (2020). Oncol Lett 20, 69.
Stadtfeld et al., "Induced Pluripotent Stem Cells Generated without Viral Integration," Science 322: 945-949 (2008).

(56) References Cited

OTHER PUBLICATIONS

Streckfuss-Bomeke et al., "Comparative Study of Human-Induced Pluripotent Stem Cells Derived from Bone Marrow Cells, Hair Keratinocytes, and Skin Fibroblasts," Eur. Heart J.
Sundar, et al. (2018). FASEB journal : official publication of the Federation of American Societies for Experimental Biology 32, 4955-4971.
Takahashi et al., Cell 126:663-676 (2006).
Takahashi et al., Cell 131:1-12 (2007.
Tannenbaum et al., "Derivation of Xeno-free and GMP-grade Human Embryonic Stem Cells—Platforms for Future Clinical Applications," PLoS One 7(6):e35325 (2012).
Thomson et al., "Embryonic Stem Cell Lines Derived from Human Blastocytes," Science 282 (5391): 1145-47 (1998).
Tkachev, D. et al., "Oligodendrocyte Dysfunction in Schizophrenia and Bipolar Disorder," Lancet 362, 798-805 (2003).
Tong, et al. (2019). TransmiR v2.0: an updated transcription factor-microRNA regulation database. Nucleic Acids Res 47, D253-D258.
Tong, X. et al. "Astrocyte Kir4.1 Ion Channel Deficits Contribute to Neuronal Dysfunction in Huntington's Disease Model Mice," Nat Neurosci 17, 694-703 (2014).
Ura et al., "Developments in Viral Vector-Based Vaccines," Vaccines 2: 624-641 (2014).
Urnov et al., "Genome Editing with Engineered Zinc Finger Nucleases," Nat. Rev. Genet. 11(9):636-646 (2010).
Vectors: A Survey of Molecular Cloning Vectors and Their Uses, Butterworths, Boston Mass. (1988).
Vega et al., Gene Targeting, CRC Press, Ann Arbor Mich. (1995).
Voineskos, A. N. et al., "Oligodendrocyte Genes, White Matter Tract Integrity, and Cognition in Schizophrenia," Cereb Cortex 23, 2044-2057 (2013).
Wang et al. Cell Stem Cell 12, 252-264, 2013.
Wang et al., "Human iPSC-Derived Oligodendrocyte Progenitors Can Myelinate and Rescue a Mouse Model of Congenital Hypomyelination," Cell Stem Cell 12(2):252-264 (2013).
Wang, et al. (2013). Cell Stem Cell 12, 252-264.
Wang, et al. (2017). Dev Cell 40, 566-582.e565.
Wang, S. et al. Human iPSC-Derived Oligodendrocyte Progenitor Cells Can Myelinate and Rescue a Mouse Model of Congenital Hypomyelination. Cell Stem Cell 12, 252-264 (2013).
Wang, Y et al. (2020b). Aging 12, 20366-20379.
Windrem et al., "Fetal and Adult Human Oligodendrocyte Progenitor Cell Isolates Myelinate the Congenitally Dysmyelinated Brain," Nature Medicine 10:93-97 (2004).
Windrem, et al. (2004). Nat Med 10, 93-974.
Windrem, et al. (2017). Cell Stem Cell 21, 195-208.e196.
Windrem, M. S. et al., "A Competitive Advantage by Neonatally Engrafted Human Glial Progenitors Yields Mice Whose Brains Are Chimeric for Human Glia," J Neurosci 34, 16153-161.
Windrem, M. S. et al., "Human Glial Progenitor Cells Effectively Remyelinate the Demyelinated Adult Brain," Cell Reports 31, 107658 (2020).
Windrem, M. S. et al., "Human iPSC Glial Mouse Chimeras Reveal Glial Contributions to Schizophrenia," Cell Stem Cell 21, 195-208.e6 (2017).
Woltjen et al., "PiggyBac Transposition Reprograms Fibroblasts to Induced Pluripotent Stem Cells," Nature 458: 786-770 (2009).
Wong, et al. (2015). Nucleic Acids Res 43, D146-152.
Yamanaka, K. et al. "Astrocytes as determinants of disease progression in inherited amyotrophic lateral sclerosis," Nat Neurosci 11: 251-253 (2008).
Yang, et al. (2005). Oncogene 24, 7869-7881.
Yattah, et al. (2020). Neurochem Res 45, 606-619.
Yeo et al., "An Enhanced CRISPR Repressor for Targeted Mammalian Gene Regulation," 15(8):611-616 (2018).
Yu et al. Science 318:1917-1920 (2007).
Yu et al., "Human Induced Pluripotent Stem Cells Free of Vector and Transgene Sequences," Science 324: 797-801 (2009).
Yusa et al., "Generation of Transgene-Free Induced Pluripotent Mouse Stem Cells by the PiggyBac Transposon," Nat. Methods 6: 363-369 (2009).
Zhao et al., Cell Stem Cell 3: 475-479 (2008).
Zhou et al., "Generation of Induced Pluripotent Stem Cells Using Recombinant Proteins," Cell Stem Cell 4: 381-384 (2009).

* cited by examiner

A

A'

C

| Cell Line | HTT CAG Length | Transgenic Insert |
|---|---|---|
| GENEA019 (WT-EGFP) | 18;15 | Puro-CAG-EGFP |
| GENEA019 (WT-mCherry) | 18;15 | Puro-CAG-mCherry |
| GENEA020 (HD-EGFP) | 48;17 | Puro-CAG-EGFP |

D

E

A

B

D

A

B

B'

C

C

E

U.S. Patent Nov. 3, 2026 Sheet 62 of 81 US 12,781,186 B2

F

A

G

C

D

C

SEQUENCE LISTING

```
Sequence total quantity: 10
SEQ ID NO: 1            moltype = DNA  length = 21
FEATURE                 Location/Qualifiers
misc_feature            1..21
                        note = Synthetic: Dna803
source                  1..21
                        mol_type = other DNA
                        organism = synthetic construct
SEQUENCE: 1
tcgacttccc ctcttccgat g                                          21

SEQ ID NO: 2            moltype = DNA  length = 21
FEATURE                 Location/Qualifiers
misc_feature            1..21
                        note = Synthetic: Dna804
source                  1..21
                        mol_type = other DNA
                        organism = synthetic construct
SEQUENCE: 2
gagcctaggg ccgggattct c                                          21

SEQ ID NO: 3            moltype = DNA  length = 22
FEATURE                 Location/Qualifiers
misc_feature            1..22
                        note = Synthetic: Dna183
source                  1..22
                        mol_type = other DNA
                        organism = synthetic construct
SEQUENCE: 3
ctcaggttct gggagagggt ag                                         22

SEQ ID NO: 4            moltype = AA  length = 1054
FEATURE                 Location/Qualifiers
REGION                  1..1054
                        note = misc_feature - human CEBPZ protein
source                  1..1054
                        mol_type = protein
                        organism = Homo sapiens
SEQUENCE: 4
MAAVKEPLEF HAKRPWRPEE AVEDPDEEDE DNTSEAENGF SLEEVLRLGG TKQDYLMLAT  60
LDENEEVIDG GKKGAIDDLQ QGELEAFIQN LNLAKYTKAS LVEEDEPAEK ENSSKKEVKI  120
PKINNKNTAE SQRTSVNKVK NKNRPEPHSD ENGSTTPKVK KDKQNIFEFF ERQTLLLRPG  180
GKWYDLEYSN EYSLKPQPQD VVSKYKTLAQ KLYQHEINLF KSKTNSQKGA SSTWMKAIVS  240
SGTLGDRMAA MILLIQDDAV HTLQFVETLV NLVKKKGSKQ QCLMALDTFK ELLITDLLPD  300
NRKLRIFSQR PFDKLEQLSS GNKDSRDRRL ILWYFEHQLK HLVAEFVQVL ETLSHDTLVT  360
TKTRALTVAH ELLCNKPEEE KALLVQVVNK LGDPQNRIAT KASHLLETLL CKHPNMKGVV  420
SGEVERLLFR SNISSKAQYY AICFLNQMAL SHEESELANK LITVYFCFFR TCVKKKDVES  480
KMLSALLTGV NRAYPYSQTG DDKVREQIDT LFKVLHIVNF NTSVQALMLL FQVMNSQQTI  540
SDRYYTALYR KMLDPGLMTC SKQAMFLNLV YKSLKADIVL RRVKAFVKRL LQVTCQQMPP  600
FICGALYLVS EILKAKPGLR SQLDDHPESD DEENFIDAND DEDMEKFTDA DKETEIVKKL  660
ETEETVPETD VETKKPEVAS WVHFDNLKGG KQLNKYDPFS RNPLFCGAEN TSLWELKKLS  720
VHFHPSVALF AKTILQGNYI QYSGDPLQDF TLMRFLDRFV YRNPKPHKGK ENTDSVVMQP  780
KRKHFIKDIR HLPVNSKEFL AKEESQIPVD EVFFHRYYKK VAVKEKQKRD ADEESIEDVD  840
DEEFEELIDT FEDDNCFSSG KDDMDFAGNV KKRTKGAKDN TLDEDSEGSD DELGNLDDDE  900
VSLGSMDDEE FAEVDEDGGT FMDVLDDESE SVPELEVHSK VSTKKSKRKG TDDFDFAGSF  960
QGPRKKKRNL NDSSLFVSAE EFGHLLDENM GSKFDNIGMN AMANKDNASL KQLRWEAERD  1020
DWLHNRDAKS IIKKKKHFKK KRIKTTQKTK KQRK                            1054

SEQ ID NO: 5            moltype = AA  length = 700
FEATURE                 Location/Qualifiers
REGION                  1..700
                        note = misc_feature - human MYBL2 protein isoform 1
source                  1..700
                        mol_type = protein
                        organism = Homo sapiens
SEQUENCE: 5
MSRRTRCEDL DELHYQDTDS DVPEQRDSKC KVKWTHEEDE QLRALVRQFG QQDWKFLASH  60
FPNRTDQQCQ YRWLRVLNPD LVKGPWTKEE DQKVIELVKK YGTKQWTLIA KHLKGRLGKQ  120
```

```
CRERWHNHLN PEVKKSCWTE EEDRIICEAH KVLGNRWAEI AKMLPGRTDN AVKNHWNSTI  180
KRKVDTGGFL SESKDCKPPV YLLLELEDKD GLQSAQPTEG QGSLLTNWPS VPPTIKEEEN  240
SEEELAAATT SKEQEPIGTD LDAVRTPEPL EEFPKREDQE GSPPETSLPY KWVVEAANLL  300
IPAVGSSLSE ALDLIESDPD AWCDLSKFDL PEEPSAEDSI NNSLVQLQAS HQQQVLPPRQ  360
PSALVPSVTE YRLDGHTISD LSRSSRGELI PISPSTEVGG SGIGTPPSVL KRQRKRRVAL  420
SPVTENSTSL SFLDSCNSLT PKSTPVKTLP FSPSQFLNFW NKQDTLELES PSLTSTPVCS  480
QKVVVTTPLH RDKTPLHQKH AAFVTPDQKY SMDNTPHTPT PFKNALEKYG PLKPLPQTPH  540
LEEDLKEVLR SEAGIELIIE DDIRPEKQKR KPGLRRSPIK KVRKSLALDI VDEDVKLMMS  600
TLPKSLSLPT TAPSNSSSLT LSGIKEDNSL LNQGFLQAKP EKAAVAQKPR SHFTTPAPMS  660
SAWKTVACGG TRDQLFMQEK ARQLLGRLKP SHTSRTLILS                        700

SEQ ID NO: 6            moltype = AA  length = 676
FEATURE                 Location/Qualifiers
REGION                  1..676
                        note = misc_feature - human MYBL2 protein isoform 2
source                  1..676
                        mol_type = protein
                        organism = Homo sapiens
SEQUENCE: 6
MSRRTRCEDL DELHYQDTDS DVPEQRDSKC KVKWTHEENR TDQQCQYRWL RVLNPDLVKG  60
PWTKEEDQKV IELVKKYGTK QWTLIAKHLK GRLGKQCRER WHNHLNPEVK KSCWTEEEDR  120
IICEAHKVLG NRWAEIAKML PGRTDNAVKN HWNSTIKRKV DTGGFLSESK DCKPPVYLLL  180
ELEDKDGLQS AQPTEGQGSL LTNWPSVPPT IKEEENSEEE LAAATTSKEQ EPIGTDLDAV  240
RTPEPLEEFP KREDQEGSPP ETSLPYKWVV EAANLLIPAV GSSLSEALDL IESDPDAWCD  300
LSKFDLPEEP SAEDSINNSL VQLQASHQQQ VLPPRQPSAL VPSVTEYRLD GHTISDLSRS  360
SRGELIPISP STEVGGSGIG TPPSVLKRQR KRRVALSPVT ENSTSLSFLD SCNSLTPKST  420
PVKTLPFSPS QFLNFWNKQD TLELESPSLT STPVCSQKVV VTTPLHRDKT PLHQKHAAFV  480
TPDQKYSMDN TPHTPTPFKN ALEKYGPLKP LPQTPHLEED LKEVLRSEAG IELIIEDDIR  540
PEKQKRKPGL RRSPIKKVRK SLALDIVDED VKLMMSTLPK SLSLPTTAPS NSSSLTLSGI  600
KEDNSLLNQG FLQAKPEKAA VAQKPRSHFT TPAPMSSAWK TVACGGTRDQ LFMQEKARQL  660
LGRLKPSHTS RTLILS                                                 676

SEQ ID NO: 7            moltype = AA  length = 454
FEATURE                 Location/Qualifiers
REGION                  1..454
                        note = misc_feature - human MYC protein isoform 1
source                  1..454
                        mol_type = protein
                        organism = Homo sapiens
SEQUENCE: 7
MDFFRVVENQ QPPATMPLNV SFTNRNYDLD YDSVQPYFYC DEEENFYQQQ QQSELQPPAP  60
SEDIWKKFEL LPTPPLSPSR RSGLCSPSYV AVTPFSLRGD NDGGGGSFST ADQLEMVTEL  120
LGGDMVNQSF ICDPDDETFI KNIIIQDCMW SGFSAAAKLV SEKLASYQAA RKDSGSPNPA  180
RGHSVCSTSS LYLQDLSAAA SECIDPSVVF PYPLNDSSSP KSCASQDSSA FSPSSDSLLS  240
STESSPQGSP EPLVLHEETP PTTSSDSEEE QEDEEEIDVV SVEKRQAPGK RSESGSPSAG  300
GHSKPPHSPL VLKRCHVSTH QHNYAAPPST RKDYPAAKRV KLDSVRVLRQ ISNNRKCTSP  360
RSSDTEENVK RRTHNVLERQ RRNELKRSFF ALRDQIPELE NNEKAPKVVI LKKATAYILS  420
VQAEEQKLIS EEDLLRKRRE QLKHKLEQLR NSCA                             454

SEQ ID NO: 8            moltype = AA  length = 453
FEATURE                 Location/Qualifiers
REGION                  1..453
                        note = misc_feature - human MYC protein isoform 2
source                  1..453
                        mol_type = protein
                        organism = Homo sapiens
SEQUENCE: 8
MDFFRVVENQ PPATMPLNVS FTNRNYDLDY DSVQPYFYCD EEENFYQQQQ QSELQPPAPS  60
EDIWKKFELL PTPPLSPSRR SGLCSPSYVA VTPFSLRGDN DGGGGSFSTA DQLEMVTELL  120
GGDMVNQSFI CDPDDETFIK NIIIQDCMWS GFSAAAKLVS EKLASYQAAR KDSGSPNPAR  180
GHSVCSTSSL YLQDLSAAAS ECIDPSVVFP YPLNDSSSPK SCASQDSSAF SPSSDSLLSS  240
TESSPQGSPE PLVLHEETPP TTSSDSEEEQ EDEEEIDVVS VEKRQAPGKR SESGSPSAGG  300
HSKPPHSPLV LKRCHVSTHQ HNYAAPPSTR KDYPAAKRVK LDSVRVLRQI SNNRKCTSPR  360
SSDTEENVKR RTHNVLERQR RNELKRSFFA LRDQIPELEN NEKAPKVVIL KKATAYILSV  420
QAEEQKLISE EDLLRKRREQ LKHKLEQLRN SCA                              453

SEQ ID NO: 9            moltype = AA  length = 207
FEATURE                 Location/Qualifiers
REGION                  1..207
                        note = misc_feature - human NFYB protein
source                  1..207
                        mol_type = protein
                        organism = Homo sapiens
SEQUENCE: 9
MTMDGDSSTT DASQLGISAD YIGGSHYVIQ PHDDTEDSMN DHEDTNGSKE SFREQDIYLP  60
IANVARIMKN AIPQTGKIAK DAKECVQECV SEFISFITSE ASERCHQEKR KTINGEDILF  120
AMSTLGFDSY VEPLKLYLQK FREAMKGEKG IGGAVTATDG LSEELTEEAF TNQLPAGLIT  180
TDGQQQNVMV YTTSYQQISG VQQIQFS                                     207
```

-continued

```
SEQ ID NO: 10          moltype = AA  length = 410
FEATURE                Location/Qualifiers
REGION                 1..410
                       note = misc_feature - human TFDP1 protein
source                 1..410
                       mol_type = protein
                       organism = Homo sapiens
SEQUENCE: 10
MAKDAGLIEA NGELKVFIDQ NLSPGKGVVS LVAVHPSTVN PLGKQLLPKT FGQSNVNIAQ  60
QVVIGTPQRP AASNTLVVGS PHTPSTHFAS QNQPSDSSPW SAGKRNRKGE KNGKGLRHFS  120
MKVCEKVQRK GTTSYNEVAD ELVAEFSAAD NHILPNESAY DQKNIRRRVY DALNVLMAMN  180
IISKEKKEIK WIGLPTNSAQ ECQNLEVERQ RRLERIKQKQ SQLQELILQQ IAFKNLVQRN  240
RHAEQQASRP PPPNSVIHLP FIIVNTSKKT VIDCSISNDK FEYLFNFDNT FEIHDDIEVL  300
KRMGMACGLE SGSCSAEDLK MARSLVPKAL EPYVTEMAQG TVGGVFITTA GSTSNGTRFS  360
ASDLTNGADG MLATSSNGSQ YSGSRVETPV SYVGEDDEED DDFNENDEDD            410
```

METHOD FOR REJUVENATING GLIAL PROGENITOR CELLS AND REJUVENATED GLIAL PROGENITOR CELLS PER SE

CROSS-REFERENCE TO RELATED APPLICATIONS

This application claims priority from U.S. provisional No. 63/257,853, filed Oct. 20, 2021, which is incorporated herein by reference.

STATEMENT REGARDING FEDERALLY SPONSORED RESEARCH

This invention was made with government support under NS110776 and AG072298 awarded by National Institutes of Health. The government has certain rights in the invention.

REFERENCE TO AN ELECTRONIC SEQUENCE LISTING

The contents of the electronic sequence listing (1134-091.xml; Size: 17,422 bytes; and Date of Creation: Oct. 13, 2022) is herein incorporated by reference in its entirety.

FIELD

This application relates to genetically modified glial progenitor cells and methods of utilizing the genetically modified glial progenitor cells to rejuvenate glial cells and to treat a variety of conditions amenable to cell therapy.

BACKGROUND

Glial dysfunction is a causal contributor to a broad spectrum of neurological conditions. Besides the many disorders of myelin, it is now clear that astrocytic and oligodendrocytic pathology underlie the genesis and progression of a number of both neurodegenerative and neuropsychiatric disorders, including conditions as varied as amyotrophic lateral sclerosis (ALS) (Giorgio, F. P. D., et al., "Non-Cell Autonomous Effect of Glia on Motor Neurons in an Embryonic Are Sensitive to the Toxic Effect of Glial Cells Carrying an ALS-Causing Mutation," Cell Stem Cell 3:637-648 (2008); Yamanaka, K. et al. "Astrocytes as determinants of disease progression in inherited amyotrophic lateral sclerosis," Nat Neurosci 11:251-253 (2008); Lee, Y. et al. "Oligodendroglia Metabolically Support Axons and Contribute to Neurodegeneration," Nature 487:443-448 (2012); and Meyer, K. et al. "Direct Conversion of Patient Fibroblasts Demonstrates Non-Cell Autonomous Toxicity of Astrocytes to Motor Neurons in Familial and Sporadic ALS," Proc National Acad Sci 111:829-832 (2014)) and Huntington's disease (HD) (Shin, J.-Y. et al. "Expression of Mutant Huntingtin in Glial Cells Contributes to Neuronal Excitotoxicity," J Cell Biology 171:1001-1012 (2005); Faideau, M. et al. "In Vivo Expression of Polyglutamine-Expanded Huntingtin by Mouse Striatal Astrocytes Impairs Glutamate Transport: A Correlation with Huntington's Disease Subjects," Hum Mol Genet 19:3053-3067 (2010); Tong, X. et al. "Astrocyte Kir4.1 Ion Channel Deficits Contribute to Neuronal Dysfunction in Huntington's Disease Model Mice," Nat Neurosci 17, 694-703 (2014); Benraiss, A. et al., Human Glia can both Induce and Rescue Aspects of Disease Phenotype in Huntington Disease," Nat Commun 7, 11758 (2016); Diaz-Castro, B., et. al., "Astrocyte Molecular Signatures in Huntington's Disease," Sci Transl Med 11, eaaw8546 (2019); Benraiss, A. et al. "Cell-intrinsic Glial Pathology is Conserved Across Human and Murine Models of Huntington's Disease," Cell Reports 36, 109308 (2021)) as well as schizophrenia and bipolar disease (Tkachev, D. et al., "Oligodendrocyte Dysfunction in Schizophrenia and Bipolar Disorder," Lancet 362, 798-805 (2003); Katsel, P. et al., "Astrocyte and Glutamate Markers in the Superficial, Deep, and White Matter Layers of the Anterior Cingulate Gyrus in Schizophrenia," Neuropsychopharmacol 36, 1171-1177 (2011); Voineskos, A. N. et al., "Oligodendrocyte Genes, White Matter Tract Integrity, and Cognition in Schizophrenia," Cereb Cortex 23, 2044-2057 (2013); Aleksovska, K. et al., "Systematic Review and Meta-Analysis of Circulating S100B Blood Levels in Schizophrenia," Plos One 9, e106342 (2014); Windrem, M. S. et al., "Human iPSC Glial Mouse Chimeras Reveal Glial Contributions to Schizophrenia," Cell Stem Cell 21, 195-208.e6 (2017).

In such conditions, the replacement of diseased glia by healthy wild-type glial progenitor cells may provide substantial therapeutic benefit (Goldman, S. A., "Stem and Progenitor Cell-Based Therapy of the Central Nervous System: Hopes, Hype, and Wishful Thinking," Cell Stem Cell 18, 174-188 (2016) and Franklin, R. J. M., et. al., "Remyelination in the CNS: from Biology to Therapy," Nat Rev Neurosci 9, 839-855 (2008)) due to the migration and expansion competence of human glial progenitor cells (hGPCs), as well as their lineage plasticity and ability to generate both astrocytes and myelin-forming oligodendrocytes in a context-dependent manner (Nunes, M. C. et al., "Identification and Isolation of Multipotential Neural Progenitor Cells from the Subcortical White Matter of the Adult Human Brain," Nat Med 9, 439-447 (2003); Sim, F. J. et al., "CD140a Identifies a Population of Highly Myelinogenic, Migration-competent and Efficiently Engrafting Human Oligodendrocyte Progenitor cells," Nat Biotechnol 29, 934-941 (2011); Windrem, M. S. et al., "A Competitive Advantage by Neonatally Engrafted Human Glial Progenitors Yields Mice Whose Brains Are Chimeric for Human Glia," J Neurosci 34, 16153-16161 (2014); and Windrem, M. S. et al., "Human Glial Progenitor Cells Effectively Remyelinate the Demyelinated Adult Brain," Cell Reports 31, 107658 (2020)). However, to effect therapeutic replacement, allogeneic hGPCs must compete against the endogenous pool, displace them, and eventually repopulate the afflicted areas of the host's brain. In prior studies of mouse-to-mouse allografts, the competitive interactions between healthy and diseased glial progenitor cells (GPCs) favor the expansion and integration of the healthy donor population (Givogri, M. I. et al., "Oligodendroglial Progenitor Cell Therapy Limits Central Neurological Deficits in Mice with Metachromatic Leukodystrophy," J Neurosci 26, 3109-3119 (2006), U.S. Pat. No. 10,279,051 to Goldman, and U.S. Pat. No. 10,779,519 to Goldman). Nonetheless, it remains unclear whether healthy human GPCs can outcompete and replace their diseased human counterparts.

The present disclosure is directed to overcoming these and other deficiencies in the art.

SUMMARY

One aspect of the present application relates to a method of rejuvenating glial cells of the brain and/or brain stem in a subject, said method comprising: introducing the population of genetically modified glial progenitor cells into the brain and/or brain stem of the subject, wherein the genetically modified glial progenitor cells have increased expression of one or more genes compared to the same type of glial progenitor cells that have not been genetically modified, wherein the one or more genes are selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, and wherein said increased expression of the one or more genes in the genetically modified glial progenitor cells confer competitive advantage over native or already resident glial progenitor cells in the subject.

Another aspect of the present application relates to an isolated population of genetically modified glial progenitor cells, wherein the genetically modified glial progenitor cells have increased expression of one or more genes compared to the same type of glial progenitor cells that have not been genetically modified, and wherein the one or more genes are selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195.

BRIEF DESCRIPTION OF THE DRAWINGS

The patent or application file contains at least one drawing executed in color. Copies of this patent or application with color drawing(s) will be provided by the Office upon request and payment of the necessary fee.

Figure 1:
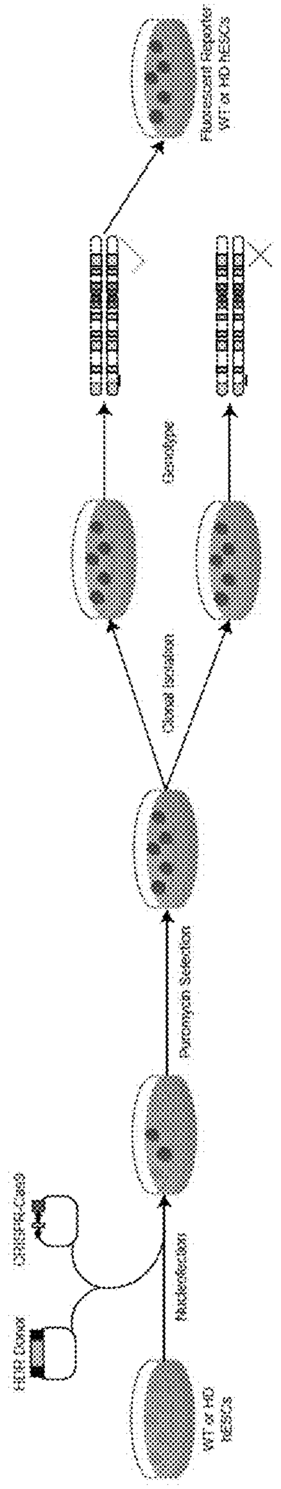
FIG. 1, Panels A-B show representative images of expression of WT-mCherry and HD-EGFP. Panel A shows workflow employed in the genetic engineering of the adeno-associated virus integration site 1 (AAVS1) locus of hESC lines to constitutively express transgenes of interest. Panel A' shows the mechanism of CRISPR-Cas9 mediated transgene integration into the AAVS1 locus (located in the first intron of the protein phosphatase 1 regulatory subunit 12C (PPP1R12C) gene). Panels B-B' show representative images of expression of WT-mCherry and HD-EGFP. Panels C-D illustrate transgene constructs driving expression of either mCherry or EGFP (enhanced green fluorescent protein) inserted into the AAVS1 safe-harbor locus of WT GENEA019 (mcherry) and HD GENEA020 (EGFP) hESCs. Panel E shows representative images of WT-mCherry (Panel B) and HD-EGFP expression in the brain (Panel B').
Figure 1:
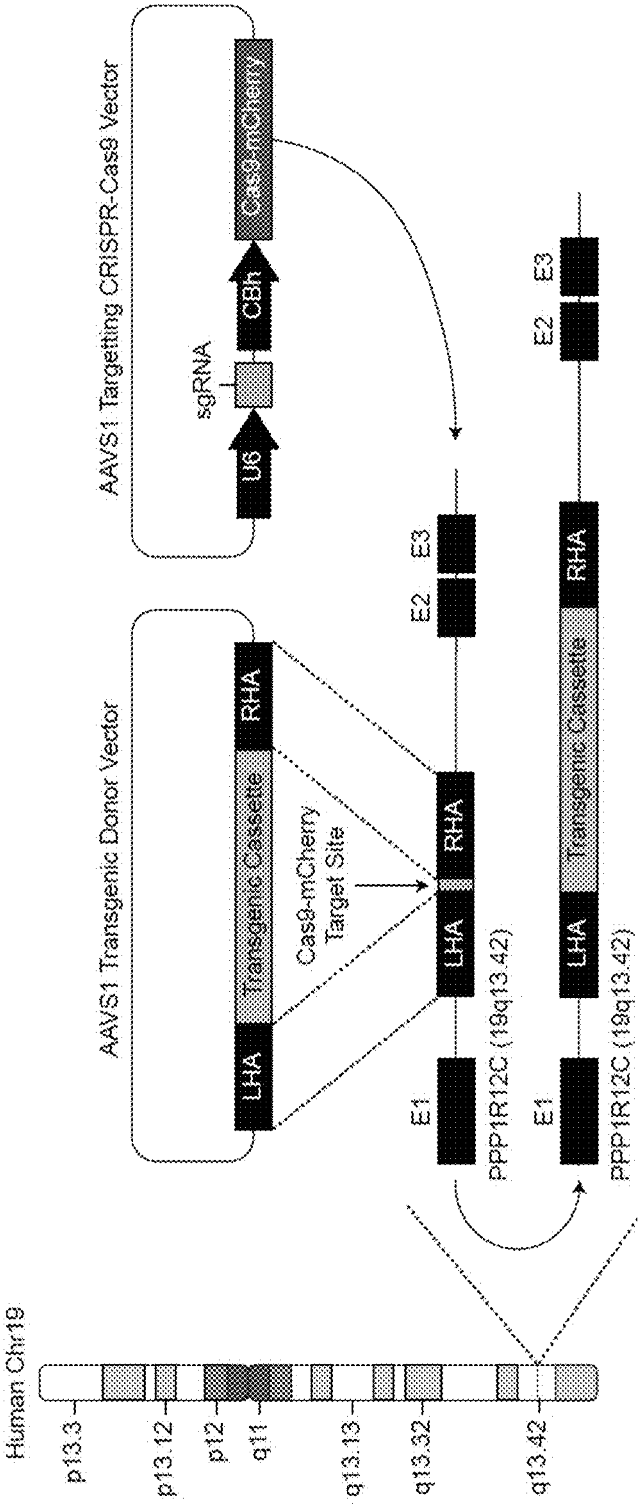
Figure 1:
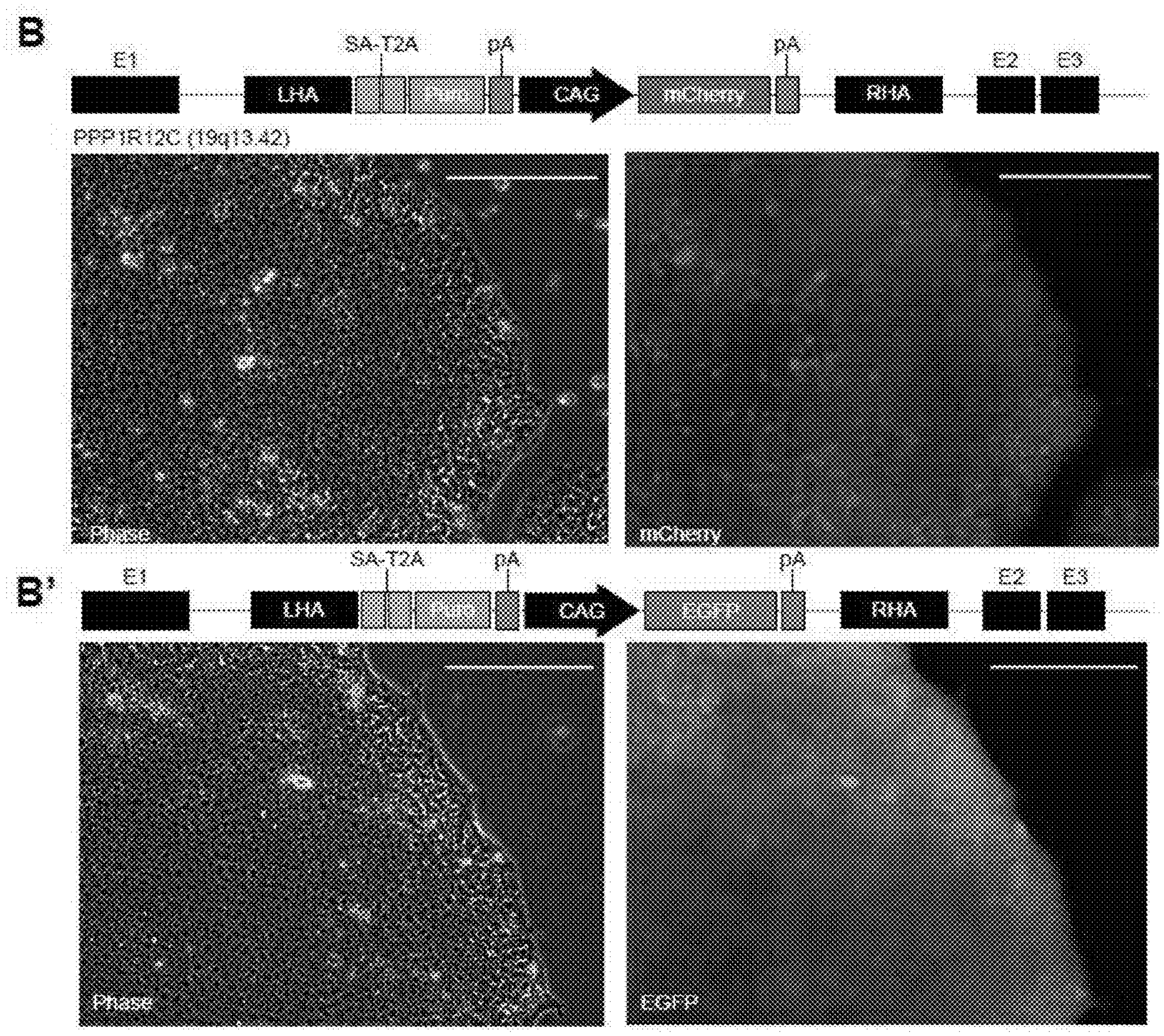
Figure 1:
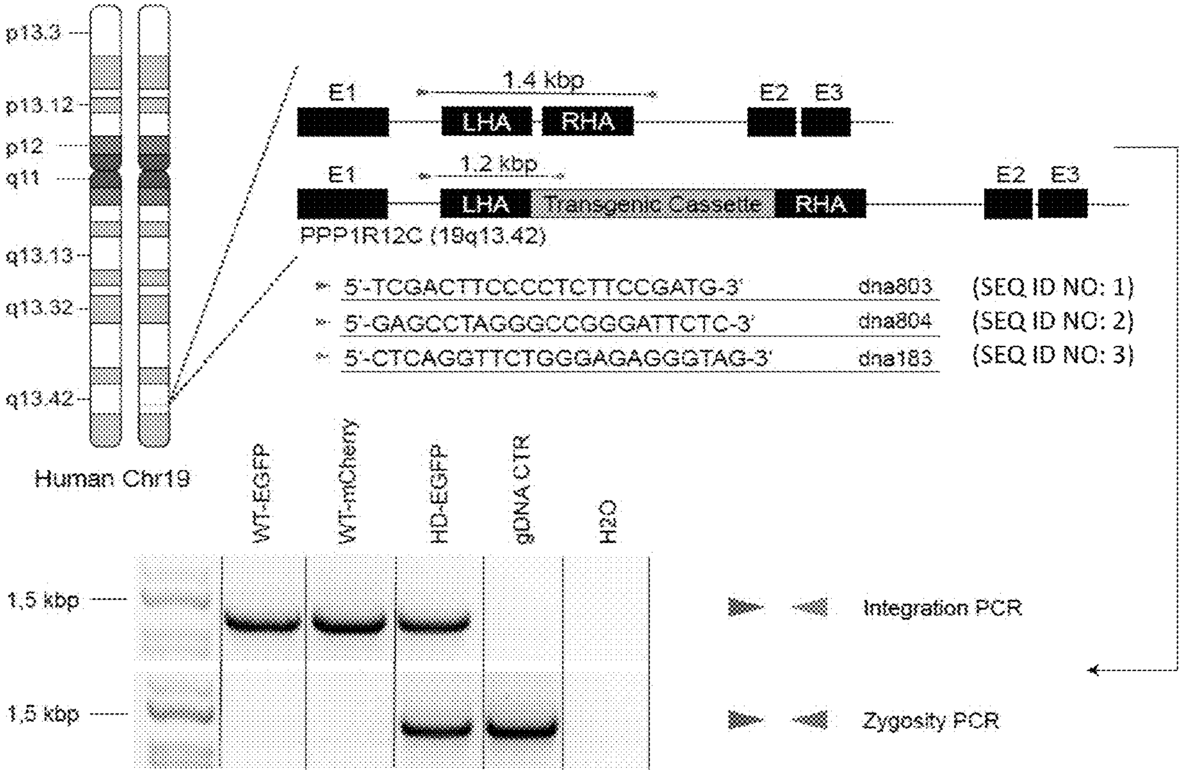
Figure 1:
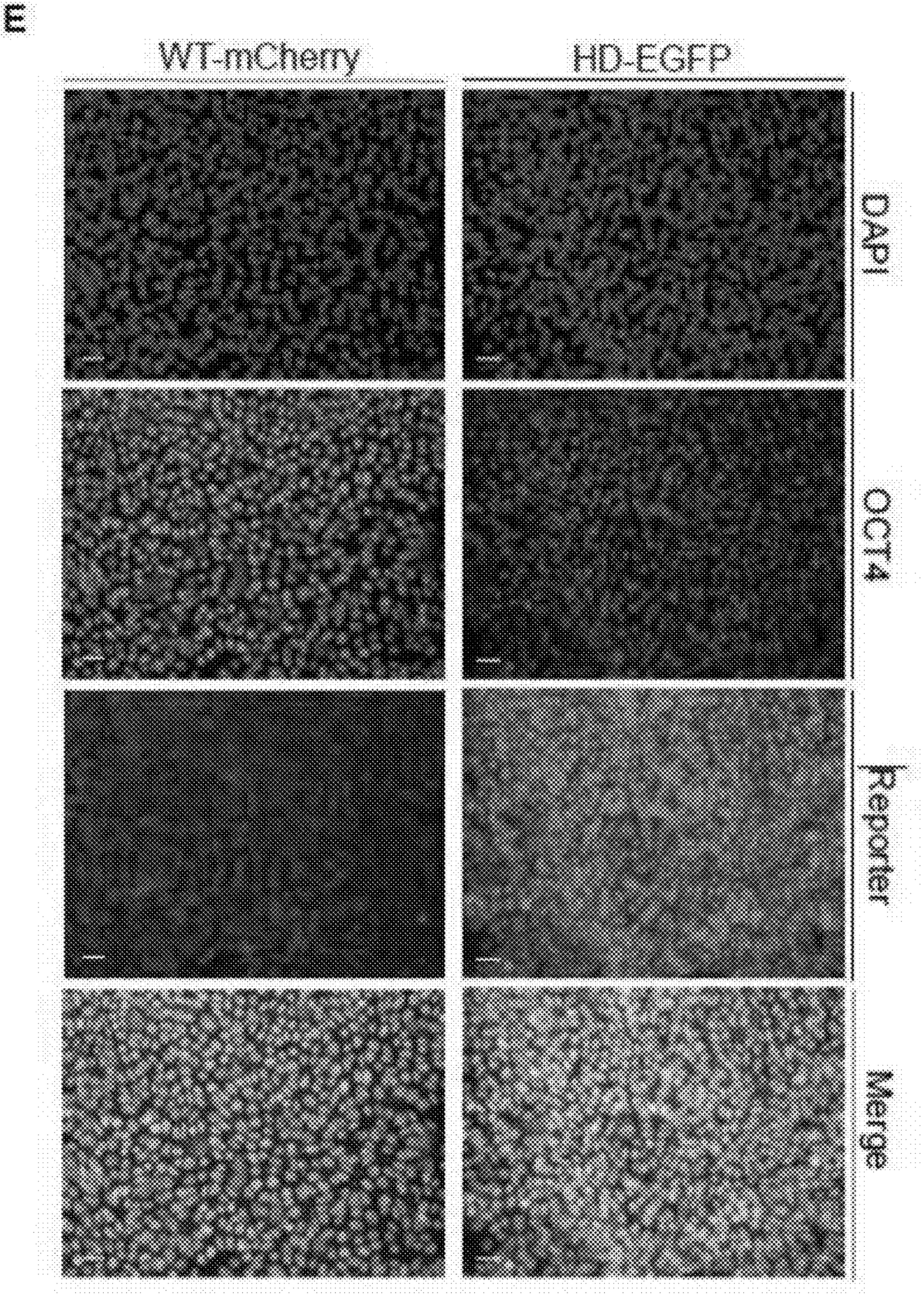

Curated signaling networks of Panel D, fetal (top) and Panel E, adult (bottom) enriched miRNAs and their predicted targets.

DETAILED DESCRIPTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting, and the scope of the application is intended to encompass all equivalents, alternatives, and modifications, either generally known, or incorporated here. The described aspects, features, advantages, and characteristics of the invention may be combined in any suitable manner in one or more further embodiments. One skilled in the relevant art will recognize that the invention may be practiced without one or more of the specific aspects or advantages of a particular embodiment. In other instances, additional aspects, features, and advantages may be recognized and claimed in certain embodiments that may not be present in all embodiments of the invention. Further, one skilled in the art will recognize many techniques and materials similar or equivalent to those described here, which could be used in the practice of the aspects and embodiments of the present application. The described aspects and embodiments of the application are not limited to the methods and materials described.

Unless otherwise defined, all technical and scientific terms used herein have the same meaning as commonly understood by one of ordinary skill in the art to which this application belongs.

Ranges may be expressed herein as from "about" one particular value and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

As used in this specification and the appended claims, the singular forms "a," "an" and "the" include plural referents unless the content clearly dictates otherwise. Thus, for example, reference to "a peptide" includes "one or more" peptides or a "plurality" of such peptides.

I. Definitions

As used herein, the following terms or phrases (in parentheses) shall have the following meanings:

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "and/or" as used herein means that the listed items are present, or used, individually or in combination. In effect, this term means that "at least one of" or "one or more" of the listed items is used or present.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, and so on. As a non-limiting example, each range discussed herein can be readily broken down into a lower third, middle third and upper third, and so on. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "involving", "having", and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. In embodiments or claims where the term comprising (or the like) is used as the transition phrase, such embodiments can also be envisioned with replacement of the term "comprising" with the terms "consisting of" or "consisting essentially of." The methods, kits, systems, and/or compositions of the present disclosure can comprise, consist essentially of, or consist of, the components disclosed.

In embodiments comprising an "additional" or "second" component, the second component as used herein is different from the other components or first component. A "third" component is different from the other, first, and second components, and further enumerated or "additional" components are similarly different.

The term "complementary" when used in connection with nucleic acid, refers to the pairing of bases, A with T or U, and G with C. The term "complementary" refers to nucleic acid molecules that are completely complementary, that is, form A to T or U pairs and G to C pairs across the entire reference sequence, as well as molecules that are partially (e.g., at least 80%, 81%, 82%, 83%, 84%, 85%, 86%, 87%, 88%, 89%, 90%, 91%, 92%, 93%, 94%, 95%, 96%, 97%, 98%, or 99%) complementary.

The terms "nucleic acid", "nucleotide", and "polynucleotide" encompass both DNA and RNA unless specified otherwise.

The term "polypeptide," "peptide" or "protein" are used interchangeably and to refer to a polymer of amino acid residues. The terms encompass all kinds of naturally occurring and synthetic proteins, including protein fragments of all lengths, fusion proteins and modified proteins, including without limitation, glycoproteins, as well as all other types of modified proteins (e.g., proteins resulting from phosphorylation, acetylation, myristoylation, palmitoylation, glycosylation, oxidation, formylation, amidation, polyglutamylation, ADP-ribosylation, pegylation, biotinylation, etc.).

The terms "abrogate", "abrogation" "eliminate", or "elimination" of expression of a gene or gene product (e.g., RNA or protein) refers to a complete loss of the transcription and/or translation of a gene or a complete loss of the gene product (e.g., RNA or protein). Expression of a gene or gene product (e.g., RNA or protein) can be detected by standard art known methods such as those described herein, as compared to a control, e.g., an unmodified cell.

The terms "express" and "expression" mean allowing or causing the information in a gene or DNA sequence to become produced, for example producing an RNA or a protein by activating the cellular functions involved in transcription and/or translation of a corresponding gene or DNA sequence. A DNA sequence is expressed in or by a cell to form an "expression product" such as an RNA or a protein. The expression product itself, e.g., the resulting protein, may also be said to be "expressed" by the cell. An expression product can be characterized as intracellular, extracellular or transmembrane.

The term "competitive advantage" as referred to herein encompasses the preferential proliferation, population expansion, durable survival and/or stable integration of a cell population placed in apposition to or admixture with a genetically and/or epigenetically-distinct cell population, to the detriment and eventual partial or complete replacement of the latter.

As used herein, the term "glial cells" refers to a population of non-neuronal cells that provide support and nutrition, maintain homeostasis, either form myelin or promote myelination, and participate in signal transmission in the nervous system. "Glial cells" as used herein encompasses fully differentiated cells of the glial lineage, such as oligodendrocytes or astrocytes, as well as glial progenitor cells, each of which can be referred to as macroglial cells.

Certain terms employed in the specification, examples, and claims are collected herein. Unless defined otherwise, all technical and scientific terms used in this disclosure have the same meanings as commonly understood by one of ordinary skill in the art to which this disclosure belongs.

Preferences and options for a given aspect, feature, embodiment, or parameter of the disclosure should, unless the context indicates otherwise, be regarded as having been disclosed in combination with any and all preferences and options for all other aspects, features, embodiments, and parameters of the disclosure.

II. Genetically Modified Cell Populations

A first aspect of the present disclosure is directed to an isolated population of progenitor cells genetically modified to have a competitive advantage over progenitor cells which have not been genetically modified. As explained above, progenitor cells genetically modified to have a "competitive advantage" are cells modified to exhibit preferential proliferation, population expansion, durable survival and/or stable integration of a cell population placed in apposition to or admixture with a genetically and/or epigenetically-distinct cell population, to the detriment and eventual partial or complete replacement of the latter.

In one embodiment, the isolated population of progenitor cells is a population of central nervous system progenitor cells. Accordingly, in some embodiments, the genetically modified cell population is an isolated population of neural progenitor cells, neuronal progenitor cells, or glial progenitor cells genetically modified to have a competitive advantage over corresponding progenitor cells which have not been genetically modified.

In one embodiment, the isolated population of progenitor cells is a population of glial progenitor cells. Accordingly, in one embodiment, the genetically modified cell population is an isolated population of glial progenitor cells genetically modified to have a competitive advantage over progenitor cells which have not been genetically modified. Suitable glial progenitor cell populations include, bi-potential glial progenitor cells, oligodendrocyte-biased glial progenitor cells, and astrocyte-biased glial progenitor cells.

Other populations of progenitor cells that can be genetically modified as described herein include, without limitation, bone marrow progenitor cells, cardiac progenitor cells, endothelial progenitor cells, epithelial progenitor cells, mesenchymal progenitor cells, hematopoietic progenitor cells, hepatic progenitor cells, osteoprogenitor cells, muscle progenitor cells, pancreatic progenitor cells, pulmonary progenitor cells, renal progenitor cells, vascular progenitor cells, and retinal progenitor cells. In accordance with the present disclosure, any one of the aforementioned progenitor cells populations can be genetically modified as described herein to have a competitive advantage over progenitor cells which have not been genetically modified.

In some embodiments, the population of progenitor cells are genetically modified to increase expression of one or more genes encoding proteins that confer to the cells a competitive advantage over progenitor cells which have not been genetically modified. In other embodiments, the progenitor cells are genetically modified so as to decrease, suppress, abrogate, or silence one or more genes encoding proteins that are associated with a competitive disadvantage over progenitor cells which have not been genetically modified. In yet another embodiment, progenitor cells of the populations described herein are genetically modified to express one or more genes that confer to the cells a competitive advantage and to suppress or silence one or more genes that are associated with a competitive disadvantage.

In some embodiments, the population of glial progenitor cells are genetically modified to express one or more genes that confer to the glial progenitor cells a competitive advantage over glial progenitor cells which have not been genetically modified. In other embodiments, the glial progenitor cells are genetically modified so as to decrease, suppress, or silence one or more genes that are associated with a competitive disadvantage over glial progenitor cells which have not been genetically modified. In yet another embodiment, glial progenitor cells of the populations described herein are genetically modified to express one or more genes that confer to the cells a competitive advantage and genetically modified to suppress or silence one or more genes that are associated with a competitive disadvantage.

In accordance with all aspects of the present disclosure, the population of progenitor cells genetically modified as described herein are mammalian progenitor cells. In some embodiment, the population of glial progenitor cells is a population of human progenitor cells. In some embodiment, the population of glial progenitor cells is a population of human glial progenitor cells.

In some embodiment, the progenitor cells genetically modified as described herein are glial progenitor cells. In some embodiments, the genetically modified glial progenitor cells are genetically modified bi-potential glial progenitor cells. In some embodiments, the genetically modified glial progenitor cells are genetically modified oligodendrocyte-biased glial progenitor cells. In some embodiments, the genetically modified glial progenitor cells are genetically modified astrocyte-biased glial progenitor cells. Methods and markers for producing and distinguishing bi-potential glial progenitor cells, astrocyte-biased glial progenitor cells, and oligodendrocyte-biased glial progenitor cells are described herein.

Glial progenitor cells suitable for genetic modification as described here can be derived from multipotent (e.g., neural stem cells) or pluripotent cells (e.g., embryonic stem cells and induced pluripotent stem cells) using methods known in the art or described herein.

In some embodiments, glial progenitor cells are derived from embryonic stem cells. Embryonic stem cells are derived from totipotent cells of the early mammalian embryo and are capable of unlimited, undifferentiated proliferation in vitro. As used herein, the term "embryonic stem cells" refer to cells isolated from an embryo, placenta, or umbilical cord, or an immortalized version of such a cells, i.e., an embryonic stem cell line. Suitable embryonic stem cell lines include, without limitation, lines WA-01 (H1), WA-07, WA-09 (H9), WA-13, and WA-14 (H14) (Thomson et al., "Embryonic Stem Cell Lines Derived from Human Blastocytes," Science 282 (5391): 1145-47 (1998) and U.S. Pat. No. 7,029,913 to Thomson et al., which are hereby incorporated by reference in their entirety). Other suitable embryonic stem cell lines includes the HAD-C100 cell line (Tannenbaum et al., "Derivation of Xeno-free and GMP-grade Human Embryonic Stem Cells-Platforms for Future Clinical Applications," PLOS One 7(6): e35325 (2012), which is hereby incorporated by reference in its entirety, the WIBR4, WIBR5, WIBR6 cell lines (Lengner et al., "Derivation of Pre-x Inactivation Human Embryonic Stem Cell Line in Physiological Oxygen Conditions," Cell 141 (5): 872-83 (2010), which is hereby incorporated by reference in its entirety), and the human embryonic stem cell lines (HUES) lines 1-17 (Cowan et al., "Derivation of Embryonic Stem-Cell Lines from Human Blastocytes," N. Engl. J. Med. 350:1353-56 (2004), which is hereby incorporated by reference in its entirety).

In some embodiments, glial progenitor cells are derived from induced pluripotential cells (iPSCs). "Induced pluripotent stem cells" as used herein refers to pluripotent cells that are derived from non-pluripotent cells, such as somatic cells or tissue stem cells. For example, and without limitation, iPSCs can be derived from embryonic, fetal, newborn, and adult tissue, from peripheral blood, umbilical cord blood, and bone marrow (see e.g., Cai et al., "Generation of Human Induced Pluripotent Stem Cells from Umbilical Cord Matrix and Amniotic Membrane Mesenchymal Cells," J. Biol. Chem. 285 (15): 112227-11234 (2110); Giorgetti et al., "Generation of Induced Pluripotent Stem Cells from Human Cord Blood Cells with only Two Factors: Oct4 and Sox2," Nature Protocols, 5 (4): 811-820 (2010); Streckfuss-Bomeke et al., "Comparative Study of Human-Induced Pluripotent Stem Cells Derived from Bone Marrow Cells, Hair Keratinocytes, and Skin Fibroblasts," Eur. Heart J. doi: 10.1093/eurheartj/ehs203 (Jul. 12, 2012); Hu et al., "Efficient Generation of Transgene-Free Induced Pluripotent Stem Cells from Normal and Neoplastic Bone Marrow and Cord Blood Mononuclear Cells," Blood doi: 10.1182/blood-2010-07-298331 (Feb. 4, 2011); Sommer et al., "Generation of Human Induced Pluripotent Stem Cells from Peripheral Blood using the STEMCCA Lentiviral Vector," J. Vis. Exp. 68: e4327 doi: 10.3791/4327 (2012), which are hereby incorporated by reference in their entirety). Exemplary somatic cells that can be used include fibroblasts, such as dermal fibroblasts obtained by a skin sample or biopsy, synoviocytes from synovial tissue, keratinocytes, mature B cells, mature T cells, pancreatic β cells, melanocytes, hepatocytes, foreskin cells, cheek cells, or lung fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," Eur. Heart J. doi: 10.1093/eurheartj/ehs203 (2012), which is hereby incorporated by reference in its entirety). Although skin and cheek provide a readily available and easily attainable source of appropriate cells, virtually any cell can be used. Exemplary stem or progenitor cells that are suitable for iPSC production include, without limitation, myeloid progenitors, hematopoietic stem cells, adipose-derived stem cells, neural stem cells, and liver progenitor cells.

Autologous, allogenic, or xenogenic non-pluripotent cells can be used in to produce the iPSCs used to generate the genetically modified glial progenitor cells. Allogenic cells for production of iPSCs, for example, are harvested from healthy, non-recipient donors and/or donor sources having suitable immunohistocompatibility. Xenogeneic cells can be harvested from a pig, monkey, or any other suitable mammal for the production if iPSCs. Autologous non-pluripotent cells can also be harvested from the same subject to be treated. Autologous cells may need to be genetically modified as described herein and further genetically modified and/or otherwise treated to correct certain dysregulations so that they exhibit normal, non-disease related expression and/or activity in addition to levels prior to administration.

Induced pluripotent stem cells can be produced by expressing a combination of reprogramming factors in a somatic cell. Suitable reprogramming factors that promote and induce iPSC generation include one or more of Oct4, Klf4, Sox2, c-Myc, Nanog, C/EBPα, Esrrb, Lin28, and Nr5a2. In certain embodiments, at least two reprogramming factors are expressed in a somatic cell to successfully reprogram the somatic cell. In other embodiments, at least three reprogramming factors are expressed in a somatic cell to successfully reprogram the somatic cell. In other embodiments, at least four reprogramming factors are expressed in a somatic cell to successfully reprogram the somatic cell.

iPSCs may be derived by methods known in the art including the use of integrating viral vectors (e.g., lentiviral vectors, inducible lentiviral vectors, and retroviral vectors), excisable vectors (e.g., transposon and floxed lentiviral vectors), and non-integrating vectors (e.g., adenoviral and plasmid vectors) to deliver the aforementioned genes that promote cell reprogramming (see e.g., Takahashi and Yamanaka, Cell 126:663-676 (2006); Okita. et al., Nature 448:313-317 (2007); Nakagawa et al., Nat. Biotechnol. 26:101-106 (2007); Takahashi et al., Cell 131:1-12 (2007); Meissner et al. Nat. Biotech. 25:1177-1181 (2007); Yu et al. Science 318:1917-1920 (2007); Park et al. Nature 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/

118820, U.S. Patent Application Publication Nos. 2011/0200568 to Ikeda et al., 2010/0156778 to Egusa et al., 2012/0276070 to Musick, and 2012/0276636 to Nakagawa, Shi et al., Cell Stem Cell 3 (5): 568-574 (2008), Kim et al., Nature 454:646-650 (2008), Kim et al., Cell 136 (3:411-419 (2009), Huangfu et al., Nature Biotechnology 26:1269-1275 (2008), Zhao et al., Cell Stem Cell 3:475-479 (2008), Feng et al., Nature Cell Biology 11:197-203 (2009), and Hanna et al., Cell 133 (2): 250-264 (2008), which are hereby incorporated by reference in their entirety.

Integration free approaches, i.e., those using non-integrating and excisable vectors, for deriving iPSCs free of transgenic sequences are particularly suitable in the therapeutic context. Suitable methods of iPSC production that utilize non-integrating vectors include methods that use adenoviral vectors (Stadtfeld et al., "Induced Pluripotent Stem Cells Generated without Viral Integration," Science 322:945-949 (2008), and Okita et al., "Generation of Mouse Induced Pluripotent Stem Cells without Viral Vectors," Science 322:949-953 (2008), which are hereby incorporated by reference in their entirety), Sendi virus vectors (Fusaki et al., "Efficient Induction of Transgene-Free Human Pluripotent Stem Cells Using a Vector Based on Sendi Virus, an RNA Virus That Does Not Integrate into the Host Genome," Proc Jpn Acad. 85:348-362 (2009), which is hereby incorporated by reference in its entirety), polycistronic minicircle vectors (Jia et al., "A Nonviral Minicircle Vector for Deriving Hyman iPS Cells," Nat. Methods 7:197-199 (2010), which is hereby incorporated by reference in its entirety), and self-replicating selectable episomes (Yu et al., "Human Induced Pluripotent Stem Cells Free of Vector and Transgene Sequences," Science 324:797-801 (2009), which is hereby incorporated by reference in its entirety). Suitable methods for iPSC generation using excisable vectors are described by Kaji et al., "Virus-Free Induction of Pluripotency and Subsequent Excision of Reprogramming Factors," Nature 458:771-775 (2009), Soldner et al., "Parkinson's Disease Patient-Derived Induced Pluripotent Stem Cells Free of Viral Reprogramming Factors," Cell 136:964-977 (2009), Woltjen et al., "PiggyBac Transposition Reprograms Fibroblasts to Induced Pluripotent Stem Cells," Nature 458:766-770 (2009), and Yusa et al., "Generation of Transgene-Free Induced Pluripotent Mouse Stem Cells by the PiggyBac Transposon," Nat. Methods 6:363-369 (2009), which are hereby incorporated by reference in their entirety. Suitable methods for iPSC generation also include methods involving the direct delivery of reprogramming factors as recombinant proteins (Zhou et al., "Generation of Induced Pluripotent Stem Cells Using Recombinant Proteins," Cell Stem Cell 4:381-384 (2009), which is hereby incorporated by reference in its entirety) or as whole-cell extracts isolated from ESCs (Cho et al., "Induction of Pluripotent Stem Cells from Adult Somatic Cells by Protein-Based Reprogramming without Genetic Manipulation," Blood 116:386-395 (2010), which is hereby incorporated by reference in its entirety).

The methods of iPSC generation described above can be modified to include small molecules that enhance reprogramming efficiency or even substitute for a reprogramming factor.

These small molecules include, without limitation, epigenetic modulators such as the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as TGF-β inhibitors and kinase inhibitors (e.g., kenpaullone) (see review by Sommer and Mostoslavsky, "Experimental Approaches for the Generation of Induced Pluripotent Stem Cells," Stem Cell Res. Ther. 1:26 doi: 10.1186/scrt26 (2010), which is hereby incorporated by reference in its entirety).

Methods of obtaining highly enriched preparations of glial progenitor cells from the iPSCs or embryonic stem cells (e.g., human embryonic stem cells) that are suitable for treating a neuropsychiatric disorder as described herein are disclosed in WO2014/124087 to Goldman and Wang, and Wang et al., "Human iPSC-Derived Oligodendrocyte Progenitors Can Myelinate and Rescue a Mouse Model of Congenital Hypomyelination," Cell Stem Cell 12(2): 252-264 (2013), which are hereby incorporated by reference in their entirety.

In yet another embodiment, glial progenitor cells can be extracted from embryonic tissue, fetal tissue, or adult brain tissue containing a mixed population of cells directly by using the promoter specific separation technique, as described in U.S. Patent Application Publication Nos. 20040029269 and 20030223972 to Goldman, which are hereby incorporated by reference in their entirety. In accordance with this embodiment, the glial progenitor cells are isolated from ventricular or subventricular zones of the brain or from the subcortical white matter.

In some embodiments, it may be preferable to enrich a cell preparation comprising glial progenitor cells prior to or after genetic modification to increase the concentration and/or purity of the glial progenitor cells exhibiting a competitive advantage for therapeutic administration. Accordingly, in one embodiment, the A2B5 monoclonal antibody (mAb) that recognizes and binds to gangliosides present on glial progenitor cells early in the developmental or differentiation process is utilized to separate glial progenitor cells from a mixed population of cells (Nunes et al., "Identification and Isolation of Multipotential Neural Progenitor Cells From the Subcortical White Matter of the Adult Human Brain.," Nat Med. 9 (4): 439-47 (2003), which is hereby incorporated by reference in its entirety). Using the A2B5 mAb, glial progenitor cells can be separated, enriched, or purified from a mixed population of cell types. In another embodiment, selection of CD140α/PDGFRα positive cells is employed to produce a purified or enriched preparation of bi-potential glial progenitor cells. In another embodiment, selection of CD9 positive cells is employed to produce a purified or enriched preparation of oligodendrocyte-biased glial progenitor cells. In yet another embodiment, both CD140α/PDGFRα and CD9 positive cell selection is employed to produce a purified or enriched preparation of oligodendrocyte-biased glial progenitor cells. In another embodiment, selection of CD44 positive cells is employed to produce a purified or enriched preparation of astrocyte-biased glial progenitor cells (Liu et al., "CD44 Expression Identifies Astrocyte-Restricted Precursor Cells," Dev. Biol. 276 (1): 31-46 (2004), which is hereby incorporated by reference in its entirety.) In another embodiment, both CD140α/PDGFRα and CD44 positive cell selection is employed to produce a purified or enriched preparation of oligodendrocyte-biased glial progenitor cells. In another embodiment, CD140α/PDGFRa, CD9, and CD44 positive cell selection is employed to produce a purified or enriched preparation of oligodendrocyte-biased glial progenitor cells.

The genetically modified glial progenitor cell population described herein is preferably negative for a PSA-NCAM marker and/or other neuronal lineage markers, and/or negative for one or more inflammatory cell markers, e.g., negative for a CD11 marker, negative for a CD32 marker, and/or negative for a CD36 marker (which are markers for microglia). Optionally, the preparation of glial progenitor cells is negative for any combination or subset of these additional markers. Thus, for example, the preparation of glial progenitor cells is negative for any one, two, three, or four of these additional markers.

In accordance with the present disclosure the population of genetically modified glial progenitor cells as described herein comprises at least about 80% glial progenitor cells, including, for example, about 80%, 85%, 90%, 95%, 96%, 97%, 98%, 99%, 100% glial progenitor cells. The population of genetically modified glial progenitor cells is preferably devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, multipotent cells, and pluripotential stem cells (like ES cells). Optionally, exemplary cell populations are substantially pure populations of glial progenitor cells.

Positive and/or negative selection for cell markers of interest (e.g., PDGFRα marker, A2B5 marker, and/or a CD44 marker) can be carried out serially or sequentially and can be performed using conventional methods known in the art such as immunopanning. The selection methods optionally involve the use of fluorescence sorting (FACS), magnetic sorting (MACS), or any other method that allows rapid, efficient cell sorting. Examples of methods for cell sorting are taught for example in U.S. Pat. No. 6,692,957 to Goldman, which is hereby incorporated by reference in its entirety, at least for compositions and methods for cell selection and sorting.

Generally, cell sorting methods use a detectable moiety. Detectable moieties include any suitable direct or indirect label, including, but not limited to, enzymes, fluorophores, biotin, chromophores, radioisotopes, colored beads, electrochemical, chemical-modifying or chemiluminescent moieties. Common fluorescent moieties include fluorescein, cyanine dyes, coumarins, phycoerythrin, phycobiliproteins, dansyl chloride, Texas Red, and lanthanide complexes or derivatives thereof.

The genetically modified glial progenitor cell populations described herein, including the enriched preparations can be optionally expanded in culture to increase the total number of cells for therapeutic administration. The cells can be expanded by either continuous or pulsatile exposure to PDGF-AA or AB as mitogens that support the expansion of oligodendrocyte progenitor cells; they can be exposed to fibroblast growth factors, including FGF2, FGF4, FGF8 and FGF9, which can support the mitotic expansion of the glial progenitor cells, but which can bias their differentiation to a mixed population of astrocytes as well as oligodendrocytes. The cells can also be expanded in media supplemented with combinations of FGF2, PDGF, and NT3, which can optionally be supplemented with either platelet-depleted or whole serum (see Nunes et al. "Identification and Isolation of Multipotent Neural Progenitor Cells from the Subcortical White Matter of the Adult Human Brain," Nature Medicine 9:239-247; Windrem et al., "Fetal and Adult Human Oligodendrocyte Progenitor Cell Isolates Myelinate the Congenitally Dysmyelinated Brain," Nature Medicine 10:93-97 (2004), which are incorporated by reference for the methods and compositions described therein).

As described supra, in some embodiments, the population of glial progenitor cells as described herein is genetically modified to have a competitive advantage over glial progenitor cells which have not been genetically modified. In some embodiments, cells of the isolated population are modified to increase expression of one or more genes that confers a competitive advantage to the modified cells relative to glial progenitor cells which have not been genetically modified. In some embodiments, cells of the isolated population are modified to decrease or silence expression of one or more genes that confers a competitive disadvantage to the modified cells relative to glial progenitor cells which have not been genetically modified.

In some embodiments, the isolated population of glial progenitor cells as described herein contains cells that have been modified to express one or more genes that confer a competitive advantage to the cells and cells that have been modified to decrease expression of one or more genes that confer a competitive disadvantage to the cells.

In some embodiments, cells of the isolated population are genetically modified to express one or more genes that confer a competitive advantage and modified to decrease expression of one or more genes that confer a competitive disadvantage to the glial progenitor cells compared to glial progenitor cells which have not been genetically modified.

Genetic Modifications to Express One or More Genes that Confer a Competitive Advantage Genes whose expression provides progenitor cells a competitive advantage were identified using the models of cell competition described in the Examples herein. In particular, differential gene expression between various cell populations utilized in the model (e.g., healthy glial progenitor cells vs. diseased glial progenitor cells and similarly aged healthy vs. diseased progenitor cells) were analyzed and compared to identify genes that confer a competitive advantage and genes that confer a competitive disadvantage to transplanted cells as compared to the resident cells.

The one or more genes identified herein as providing cells a competitive advantage over resident cells upon transplantation (advantage genes) are provided in Table 1 below by their gene name. Also provided in Table 1 is the Entrez ID accession number and Ensembl ID for each gene, which are each hereby incorporated by reference in their entirety for their disclosure of the gene sequences and the corresponding protein encoded by each sequence. All gene products referred to in this application include the wild type gene product and functional variants thereof. A "functional variant of a gene product" refers to a modified gene product (e.g., by deletion, substitution, insertion, glycosylation, etc.) that retains at least 50% of the biological activity of the unmodified (wild-type) gene product in a competition assay.

TABLE 1

Genes That Confer A Competitive Advantage to Cells (advantage genes)

| Gene | Ensembl ID | Entrez ID |
|---|---|---|
| ACTB | ENSG00000075624 | 60 |
| AKR1C1 | ENSG00000187134 | 1645 |
| ANAPC11 | ENSG00000141552 | 51529 |
| AP2B1 | ENSG00000006125 | 163 |
| APLP2 | ENSG00000084234 | 334 |
| ARF5 | ENSG00000004059 | 381 |
| ARL4A | ENSG00000122644 | 10124 |
| ARPC3 | ENSG00000111229 | 10094 |
| ARPP19 | ENSG00000128989 | 10776 |
| ATOX1 | ENSG00000177556 | 475 |
| ATP5F1E | ENSG00000124172 | 514 |
| ATP5MC1 | ENSG00000159199 | 516 |
| ATP5MC3 | ENSG00000154518 | 518 |
| ATP5MD | ENSG00000173915 | 84833 |
| ATP5ME | ENSG00000169020 | 521 |
| ATP5MF | ENSG00000241468 | 9551 |
| ATP5MG | ENSG00000167283 | 10632 |

TABLE 1-continued

Genes That Confer A Competitive Advantage to Cells (advantage genes)

| Gene | Ensembl ID | Entrez ID |
|---|---|---|
| ATP5MPL | ENSG00000156411 | 9556 |
| ATP5PF | ENSG00000154723 | 522 |
| ATP6V0B | ENSG00000117410 | 533 |
| ATP6V0E1 | ENSG00000113732 | 8992 |
| ATXN7L3B | ENSG00000253719 | 552889 |
| B2M | ENSG00000166710 | 567 |
| BSGAT2 | ENSG00000112309 | 135152 |
| BEX1 | ENSG00000133169 | 55859 |
| BEX3 | ENSG00000166681 | 27018 |
| BLOC1S1 | ENSG00000135441 | 2647 |
| BMERB1 | ENSG00000166780 | 89927 |
| C18orf32 | ENSG00000177576 | 497661 |
| C1orf122 | ENSG00000197982 | 127687 |
| C1QBP | ENSG00000108561 | 708 |
| C4orf48 | ENSG00000243449 | 401115 |
| CADM4 | ENSG00000105767 | 199731 |
| CALM1 | ENSG00000198668 | 801 |
| CALM3 | ENSG00000160014 | 808 |
| CALR | ENSG00000179218 | 811 |
| CANX | ENSG00000127022 | 821 |
| CAV2 | ENSG00000105971 | 858 |
| CC2D1A | ENSG00000132024 | 54862 |
| CCND1 | ENSG00000110092 | 595 |
| CCNI | ENSG00000118816 | 10983 |
| CD63 | ENSG00000135404 | 967 |
| CD82 | ENSG00000085117 | 3732 |
| CDC42 | ENSG00000070831 | 998 |
| CDH2 | ENSG00000170558 | 1000 |
| CFL1 | ENSG00000172757 | 1072 |
| CHCHD2 | ENSG00000105153 | 51142 |
| CHGB | ENSG00000089199 | 1114 |
| CIAO2B | ENSG00000166595 | 51647 |
| CLCN3 | ENSG00000109572 | 1182 |
| CLTA | ENSG00000122705 | 1211 |
| CLTC | ENSG00000141367 | 1213 |
| CNN3 | ENSG00000117519 | 1266 |
| CNTN1 | ENSG00000018236 | 1272 |
| COTL1 | ENSG00000103187 | 23406 |
| COX4I1 | ENSG00000131143 | 1327 |
| COX6A1 | ENSG00000111775 | 1337 |
| COX6C | ENSG00000164919 | 1345 |
| COX7A2 | ENSG00000112695 | 1347 |
| COX7C | ENSG00000127184 | 1350 |
| COX8A | ENSG00000176340 | 1351 |
| CPNE8 | ENSG00000139117 | 144402 |
| CPS1 | ENSG00000021826 | 1373 |
| CRNDE | ENSG00000245694 | 643911 |
| CSPG4 | ENSG00000173546 | 1464 |
| CTHRC1 | ENSG00000164932 | 115908 |
| CUL4B | ENSG00000158290 | 8450 |
| CYP51A1 | ENSG00000001630 | 1595 |
| DBI | ENSG00000155368 | 1622 |
| DCX | ENSG00000077279 | 1641 |
| DDAH1 | ENSG00000153904 | 23576 |
| DDX1 | ENSG00000079785 | 1653 |
| DENND10 | ENSG00000119979 | 404636 |
| DMD | ENSG00000198947 | 1756 |
| DMRT2 | ENSG00000173253 | 10655 |
| DNAJA2 | ENSG00000069345 | 10294 |
| DPYSL2 | ENSG00000092964 | 1808 |
| DRAP1 | ENSG00000175550 | 10589 |
| DSTN | ENSG00000125868 | 11034 |
| DYNC1I2 | ENSG00000077380 | 1781 |
| EDF1 | ENSG00000107223 | 8721 |
| EEF1A1 | ENSG00000156508 | 1915 |
| EEF1B2 | ENSG00000114942 | 1933 |
| EEF2 | ENSG00000167658 | 1938 |
| EID1 | ENSG00000255302 | 23741 |
| EIF3J | ENSG00000104131 | 8669 |
| ELOB | ENSG00000103363 | 6923 |
| EMP2 | ENSG00000213853 | 2013 |
| ESD | ENSG00000139684 | 2098 |
| ETV1 | ENSG00000006468 | 2115 |
| FABP7 | ENSG00000164434 | 2173 |
| FAM171B | ENSG00000144369 | 165215 |

TABLE 1-continued

Genes That Confer A Competitive Advantage to Cells (advantage genes)

| Gene | Ensembl ID | Entrez ID |
|---|---|---|
| FAM177A1 | ENSG00000151327 | 283635 |
| FAU | ENSG00000149806 | 2197 |
| FIS1 | ENSG00000214253 | 51024 |
| FXYD6 | ENSG00000137726 | 53826 |
| GAP43 | ENSG00000172020 | 2596 |
| GCSH | ENSG00000140905 | 2653 |
| GNAS | ENSG00000087460 | 2778 |
| GOLM1 | ENSG00000135052 | 51280 |
| GPM6B | ENSG00000046653 | 2824 |
| GSTP1 | ENSG00000084207 | 2950 |
| H3-3A | ENSG00000163041 | 3020 |
| H3-3B | ENSG00000132475 | 3021 |
| HINT1 | ENSG00000169567 | 3094 |
| HNRNPA1 | ENSG00000135486 | 3178 |
| HNRNPA3 | ENSG00000170144 | 220988 |
| HNRNPAB | ENSG00000197451 | 3182 |
| HNRNPC | ENSG00000092199 | 3183 |
| HNRNPK | ENSG00000165119 | 3190 |
| HNRNPM | ENSG00000099783 | 4670 |
| HNRNPR | ENSG00000125944 | 10236 |
| HSPA5 | ENSG00000044574 | 3309 |
| IGFBP2 | ENSG00000115457 | 3485 |
| ITGB8 | ENSG00000105855 | 3696 |
| ITM2A | ENSG00000078596 | 9452 |
| ITM2B | ENSG00000136156 | 9445 |
| JPT1 | ENSG00000189159 | 51155 |
| KDELR1 | ENSG00000105438 | 10945 |
| KLRK1-AS1 | ENSG00000245648 | 101928100 |
| KRTCAP2 | ENSG00000163463 | 200185 |
| KTN1 | ENSG00000126777 | 3895 |
| LDH8 | ENSG00000111716 | 3945 |
| LHFPL3 | ENSG00000187416 | 375612 |
| LRRC4B | ENSG00000131409 | 94030 |
| MAP2 | ENSG00000078018 | 4133 |
| MARCKS | ENSG00000277443 | 4082 |
| MARCKSL1 | ENSG00000175130 | 65108 |
| MIA | ENSG00000261857 | 8190 |
| MICOS10 | ENSG00000173436 | 440574 |
| MIF | ENSG00000240972 | 4282 |
| MIR9-1HG | ENSG00000125462 | 10485 |
| MMGT1 | ENSG00000169446 | 93380 |
| MPZL1 | ENSG00000197965 | 9019 |
| MTLN | ENSG00000175701 | 205251 |
| MTRNR2L12 | ENSG00000269028 | 100462981 |
| GADD45A | ENSG00000116717 | 1647 |
| LY6H | ENSG00000176956 | 4062 |
| MTRNR2L8 | ENSG00000255823 | 100463486 |
| MYL12A | ENSG00000101608 | 10627 |
| MYL12B | ENSG00000118680 | 103910 |
| NACA | ENSG00000196531 | 4666 |
| NARS1 | ENSG00000134440 | 4677 |
| NCL | ENSG00000115053 | 4691 |
| NDUFA1 | ENSG00000125356 | 4694 |
| NDUFA11 | ENSG00000174886 | 126328 |
| NDUFA13 | ENSG00000186010 | 51079 |
| NDUFA3 | ENSG00000170906 | 4696 |
| NDUFA4 | ENSG00000189043 | 4697 |
| NDUFH1 | ENSG00000183648 | 4707 |
| NDUFB11 | ENSG00000147123 | 54539 |
| NDUFB2 | ENSG00000090266 | 4708 |
| NDUFB6 | ENSG00000165264 | 4712 |
| NDUFB7 | ENSG00000099795 | 4713 |
| NDUFC2 | ENSG00000151366 | 4718 |
| NDUFS5 | ENSG00000168653 | 4725 |
| NUCKS1 | ENSG00000069275 | 64710 |
| OAZ1 | ENSG00000104904 | 4946 |
| OLFM2 | ENSG00000105088 | 93145 |
| OSBPL8 | ENSG00000091039 | 114882 |
| OST4 | ENSG00000228474 | 100128731 |
| OSTC | ENSG00000198856 | 58505 |
| PABPC1 | ENSG00000070756 | 26986 |
| PCBP2 | ENSG00000197111 | 5094 |
| PCDH10 | ENSG00000138650 | 57575 |
| PCDH11X | ENSG00000102290 | 27328 |
| PCDH17 | ENSG00000118946 | 27253 |

TABLE 1-continued

| Genes That Confer A Competitive Advantage to Cells (advantage genes) | | |
|---|---|---|
| Gene | Ensembl ID | Entrez ID |
| PCDHB2 | ENSG00000112852 | 56133 |
| PCDHGB6 | ENSG00000253305 | 56100 |
| PDGFRA | ENSG00000134853 | 5156 |
| PDIA6 | ENSG00000143870 | 10130 |
| PEG10 | ENSG00000242265 | 23089 |
| PFN1 | ENSG00000108518 | 5216 |
| PGRMC1 | ENSG00000101856 | 10857 |
| PKIA | ENSG00000171033 | 5569 |
| PLPP3 | ENSG00000162407 | 8613 |
| PLPPR1 | ENSG00000148123 | 54886 |
| PPIA | ENSG00000196262 | 5478 |
| PRDX1 | ENSG00000117450 | 5052 |
| PRDX2 | ENSG00000167815 | 7001 |
| PRDX5 | ENSG00000126432 | 25824 |
| PSMB1 | ENSG00000008018 | 5689 |
| PSMB9 | ENSG00000240065 | 5698 |
| PTMS | ENSG00000159335 | 5763 |
| PTN | ENSG00000105894 | 5764 |
| PTPRA | ENSG00000132670 | 5786 |
| RAB10 | ENSG00000084733 | 10890 |
| RAB14 | ENSG00000119396 | 51552 |
| RAB2A | ENSG00000104388 | 5862 |
| RAB31 | ENSG00000168461 | 11031 |
| RAC1 | ENSG00000136238 | 5879 |
| RACK1 | ENSG00000204628 | 10399 |
| RMDN2 | ENSG00000115841 | 151393 |
| RO60 | ENSG00000116747 | 6738 |
| ROBO1 | ENSG00000169855 | 6091 |
| RRAGB | ENSG00000083750 | 10325 |
| RTN3 | ENSG00000133318 | 10313 |
| S100B | ENSG00000160307 | 6285 |
| SARAF | ENSG00000133872 | 51669 |
| SAT1 | ENSG00000130066 | 6303 |
| SBDS | ENSG00000126524 | 51119 |
| SCARB2 | ENSG00000138760 | 950 |
| SCP2 | ENSG00000116171 | 6342 |
| SCRG1 | ENSG00000164106 | 11341 |
| SEC62 | ENSG00000008952 | 7095 |
| SELENOK | ENSG00000113811 | 58515 |
| SELENOT | ENSG00000198843 | 51714 |
| SELENOW | ENSG00000178980 | 6415 |
| SERF2 | ENSG00000140264 | 10169 |
| SERPINE2 | ENSG00000135919 | 5270 |
| SET | ENSG00000119335 | 6418 |
| SH3BGRL | ENSG00000131171 | 6451 |
| SKP1 | ENSG00000113558 | 6500 |
| SLC25A6 | ENSG00000169100 | 293 |
| SLIT2 | ENSG00000145147 | 9353 |
| SLITRK2 | ENSG00000185985 | 84631 |
| SMC3 | ENSG00000108055 | 9126 |
| SMDT1 | ENSG00000183172 | 91689 |
| SMOC1 | ENSG00000198732 | 64093 |
| SMS | ENSG00000102172 | 6611 |
| SNCA | ENSG00000145335 | 6622 |
| SNHG29 | ENSG00000175061 | 125144 |
| SNHG6 | ENSG00000245910 | 641638 |
| SNX22 | ENSG00000157734 | 79856 |
| SNX3 | ENSG00000112335 | 8724 |
| SOD1 | ENSG00000142168 | 6647 |
| SOX11 | ENSG00000176887 | 6664 |
| SOX2 | ENSG00000181449 | 6657 |
| SOX9 | ENSG00000125398 | 6662 |
| SPCS2 | ENSG00000118363 | 9789 |
| SPCS3 | ENSG00000129128 | 50559 |
| SRP14 | ENSG00000140319 | 6727 |
| SSR4 | ENSG00000180879 | 6748 |
| STAG2 | ENSG00000101972 | 10735 |
| STMN1 | ENSG00000117632 | 3925 |
| SUPT16H | ENSG00000092201 | 11198 |
| TALDO1 | ENSG00000177156 | 6888 |
| TBCB | ENSG00000105254 | 1155 |
| TCEAL7 | ENSG00000182916 | 56849 |
| TCEAL8 | ENSG00000180964 | 90843 |
| TCEAL9 | ENSG00000185222 | 51186 |
| TIMP1 | ENSG00000102265 | 7076 |

TABLE 1-continued

| Genes That Confer A Competitive Advantage to Cells (advantage genes) | | |
|---|---|---|
| Gene | Ensembl ID | Entrez ID |
| TLE5 | ENSG00000104964 | 166 |
| TM4SF1 | ENSG00000169908 | 4071 |
| TM9SF3 | ENSG00000077147 | 56889 |
| TMA7 | ENSG00000232112 | 51372 |
| TMBIM6 | ENSG00000139644 | 7009 |
| TMCO1 | ENSG00000143183 | 54499 |
| TMEM147 | ENSG00000105677 | 10430 |
| TMEM258 | ENSG00000134825 | 746 |
| TMEM50A | ENSG00000183726 | 23585 |
| TMOD2 | ENSG00000128872 | 29767 |
| TMSB10 | ENSG00000034510 | 9168 |
| TMSB4X | ENSG00000205542 | 7114 |
| TPT1 | ENSG00000133112 | 7178 |
| TRAF4 | ENSG00000076604 | 9618 |
| TSC22D4 | ENSG00000166925 | 81628 |
| TSPAN6 | ENSG00000000003 | 7105 |
| TSPAN7 | ENSG00000156298 | 7102 |
| TTC3 | ENSG00000182670 | 7267 |
| TUBB | ENSG00000196230 | 203068 |
| UBA52 | ENSG00000221983 | 7311 |
| UBL5 | ENSG00000198258 | 59286 |
| UQCR10 | ENSG00000184076 | 29796 |
| UQCR11 | ENSG00000127540 | 10975 |
| UQCRB | ENSG00000156467 | 7381 |
| VIM | ENSG00000026025 | 7431 |
| WSB2 | ENSG00000176871 | 55884 |
| WSCD1 | ENSG00000179314 | 23302 |
| YBX1 | ENSG00000065978 | 4904 |
| YWHAB | ENSG00000166913 | 7529 |
| YWHAE | ENSG00000108953 | 7531 |
| ZFAS1 | ENSG00000177410 | 441951 |
| ZNF428 | ENSG00000131116 | 126299 |
| ZNF462 | ENSG00000148143 | 58499 |

In some embodiments, glial progenitor cells of the isolated populations described herein are genetically modified to increase expression of one or more genes listed in Table 1, relative to non-genetically modified progenitor cells. In some embodiments, glial progenitor cells of the isolated populations described herein are genetically modified to increase expression of any two of the above noted genes relative to non-genetically modified progenitor cells. In some embodiments, the glial progenitor cells of the isolated population are modified to increase expression of any 3 of the above noted genes. In some embodiments, the glial progenitor cells of the isolated population are modified to increase expression of any 4 of the above noted genes. In some embodiments, glial progenitor cells of the isolated population are modified to increase expression of any 5, 6, 7, 8, 9, 10, 11, 12, 13, 14, or more of the above identified genes.

Besides the genes provided in Table 1, a top-ranked set of genes is provided in Table 2 below, which additionally includes genes upregulated in advantaged cells ("winners") while concurrently suppressed in disadvantaged cells ("losers"). In some embodiments, the glial progenitor cells of the isolated population are modified to increase expression of any one of the genes provided in Table 2 below relative to non-genetically modified progenitor cells. In some embodiments, the glial progenitor cells of the isolated population are modified to increase expression of any one, two or more genes selected from the genes of Table 2 relative to non-genetically modified progenitor cells. In some embodiments, the glial progenitor cells of the isolated population are modified to increase expression of any 3 of the below noted genes. In some embodiments, the glial progenitor cells of the isolated population are modified to increase expression of any 4 of the below noted genes. In some embodiments, glial progenitor cells of the isolated population are modified to increase expression of any 1, 2, 3, 4, 5, 6, 7, 8, 9, 10, 11, 12, 13, 14, 15, 16, 17, 18, 19, 20, 21, 22, 23, or all 24 of these genes, relative to non-genetically modified progenitor cells.

TABLE 2

Top-ranked Genes that Confer a Competitive Advantage

| Gene | Ensembl ID | Entrez ID |
|---|---|---|
| TRIO | ENSG00000038382 | 7204 |
| ITM2A | ENSG00000078596 | 9452 |
| BEX5 | ENSG00000184515 | 340542 |
| BEX3 | ENSG00000166681 | 27018 |
| CTHRC1 | ENSG00000164932 | 115908 |
| EDIL3 | ENSG00000164176 | 10085 |
| MIA | ENSG00000261857 | 8190 |
| EMC10 | ENSG00000161671 | 284361 |
| CCND1 | ENSG00000110092 | 595 |
| GADD45A | ENSG00000116717 | 1647 |
| APOD | ENSG00000189058 | 347 |
| TRAF4 | ENSG00000076604 | 9618 |
| YWHAB | ENSG00000166913 | 7529 |
| B2M | ENSG00000166710 | 567 |
| PTMS | ENSG00000159335 | 5763 |
| OLFM2 | ENSG00000105088 | 93145 |
| LY6H | ENSG00000176956 | 4062 |
| MT3 | ENSG00000087250 | 4504 |
| UBA52 | ENSG00000221983 | 7311 |
| SNX3 | ENSG00000112335 | 8724 |
| FABP7 | ENSG00000164434 | 2173 |
| LRRC4B | ENSG00000131409 | 94030 |
| RAMP1 | ENSG00000132329 | 10267 |
| NEU4 | ENSG00000204099 | 129807 |

In some embodiments, the glial progenitor cells of the isolated population are modified to increase expression of one or more genes selected from the genes listed in Table 2, relative to non-genetically modified progenitor cells.

Table 3 provides another embodiment of transcripts conferring advantage, which includes top-ranked genes exhibiting significant transcriptional upregulation in WT cells presented with diseased and disadvantaged HD-derived cells, relative to singly engrafted WT cells, that also manifest significant transcriptional downregulation in the disadvantaged HD cells, relative to singly engrafted HD cells.

TABLE 3

Genes that Confer a Competitive Advantage

| Gene | Ensembl ID | Entrez ID |
|---|---|---|
| ANAPC11 | ENSG00000141552 | 51529 |
| APOD | ENSG00000189058 | 347 |
| ATP5MC3 | ENSG00000154518 | 518 |
| B2M | ENSG00000166710 | 567 |
| CALM1 | ENSG00000198668 | 801 |
| MT3 | ENSG00000087250 | 4504 |
| NEU4 | ENSG00000204099 | 129807 |
| PEBP1 | ENSG00000089220 | 5037 |
| RAMP1 | ENSG00000132329 | 10267 |
| SOD1 | ENSG00000142168 | 6647 |
| TBCB | ENSG00000105254 | 1155 |

In some embodiments, the glial progenitor cells of the isolated population are modified to increase expression of one or more genes selected from the genes listed in Table 3, relative to non-genetically modified progenitor cells. In some embodiments, the glial progenitor cells of the isolated population are modified to increase the expression of any 3, 4, 5, 6, 7, 8, 9, 10 or 11 of the genes in Table 3.

Table 4 provides another set of genes that confer a competitive advantage.

TABLE 4

Genes that Confer a Competitive Advantage

| Gene | Ensembl ID | Entrez ID |
|---|---|---|
| APOD | ENSG00000189058 | 347 |
| BEX3 | ENSG00000166681 | 27018 |
| BEX5 | ENSG00000184515 | 340542 |
| CCND1 | ENSG00000110092 | 595 |
| CTHRC1 | ENSG00000164932 | 115908 |
| EDIL3 | ENSG00000164176 | 10085 |
| EMC10 | ENSG00000161671 | 284361 |
| GADD45A | ENSG00000116717 | 1647 |
| ITM2A | ENSG00000078596 | 9452 |
| MIA | ENSG00000261857 | 8190 |
| TRAF4 | ENSG00000076604 | 9618 |
| TRIO | ENSG00000038382 | 7204 |

In some embodiments, the glial progenitor cells of the isolated population are modified to increase expression of one or more genes selected from the genes listed in Table 4, relative to non-genetically modified progenitor cells. In some embodiments, the glial progenitor cells of the isolated population are modified to increase the expression of any 3, 4, 5, 6, 7, 8, 9, 10, 11 or 12 of the genes in Table 4.

Table 5 provides another set of genes that confer a competitive advantage In some embodiments, the glial progenitor cells of the isolated population are modified to increase expression of one or more genes selected from the genes listed in Table 5, relative to non-genetically modified progenitor cells. In some embodiments, the glial progenitor cells of the isolated population are modified to increase the expression of any 3, 4, 5, 6, 7, 8, 9, 10, 11 or 12 of the genes in Table 5.

TABLE 5

Genes that Confer a Competitive Advantage

| Gene | Ensembl ID | Entrez ID |
|---|---|---|
| B2M | ENSG00000166710 | 567 |
| FABP7 | ENSG00000164434 | 2173 |
| LRRC4B | ENSG00000131409 | 94030 |
| LY6H | ENSG00000176956 | 4062 |
| MT3 | ENSG00000087250 | 4504 |
| NEU4 | ENSG00000204099 | 129807 |
| OLFM2 | ENSG00000105088 | 93145 |
| PTMS | ENSG00000159335 | 5763 |
| RAMP1 | ENSG00000132329 | 10267 |
| SNX3 | ENSG00000112335 | 8724 |
| UBA52 | ENSG00000221983 | 7311 |
| YWHAB | ENSG00000166913 | 7529 |

In some embodiments, the glial progenitor cells of the isolated population are modified to increase expression of one or more genes selected from the genes listed in Table 5, relative to non-genetically modified progenitor cells. In some embodiments, the glial progenitor cells of the isolated population are modified to increase the expression of any 3, 4, 5, 6, 7, 8, 9, 10, 11 or 12 of the genes in Table 5.

In some embodiments, the glial progenitor cells of the isolated population are modified to increase expression of one or more genes selected from the group consisting of LY6H, MIA, GADD45A, ITM2A and ITM2B.

In some embodiments, the glial progenitor cells of the isolated population are modified to increase expression of one or more genes by 50% or greater, 100% or greater, 150% or greater, 200% or greater, 300% or greater, 400% or greater, 500% or greater, 600% or greater, 700% or greater, 800% or greater, 900% or greater, or 1000% or greater at the mRNA level.

In some embodiments, the glial progenitor cells of the isolated population are modified to increase expression of one or more genes by 10% or greater, 20% or greater, 30% or greater, 40% or greater, 50% or greater, 60% or greater, 70% or greater, 80% or greater, 90% or greater, or 100% or greater at the protein level.

To express the one or more genes conferring a competitive advantage in the glial progenitor cells described herein, polynucleotides which encode the one or more genes are ligated into a nucleic acid construct suitable for glial progenitor cell expression. The nucleic acid construct is then introduced into the glial progenitor cells or into a less differentiated progenitor/stem population, e.g., neural progenitor cells, embryonic stem cells, induced pluripotent stem cells, etc., from which the glial progenitor cells will be derived from.

Nucleic acid constructs comprising one or more polynucleotide encoding any one or more of the genes in Table 1 or Table 2 further include one or more promoter and/or enhancer sequences for directing transcription of the polynucleotide sequence in the cell in a constitutive or inducible manner.

In some embodiments, the promoter sequence for directing transcription of the polynucleotide sequence in the glial progenitor cells includes a constitutive promoter. Constitutive promoters suitable for use with some embodiments described herein include promoter sequences which are active under most environmental conditions and most types of cells such as the cytomegalovirus (CMV) and Rous sarcoma virus (RSV). Other suitable promoters for inclusion in the genetically modified glial progenitor cells of the present disclosure include, without limitation, human elongation factor 1α promoter ("EF1A"), human ubiquitin C promoter ("UBC"), and phosphoglycerokinase ("PGK") promoter.

In some embodiments, the promoter sequence for directing transcription of the polynucleotide sequence in the glial progenitor cells includes an inducible promoter and/or operator system. Suitable inducible promoter and/or operator systems for inclusion in the genetically modified cells of the present disclosure are well known in the art and include, without limitation, a tetracycline-controlled operator system, a cumate-controlled operator system, rapamycin inducible system, a FKCsA inducible system, and an ABA inducible system (see, e.g., Kallunki et al., "How to Choose the Right Inducible Gene Expression System for Mammalian Studies?" Cells 8 (8): 796 (2019); U.S. Pat. Nos. 8,728,759; and 7,745,592, which are hereby incorporated by reference in their entirety).

In some embodiments, the inducible promoter is a tetracycline-controlled operator system that comprises a repression-based configuration, in which a Tet operator ("TetO") is inserted between a constitutive promoter and gene of interest and where the binding of the Tet repressor ("TetR") to the operator suppresses downstream transcription of a nucleic acid sequence of interest (see, e.g., Kallunki et al., "How to Choose the Right Inducible Gene Expression System for Mammalian Studies?" Cells 8 (8): 796 (2019), which is hereby incorporated by reference in its entirety). In accordance with such embodiments, the addition of tetracycline (or the synthetic tetracycline derivative doxycycline) results in the disruption of the association between TetR and TetO, thereby triggering TetO-dependent transcription of the nucleic acid sequence of interest.

In some embodiments, the tetracycline-controlled operator system comprises a Tet-off configuration, where tandem TetO sequences are positioned upstream of a minimal promoter followed by a nucleic acid sequence of interest (see, e.g., Kallunki et al., "How to Choose the Right Inducible Gene Expression System for Mammalian Studies?" Cells 8 (8): 796 (2019), which is hereby incorporated by reference in its entirety). In accordance with such embodiments, a chimeric protein consisting of TetR and VP16 ("tTA"), a eukaryotic transactivator derived from herpes simplex virus type 1, is converted into a transcriptional activator, and the expression plasmid is transfected together with the operator plasmid. Thus, culturing cells with tetracycline (or the synthetic tetracycline derivative doxycycline) switches off the expression of a nucleic acid sequence of interest, while removing tetracycline switches it on.

In some embodiments, the tetracycline-controlled operator system comprises a Tet-on configuration, where a nucleic acid sequence of interest is transcribed when tetracycline is present (see, e.g., Kallunki et al., "How to Choose the Right Inducible Gene Expression System for Mammalian Studies?" Cells 8 (8): 796 (2019), which is hereby incorporated by reference in its entirety). In accordance with such embodiments, tandem TetO sequences are positioned upstream of a minimal promoter followed by a nucleic acid sequence of interest. In the presence of tetracycline (or the synthetic tetracycline derivative doxycycline), a mutant rTa ("rtTa") binds to TetO sequences, thereby activating the minimal promoter.

In some embodiments, the inducible promoter and/or operator system is a cumate-controlled operator system. Similar to the tetracycline-controlled operator system, the cumate-controlled operator system, the cumate operator ("CuO") and its repressor ("CymR") may be engineered into a repressor configuration, an activator configuration, and a reverse activator configuration (see, e.g., Kallunki et al., "How to Choose the Right Inducible Gene Expression System for Mammalian Studies?" Cells 8 (8): 796 (2019), which is hereby incorporated by reference in its entirety).

In some embodiments, the cumate-controlled operator system comprises a repression-based configuration, in which the cumate operator ("CuO") is inserted between a constitutive promoter and gene of interest and where the binding of the cumate repressor ("CymR") to the operator suppresses downstream transcription of a nucleic acid sequence of interest. In accordance with such embodiments, the addition of cumate releases CymR thereby triggering CuO-dependent gene expression.

In some embodiments, the cumate-controlled operator system comprises an activator configuration, where chimeric molecular ("cTA") is formed via the fusion of CymR and VP16. In this configuration, a minimal promoter is placed downstream of the multimerized operator binding sites (e.g., 6xCuO). Transcription of a nucleic acid sequence of interest is controlled by the minimal promoter, which is activated in the absence of cumate.

In some embodiments, the cumate-controlled operator system comprises a reverse activator configuration, where a nucleic acid sequence is transcribed when cumate is present. In accordance with such embodiments, tandem CuO sequences are positioned upstream of a minimal promoter followed by a nucleic acid sequence of interest. In the presence of cumate, a cTA mutant ("rcTA") binds to CuO sequences, thereby activating the minimal promoter.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

In aspects where it is desirable to limit expression of a particular gene to only glial progenitor cells and not differentiated cells that arise therefrom, the promoter utilized in the nucleic acid construct to produce the genetically modified glial progenitor cells, including bi-potential glial progenitor cells, oligodendrocyte-biased glial progenitor cells, and astrocyte-biased glial progenitor cells, is a promoter of a gene that is selectively or specifically expressed by glial progenitor cells. Promoter sequences suitable for driving expression of the genes providing a competitive advantage as described herein include, without limitation, the platelet derived growth factor alpha (PDGFRA) promoter, the zinc finger protein 488 (ZNF488), the G protein-coupled receptor (GPR17) promoter, the oligodendrocyte Transcription Factor 2 (OLIG2) promoter, the chondroitin sulfate proteoglycan 4 (CSPG4) promoter, and the SRY-box transcription factor 10 (SOX10).

The nucleic acid constructs utilized to genetically modify the glial progenitor cells described herein can further comprise enhancer elements. Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. Suitable enhancer elements for use in producing the genetically modified glial progenitor cells as described herein include, for example, the SV40 early gene enhancer which is suitable for many cell types. Other enhancer/promoter combinations that are suitable for use include those derived from polyoma virus, human or murine cytomegalovirus (CMV), the long-term repeat from various retroviruses such as murine leukemia virus, murine or Rous sarcoma virus and HIV (see e.g., Enhancers and Eukaryotic Expression, Cold Spring Harbor Press, Cold Spring Harbor, N.Y. 1983, which is incorporated herein by reference in its entirety).

In the construction of the nucleic acid construct, the promoter is preferably positioned approximately the same distance from the heterologous transcription start site as it is from the transcription start site in its natural setting. As is known in the art, however, some variation in this distance can be accommodated without loss of promoter function.

Suitable expression vectors for introducing the nucleic acid construct of interest to genetically modify the glial progenitor cells describe herein can optionally contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1 (+/−), pGL3, pZeoSV2 (+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p205. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein.

Suitable viral expression vectors include, without limitation, adenovirus vectors, adeno-associated virus ("AAV") vectors, retrovirus vectors, lentivirus vectors, vaccinia virus vectors, herpes virus vectors, and any other vector suitable for introduction of the encoded nucleic acid inhibitor described herein into a given organism or genetic background by any means to facilitate expression of the encoded nucleic acid inhibitor.

In some embodiments, the vector is a lentiviral vector (see, e.g., U.S. Pat. No. 748,529 to Fang et al.; Ura et al., "Developments in Viral Vector-Based Vaccines," Vaccines 2: 624-641 (2014); and Hu et al., "Immunization Delivered by Lentiviral Vectors for Cancer and Infection Diseases," Immunol. Rev. 239:45-61 (2011), which are hereby incorporated by reference in their entirety).

In some embodiments, the vector is a retroviral vector (see e.g., U.S. Pat. No. 748,529 to Fang et al., and Ura et al., "Developments in Viral Vector-Based Vaccines," Vaccines 2:624-641 (2014), which are hereby incorporated by reference in their entirety), a vaccinia virus, a replication deficient adenovirus vector, and a gutless adenovirus vector (see e.g., U.S. Pat. No. 5,872,005, which is incorporated herein by reference in its entirety).

In other embodiments, the vector is an adeno-associated virus (AAV) vector (see, e.g., Krause et al., "Delivery of Antigens by Viral Vectors for Vaccination," Ther. Deliv. 2 (1): 51-70 (2011); Ura et al., "Developments in Viral Vector-Based Vaccines," Vaccines 2:624-641 (2014); Buning et al, "Recent Developments in Adeno-associated Virus Vector Technology," J. Gene Med. 10:717-733 (2008), each of which is incorporated herein by reference in its entirety).

Methods for generating and isolating viral expression vectors suitable for use as vectors are known in the art (see, e.g., Bulcha et al., "Viral Vector Platforms within the Gene Therapy Landscape," Nature 6:53 (2021); Bouard et al., "Viral Vectors: From Virology to Transgene Expression," Br. J. Pharmacol. 157 (2): 153-165 (2009); Grieger & Samulski, "Adeno-associated Virus as a Gene Therapy Vector: Vector Development, Production and Clinical Applications," Adv. Biochem. Engin/Biotechnol. 99:119-145 (2005); Buning et al, "Recent Developments in Adeno-associated Virus Vector Technology," J. Gene Med. 10:717-733 (2008), each of which is incorporated herein by reference in its entirety).

Various methods can be used to introduce the expression vector of some embodiments of the invention into glial progenitor cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et al. Biotechniques 4 (6): 504-512, 1986 (which are hereby incorporated by reference in their entirety) and include, for example, stable or transient transfection, lipofection, electroporation and infection with recombinant viral vectors. In addition, see U.S. Pat. Nos. 5,464,764 and 5,487,992 for positive-negative selection methods. Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers. Nanoparticles are also contemplated.

The genetically modified glial progenitor cells described herein are modified in accordance with the present disclosure to comprise the recombinant genetic vector at any point prior to transplantation into the subject in need thereof. For example, in one embodiment, the recombinant genetic construct is introduced into the bi-potential glial progenitor, oligodendrocyte-biased progenitor cells, or astrocyte-biased progenitor cells just prior to transplant. In another embodiment, the recombinant genetic construct is introduced into a precursor cell of the glial progenitor cells, e.g., neural progenitor or pluripotent stem cells.

Genetic Modifications to Suppress Expression of One or More Genes that Confer a Competitive Disadvantage As described supra, in some embodiments, the population of glial progenitor cells as described herein is genetically modified to suppress, i.e., suppress or silence one or more genes encoding a protein that confers a competitive disadvantage to the modified cells relative to glial progenitor cells which have not been genetically modified (disadvantage genes). The one or more genes identified herein as providing cells a competitive disadvantage over resident cells upon transplantation are provided in Table 6 below by their gene name. Also provided in Table 3 is the Entrez ID accession number and Ensembl ID for each gene, which are each hereby incorporated by reference in their entirety for their disclosure of the gene sequences and the corresponding protein encoded by each sequence. All gene products referred to in this application include the wild type gene product and functional variants thereof. A "functional variant of a gene product" refers to a modified gene product (e.g., by deletion, substitution, insertion, glycosylation, etc.) that retains at least 50% of the biological activity of the unmodified (wild-type) gene product in an competition assay.

TABLE 6

Genes that Confer a Competitive Disadvantage (disadvantage genes)

| Gene | Ensembl ID | Entrez ID |
|---|---|---|
| ABCG1 | ENSG00000160179 | 9619 |
| ADGRB1 | ENSG00000181790 | 575 |
| AKAP9 | ENSG00000127914 | 10142 |
| AL360181.3 | ENSG00000254536 | NA |
| ANKRD10 | ENSG00000088448 | 55608 |
| ARGLL1 | ENSG00000134884 | 55082 |
| ARL16 | ENSG00000214087 | 339231 |
| ATP10B | ENSG00000118322 | 23120 |
| B3GNT7 | ENSG00000156966 | 93010 |
| BHLHE41 | ENSG00000123095 | 79365 |
| BPTF | ENSG00000171634 | 2186 |
| BRI3 | ENSG00000164713 | 25798 |
| BX664615.2 | ENSG00000283886 | NA |
| BX890604.1 | ENSG00000285756 | NA |
| C1QL2 | ENSG00000144119 | 165257 |
| CAMK2N1 | ENSG00000162545 | 55450 |
| CCDC85B | ENSG00000175602 | 11007 |
| CCNL1 | ENSG00000163660 | 57018 |
| CHCHD10 | ENSG00000250479 | 400916 |
| CHORDC1 | ENSG00000110172 | 26973 |
| CIRBP | ENSG00000099622 | 1153 |
| CLDN10 | ENSG00000134873 | 9071 |
| COL9A1 | ENSG00000112280 | 1297 |
| COL9A2 | ENSG00000049089 | 1298 |
| DANCR | ENSG00000226950 | 57291 |
| DCXR | ENSG00000169738 | 51181 |
| DHX36 | ENSG00000174953 | 170506 |
| DLL3 | ENSG00000090932 | 10683 |
| DNAJA1 | ENSG00000086061 | 3301 |
| DNM3 | ENSG00000197959 | 26052 |
| ECH1 | ENSG00000104823 | 1891 |
| EGR1 | ENSG00000120738 | 1958 |
| EIF1AX | ENSG00000173674 | 1964 |
| ELAVL3 | ENSG00000196361 | 1995 |
| EMID1 | ENSG00000156998 | 129080 |
| ETFB | ENSG00000105379 | 2109 |
| FAM133A | ENSG00000179083 | 286499 |
| FAM133B | ENSG00000234545 | 257415 |
| FBXO2 | ENSG00000116661 | 26232 |
| FERMT1 | ENSG00000101311 | 55612 |
| FOS | ENSG00000170345 | 2353 |
| FOSB | ENSG00000125740 | 2354 |
| FSCN1 | ENSG00000075618 | 6624 |
| FSIP2 | ENSG00000188738 | 401024 |
| GABPB1-AS1 | ENSG00000244879 | NA |
| GALR1 | ENSG00000166573 | 2587 |
| GNG8 | ENSG00000167414 | 94235 |
| GNPTAB | ENSG00000111670 | 79158 |
| GOLGA8A | ENSG00000175265 | 23015 |
| GOLGA8B | ENSG00000215252 | 440270 |
| GPR155 | ENSG00000163328 | 151556 |
| GRID2 | ENSG00000152208 | 2895 |
| GRM7 | ENSG00000196277 | 2917 |
| HAPLN1 | ENSG00000145851 | 1404 |
| HMX1 | ENSG00000215612 | 3166 |
| HSPA1A | ENSG00000204389 | 3303 |
| HSPA1B | ENSG00000204388 | 3304 |
| HTRA1 | ENSG00000166033 | 5654 |
| JAG1 | ENSG00000101384 | 182 |
| JUN | ENSG00000177606 | 3725 |
| JUNB | ENSG00000171223 | 3726 |
| KCNIP4 | ENSG00000185774 | 80333 |
| KCNQ1OT1 | ENSG00000269821 | 10984 |
| KLF3-AS1 | ENSG00000231160 | NA |
| LAMP2 | ENSG00000005893 | 3920 |
| LINC01116 | ENSG00000163364 | NA |
| LINC01301 | ENSG00000251396 | NA |
| LINC01896 | ENSG00000263146 | NA |
| LRP4 | ENSG00000134569 | 4038 |
| LRRC7 | ENSG00000033122 | 57554 |
| MACF1 | ENSG00000127603 | 23499 |
| MALAT1 | ENSG00000251562 | 378938 |
| MASP1 | ENSG00000127241 | 5648 |
| MDH1 | ENSG00000014641 | 4190 |
| MT1E | ENSG00000169715 | 4493 |

TABLE 6-continued

| Genes that Confer a Competitive Disadvantage (disadvantage genes) | | |
|---|---|---|
| Gene | Ensembl ID | Entrez ID |
| MYT1 | ENSG00000196132 | 4661 |
| NASP | ENSG00000132780 | 4678 |
| NKTR | ENSG00000114857 | 4820 |
| NUTM2A-AS1 | ENSG00000223482 | 728190 |
| OFD1 | ENSG00000046651 | 8481 |
| PCDHB5 | ENSG00000113209 | 26167 |
| PCDHGA3 | ENSG00000254245 | 56112 |
| PEPD | ENSG00000124299 | 5184 |
| PHGDH | ENSG00000092621 | 26227 |
| PMP2 | ENSG00000147588 | 5375 |
| PNISR | ENSG00000132424 | 25957 |
| PPP1R14A | ENSG00000167641 | 94274 |
| PTGDS | ENSG00000107317 | 5730 |
| RAB3IP | ENSG00000127328 | 117177 |
| RAF1 | ENSG00000132155 | 5894 |
| RAP1GAP | ENSG00000076864 | 5909 |
| RARRES2 | ENSG00000106538 | 5919 |
| RBM25 | ENSG00000119707 | 58517 |
| RBMX | ENSG00006147274 | 27316 |
| REV3L | ENSG00000009413 | 5980 |
| RHOBTB3 | ENSG00000164292 | 22836 |
| RIMS2 | ENSG00000176406 | 9699 |
| RIT2 | ENSG00000152214 | 6014 |
| RRBP1 | ENSG00000125844 | 6238 |
| RSRP1 | ENSG00000117616 | 57035 |
| 5100A1 | ENSG00000160678 | 6271 |
| S100A16 | ENSG00000188643 | 140576 |
| SCG2 | ENSG00000171951 | 7857 |
| SEMA3E | ENSG00000170381 | 9723 |
| SERTAD1 | ENSG00000197019 | 29950 |
| SEZ6L | ENSG00000100095 | 23544 |
| SEZ6L2 | ENSG00000174938 | 26470 |
| SH3GLB2 | ENSG00000148341 | 56904 |
| SNHG15 | ENSG00000232956 | 285958 |
| SNRNP70 | ENSG00000104552 | 6625 |
| SRSF5 | ENSG00000100650 | 6430 |
| STXBP6 | ENSG00000168952 | 29091 |
| SYNRG | ENSG00000275066 | 11276 |
| TLE4 | ENSG00000106829 | 7091 |
| TMEM176B | ENSG00000106565 | 28959 |
| TPI1 | ENSG00000111669 | 7167 |
| TSC22D3 | ENSG00000157514 | 1831 |
| USP11 | ENSG00000102226 | 8237 |
| VCAN | ENSG00000038427 | 1462 |
| WFDC1 | ENSG00000103175 | 58189 |
| WSB1 | ENSG00000109046 | 26118 |
| ZFYVE16 | ENSG00000039319 | 9765 |
| ZNF528 | ENSG00000167555 | 84436 |
| ZNF528-AS1 | ENSG00000269834 | NA |

Thus, in some embodiments, glial progenitor cells of the isolated populations described herein are genetically modified to decrease or silence the expression of one or more genes listed in Table 6 relative to non-genetically modified progenitor cells. In some embodiments, glial progenitor cells of the isolated populations described herein are genetically modified to decrease or silence expression of any two or more of the above noted genes of Table 6 relative to non-genetically modified progenitor cells. In some embodiments, glial progenitor cells of the isolated population are modified to decrease or silence the expression of any 1, 2, 3, 4, 5, 6, 7, 8, 9, 10, 11, 12, 13, 14, or more of the above identified genes. In some embodiments, the glial progenitor cells of the isolated population are modified to decrease or silence the expression of any 3 of the above noted genes. In some embodiments, the glial progenitor cells of the isolated population are modified to suppress or silence the expression of any 4 of the above noted genes.

Besides the genes provided in Table 6, a top-ranked group of those genes is provided in Table 7 below, which additionally includes top-ranked genes downregulated in advantaged cells ("winners") while concurrently upregulated in disadvantaged cells ("losers"). In some embodiments, the glial progenitor cells of the isolated population are modified to decrease or silence the expression of any one of the genes provided in Table 6 relative to non-genetically modified progenitor cells. In some embodiments, glial progenitor cells of the isolated population are modified to decrease expression or silence any two or more genes provided in Table 6 relative to non-genetically modified progenitor cells. In some embodiments, glial progenitor cells of the isolated population are modified to decrease expression or silence any 1, 2, 3, 4, 5, 6, 7, 8, 9, 10, 11, 12, 13, 14, 15, 16, 17, 18, 19, 20, 21, 22, 23, or all 24 of these genes. In some embodiments, the glial progenitor cells of the isolated population are modified to decrease or silence the expression of any 3 of the genes in Table 7. In some embodiments, the glial progenitor cells of the isolated population are modified to decrease or silence the expression of any 4 of the genes in Table 7.

TABLE 7

| Top-ranked Genes that Confer a Competitive Disadvantage | | |
|---|---|---|
| Gene | Ensembl ID | Entrez ID |
| CXADR | ENSG00000154639 | 1525 |
| SEZ6L | ENSG00000100095 | 23544 |
| FABP5 | ENSG00000164687 | 2171 |
| PTGDS | ENSG00000107317 | 5730 |
| THBS4 | ENSG00000113296 | 7060 |
| MT2A | ENSG00000125148 | 4502 |
| MT1E | ENSG00000169715 | 4493 |
| ADGRG1 | ENSG00000205336 | 9289 |
| DLL3 | ENSG00000090932 | 10683 |
| ATP1B3 | ENSG00000069849 | 483 |
| ATP1A2 | ENSG00000018625 | 477 |
| B3GNT7 | ENSG00000156966 | 93010 |
| SAT1 | ENSG00000130066 | 6303 |
| TLE4 | ENSG00000106829 | 7091 |
| ARMCX6 | ENSG00000198960 | 54470 |
| SPARCL1 | ENSG00000152583 | 8404 |
| FIBIN | ENSG00000176971 | 387758 |
| PCDHGA3 | ENSG00000254245 | 56112 |
| PCDHGB6 | ENSG00000253305 | 56100 |
| PLCG2 | ENSG00000197943 | 5336 |
| LRRC7 | ENSG00000033122 | 57554 |
| MAP3K13 | ENSG00000073803 | 9175 |
| IGFBP2 | ENSG00000115457 | 3485 |
| ARL4C | ENSG00000188042 | 10123 |

In some embodiments, the glial progenitor cells of the isolated population are modified to decrease expression of one or more genes selected from the genes listed in Table 7, relative to non-genetically modified progenitor cells.

Table 8 provides another embodiment of transcripts conferring disadvantage, includes top-ranked genes exhibiting significant transcriptional downregulation in WT cells presented with diseased HD-derived cells, relative to singly engrafted WT cells, that also manifest significant transcriptional upregulation in the disadvantaged HD cells, relative to singly engrafted HD cells.

TABLE 8

| Genes that Confer a Competitive Disadvantage | | |
|---|---|---|
| Gene | Ensembl ID | Entrez ID |
| EGR1 | ENSG00000120738 | 1958 |
| HSPH1 | ENSG00000129694 | 10808 |
| WSB1 | ENSG00000109046 | 26118 |

TABLE 8-continued

| Genes that Confer a Competitive Disadvantage | | |
|---|---|---|
| Gene | Ensembl ID | Entrez ID |
| RBMX | ENSG00000147274 | 27316 |
| ARGLU1 | ENSG00000134884 | 55082 |
| TLE4 | ENSG00000106829 | 7091 |
| MACF1 | ENSG00000127603 | 23499 |
| STAT3 | ENSG00000168610 | 6774 |
| FSIP2 | ENSG00000188738 | 401024 |
| NKTR | ENSG00000114857 | 4820 |

In some embodiments, the glial progenitor cells of the isolated population are modified to decrease expression of one or more genes selected from the genes listed in Table 8. In some embodiments, the glial progenitor cells of the isolated population are modified to decrease or silence the expression of any 3, 4, 5, 6, 7, 8, 9 or 10 of the genes in Table 8.

Table 9 provides another set of genes that confer a competitive disadvantage.

TABLE 9

| Genes that Confer a Competitive Disadvantage | | |
|---|---|---|
| Gene | Ensembl ID | Entrez ID |
| ADGRG1 | ENSG00000205336 | 9289 |
| ATP1A2 | ENSG00000018625 | 477 |
| ATP1B3 | ENSG00000069849 | 483 |
| B3GNT7 | ENSG00000156966 | 93010 |
| CXADR | ENSG00000154639 | 1525 |
| DLL3 | ENSG00000090932 | 10683 |
| FABP5 | ENSG00000164687 | 2171 |
| MT1E | ENSG00000169715 | 4493 |
| MT2A | ENSG00000125148 | 4502 |
| PTGDS | ENSG00000107317 | 5730 |
| SEZ6L | ENSG00000100095 | 23544 |
| THBS4 | ENSG00000113296 | 7060 |

In some embodiments, the glial progenitor cells of the isolated population are modified to decrease expression of one or more genes selected from the genes listed in Table 9, relative to non-genetically modified progenitor cells. In some embodiments, the glial progenitor cells of the isolated population are modified to decrease or silence the expression of any 3, 4, 5, 6, 7, 8, 9, 10, 11 or 12 of the genes in Table 9.

Table 10 provides another set of genes that confer a competitive disadvantage.

TABLE 10

| Genes that Confer a Competitive Disadvantage | | |
|---|---|---|
| Gene | Ensembl ID | Entrez ID |
| ARL4C | ENSG00000188042 | 10123 |
| ARMCX6 | ENSG00000198960 | 54470 |
| FIBIN | ENSG00000176971 | 387758 |
| IGFBP2 | ENSG00000115457 | 3485 |
| LRRC7 | ENSG00000033122 | 57554 |
| MAP3K13 | ENSG00000073803 | 9175 |
| PCDHGA3 | ENSG00000254245 | 56112 |
| PCDHGB6 | ENSG00000253305 | 56100 |
| PLCG2 | ENSG00000197943 | 5336 |
| SAT1 | ENSG00000130066 | 6303 |
| SPARCL1 | ENSG00000152583 | 8404 |
| TLE4 | ENSG00000106829 | 7091 |

In some embodiments, the glial progenitor cells of the isolated population are modified to decrease expression of one or more genes selected from the genes listed in Table 10, relative to non-genetically modified progenitor cells. In some embodiments, the glial progenitor cells of the isolated population are modified to decrease or silence the expression of any 3, 4, 5, 6, 7, 8, 9, 10, 11 or 12 of the genes in Table 10.

In some embodiments, the glial progenitor cells of the isolated population are modified to decrease expression of the one or more disadvantage genes by 50% or greater, 60% or greater, 70% or greater, 80% or greater, or 90% or greater at the mRNA level.

In some embodiments, the glial progenitor cells of the isolated population are modified to decrease expression of the one or more disadvantage genes by 10% or greater, 20% or greater, 30% or greater, 40% or greater, 50% or greater, 60% or greater, 70% or greater, 80% or greater, or 90% or greater at the protein level.

In some embodiments, glial progenitor cells of the isolated populations described herein are genetically modified using a nuclease-based gene editing system to suppress the expression of one or more of the aforementioned genes involved in conferring a competitive disadvantage to glial progenitor cells. As used herein, the term "nuclease-based gene editing system" refers to a system comprising a nuclease or a derivative thereof, including a catalytically inactivated nuclease, that is recruited to a target sequence in the genome. Suitable nuclease-based systems that can be utilized to genetically modify the glial progenitor cell populations as described herein include, without limitation, a Clustered Regularly Interspaced Short Palindromic Repeat-associated ("Cas") protein (e.g., Cas9, Cas12a, and Cas12b) system, a zinc finger nuclease ("ZFNs") system, or a transcription activator-like effector nucleases ("TALEN") system.

In some embodiments, the nuclease-based gene editing system is a CRISPR/Cas system targeted to suppress or silence the expression of the one or more genes identified above to confer a competitive disadvantage to glial progenitor cells. The CRISPR/Cas system may comprise a Cas protein or a nucleic acid molecule encoding the Cas protein and a guide RNA comprising a nucleotide sequence that is complementary to a portion of a target DNA sequence of the one or more identified genes of Table 3 or Table 4.

As described herein, Cas proteins form a ribonucleoprotein complex with a guide RNA, which guides the Cas protein to a target DNA sequence. Suitable Cas proteins include Cas nucleases (i.e., Cas proteins capable of introducing a double strand break at a target nucleic acid sequence), Cas nickases (i.e., Cas protein derivatives capable of introducing a single strand break at a target nucleic acid sequence), and nuclease dead Cas (dCas) proteins (i.e., Cas protein derivatives that do not have any nuclease activity).

In some embodiments, the Cas protein is a Cas9 protein. As used herein, the term "Cas9 protein" or "Cas9" includes any of the recombinant or naturally-occurring forms of the CRISPR-associated protein 9 (Cas9) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas9 protein. In some embodiments, the Cas9 protein is substantially identical to the protein identified by the UniProt reference number Q99ZW2, G3ECR1, J7RUA5, A0Q5Y3, or J3F2B0 (which are hereby incorporated by reference in their entirety) or a variant or homolog having substantial identity thereto. In some embodiments, the Cas9 protein is selected from the group consisting of a Cas9 nuclease, a Cas9 nickases, and a nuclease dead Cas 9 ("dCas9").

In some embodiments, the Cas protein is a Cas12a protein. As used herein, the term "Cas12a protein" or "Cas12a" includes any of the recombinant or naturally-occurring forms of the CRISPR-associated protein 12 (Cas12a) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas12a protein. In some embodiments, the Cas12a protein is substantially identical to the protein identified by the UniProt reference number A0Q7Q2, U2UMQ6, A0A7C6JPC1, A0A7C9HOZ9, or A0A7JOAY55 (which are hereby incorporated by reference in their entirety) or a variant or homolog having substantial identity thereto. In some embodiments, the Cas12a protein is selected from the group consisting of a Cas12a nuclease, a Cas12a nickase, and a nuclease dead Cas12a ("dCas12a").

In some embodiments, the Cas protein is a Cas12b protein. As used herein, the term "Cas12b protein" or "Cas12b" includes any of the recombinant or naturally-occurring forms of the CRISPR-associated protein 12 (Cas12b) or variants or homologs thereof. In some embodiments, the variants or homologs have at least 90%, 95%, 96%, 97%, 98%, 99% or 100% amino acid sequence identity across the whole sequence or a portion of the sequence (e.g., a 50, 100, 150, or 200 continuous amino acid portion) compared to a naturally occurring Cas12b protein. In some embodiments, the Cas12b protein is substantially identical to the protein identified by the UniProt reference number T0D7A2, A0A613SPI6, A0A617FUC4, A0A6N9TP17, A0A6M1UF64, A0A7Y8V748, A0A7X7KIS4, A0A7X8X2U5, or A0A7X8UMW7 (which are hereby incorporated by reference in their entirety) or a variant or homolog having substantial identity thereto. In some embodiments, the Cas 12b protein is selected from the group consisting of a Cas12b nuclease, a Cas12b nickase, and a nuclease dead Cas12b ("dCas12b").

As used herein, the term "guide RNA" or "gRNA" refers to a ribonucleotide sequence capable of binding a nucleoprotein, thereby forming ribonucleoprotein complex. The guide RNA comprises (i) a DNA-targeting sequence that is complementary to a target nucleic acid sequence (e.g., sequence of a gene identified to confer a competitive disadvantage to glial progenitor cells) and (ii) a binding sequence for the Cas protein (e.g., Cas9 nuclease, Cas9 nickase, dCas9, Cas12a nuclease, Cas12a nickase, or dCas12a).

In some embodiments, the guide RNA is a single guide RNA molecule (single RNA nucleic acid), which may include a "single-guide RNA" or "sgRNA". In other embodiments, the nucleic acid of the present disclosure includes two RNA molecules (e.g., joined together via hybridization at the binding sequence). Thus, the term guide RNA is inclusive, referring both to two-molecule nucleic acids and to single molecule nucleic acids (e.g., sgRNAs).

In some embodiments, the gRNA is 10, 20, 30, 40, 50, 60, 70, 80, 90, 100 or more nucleic acid residues in length. In some embodiments, the gRNA is from 10 to 30 nucleic acid residues in length. In some embodiments, the gRNA is 20 nucleic acid residues in length. In some embodiments, the length of the gRNA is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleic acid residues or sugar residues in length. In some embodiments, the gRNA is from 5 to 50, 10 to 50, 15 to 50, 20 to 50, 25 to 50, 30 to 50, 35 to 50, 40 to 50, 45 to 50, 5 to 75, 10 to 75, 15 to 75, 20 to 75, 25 to 75, 30 to 75, 35 to 75, 40 to 75, 45 to 75, 50 to 75, 55 to 75, 60 to 75, 65 to 75, 70 to 75, 5 to 100, 10 to 100, 15 to 100, 20 to 100, 25 to 100, 30 to 100, 35 to 100, 40 to 100, 45 to 100, 50 to 100, 55 to 100, 60 to 100, 65 to 100, 70 to 100, 75 to 100, 80 to 100, 85 to 100, 90 to 100, 95 to 100, or more residues in length. In some embodiments, the gRNA is from 10 to 15, 10 to 20, 10 to 30, 10 to 40, or 10 to 50 residues in length.

In some embodiments, where the CRISPR/Cas system is targeted to silence any one or more genes selected from the genes provided in Table 3. In some embodiments, where the CRISPR/Cas system is targeted to silence any one or more genes selected from the genes provided in Table 4.

In some embodiments, the nuclease-based gene editing system utilized to suppress or silence expression of the one or more genes identified above in Table 3 or Table 4 is a CRISPR interference or "CRISPRi" system. The CRISPRi system allows for sequence-specific repression of gene expression. CRISPRi systems comprise nuclease dead Cas ("dCas") proteins (i.e., , nuclease-inactivated Cas proteins) to block the transcription of a target gene, without cutting the target DNA sequence. Nuclease inactivated Cas proteins and methods of generating nuclease-inactivated Cas proteins are well known in the art (see, e.g., Qi et al., "Repurposing CRISPR as an RNA-Guided Platform for Sequence-Specific Control of Gene Expression," Cell 152 (5): 1173-1183 (2013), which is hereby incorporated by reference in its entirety).

The CRISPRi system suitable for genetically modifying glial progenitor cells as described herein may comprise (i) a nuclease dead Cas (dCas) protein (i.e., a nuclease-inactivated Cas protein) or nucleic acid molecule encoding the dCas protein and (ii) a guide RNA comprising a nucleotide sequence that is complementary to a portion of a target gene, i.e., any one or more of the genes identified above to confer a competitive disadvantage to glial progenitor cells.

In some embodiments, the nuclease dead Cas (dCas) protein is selected from the group consisting of dCas9, dCas12a, and dCas12b.

In some embodiments, the nuclease dead Cas (dCas) protein is a fusion protein comprising a Cas protein and one or more epigenetic modulators suitable for suppressing or silencing expression of one or more genes identified above in Table 3 or identified in Table 4. Suitable epigenetic modulators include, without limitation, DNA methyltransferase enzymes (e.g., DNA methyltransferase 3 alpha ("DNMT3A") and DNA methyltransferase 3 like ("DNMT3L")), histone demethylation enzymes (e.g., lysine-specific histone demethylase 1 ("LSD1")), histone methyltransferase enzymes (e.g., G9A and SuV39 h1), transcription factor recruitment domains (e.g., Krüppel-associated box domain ("KRAB"), KRAB-Methyl-CpG binding protein 2 domain ("KRAB-MeCP2"), enhancer of Zeste 2 ("EZH2")), zinc finger transcriptional repressor domains (e.g., spalt like transcription factor 1 ("SALL1") and suppressor of defective silencing protein 3 ("SDS3")) (see, e.g., Brezgin et al., "Dead Cas Systems: Types, Principles, and Applications," Int. J. Mol. Sci. 20:6041 (2019), which is hereby incorporated by reference in its entirety).

In some embodiments, the epigenetic modulator is selected from the group consisting of DNMT3A, DNMT2L, LSD1, KRAB, KRAB-MeCP2, EZH2, SALLI, SDS3, G9A, and Suv39 h1 (see, e.g., Yeo et al., "An Enhanced CRISPR Repressor for Targeted Mammalian Gene Regulation," 15(8):611-616 (2018); Alerasool et al., "An Efficient KRAB Domain for CRISPRi Applications in Human Cells," Nature Methods 17:1093-1096 (2020); and Duke et al., "An Improved CRISPR/dCas9 Interference Tool for Neuronal Gene Suppression," Frontiers in Genome Editing 2:9 (2020), which are hereby incorporated by reference in their entirety).

In some embodiments, the isolated glial progenitor cell population as described herein is genetically modified with a CRISPRi system targeted to silence one or more genes selected from the genes provided in Table 3 or the genes provided in Table 4 above.

In some embodiments, the nuclease-based gene editing system suitable for genetically modifying glial progenitor cells as described herein comprises the FokI nuclease editing system. In this system, glial progenitor cells are genetically modified to contain a first nucleic acid molecule encoding a first sequence specific gene editing nuclease and a first DNA binding motif, where the first DNA binding motif hybridizes to a first DNA sequence of any one the genes in Table 3 or Table 4 identified as conferring a competitive disadvantage to glial progenitor cells. The glial progenitor cells further comprise or contain a second nucleic acid molecule encoding a second sequence specific gene editing nuclease and a second DNA binding motif, where the second DNA binding motif binds a second DNA sequence the gene bound by the first DNA binding motif. The first, second, or both nucleotide sequences further comprise an inducible promoter system sequence that is operatively coupled to the respective sequences to allow for controlled suppression of the one or more target genes.

Suitable sequence specific gene editing nuclease systems for use in preparing the genetically modified cells as described herein are well known in the art and include, without limitation, zinc finger nucleases ("ZFNs") and transcription activator-like effector nucleases ("TALENs").

In some embodiments, the first and second gene editing nucleases are ZFNs. In accordance with such embodiments, the first and second DNA binding motifs are zinc finger motifs. ZFNs are artificial endonucleases that comprise at least 1 zinc finger motif (e.g., at least 2, 3, 4, or 5 zinc finger motifs) fused to a nuclease domain (e.g., the cleavage domain of the FokI restriction enzyme). Heterodimerization of two individual ZFNs at a target nucleic acid sequence can result in cleavage of the target sequence. For example, two individual ZFNs may bind opposite strands of a target DNA sequence to induce a double-strand break in the target nucleic acid sequence. Methods of designing suitable ZFNs genetically modifying glial progenitor cells as described herein are well known in the art (see, e.g., Urnov et al., "Genome Editing with Engineered Zinc Finger Nucleases," Nat. Rev. Genet. 11 (9): 636-646 (2010); Gaj et al., "Targeted Gene Knockout by Direct Delivery of Zinc-Finger Nuclease Proteins," Nat. Methods 9(8): 805-807 (2012); U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; and 6,479,626, which are hereby incorporated by reference in their entirety). In some embodiments, the first and second gene editing nucleases are ZFNs. In accordance with such embodiments, the first and second DNA binding motifs are zinc finger motifs.

In some embodiments, the first and second gene editing nucleases are transcription activator-like effector nucleases (TALENs). TALENs are engineered transcription activator-like effector nucleases that comprise a DNA-binding domain and a nuclease domain (e.g., a cleavage domain of the FokI restriction enzyme). The DNA-binding domain comprises a series of 33-35 amino acid repeat domains that each recognize a single bp. Heterodimerization of two individual TALENs at a target nucleic acid sequence can result in cleavage of the target sequence. For example, two individual TALENs may bind opposite strands of a target DNA sequence to induce a double-strand break in the target nucleic acid sequence. Methods of designing suitable TALENs for inclusion in the genetically modified cells of the presently disclosure are well known in the art (see, e.g., Scharenberg et al., "Genome Engineering with TAL-Effector Nucleases and Alternative Modular Nuclease Technologies," Curr. Gene Ther. 13 (4): 291-303 (2013); Gaj et al., "Targeted Gene Knockout by Direct Delivery of Zinc-Finger Nuclease Proteins," Nat. Methods 9 (8): 805-807 (2012); Beurdeley et al., "Compact Designer TALENs for Efficient Genome Engineering," Nat. Commun. 4:1762 (2013); U.S. Pat. Nos. 8,440,431; 8,440,432; 8,450,471; 8,586,363; and 8,697,853, which are hereby incorporated by reference in their entirety). In some embodiments, the first and second gene editing nucleases are TALENs. In accordance with such embodiments, the first and second DNA binding motifs are TAL motifs.

In some embodiments, the first and second sequence specific gene editing nucleases comprise a FokI nuclease domain.

Genetically modified glial progenitor cells according to this embodiment, are produced by introducing one or more expression vectors comprising the first and second nucleotide sequences encoding the nuclease editing proteins linked to the DNA binding motifs. Suitable expression vectors and methods for introducing such vectors into the glial progenitor cells are described supra. As noted above, in some embodiments, these nucleotide sequences can be operatively coupled to an inducible promoter/operator sequence. Suitable inducible promoter sequences for use in the systems according to the present disclosure are well known in the art and described in more detail supra.

Genetic Modification to Express One or More Youth-Related Genes that Confer Competitive Advantage in Young GPCs Another aspect of the present application relates to an isolated population of genetically modified glial progenitor cells and their competitive advantage over the same type of glial progenitor cells that have not been genetically modified.

In some embodiments, the glial progenitor cells of the isolated population are modified to increase expression of one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195. These genes are listed in Table 11. Expression of these genes are closely related to the dominance of transplanted young human glial progenitor cells over the residential older human glial progenitor cells.

TABLE 11

| Genes related to the dominance of young human glial progenitor cells | | |
|---|---|---|
| Gene | Ensembl ID | Entrez ID |
| ARX | ENSG00000004848 | 170302 |
| CEBPZ | ENSG00000115816 | 10153 |
| DLX1 | ENSG00000144355 | 1745 |
| DLX2 | ENSG00000115844 | 1746 |
| ELK1 | ENSG00000126767 | 2002 |
| ETS1 | ENSG00000134954 | 2113 |
| ETV4 | ENSG00000175832 | 2118 |
| KLF16 | ENSG00000129911 | 83855 |
| MYBL2 | ENSG00000101057 | 4605 |
| MYC | ENSG00000136997 | 4609 |
| NFYB | ENSG00000120837 | 4801 |
| POU3F1 | ENSG00000185668 | 5453 |
| SMAD1 | ENSG00000170365 | 4086 |
| SOX3 | ENSG00000134595 | 6658 |
| SP5 | ENSG00000204335 | 389058 |
| TCF12 | ENSG00000140262 | 6938 |
| TFDP1 | ENSG00000198176 | 7027 |
| TP53 | ENSG00000141510 | 7157 |
| ZIC3 | ENSG00000156925 | 7547 |
| ZNF195 | ENSG00000005801 | 7748 |

In some embodiments, the glial progenitor cells of the isolated population are modified to increase expression of one or more youth-related genes selected from the group consisting of CEBPZ, MYBL2, MYC, NFYB and TFDP1.

In some embodiments, the glial progenitor cells of the isolated population are modified to increase expression of CEBPZ, MYBL2, MYC, NFYB or TFDP1.

In some embodiments, the glial progenitor cells of the isolated population are modified to increase expression of a combination of CEBPZ and MYBL2, CEBPZ and MYC, CEBPZ, CEBPZ and NFYB, CEBPZ and TFDP1, MYBL2 and MYC, MYBL2 and NFYB, MYBL2 and TFDP1, MYC and NFYB, MYC and TFDP1, or NFYB and TFDP1.

In some embodiments, the glial progenitor cells of the isolated population are modified to increase expression of a combination of CEBPZ, MYBL2 and MYC; CEBPZ, MYBL2 and NFYB; CEBPZ, MYBL2 and TFDP1; CEBPZ, MYC and NFYB; CEBPZ, MYC and TFDP1; CEBPZ, NFYB and TFDP1; MYBL2, MYC and NFYB; MYBL2, MYC and TFDP1; or MYC, NFYB and TFDP1.

In some embodiments, the glial progenitor cells of the isolated population are modified to increase expression of a combination of CEBPZ, MYBL2, MYC and NFYB, CEBPZ, MYBL2, MYC and TFDP1; or MYBL2, MYC, NFYB and TFDP1.

In some embodiments, the CEBPZ, MYBL2, MYC, NFYB and/or TFDP1 described above are human gene products with their respective protein sequences listed in SEQ ID NOS: 4-10.

All gene products referred to in this application include the wild type gene product and functional variants thereof. A "functional variant of a gene product" refers to a modified gene product (e.g., by deletion, substitution, insertion, glycosylation, etc.) that retains at least 50% of the biological activity of the unmodified (wild-type) gene product in a competition assay.

In some embodiments, the glial progenitor cells of the isolated population are modified to increase expression of one or more youth-related genes that selectively activate one or more signaling pathways selected from the group consisting of YAP1, MYC and MYCN, so as to confer a competitive advantage to the glial cells, while not leading to uncontrolled growth of these cells. In some embodiments, the glial progenitor cells of the isolated population are modified to increase expression of TEAD2 and one or more genes that selectively activate the YAP1 signaling pathway.

As used herein the term "healthy human glial progenitor cells" refers to glial progenitor cells, which may function normally to expand and/or differentiate into functional oligodendrocytes and astrocytes. In some embodiments, transplanted healthy human glial progenitor cells can outcompete the host glial pool to ultimately colonize and dominate recipient brains.

As used hereinafter, the term "youth-related genes" refers to genes with significantly increased expression in young glial progenitor cells compared to older glial progenitor cells.

In some embodiments, the term "young glial progenitor cells" refers to stem cells that are induced to start differentiation into glial progenitor cell in an in vitro setting at differentiation stage 6 based on the protocol of Wang et al. Cell Stem Cell 12, 252-264, 2013, or at the equivalent differentiation stage based on other protocols. Compared with old glial progenitor cells, young glial progenitor cells may have one or more of the following characteristics: (i) growing or proliferating or dividing faster, (ii) longer telomeres and/or higher telomerase activity, and (iii) having lower levels than old of senescence-associated transcripts encoding CDKNIA (p21Cip1) and CDKN2/p16 (INK4) and p14 (ARF).

In some embodiments, the term "young glial progenitor cells" refers to glial progenitor cells that are within 1-20 weeks of transplantation into a host. The term "older glial progenitor cells" or "old glial progenitor cells" is used in relative to the term "young glial progenitor cells".

In some embodiments, the young glial progenitor cells are glial progenitor cells that have been cultured for 1-5, 5-10, 5-20, 5-30, 10-20, 10-30, or 20-30 weeks at differentiation stage 6 based on the protocol of Wang et al. Cell Stem Cell 12, 252-264, 2013, or at the equivalent differentiation stage based on other protocols.

In some embodiments, old glial progenitor cells are glial progenitor cells that have been cultured for 5-100, 5-10, 5-20, 5-30, 5-40, 5-50, 5-60, 5-70, 5-80, 5-90, 10-20, 10-30, 10-40, 10-50, 10-60, 10-70, 10-80, 10-90, 10-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90,60-100, 70-80, 70-90, 70-100, 80-90, 80-100, or 90-100 weeks at differentiation stage 6 based on the protocol of Wang et al. Cell Stem Cell 12, 252-264, 2013, or at the equivalent differentiation stage based on other protocol.

In some embodiments, old glial progenitor cells are glial progenitor cells (including cells derived therefrom) that have been transplanted into a host for 5-10, 5-20, 5-30, 5-40, 5-50, 5-60, 5-70, 5-80, 5-90, 5-100, 10-20, 10-30, 10-40, 10-50, 10-60, 10-70, 10-80, 10-90, 10-100, 20-30, 20-40, 20-50, 20-60, 20-70, 20-80, 20-90, 20-100, 30-40, 30-50, 30-60, 30-70, 30-80, 30-90, 30-100, 40-50, 40-60, 40-70, 40-80, 40-90, 40-100, 50-60, 50-70, 50-80, 50-90, 50-100, 60-70, 60-80, 60-90,60-100, 70-80, 70-90, 70-100, 80-90, 80-100, or 90-100 weeks.

In some embodiments, old glial progenitor cells refer to native glial progenitor cells in a host, while young glial progenitor cells refer to glial progenitor cells engrafted or transplanted into the host.

As used hereinafter, the term "significantly increased expression" refers to an at least 20% increase at the mRNA or protein level. In some embodiments, the term "significantly increased expression" refers to at least 50%, 100%, 150%, 200%, 300%, 400%, 500%, 600%, 700%, 800%, 900% or 1000% at the mRNA level.

As used hereinafter, the term "significantly increased expression" refers to an at least 20% increase at the mRNA or protein level. In some embodiments, the term "significantly increased expression" refers to at least 10%, 20%, 30%, 40%, 50%, 60%, 70%, 80%, 90%, or 100% at the protein level.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes selected from the group consisting ACTB, AKRIC1, ANAPC11, AP2B1, APLP2, APOD, ARF5, ARL4A, ARPC3, ARPP19, ATOXI, ATP5FIE, ATP5MC1, ATP5MC3, ATP5MD, ATP5ME, ATP5MF, ATP5MG, ATP5MPL, ATP5PF, ATP6V0B, ATP6VOE1, ATXN7L3B, B2M, B3GAT2, BEX1, BEX3, BEX5, BLOC1S1, BMERB1, C18orf32, Clorf122, C1QBP, C4orf48, CADM4, CALM1, CALM3, CALR, CANX, CAV2, CC2D1A, CCND1, CCNI, CD63, CD82, CDC42, CDH2, CFL1, CHCHD2, CHGB, CIAO2B, CLCN3, CLTA, CLTC, CNN3, CNTN1, COTL1, COX411, COX6A1, COX6C, COX7A2, COX7C, COX8A, CPNE8, CPS1, CRNDE, CSPG4, CTHRC1, CUL4B, CYP51A1, DBI, DCX, DDAH1, DDX1, DENND10, DMD, DMRT2, DNAJA2, DPYSL2, DRAP1, DSTN, DYNC112, EDF1, EDIL3, EEF1A1, EEF1B2, EEF2, EID1, EIF3J, ELOB, EMC10, EMP2, ESD, ETVI, FABP7, FAM171B, FAM177A1, FAU, FIS1, FXYD6, GADD45A, GAP43, GCSH, GNAS, GOLM1, GPM6B, GSTP1, H3-3A, H3-3B, HINT1, HNRNPA1, HNRNPA3, HNRNPAB, HNRNPC, HNRNPK, HNRNPM, HNRNPR, HSPA5, IGFBP2, ITGB8, ITM2A, ITM2B, JPT1, KDELR1, KLRK1-AS1, KRTCAP2, KTN1, LDHB, LHFPL3, LRRC4B, LY6H, MAP2, MARCKS, MARCKSL1, MIA, MICOS10, MIF, MIR9-1HG, MMGT1, MPZL1, MT3, MTLN, MTRNR2L12, MTRNR2L8, MYL12A, MYL12B, NACA, NARS1, NCL, NDUFA1, NDUFA11, NDUFA13, NDUFA3, NDUFA4, NDUFB1, NDUFB11, NDUFB2, NDUFB6, NDUFB7, NDUFC2, NDUFS5, NEU4, NUCKS1, OAZ1, OLFM2, OSBPL8, OST4, OSTC, PABPC1, PCBP2, PCDH10, PCDH11X, PCDH17, PCDHB2, PCDHGB6, PDGFRA, PDIA6, PEBP1, PEG10, PFN1, PGRMC1, PKIA, PLPP3, PLPPR1, PPIA, PRDX1, PRDX2, PRDX5, PSMB1, PSMB9, PTMS, PTN, PTPRA, RAB10, RAB14, RAB2A, RAB31, RAC1, RACK1, RMDN2, RAMP1, RO60, ROBO1, RRAGB, RTN3, S100B, SARAF, SAT1, SBDS, SCARB2, SCP2, SCRG1, SEC62, SELENOK, SELENOT, SELENOW, SERF2, SERPINE2, SET, SH3BGRL, SKP1, SLC25A6, SLIT2, SLITRK2, SMC3, SMDT1, SMOC1, SMS, SNCA, SNHG29, SNHG6, SNX3, SNX22, SOD1, SOX11, SOX2, SOX9, SPCS2, SPCS3, SRP14, SSR4, STAG2, STMN1, SUPT16H, TALDO1, TBCB, TCEAL7, TCEAL8, TCEAL9, TIMP1, TLE5, TM4SF1, TM9SF3, TMA7, TMBIM6, TMCO1, TMEM147, TMEM258, TMEM50A, TMOD2, TMSB10, TMSB4X, TPT1, TRAF4, TRIO, TSC22D4, TSPAN6, TSPAN7, TTC3, TUBB, UBA52, UBL5, UQCR10, UQCR11, UQCRB, VIM, WSB2, WSCD1, YBX1, YWHAB, YWHAE, ZFAS1, ZNF428, and ZNF462.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes elected from the group consisting of APOD, B2M, BEX3, BEX5, CCND1, CTHRC1, EDIL3, EMC10, FABP7, GADD45A, ITM2A, LRRC4B, LY6H, MIA, MT3, NEU4, OLFM2, PTMS, RAMP1, SNX3, TRAF4, TRIO, UBA52, and YWHAB.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes elected from the group consisting of ANAPC11, APOD, ATP5MC3, B2M, CALM1, MT3, NEU4, PEBP1, RAMP1, SOD1 and TBCB.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes elected from the group consisting of APOD, BEX3, BEX5, CCND1, CTHRC1, EDIL3, EMC10, GADD45A, ITM2A, MIA, TRAF4, and TRIO.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes elected from the group consisting of B2M, FABP7, LRRC4B, LY6H, MT3, NEU4, OLFM2, PTMS, RAMP1, SNX3, UBA52, and YWHAB.

In some embodiments, the glial progenitor cells of the isolated population are modified to increase expression of (1) one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) one or more additional genes elected from the group consisting of LY6H, MIA, GADD45A, ITM2A and ITM2B.

In some embodiments, the glial progenitor cells of the isolated population are modified to (1) increase expression of one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) decrease expression of one or more disadvantage genes selected from the group consisting of ABCG1, ADGRB1, ADGRG1, AKAP9, AL360181.3, ANKRD10, ARGLUI, ARL4C, ARL16, ARMCX6, ATP1A2, ATP1B3, ATP10B, B3GNT7, BHLHE41, BPTF, BRI3, BX664615.2, BX890604.1, C1QL2, CAMK2N1, CCDC85B, CCNL1, CHCHD10, CHORDC1, CIRBP, CLDN10, COL9A1, COL9A2, CXADR, DANCR, DCXR, DHX36, DLL3, DNAJA1, DNM3, ECH1, EGR1, EIF1AX, ELAVL3, EMID1, ETFB, FABP5, FAM133A, FAM133B, FBX02, FERMT1, FIBIN, FOS, FOSB, FSCN1, FSIP2, GABPB1-AS1, GALR1, GNG8, GNPTAB, GOLGA8A, GOLGA8B, GPR155, GRID2, GRM7, HAPLN1, HMX1, HSPA1A, HSPA1B, HSPH1, HTRA1, IGFBP2, JAG1, JUN, JUNB, KCNIP4, KCNQ1OT1, KLF3-AS1, LAMP2, LINC01116, LINC01301, LINC01896, LRP4, LRRC7, MACF1, MALATI, MAP3K13, MASP1, MDH1, MTIE, MT2A, MYT1, NASP, NKTR, NUTM2A-AS1, OFD1, PCDHB5, PCDHGA3, PCDHGB6, PEPD, PHGDH, PLCG2, PMP2, PNISR, PPP1R14A, PTGDS, RAB3IP, RAF1, RAPIGAP, RARRES2, RBM25, REV3L, RHOBTB3, RIMS2, RIT2, RBMX, RRBP1, RSRP1, S100A1, S100A16, SATI, SCG2, SEMA3E, SERTAD1, SEZ6L, SEZ6L2, SH3GLB2, SNHG15, SNRNP70, SPARCL1, SRSF5, STAT3, STXBP6, SYNRG, THBS4, TLE4, TMEM176B, TPI1, TSC22D3, USP11, VCAN, WFDC1, WSB1, ZFYVE16, ZNF528, and ZNF528-AS1.

In some embodiments, the glial progenitor cells of the isolated population are modified to (1) increase expression of one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) decrease expression of one or more genes selected from the group consisting of ADGRG1 ARL4C, ARMCX6, ATP1A2, ATP1B3, B3GNT7, CXADR, DLL3, FABP5, FIBIN, IGFBP2, LRRC7, MAP3K13, MTIE, MT2A, PCDHGA3, PCDHGB6, PLCG2, PTGDS, SAT1, SEZ6L, SPARCL1, THBS4, and TLE4.

In some embodiments, the glial progenitor cells of the isolated population are modified to (1) increase expression of one or more youth-related genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, and (2) decrease expression of one or more genes selected from the group consisting of EGR1, HSPHI, WSB1, RBMX, ARGLUI, TLE4, MACF1, STAT3, FSIP2 and NKTR.

In some embodiments, glial progenitor cells of the isolated population are modified to (1) increase expression of one or more advantage genes selected from the group consisting of ARX, CEBPZ, DLX1, DLX2, ELK1, ETS1, ETV4, KLF16, MYBL2, MYC, NFYB, POU3F1, SMAD1, SOX3, SP5, TCF12, TFDP1, TP53, ZIC3 and ZNF195, preferably selected from the group consisting of CEBPZ, MYBL2, MYC, NFYB and TFDP1, (2) increase expression of one or more advantage genes selected from the group consisting of ACTB, AKR1C1, ANAPC11, AP2B1, APLP2, APOD, ARF5, ARL4A, ARPC3, ARPP19, ATOXI, ATP5F1E, ATP5MC1, ATP5MC3, ATP5MD, ATP5ME, ATP5MF, ATP5MG, ATP5MPL, ATP5PF, ATP6V0B, ATP6VOE1, ATXN7L3B, B2M, B3GAT2, BEX1, BEX3, BEX5, BLOC1S1, BMERB1, C18orf32, Clorf122, C1QBP, C4orf48, CADM4, CALM1, CALM3, CALR, CANX, CAV2, CC2D1A, CCND1, CCNI, CD63, CD82, CDC42, CDH2, CFL1, CHCHD2, CHGB, CIAO2B, CLCN3, CLTA, CLTC, CNN3, CNTN1, COTL1, COX4I1, COX6A1, COX6C, COX7A2, COX7C, COX8A, CPNE8, CPS1, CRNDE, CSPG4, CTHRC1, CUL4B, CYP51A1, DBI, DCX, DDAHI, DDX1, DENND10, DMD, DMRT2, DNAJA2, DPYSL2, DRAP1, DSTN, DYNC112, EDF1, EDIL3, EEF1A1, EEF1B2, EEF2, EID1, EIF3J, ELOB, EMC10, EMP2, ESD, ETV1, FABP7, FAM171B, FAM177A1, FAU, FIS1, FXYD6, GADD45A, GAP43, GCSH, GNAS, GOLM1, GPM6B, GSTP1, H3-3A, H3-3B, HINT1, HNRNPA1, HNRNPA3, HNRNPAB, HNRNPC, HNRNPK, HNRNPM, HNRNPR, HSPA5, IGFBP2, ITGB8, ITM2A, ITM2B, JPT1, KDELR1, KLRK1-AS1, KRTCAP2, KTN1, LDHB, LHFPL3, LRRC4B, LY6H, MAP2, MARCKS, MARCKSL1, MIA, MICOS10, MIF, MIR9-1HG, MMGT1, MPZL1, MT3, MTLN, MTRNR2L12, MTRNR2L8, MYL12A, MYL12B, NACA, NARS1, NCL, NDUFA1, NDUFA11, NDUFA13, NDUFA3, NDUFA4, NDUFB1, NDUFB11, NDUFB2, NDUFB6, NDUFB7, NDUFC2, NDUFS5, NEU4, NUCKS1, OAZ1, OLFM2, OSBPL8, OST4, OSTC, PABPC1, PCBP2, PCDH10, PCDH11X, PCDH17, PCDHB2, PCDHGB6, PDGFRA, PDIA6, PEBP1, PEG10, PFN1, PGRMC1, PKIA, PLPP3, PLPPR1, PPIA, PRDX1, PRDX2, PRDX5, PSMB1, PSMB9, PTMS, PTN, PTPRA, RAB10, RAB14, RAB2A, RAB31, RAC1, RACK1, RMDN2, RAMP1, RO60, ROBO1, RRAGB, RTN3, S100B, SARAF, SAT1, SBDS, SCARB2, SCP2, SCRG1, SEC62, SELENOK, SELENOT, SELENOW, SERF2, SERPINE2, SET, SH3BGRL, SKP1, SLC25A6, SLIT2, SLITRK2, SMC3, SMDT1, SMOC1, SMS, SNCA, SNHG29, SNHG6, SNX3, SNX22, SOD1, SOX11, SOX2, SOX9, SPCS2, SPCS3, SRP14, SSR4, STAG2, STMN1, SUPT16H, TALDO1, TBCB, TCEAL7, TCEAL8, TCEAL9, TIMP1, TLE5, TM4SF1, TM9SF3, TMA7, TMBIM6, TMCO1, TMEM147, TMEM258, TMEM50A, TMOD2, TMSB10, TMSB4X, TPT1, TRAF4, TRIO, TSC22D4, TSPAN6, TSPAN7, TTC3, TUBB, UBA52, UBL5, UQCR10, UQCR11, UQCRB, VIM, WSB2, WSCD1, YBX1, YWHAB, YWHAE, ZFAS1, ZNF428, and ZNF462, and (3) decrease expression of one or more disadvantage genes selected from the group consisting of ABCG1, ADGRB1, ADGRG1, AKAP9, AL360181.3, ANKRD10, ARGLUI, ARL4C, ARL16, ARMCX6, ATP1A2, ATP1B3, ATP10B, B3GNT7, BHLHE41, BPTF, BRI3, BX664615.2, BX890604.1, C1QL2, CAMK2N1, CCDC85B, CCNL1, CHCHD10, CHORDC1, CIRBP, CLDN10, COL9A1, COL9A2, CXADR, DANCR, DCXR, DHX36, DLL3, DNAJA1, DNM3, ECH1, EGR1, EIF1AX, ELAVL3, EMID1, ETFB, FABP5, FAM133A, FAM133B, FBXO2, FERMT1, FIBIN, FOS, FOSB, FSCN1, FSIP2, GABPB1-AS1, GALRI, GNG8, GNPTAB, GOLGA8A, GOLGA8B, GPR155, GRID2, GRM7, HAPLN1, HMX1, HSPA1A, HSPA1B, HSPH1, HTRA1, IGFBP2, JAG1, JUN, JUNB, KCNIP4, KCNQ1OT1, KLF3-AS1, LAMP2, LINC01116, LINC01301, LINC01896, LRP4, LRRC7, MACF1, MALATI, MAP3K13, MASP1, MDH1, MTIE, MT2A, MYT1, NASP, NKTR, NUTM2A-AS1, OFD1, PCDHB5, PCDHGA3, PCDHGB6, PEPD, PHGDH, PLCG2, PMP2, PNISR, PPP1R14A, PTGDS, RAB3IP, RAF1, RAPIGAP, RARRES2, RBM25, REV3L, RHOBTB3, RIMS2, RIT2, RBMX, RRBP1, RSRP1, S100A1, S100A16, SAT1, SCG2, SEMA3E, SERTAD1, SEZ6L, SEZ6L2, SH3GLB2, SNHG15, SNRNP70, SPARCL1, SRSF5, STAT3, STXBP6, SYNRG, THBS4, TLE4, TMEM176B, TPI1, TSC22D3, USP11, VCAN, WFDC1, WSB1, ZFYVE16, ZNF528, and ZNF528-AS1.

In some embodiments, the glial progenitor cells of the isolated population are modified to increase expression of the one or more youth-related genes and/or advantage genes by 50% or greater, 100% or greater, 150% or greater, 200% or greater, 300% or greater, 400% or greater, 500% or greater, 600% or greater, 700% or greater, 800% or greater, 900% or greater, or 1000% or greater, at the mRNA or protein level.

In some embodiments, the glial progenitor cells of the isolated population are modified to decrease expression of the one or more disadvantage genes by 50% or greater, 60% or greater, 70% or greater, 80% or greater, or 90% or greater at the mRNA level, or by 10% or greater, 20% or greater, 30% or greater, 40% or greater, 50% or greater, 60% or greater, 70% or greater, 80% or greater, or 90% or greater at the protein level.

Methods of Treatment

Another aspect of the present disclosure is directed to methods of treatment using the genetically modified cells described herein. In one aspect, the present application is directed to a method of treating a disorder in a subject that involves providing a population of isolated glial progenitor cells genetically modified to have a competitive advantage over native or already resident progenitor cells and introducing the population of isolated glial or glial progenitor cells into the subject to treat the disorder. In another aspect, the present application provides method of rejuvenating glial cells of the brain and/or brain stem in a subject using the genetically modified glial progenitor cells described herein.

In accordance with this aspect of the disclosure, the isolated genetically modified progenitor cells can be a genetically modified population of bone marrow progenitor cells, cardiac progenitor cells, endothelial progenitor cells, epithelial progenitor cells, mesenchymal progenitor cells, hematopoietic progenitor cells, hepatic progenitor cells, osteoprogenitor cells, muscle progenitor cells, pancreatic progenitor cells, pulmonary progenitor cells, renal progenitor cells, vascular progenitor cells, retinal progenitor cells. These progenitor cell populations can be derived from fetal tissue, embryonic stem cells, or induced pluripotent stem cells.

In some embodiments, the isolated glial progenitor cells are genetically modified to increase the expression of one or more genes provided in Table 1 or Table 2 supra that confer a competitive advantage to the progenitor cells compared to glial progenitor cells which have not been genetically modified.

In some embodiments, the isolated glial progenitor cells are genetically modified to decrease expression of one or more genes as provided in Table 3 or Table 4 supra that confer a competitive disadvantage to the glial progenitor cells compared to the glial progenitor cells which have not been genetically modified.

In some embodiments, the isolated glial progenitor cells of the population are genetically modified to express one or more genes that confer a competitive advantage and genetically modified to decrease expression of one or more genes that confer a competitive disadvantage to the glial or glial progenitor cells compared to glial progenitor cells which have not been genetically modified.

In some embodiments, the isolated glial progenitor cells are genetically modified to increase expression of one or more youth-genes compared to glial progenitor cells which have not been genetically modified.

In some embodiments, the isolated glial progenitor cells are genetically modified to increase expression of one or more youth-genes and one or more advantage genes compared to glial progenitor cells which have not been genetically modified.

In some embodiments, the isolated glial progenitor cells are genetically modified to increase expression of one or more youth-genes and decrease expression of one or more disadvantage genes compared to glial progenitor cells which have not been genetically modified.

In some embodiments, the isolated glial progenitor cells are genetically modified to increase expression of one or more youth-genes and one or more advantage genes, and decrease expression of one or more disadvantage genes compared to glial progenitor cells which have not been genetically modified.

Suitable disorders to be treated in accordance with this aspect of the disclosure include any condition amendable to cell therapy treatment. In one embodiment, the condition to be treated is a liver condition, e.g., chronic liver failure, al-antitrypsin deficiency, familial hypercholesterolemia, hereditary tyrosinemia, and chronic biliary disorders such as primary sclerosing cholangitis, primary biliary cirrhosis, or ischemic cholangiopathy after transplant, that is amendable to treatment with progenitor cell therapy. These conditions can be treated with genetically modified hepatocyte and liver stem/progenitor cells, mesenchymal stem cells or bone marrow stem cells.

In another embodiment, the condition to be treated is a pancreatic condition that is amendable to treatment with progenitor cell therapy. Suitable conditions include, without limitation, acute pancreatitis, chronic pancreatitis, and diabetes. These conditions can be treated with genetically modified pancreatic progenitor cells populations, e.g., genetically modified islet progenitor cells, stem cell derived β cell, or mesenchymal stem cells.

In another embodiment, the condition to be treated is a heart condition that is amendable to treatment with progenitor cell therapy. Suitable conditions include, without limitation, chronic heart failure and related conditions. These conditions can be treated with genetically modified cardiac progenitor cells populations, e.g., genetically modified cardiac progenitor cells, mesenchymal stromal cells, endothelial progenitor cells and bone marrow derived progenitor cells.

In another embodiment, the condition to be treated is a kidney condition that is amendable to treatment with progenitor cell therapy. Suitable conditions include, without limitation, acute and chronic kidney disease including end-stage renal disease. These conditions can be treated with genetically modified renal progenitor cells populations, e.g., genetically modified renal progenitor cells, mesenchymal stromal cells, and hematopoietic stem cells.

In another embodiment, the condition to be treated is a lung condition that is amendable to treatment with progenitor cell therapy. Suitable conditions include, without limitation, chronic obstructive pulmonary disease (COPD), pulmonary fibrosis, cystic fibrosis, pulmonary arterial hypertension and bronchiolitis obliterans. These conditions can be treated with genetically modified pulmonary progenitor cells populations, e.g., genetically modified pulmonary progenitor cells, alveolar type 2 progenitor cells, alveolar type 1 progenitor cells, endothelial progenitor cells.

In another embodiment, the condition to be treated is a bone marrow condition that is amendable to treatment with progenitor cell therapy. Suitable conditions include, without limitation, leukemias, lymphomas, aplastic anemia, and immune deficiency disorders. These conditions can be treated with genetically modified pulmonary progenitor cells populations, e.g., genetically modified bone marrow stem cells and hematopoietic stem cells.

In another embodiment, the condition to be treated is a skin condition that is amendable to treatment with progenitor cell therapy. Suitable conditions include, without limitation, acute and chronic inflammatory skin conditions including psoriasis and atopic dermatitis. These conditions can be treated with genetically modified mesenchymal stem cell populations.

Another aspect of the present disclosure is directed to a method of treating a disorder of the brain and/or brain stem in a subject. This method comprises providing a population of isolated glial progenitor cells genetically modified to have a competitive advantage over native or already resident glial progenitor cells and introducing the population of isolated glial progenitor cells into the brain and/or brain stem of the subject to treat the disorder.

In accordance with this aspect of the disclosure, the isolated genetically modified glial progenitor cells can be a genetically modified population of bi-potential glial progenitor cells, oligodendrocyte-biased glial progenitor cells, or astrocyte-biased glial progenitor cells. As described in detail supra, these progenitor cell populations can be derived from fetal tissue, embryonic stem cells, or induced pluripotent stem cells.

In some embodiments, the isolated glial progenitor cells are genetically modified to increase the expression of one or more genes as provided in Table 1 or Table 2 above that confer a competitive advantage to the glial progenitor cells compared to glial progenitor cells which have not been genetically modified.

In some embodiments, the isolated glial progenitor cells are genetically modified to decrease or silence the expression of one or more genes provided in Table 3 or Table 4 above that confer a competitive disadvantage to the glial progenitor cells compared to glial progenitor cells which have not been genetically modified.

In some embodiments, the isolated glial progenitor cells of the population are genetically modified to increase the expression one or more genes that confer a competitive advantage and genetically modified to decrease or silence the expression of one or more genes that confer a competitive disadvantage to the glial progenitor cells compared to glial progenitor cells which have not been genetically modified.

Conditions of the brain and/or brain stem that can be treated in accordance with the methods described herein include, without limitation, neurodegenerative disorders, neuropsychiatric disorders, conditions associate with myelin loss or deficiency.

Exemplary neurodegenerative diseases that can be treated with the genetically modified glial progenitor cell populations as described herein include, without limitation, Huntington's disease, frontotemporal dementia, Parkinson's disease, multisystem atrophy, and amyotrophic lateral sclerosis.

Exemplary neuropsychiatric disorders that can be treated with the genetically modified glial progenitor cell populations as described herein include, without limitation, schizophrenia, autism spectrum disorder, and bipolar disorder.

Exemplary conditions associated with myelin loss or myelin deficiency that can be treated with the genetically modified cell glial progenitor cell populations as described herein include, without limitation, hypomyelination disorders and demyelinating disorders. In one embodiment, the condition is an autoimmune demyelination condition, such as e.g., multiple sclerosis, neuromyelitis optica, transverse myelitis, and optic neuritis. In another embodiment, the myelin-related disorder is a vascular leukoencephalopathy, such as e.g., subcortical stroke, diabetic leukoencephalopathy, hypertensive leukoencephalopathy, age-related white matter disease, and spinal cord injury. In another embodiment, the myelin-related condition is a radiation induced demyelination condition. In another embodiment, the myelin-related disorder is a pediatric leukodystrophy, such as e.g., Pelizaeus-Merzbacher Disease, Tay-Sach Disease, Sandhoff's gangliosidoses, Krabbe's disease, metachromatic leukodystrophy, mucopolysaccharidoses, Niemann-Pick A disease, adrenoleukodystrophy, Canavan's disease, Vanishing White Matter Disease, and Alexander Disease. In yet another embodiment, the myelin-related condition is periventricular leukomalacia or cerebral palsy.

The number of genetically modified glial progenitor cells administered to the subject can range from about $102\text{-}10^{8}$ cells at each transplantation (e.g., injection site), depending on the size and species of the recipient, and the volume of tissue requiring myelin production or replacement.

Single transplantation (e.g., injection) doses can span ranges of $10^{3}$-$10^{5}$, $10^{4}$-$10^{7}$, and $10^{5}$-$10^{8}$ cells, or any amount in total for a transplant recipient patient.

Delivery of the genetically modified glial progenitor cells to the subject can include either a single step or a multiple step injection directly into the nervous system. Specifically, the cells can be delivered directly to one or more sites of the brain, the brain stem, the spinal cord, and/or any combination thereof. For localized disorders such as demyelination of the optic nerve, a single injection can be used. Although the genetically modified glial progenitor cells disperse widely within a transplant recipient's brain, for widespread demyelinating or hypomyelination disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles via intraventricular, intracallosal, or intraparenchymal injections. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

The genetically modified glial progenitor cell transplants are optionally injected as dissociated cells but can also be provided by local placement of non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Ringer's solution, dextrose solution, and culture media. The pH of the solution is preferably from about 5 to about 8, and more preferably from about 7 to about 7.5.

The injection of the genetically modified glial progenitor cell transplant can be a streaming injection made across the entry path, the exit path, or both the entry and exit paths of the injection device (e.g., a cannula, a needle, or a tube). Automation can be used to provide a uniform entry and exit speed and an injection speed and volume.

Optionally a multifocal delivery strategy can be used to deliver the genetically modified glial progenitor cell transplants. Such a multifocal delivery strategy is designed to achieve widespread, dense, whole neuraxis donor cell engraftment throughout the recipient central nervous system. Injection sites can be chosen to permit contiguous infiltration of migrating donor cells into one or more of the major brain areas, brainstem, and spinal cord white matter tracts, without hindrance (or with limited hindrance) from intervening gray matter structures. For example, injection sites optionally include four locations in the forebrain subcortex, specifically into the anterior and posterior anlagen of the corpus callosum bilaterally, and into a fifth location in the cerebellar peduncle dorsally.

The present application is further illustrated by the following examples that should not be construed as limiting. The contents of all references, patents, and published patent applications cited throughout this application, as well as the Figures and Tables, are incorporated herein by reference.

EXAMPLES

Example 1: Materials and Methods

Human Embryonic Stem Cell Lines and Culture Conditions

Sibling human embryonic stem cells (hESCs) lines GENEA019 (WT: 18;15 CAG; Giorgio, F. P. D., et al., "Non-Cell Autonomous Effect of Glia on Motor Neurons in an Embryonic Stem Cell-Based ALS Model," Nat Neurosci 10:608-614 (2007), which is hereby incorporated by reference in its entirety) and GENEA020 (HD: 48;17 CAG; Giorgio, F. P. D., et al., "Human Embryonic Stem Cell-Derived Motor Neurons Are Sensitive to the Toxic Effect of Glial Cells Carrying an ALS-Causing Mutation," Cell Stem Cell 3:637-648 (2008), which is hereby incorporated by reference in its entirety) were obtained from GENEA, Inc. (Sydney, Australia). hESC were regularly cultured under feeder-free conditions on 0.55 μg/cm2 human recombinant laminin 521 (Biolamina, cat. no. LN521) coated cell culture flasks with mTeSRTM1 medium (StemCell Technologies, cat. no. 85850). Daily medium changes were performed. hESCs were routinely passaged at 80% confluency onto freshly coated flasks. Passaging was performed using ReLeSR™ (StemCell Technologies, cat. no. 05872). All hESCs and differentiated cultures were maintained in a 5% $CO_2$ incubator at 37° C. and routinely checked for contamination and mycoplasma free status.

Generation of Fluorescent Reporter hESCs

For ubiquitous and distinct fluorescent labeling of wild-type (WT) and Huntington's disease (HD) cells (FIG. 1), reporter constructs driving expression of either mCherry or EGFP (enhanced green fluorescent protein) were inserted into the AAVS1 safe-harbor locus of WT GENEA019 and HD GENEA020 hESCs, respectively, using a modified version of the CRISPR-Cas9 (clustered regularly interspaced short palindromic repeats-CRISPR associated protein 9) mediated strategy previously described in (Yamanaka, K. et al., "Astrocytes as Determinants of Disease Progression in Inherited Amyotrophic Lateral Sclerosis," Nat Neurosci 11:251-253 (2008), which is hereby incorporated by reference in its entirety). To prepare hESCs for plasmid delivery by electroporation, hESC were harvested as single cell suspension following dissociation with Accutase™ (StemCell Technologies, cat. no. 07920), washed in culture medium, and counted with the automated cell counter NucleoCounter® NC-200 (ChemoMetec). Per electroporation, a total of $1.5\times10^6$ cells were mixed with 5 μg of the AAVS1 targeting CRISPR-Cas9 plasmid (pXAT2) and 5 μg of reporter donor plasmid (pAAVS1-P-CAG-mCh or pAAVS1-P-CAG-GFP). pXAT2 (Addgene plasmid no. 80494), pAAVS1-P-CAG-mCh (Addgene plasmid no. 80491) and pAAVS1-P-CAG-GFP (Addgene plasmid no. 80492) were a gift from Knut Woltjen. Electroporation was performed using an Amaxa® 4D-Nucleofector® (Lonza) with the P3 primary cell kit (Lonza, cat. no. V4XP-3024) according to manufacturer's guidelines. After nucleofection, the electroporated hESC suspensions were transferred to 10 cm cell culture dishes and cultured with mTeSRTM1 supplemented with 10 μM Y-27632 (Tocris, Scat. no. 1254) for the first 24 h. Electroporated hESCs were grown for 48-72 h and then treated with 0.5 μg/μL puromycin (ThermoFisher, cat. no. A1113803). Electroporated hESC cultures were kept under puromycin until individual colonies were large enough to be picked manually. Colonies were assessed by fluorescent microscopy and transferred to a 96-well plate based on uniformity of fluorescent protein expression. Following their expansion, each clone was split for further expansion and for genotyping. For genotyping, DNA was extracted using the prepGEM® Tissue DNA extraction kit (Zygem). Correctly targeted transgenic integrations in the AAVS1 locus were detected by PCR using the following primers: dna803: TCGACTTCCCCTCTTCCGATG (SEQ ID NO: 1) and dna804: CTCAGGTTCTGG-GAGAGGGTAG (SEQ ID NO: 2); while the zygosity of the integrations was determined by the presence or absence of a WT allele using an additional primer: (dna803 and dna183: GAGCCTAGGGCCGGGATTCTC (SEQ ID NO:3)). hESC clones with correctly targeted insertions were cryopreserved with ProFreeze® CDM medium (Lonza, cat. no. BEBP12-769E) and expanded for karyotyping and array comparative genomic hybridization (aCGH) characterization prior to experimental application.

Karyotyping and aCGH

The karyogram of generated reporter hESC lines was analyzed on metaphase spreads by G-banding (Institut für Medizinishche Genetik und Angewandte Genomik, Universitätsklinikum Tübingen). All hESC lines used in this study harbor a normal karyotype. Additionally, acquired copy number variants (CNVs) and loss-of-heterozygosity regions (LOH) were assessed by aCGH (Cell Line Genetics). A variety of CNVs and LOH within and outside of normal range were identified (FIG. 2), but none that are expected to influence the outcomes of competitive interactions between the clones.

Derivation of hGPCs from Reporter WT and HD hESCs

Human GPCs were derived from both reporter WT and HD hESCs using our well-established protocol (Lee, Y. et al., "Oligodendroglia Metabolically Support Axons and Contribute to Neurodegeneration," Nature 487:443-448 (2012), which is hereby incorporated by reference in its entirety). with minor modifications to the embryoid body (EB) generation step. Details on the EB generation step are included in the supplementary information. Cells were collected for xenotransplantation between 150 and 200 DIV, at which time the cultures derived from both WT-mCherry and HD-EGFP hESCs were rich in PDGFRα+/CD44+ bipotential glial progenitor cells. A detailed characterization of the generated cultures by flow cytometry and immunocytochemistry can be found in FIG. 3 and FIG. 18, Panel A and Panel B.

Cell Preparation for Xenotransplantation

To prepare cells for xenotransplantation, glial cultures were collected in $Ca^{2+}/Mg^{2+}$-free Hanks' balanced salt solution (HBSS (−/−); ThermoFisher, cat. no. 14170112), mechanically dissociated to small clusters by gentle pipetting and counted with a hemocytometer. The cell suspension was then spun and resuspended in cold HBSS (−/−) at a final concentration of $10^5$ cells/μL and kept on ice until transplanted.

Hosts and Xenotransplantation Paradigms

In vivo modelling of human glial striatal repopulation: To generate human-mouse chimeras harboring mHTT-expressing human glia (HD chimeras), newborn immunocompromised Rag1(−/−) pups (Meyer, K. et al. "Direct Conversion Of Patient Fibroblasts Demonstrates Non-Cell Autonomous Toxicity Of Astrocytes To Motor Neurons In Familial And Sporadic ALS." Proc National Acad Sci 111:829-832 (2014), which is hereby incorporated by reference in its entirety) were cryoanesthetized, secured in a custom baked clay stage, and injected bilaterally with 100,000 HD-EGFP glia (50,000 per hemisphere) into the presumptive striatum within 48 h from birth. Cells were delivered using a 10 μL syringe (Hamilton, cat. no. 7653-01) with pulled glass pipettes at a depth of 1.2 to 1.4 mm. The pups were then returned to their mother, until weaned. To model human glial striatal repopulation, 36 weeks old HD chimeras were anesthetized by ketamine/xylazine and secured in a stereotaxic frame. 200,000 WT glia were delivered bilaterally using a 10 μL syringe and metal needle into the humanized striatum (AP: +0.8 mm; ML: ±1.8 mm; DV: −2.5 to −2.8 mm). To minimize damage, cells were infused at a controlled rate of 175 nL/min using a controlled micropump system (World Precision Instruments). Backflow was prevented by leaving the needle in place for an additional 5 min. Experimental animals were compared to HD chimeric littermates that did not receive WT glia and to non-chimeric Rag1(−/−) mice that received WT glia at 36 weeks of age following this exact procedure.

Neonatal Striatal Co-Engraftments

To model the cell-intrinsic effects of mHTT-expression on the outcomes of competition between human glia, newborn Rag1(−/−) mice were injected following the same neonatal striatal xenotransplant protocol above described, but instead a total of 200,000 human glia (100,000 per hemisphere) composed of a 1:1 mixture of glia derived from WT-mCherry and HD-EGFP hESCs were delivered. Control littermates received injections composed of either WT-mCherry or HD-EGFP human glia.

Aseptic technique was used for all xenotransplants. All mice were housed in a pathogen-free environment, with ad libitum access to food and water, and all procedures were performed in agreement with protocols approved by the University of Rochester Committee on Animal Resources.

Tissue Processing

Experimental animals were perfused with HBSS (−/−) followed by 4% PFA. The brains were removed, post-fixed for 2 h in 4% PFA and rinsed 3× with PBS. They were then incubated in 30% sucrose solution (Sigma-Aldrich, cat. no. S9378) until equilibrated at which point, they were embedded in OCT in a sagittal orientation (Sakura, cat. no. 4583), frozen in 2-methylbutane (Fisher Scientific, cat. no. 11914421) at temperatures between −60 and −70° C. and transferred to a −80° C. freezer. The resulting blocks were then cut in 20 μm sections on a CM1950 cryostat (Leica), serially collected on adhesion slides and stored at −20° C. until further use.

Immunostaining

Figure 4:
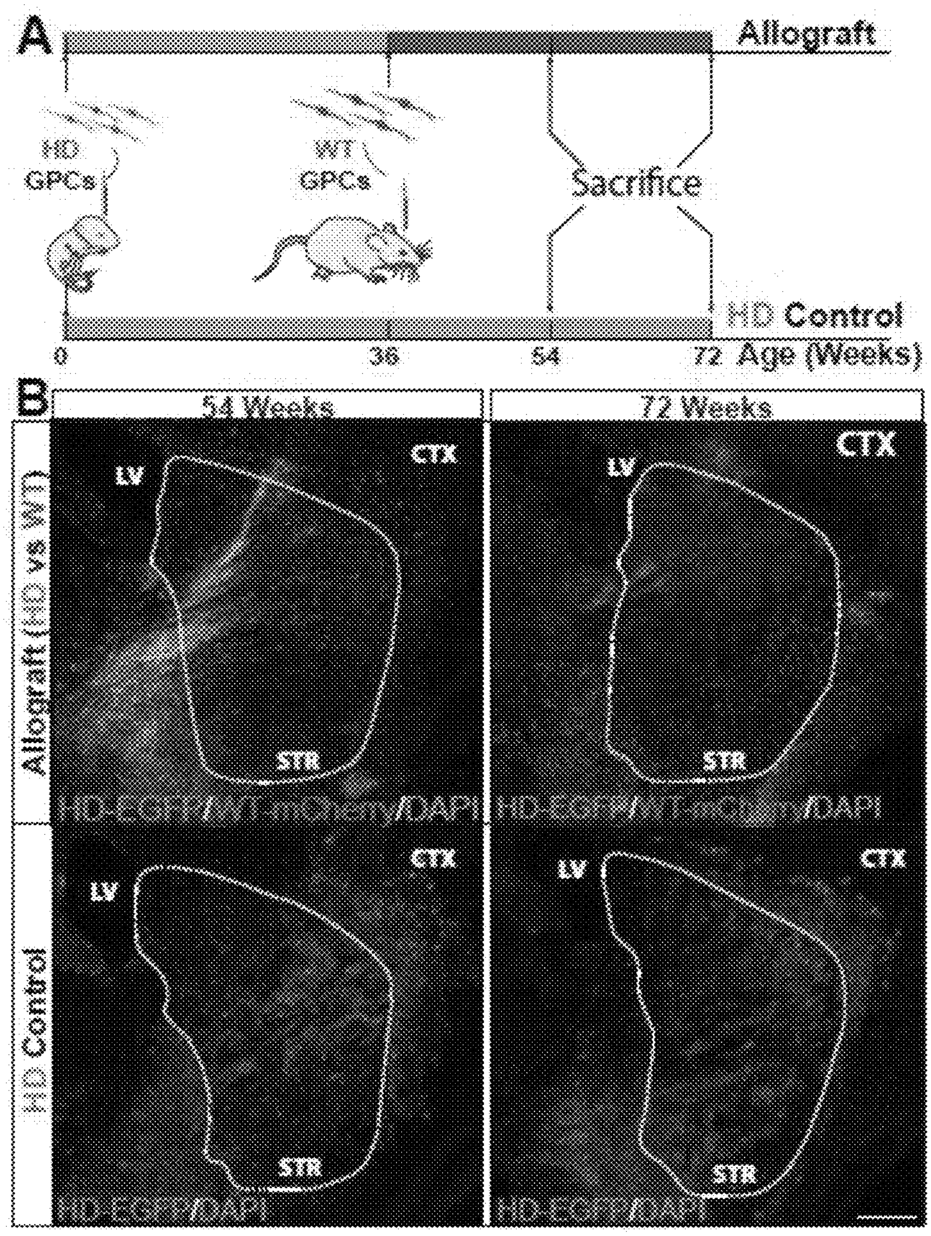
FIG. 4 shows adult-transplanted WT human GPCs outcompete and replace neonatally resident HD hGPCs. Panel A. Experimental design and analytical endpoints. Panel B-Engraftment of WT glia (mCherry+, red) into the striatum of HD chimeras yielded progressive replacement of HD glia (EGFP+, green) creating extensive exclusive domains in their advance. Dashed outlines (white) demarcate the striatal outlines within which human cells were mapped and quantified. Panel C-D. The border between advancing WT and retreating HD hGPCs was typically well-delineated, such that exclusive domains are formed as WT GPCs (Olig2+, white) displace their HD counterparts. Panel E. GPC replacement precedes astrocytic replacement, as within regions colonized by WT hGPCs, stray HD astrocytes (hGFAP+, white) could still be found. Panel F. Mapped distributions of human glia in host striata. Human glia were mapped in 15 equidistant sections (5 are shown as example) and reconstructed in 3D. Their distribution was measured radially as a function of distance to the injection site. Panel G. Rendered examples of mapped striata. Panel H. Volumetric quantification shows that WT gradually replaced their HD counterparts as they expanded from their implantation site; H1: WT vs. HD (Allograft; n=8 for 54 weeks, n=7 for 72 weeks). The advance of WT cells was accompanied by a progressive elimination of HD glia from the tissue, relative to untransplanted HD chimeras (HD control); H2: HD (Allograft; n=8 for 54 weeks, n=7 for 72 weeks) vs. HD Control (n=4 for both timepoints; 2-way ANOVA with Šidák's multiple comparisons tests. ** P<0.0001, * P<0.001, ** P<0.01, *P<0.05; data are presented as means±SEM). Panel I. At the boundary between WT and HD glia, a high incidence of Ki67+ (white) cells can be seen exclusively within the WT glial population. Panel I'. Higher magnification of two WT daughter cells at the edge of the competitive boundary. Panel J. Quantification of Ki67+ glia within each population as a function of time shows a significant proliferative advantage by WT glia, that is sustained throughout the experiment. HD control: 54 wks (n=4), 72 wks (n=4); WT control: 54 wks (n=5), 72 wks: n=3; WT vs. HD allograft: 54 wks (n=5), 72 wks (n=3). Comparisons by 2-way ANOVA with Šidák's multiple comparisons tests; mean±SEM. STR, striatum (caudate-putamen); LV, lateral ventricle; CTX, cortex. Dashed rectangle (orange) represents inset (Panel B'). Scale: Panel B, 500 μm; Panel C', 100 μm; Panel D, 50 μm; Panel E, 10 μm; Panel I, 100 μm; Panel I', 10 μm.
Figure 4:
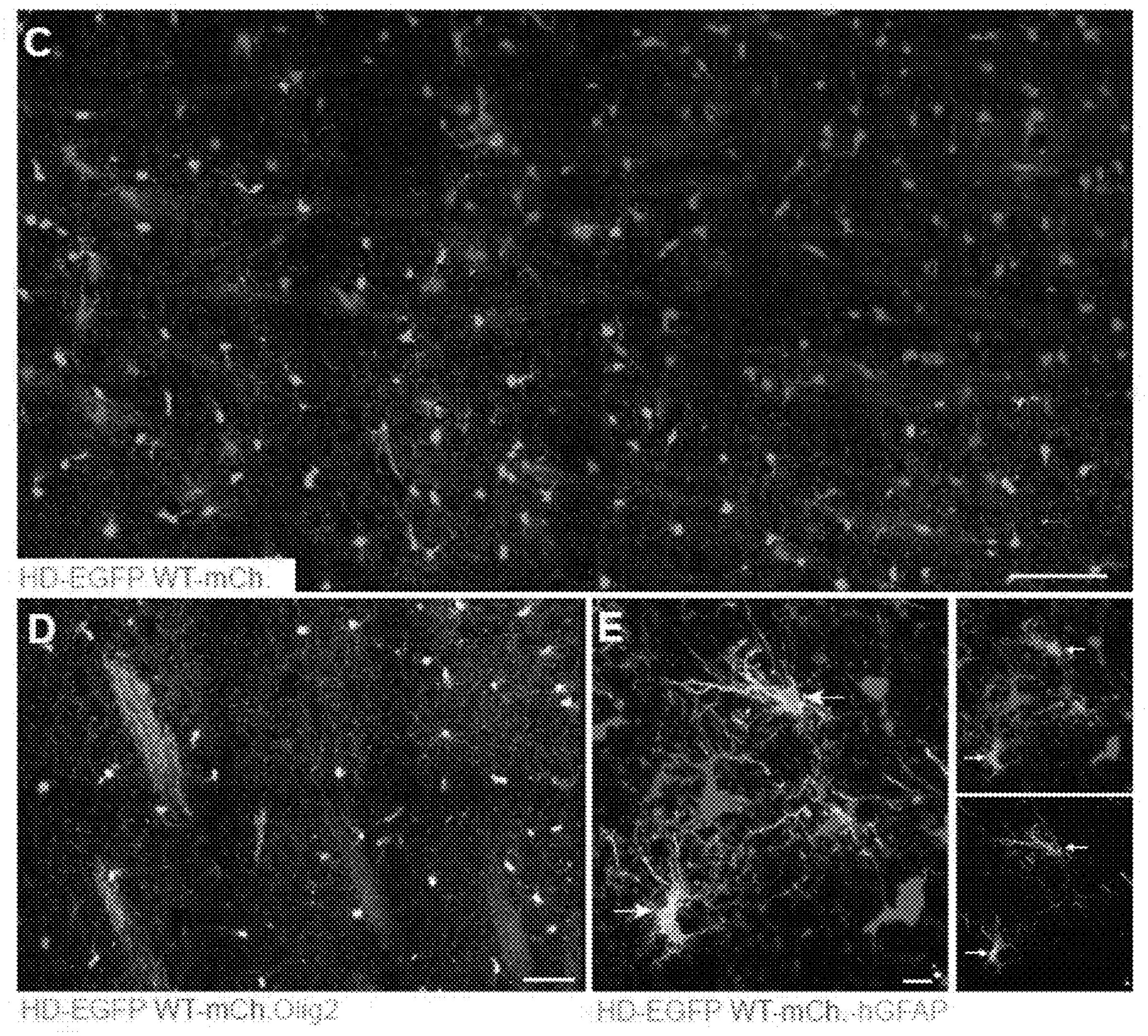
Figure 4:
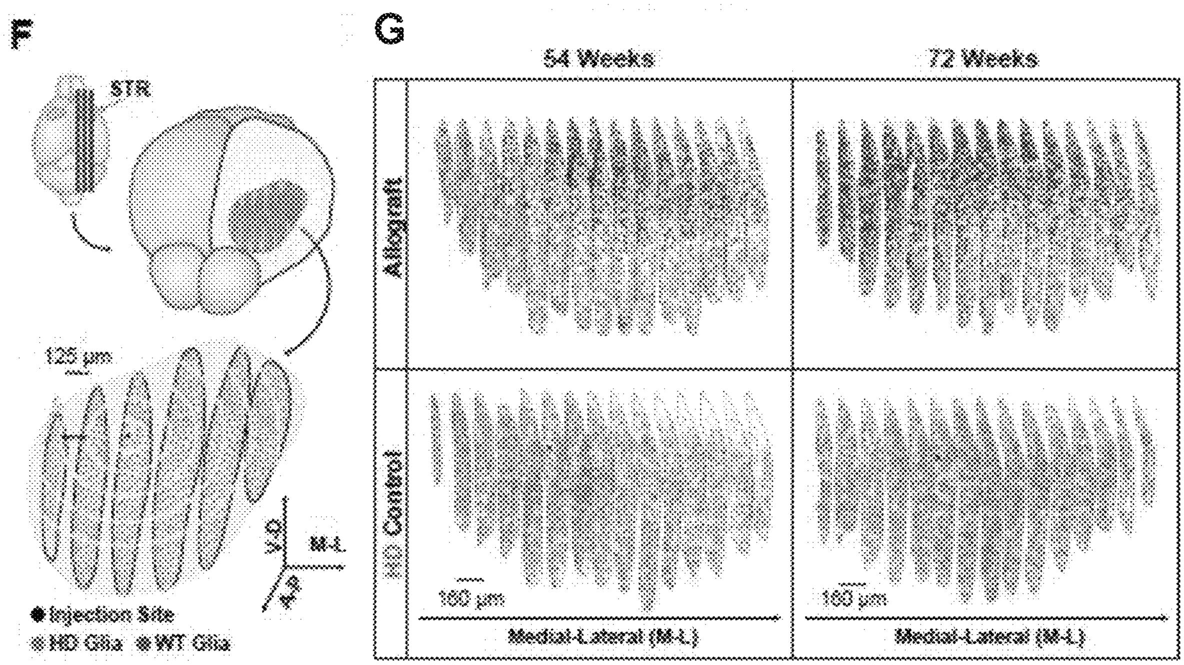
Figure 4:
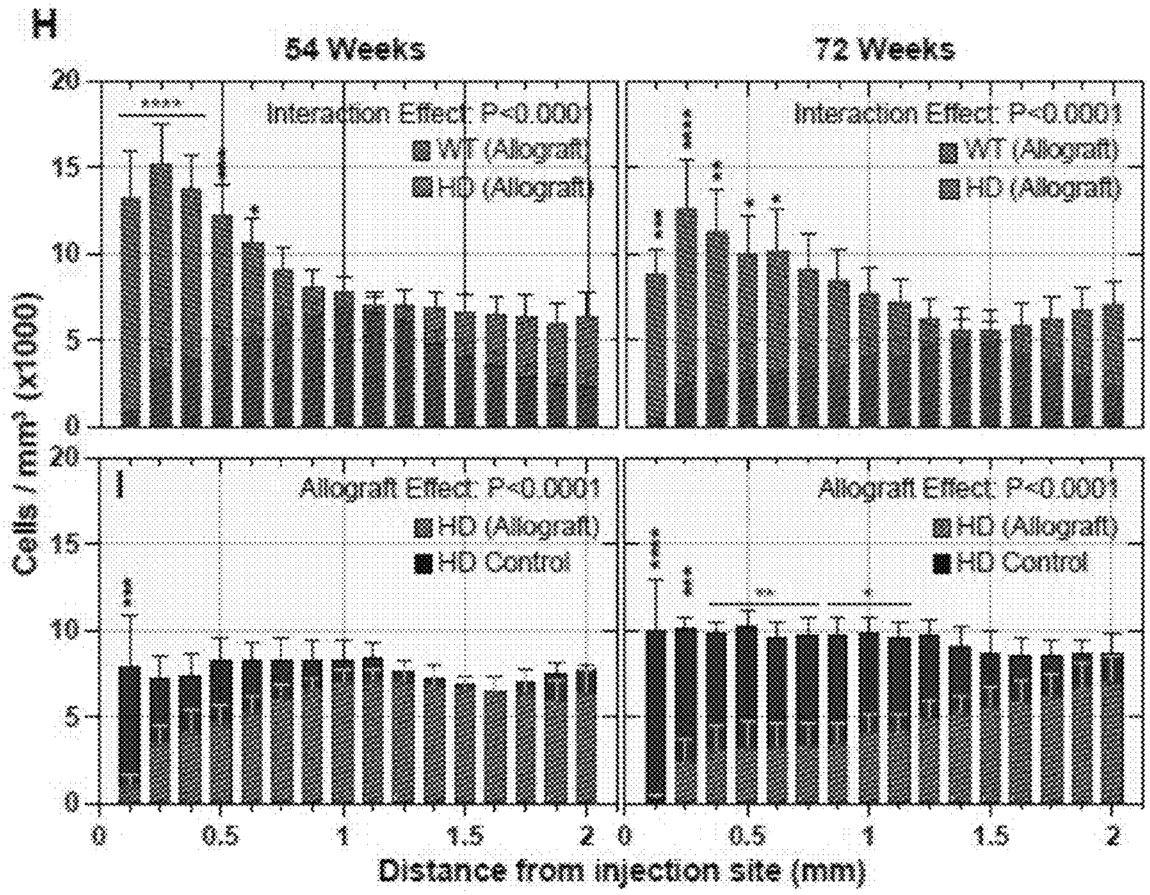
Figure 4:
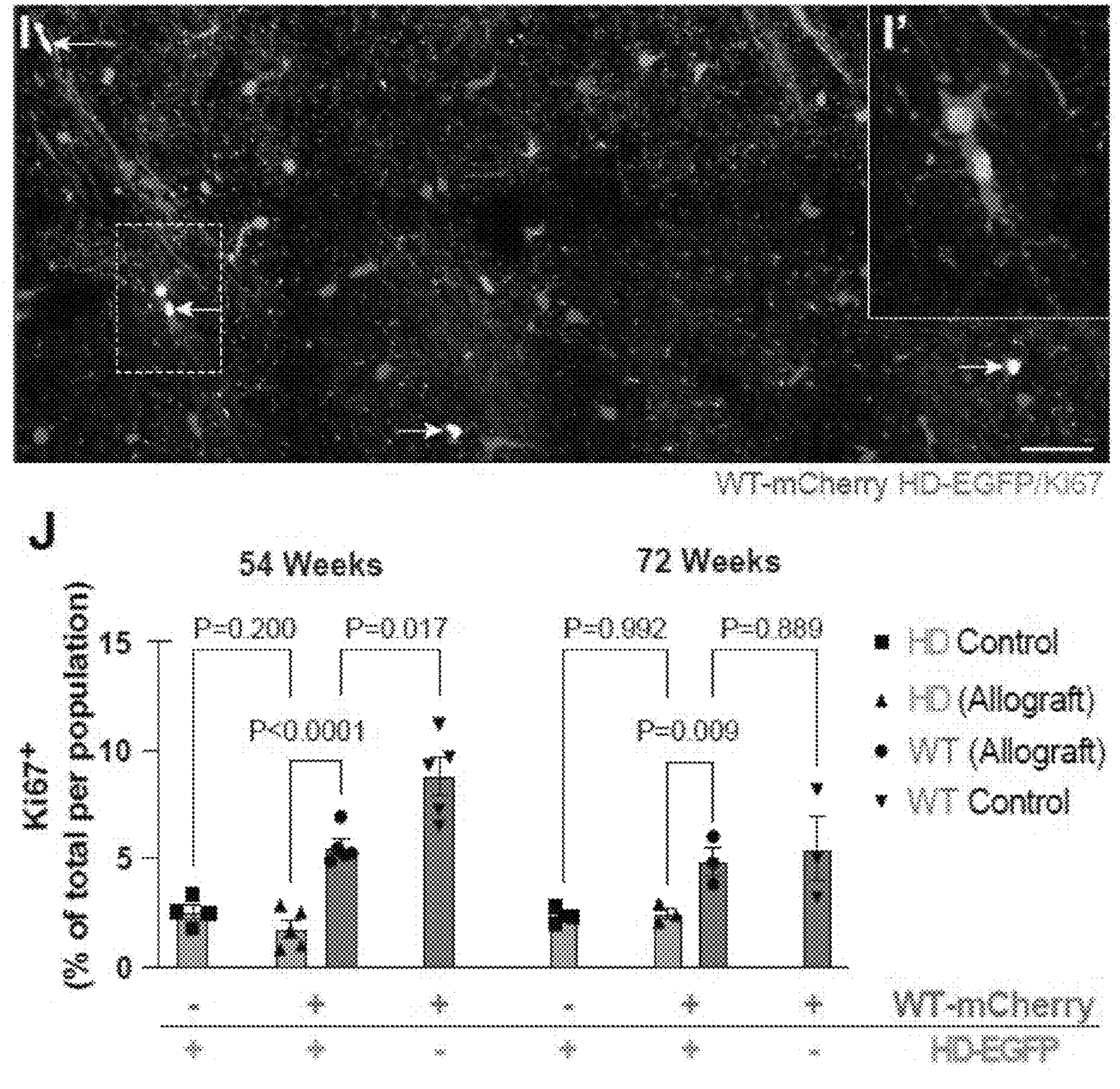

Phenotyping of human cells was accomplished by immunostaining for their respective fluorescent reporter, together with a specific phenotype marker: Olig2 (oligodendrocyte transcription factor, marking GPCs) and GFAP (glial fibrillary acidic protein, marking astrocytes). Fluorescent reporters were used as makers for human cells as their expression remained ubiquitous throughout the animal's life (FIG. 4). In animals that received a 1:1 mixture of WT-mCherry and WT-untagged human glia, the latter were identified by the expression of human nuclear antigen and the lack of fluorescent reporter expression. To immunolabel, sections were rehydrated with PBS, then permeabilized and blocked using a permeabilization/blocking buffer (PBS+0.1% Triton™ X-100 (Sigma-Aldrich cat. no. T8787)+10% Normal Goat Serum (ThermoFisher, cat. no. 16210072)) for 2h. Sections were then incubated overnight with primary antibodies targeting phenotypic makers at 4° C. The following day, the primary antibodies were thoroughly rinsed from the sections with PBS and secondary antibodies were applied to the sections for 1 h. After thoroughly rinsing out the secondary antibodies with PBS, a second round of primary antibodies, this time against fluorescent reporters, were applied to the sections overnight at 4° C. These were rinsed with PBS the following day and the sections were incubated with secondary antibodies for 1 h. The slides were again thoroughly washed with PBS and mounted with VECTASHIELD® Vibrance® (Vector Labs, cat. no. H-1800).

Xenotransplant Mapping and 3D Reconstruction

To map human cell distribution within the murine striatum, whole brain montages of 15 equidistantly spaced 160 μm apart sagittal sections spanning the entire striatum were captured using a Nikon Ni-E Eclipse microscope equipped with a DS-Fil camera at 10× magnification and processed in the NIS-Elements imaging software (Nikon). The striatum within each section was outlined and immunolabeled human cells were identified and mapped within the outlined striatum using the Stereo Investigator® software (MicroBrightField Bioscience). When applicable, the injection site for WT glia was mapped as a reference point for further volumetric quantification of human cell distribution. Mapped sections were then aligned using the lateral ventricle as a reference to produce a 3D reconstructed model of the humanized murine striatum.

After 3D reconstruction, the cartesian coordinates for each human cell marker, injection site and striatal outlines were exported for further analysis.

To assess the distribution and proportion of proliferative cells in each human cell population within the striatum, immunolabeled human cells expressing Ki67 were mapped in every third section of the 15 sections when performing the 3D reconstructions.

Volumetric Quantification

To quantify the spatial distribution of HD glia in HD chimeras, the volumes for each quantified striatal section were calculated by multiplying the section thickness (20 μm) by the section area. The cell density for each section was then calculated by dividing the number of marked cells in each section by their respective volume.

To quantify the spatial-temporal dynamics of competing WT and HD glia, a program was developed to calculate the volumetric distribution of each cell population as a function of distance to the WT glia delivery site in 3D reconstructed datasets (FIG. 4). To that end, each quantified section was given an upper and lower boundary Zu, Zi, by representing the striatal outline as two identical polygons separated from each other by the section thickness (20 μm). Then, since the depth-wise location of each cell marker within each individual section is unknown, marked cells within each section were represented as uniform point probability functions with constant probability across the section. I.e., each cell marker in a section from ZZu to ZZuu has a probability function:

$$P(z) = \begin{cases} \frac{1}{z_u - z_l}, & z_l \le z < z_u \\ 0, & \text{otherwise} \end{cases}.$$

The spatial distribution of each cell population was then measured by counting the number of marked cells within concentric spherical shells radiating from the WT glia delivery site in radial increments of 125 μm (For control HD chimeras, an average of the coordinates of the WT glia delivery site was used). Marked cells were counted if their respective representative line segments are fully inside, fully outside or intersecting the spherical shell at either the upper or lower boundary. The density of each cell population $\rho_{a,b}$—where a,b represents the minimum and maximum radii of the spherical shell—was then calculated by dividing number of marked cells within the spherical shell by the combined section volume within the shell:

$$\sigma_{a,b}=N_{a,b}/V_{a,b}$$

where $N_{a,b}$ is the sum of integrated point probability functions over each section for each point and $V_{a,b}$ is the combined section volume within the spherical shell. Subsequent analyses were restricted to a 2 mm spherical radius. The code was implemented in Python 3.8 and the package Shapely 1.7 to represent polygons and calculate circle intersections of the polygons.

Stereological Estimations and Phenotyping

Estimations of the total amount of human cells and their respective phenotyping were performed stereologically using the optical fractionator method (Shin, J.-Y. et al. "Expression Of Mutant Huntingtin In Glial Cells Contributes To Neuronal Excitotoxicity" J Cell Biology 171, 1001-1012 (2005), which is hereby incorporated by reference in its entirety) in 5 equidistantly separated 480 μm apart sections spanning the entire striatum. First, whole striatum z-stacked montages were captured using a Nikon Ni-E Eclipse microscope equipped with a DS-Fil camera at 20× magnification and processed in the NIS-Elements imaging software (Nikon). Each z-stack tile was captured using a 0.9 μm step size. The montages were then loaded onto Stereo-Investigator and outlines of the striatum were defined. A set of 200×200 μm counting frames was placed by the software in a systematic random fashion within a 400×400 μm grid covering the outlined striatum of each section. Counting was performed in the entire section height (without guard zones) and cells were counted based on their immunolabelling in the optical section in which they first came into focus.

Statistical Analysis and Reproducibility

Samples exhibiting artifacts related to technical issues from experimental procedures—such as mistargeted injections, overt surgical damage, or injections into gliotic foci —were excluded from this study. Statistical tests were performed using GraphPad Prism™ 9. For comparisons between more than two groups, one-way analysis of variance (Tukey's multiple comparison test) was applied. For comparisons between two groups with more than two factors, two-way analysis of variance (Sidák's multiple comparison test) was applied. When comparing between two matched groups, paired two-tailed t-tests were applied for normally distributed data sets, while for unmatched groups, unpaired two-tailed t-tests were applied. Significance was defined as P<0.05. Respective P values were stated in the figures whenever possible, otherwise, P<0.0001, * P<0.001,  P<0.01, *P<0.05. The number of replicates is indicated in the figure legends, with n denoting the number of independent experiments. Data are represented as the mean±standard error of mean (s.e.m).

Figure 2:
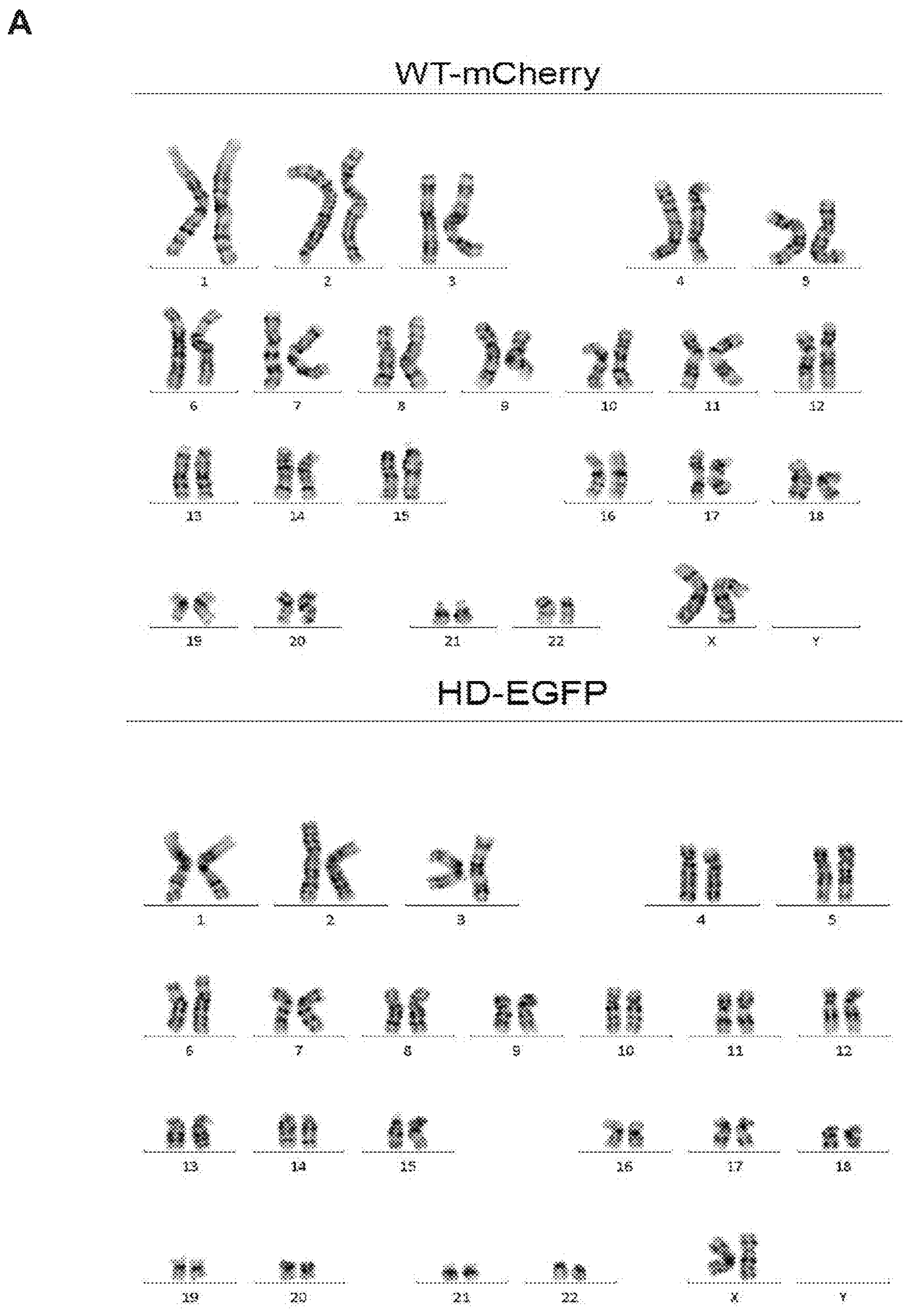
FIG. 2, Panel A shows representative karyotypes from WT-mCherry and HD-EGFP to assess acquired copy number variants (CNVs) and loss-of-heterozygosity regions (LOH). Panels B-C show karyotype analysis.
Figure 2:
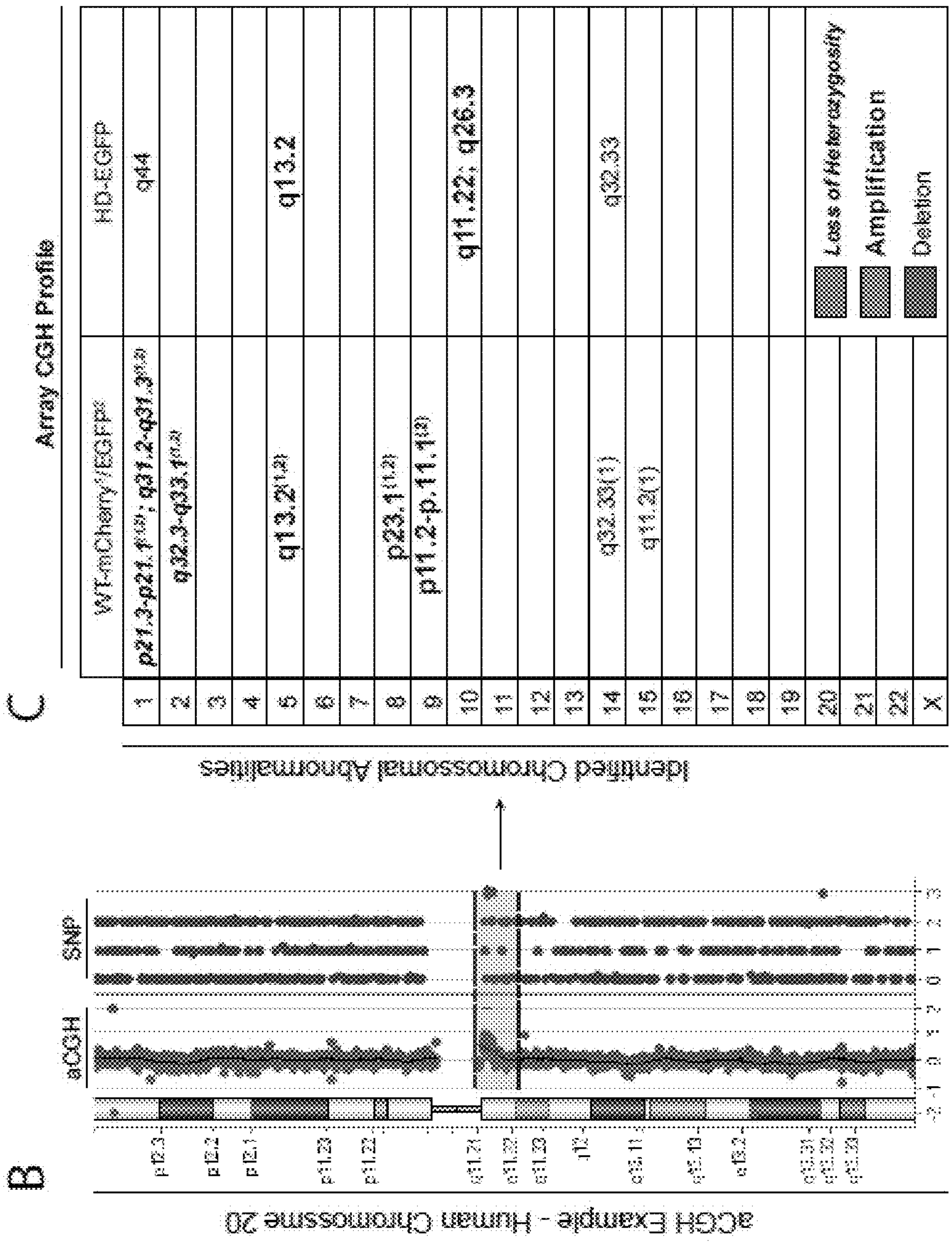

Example 2: Generation of Distinctly Color-Tagged Human Glia from WT and HD hESCs To assess the ability of healthy glia to replace their diseased counterparts in vivo, fluorophore-tagged reporter lines of WT and HD human embryonic stem cells (hESC) were first generated, so as to enable the production of spectrally-distinct GPCs of each genotype, whose growth in vivo could then be independently monitored. A CRISPR-Cas9-mediated knock-in strategy was first used to integrate EGFP and mCherry reporter cassettes into the AAVS1 locus of matched, female sibling wild-type (WT, GENEA019) and mHTT-expressing (HD, GENEA020) hESCs (FIG. 1, Panel A). The reporter cassettes were verified as stably integrated into each of these clones (FIG. 1, Panel D), and that editing did not influence the self-renewal, pluripotency, or karyotypic stability of the tagged hESCs (FIG. 1, Panel E and FIG. 2 Panel A). From these tagged and spectrally-distinct lines, a differentiation protocol was used (Benraiss, A. et al. Human glia can both induce and rescue aspects of disease phenotype in Huntington disease. Nature Communications 7, 11758 (2016)) to produce color-coded human glial progenitor cells (hGPCs) from each line, whose behaviors in vivo could be compared, both alone and in competition. The ability of each line to maintain EGFP or mCherry expression after maturation as astrocytes or oligodendrocytes was validated, and their lack of any significant differentially-expressed oncogenic mutations, or copy number variants (CNVs) that could bias growth (FIG. 2, Panel B-Panel C); it was also verified that both the WT and mHTT-expressing hGPCs, when injected alone, colonized the murine host brains (FIG. 15, Panel A-B, FIG. 5, and FIG. 6, Panel A).

Figure 3:
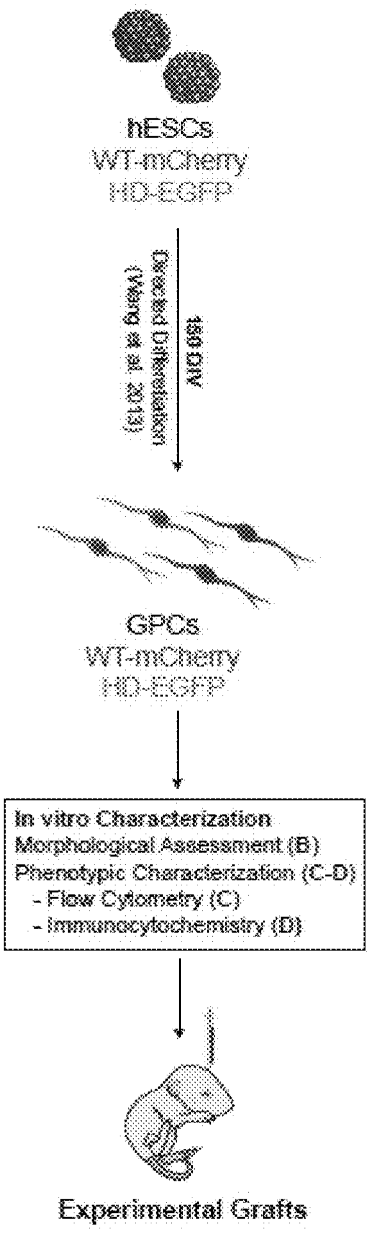
FIG. 3, Panel A illustrates creation of HD-chimeric mice. Panels B-C show characterization of cells in HD-chimeric mice. Panel D shows representative images and characterization of cells in HD-chimeric mice.
Figure 3:
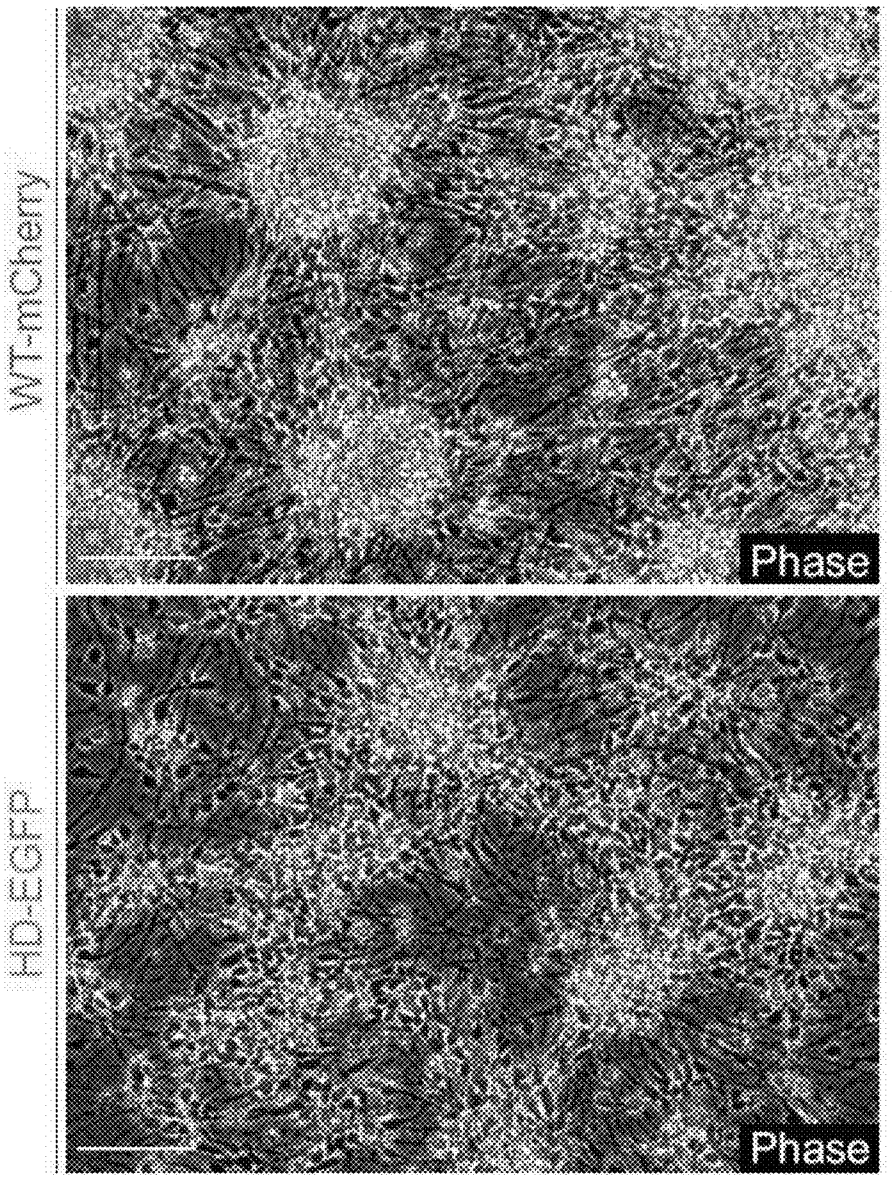
Figure 3:
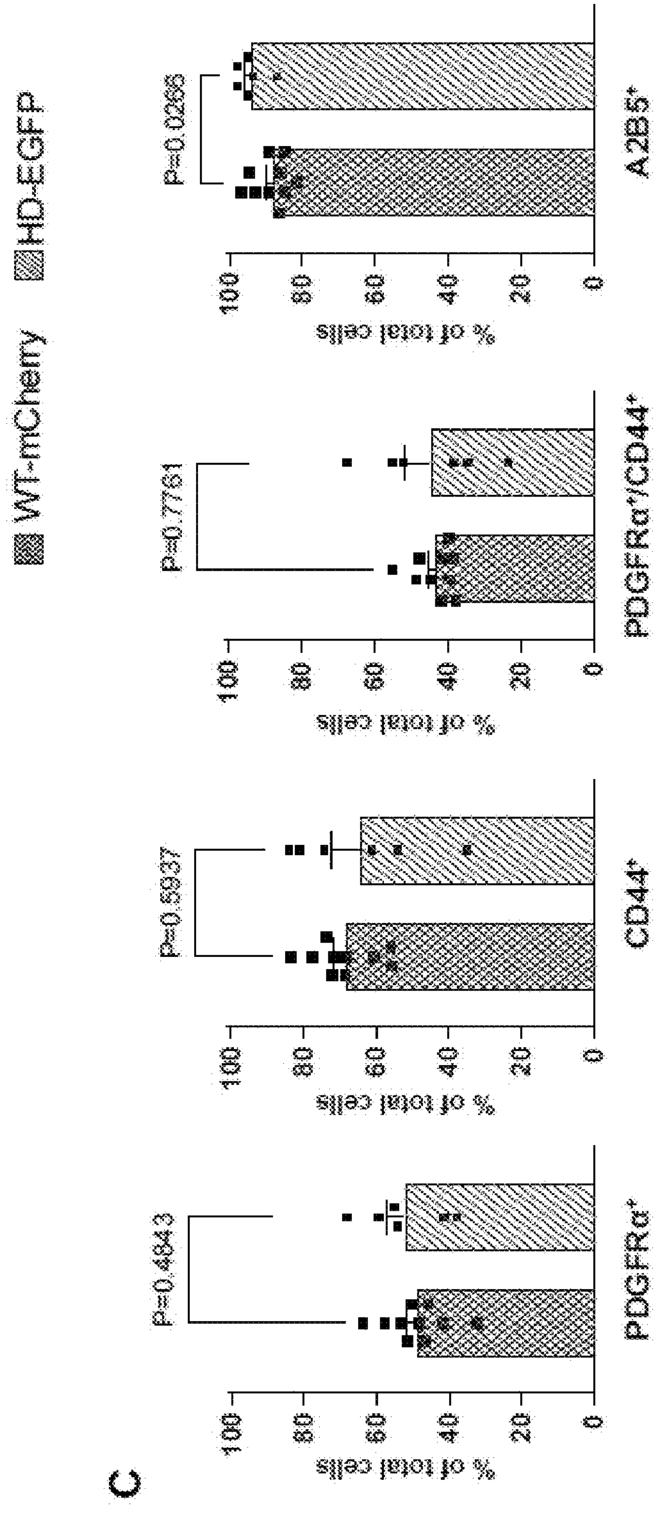
Figure 3:
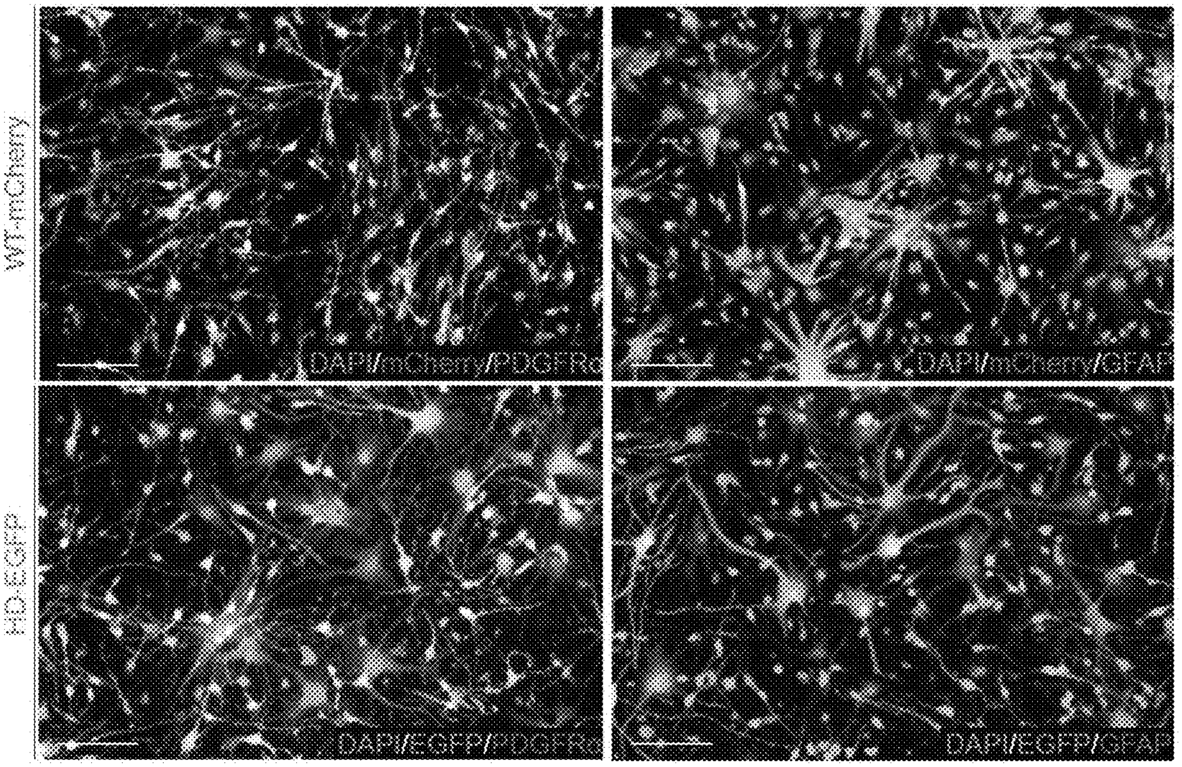
Figure 18:
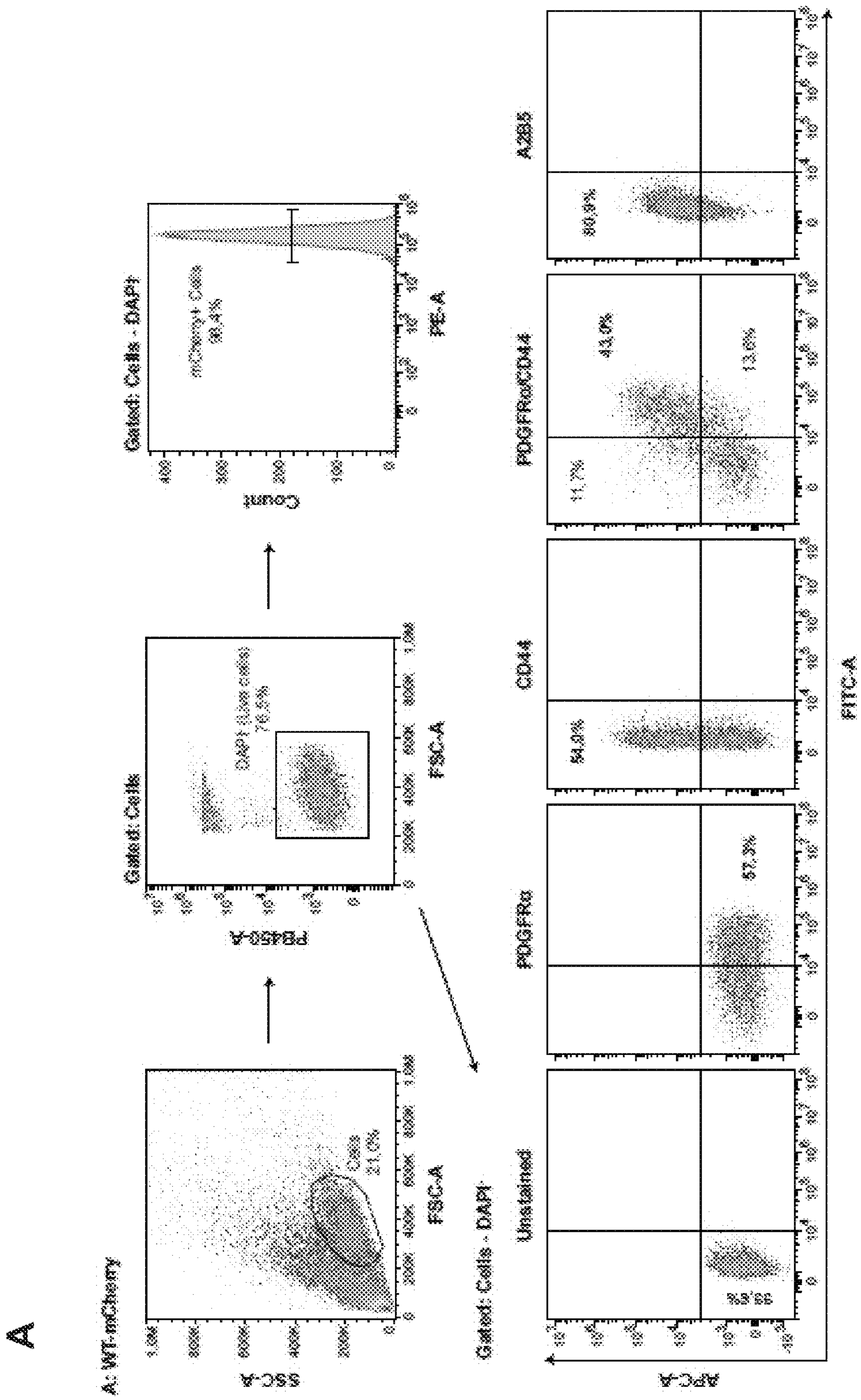
FIG. 18, Panels A-B show gating strategy flow cytometry analysis.
Figure 18:
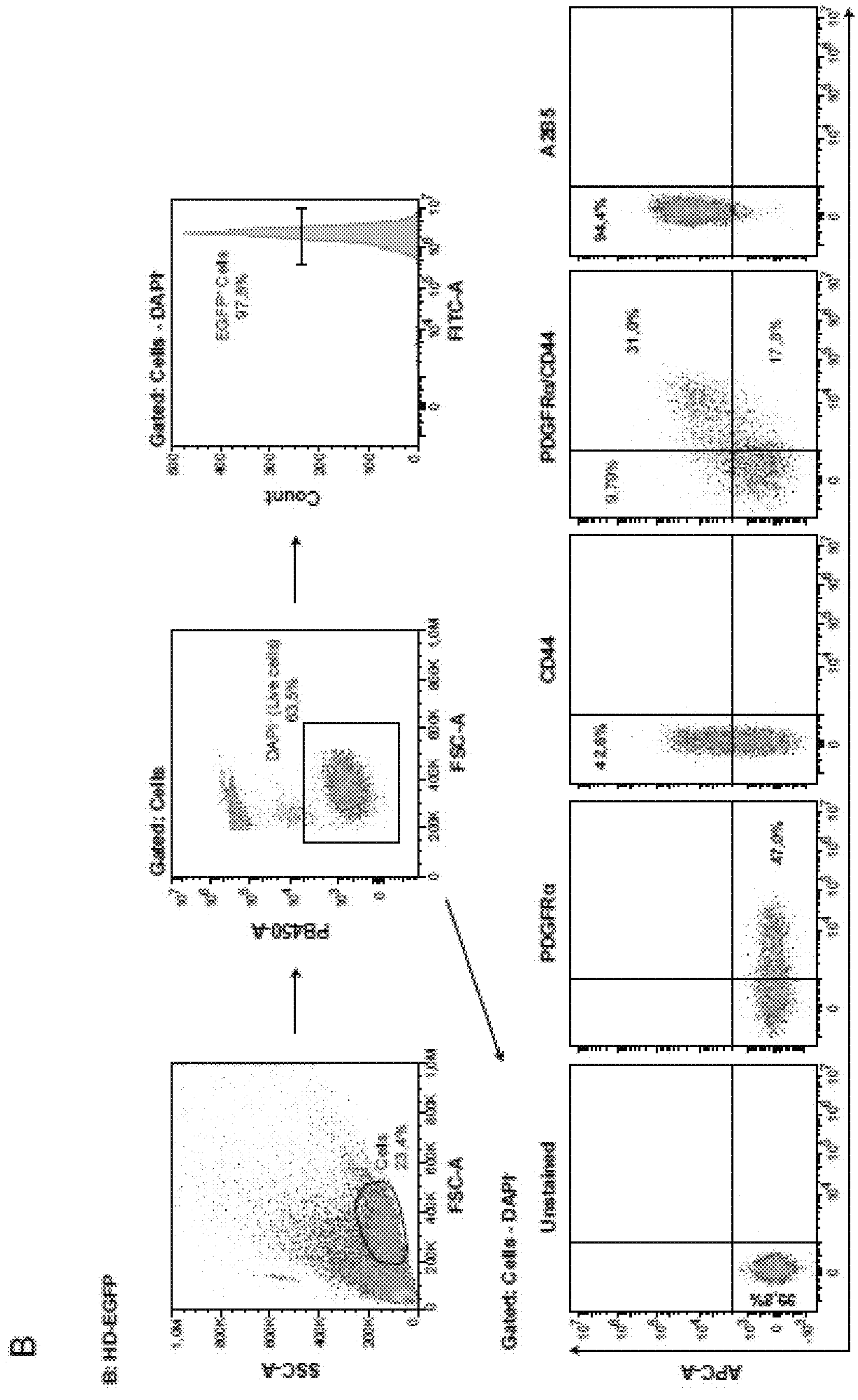

Both WT-mCherry and HD-EGFP hESCs were differentiated using a protocol for generating hGPCs (Wang, S. et al. Human iPSC-Derived Oligodendrocyte Progenitor Cells Can Myelinate and Rescue a Mouse Model of Congenital Hypomyelination. Cell Stem Cell 12, 252—264 (2013)) and both their capacity to differentiate into glia and the stability of their reporter expression upon acquisition of glial fate were assessed (FIG. 3, Panels A-D). By 150 days in vitro (DIV), glial cultures derived from both WT-mCherry and HD-EGFP were equally enriched for PDGFRα+/CD44+ bipotential GPCs (P-0.78), comprising around half of the cells in the cultures, with the rest being immature A2B5+ GPCs 27 and PDGFRα−/CD44+ astrocytes and their progenitors (FIG. 3, Panel C and FIG. 18, Panels A-B). Importantly, virtually all immune-phenotyped cells derived from WT-mCherry and HD-EGFP hESCs-including mature astrocytes as well as GPCs-continued to express their respective fluorescent reporter, indicating that transgene expression remained stable upon acquisition of terminal glial identity (FIG. 3, Panel D).

Example 3: Establishment of Human HD Glial Chimeric Mice

Figure 15:
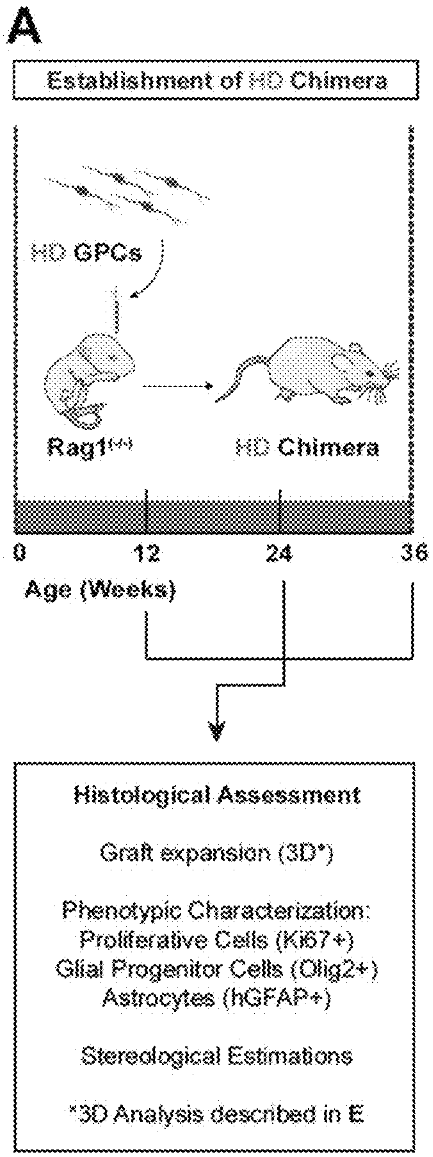
FIG. 15, Panels A-D show murine chimeras with striata substantially humanized by HD glia were generated to provide an in vivo model by which to assess the replacement of diseased human glia by their healthy counterparts. hGPCs derived from mHTT-expressing hESCs engineered to express EGFP were implanted into the neostriatum of immunocompromised Rag1(−/−) mice and their expansion histologically was monitored. Panels E-J show murine chimeras with striata substantially humanized by HD glia were generated to provide an in vivo model by which to assess the replacement of diseased human glia by their healthy counterparts. hGPCs derived from mHTT-expressing hESCs engineered to express EGFP were implanted into the neostriatum of immunocompromised Rag1(−/−) mice and their expansion histologically was monitored.
Figure 15:
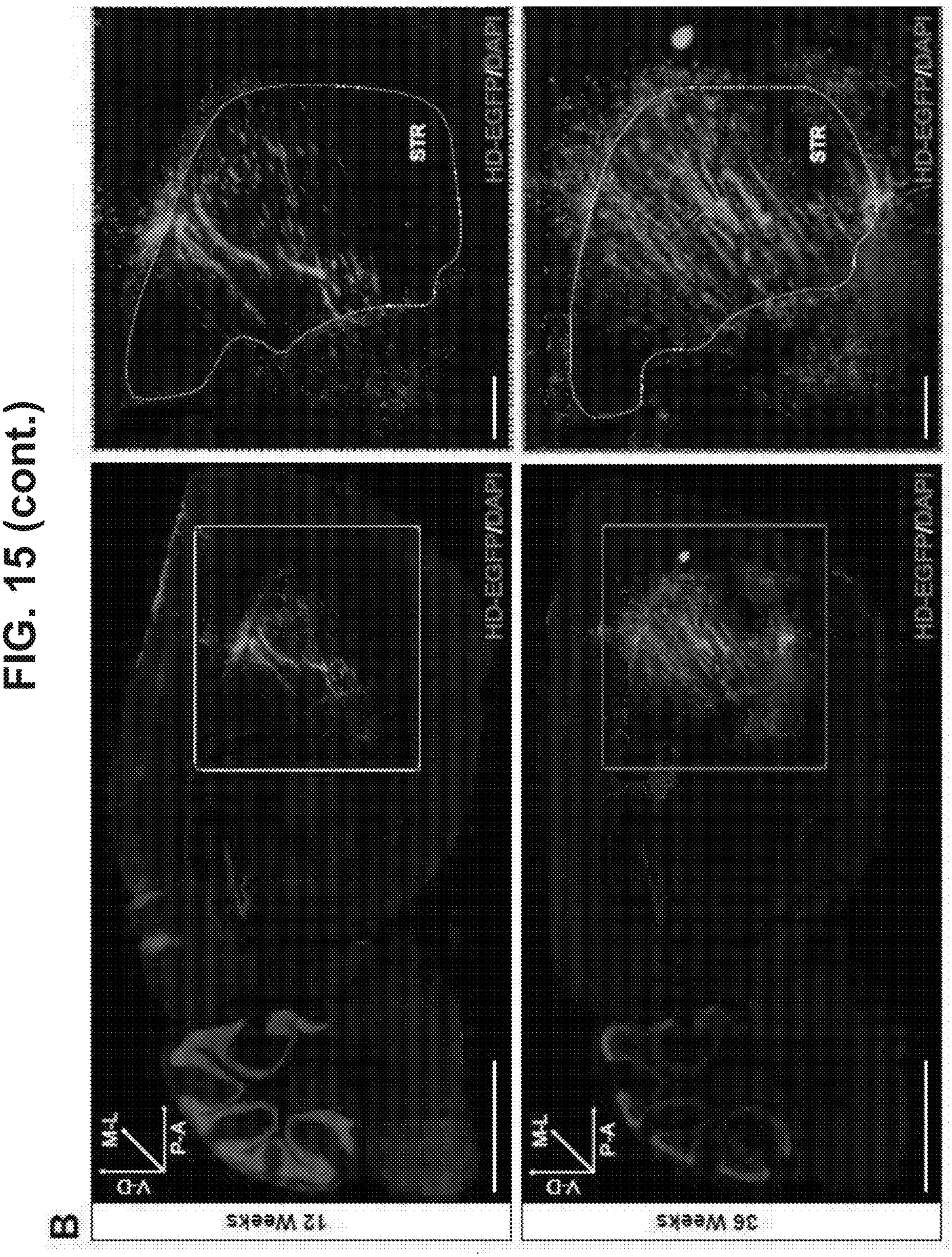
Figure 15:
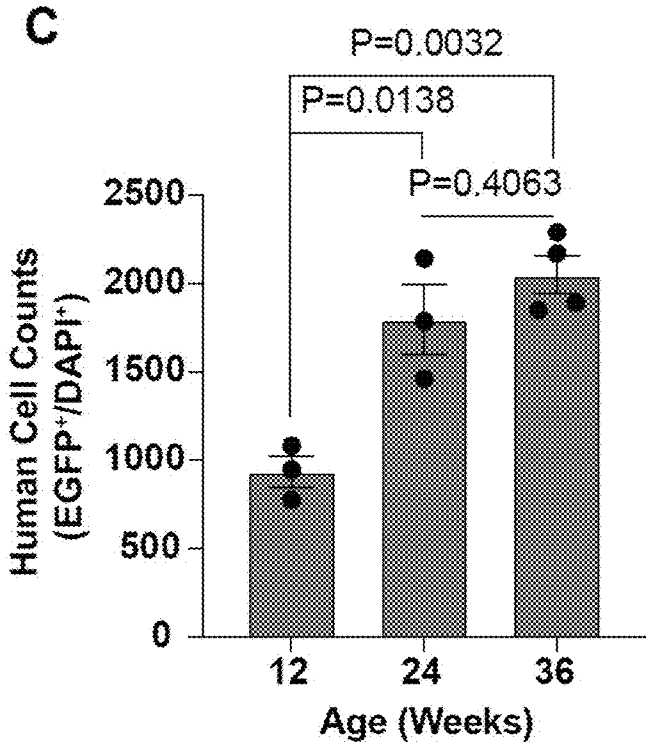
Figure 15:
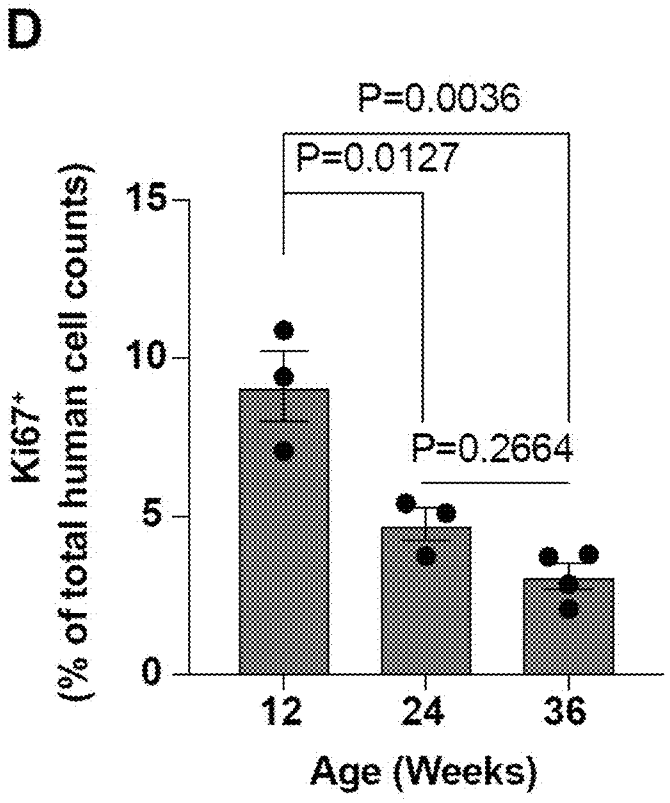
Figure 15:
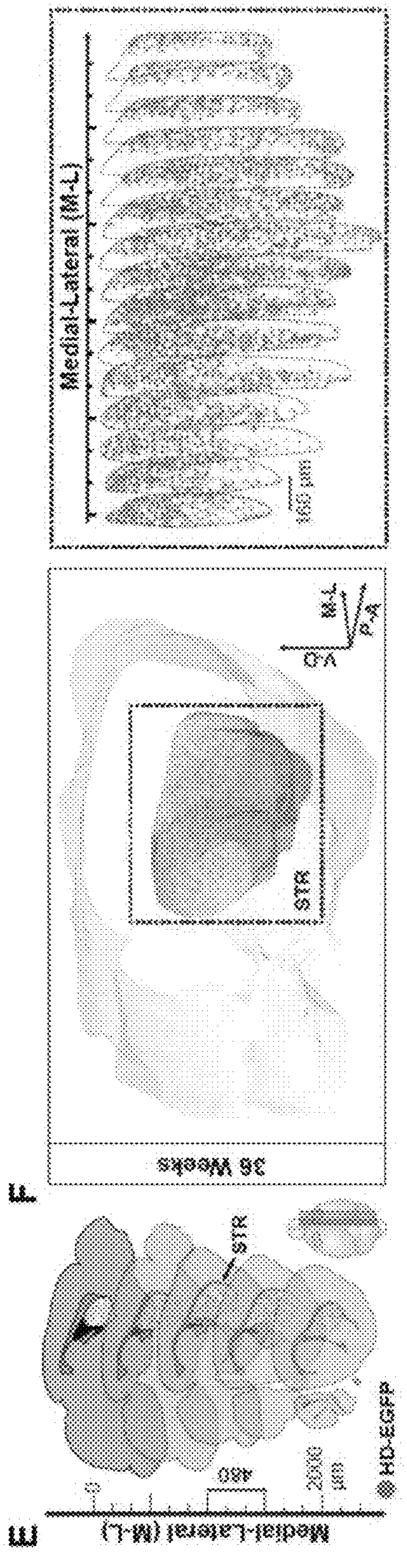
Figure 15:
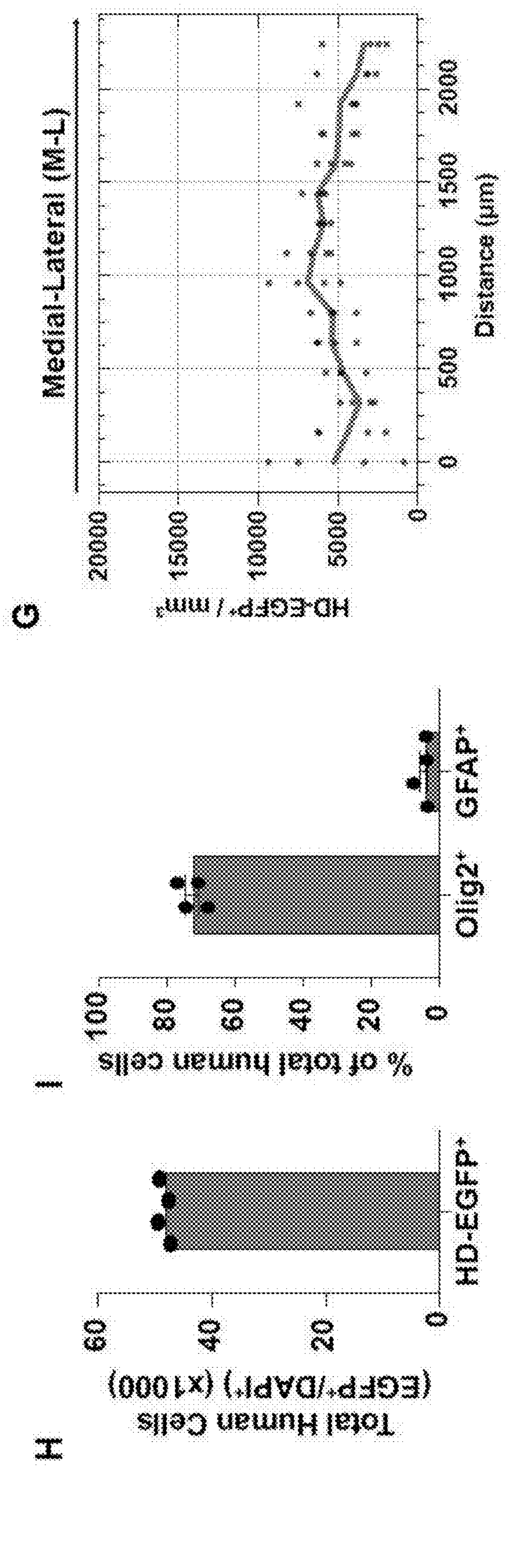
Figure 15:
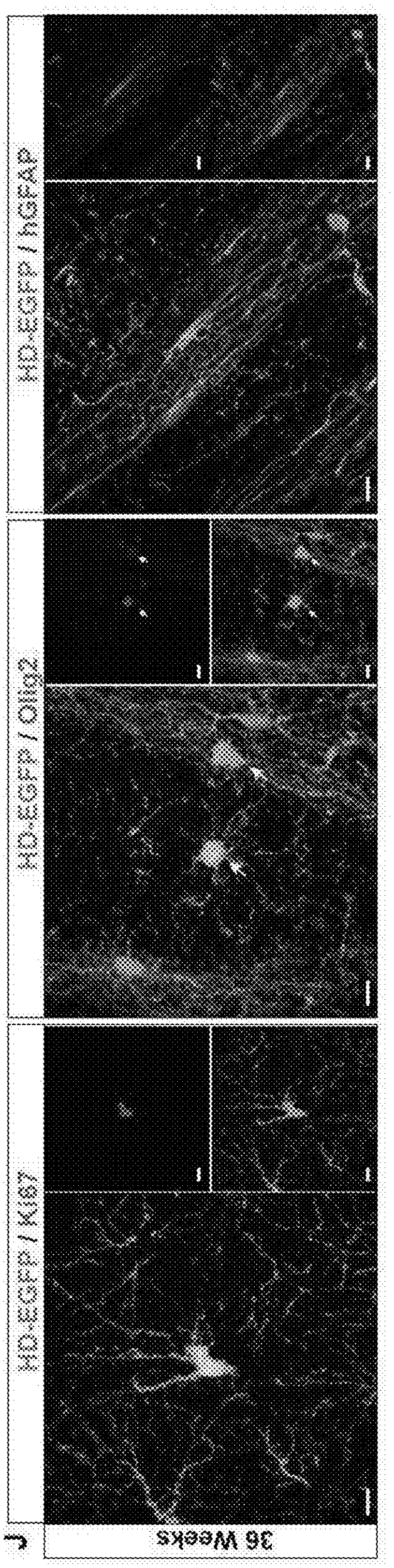
Figure 16:
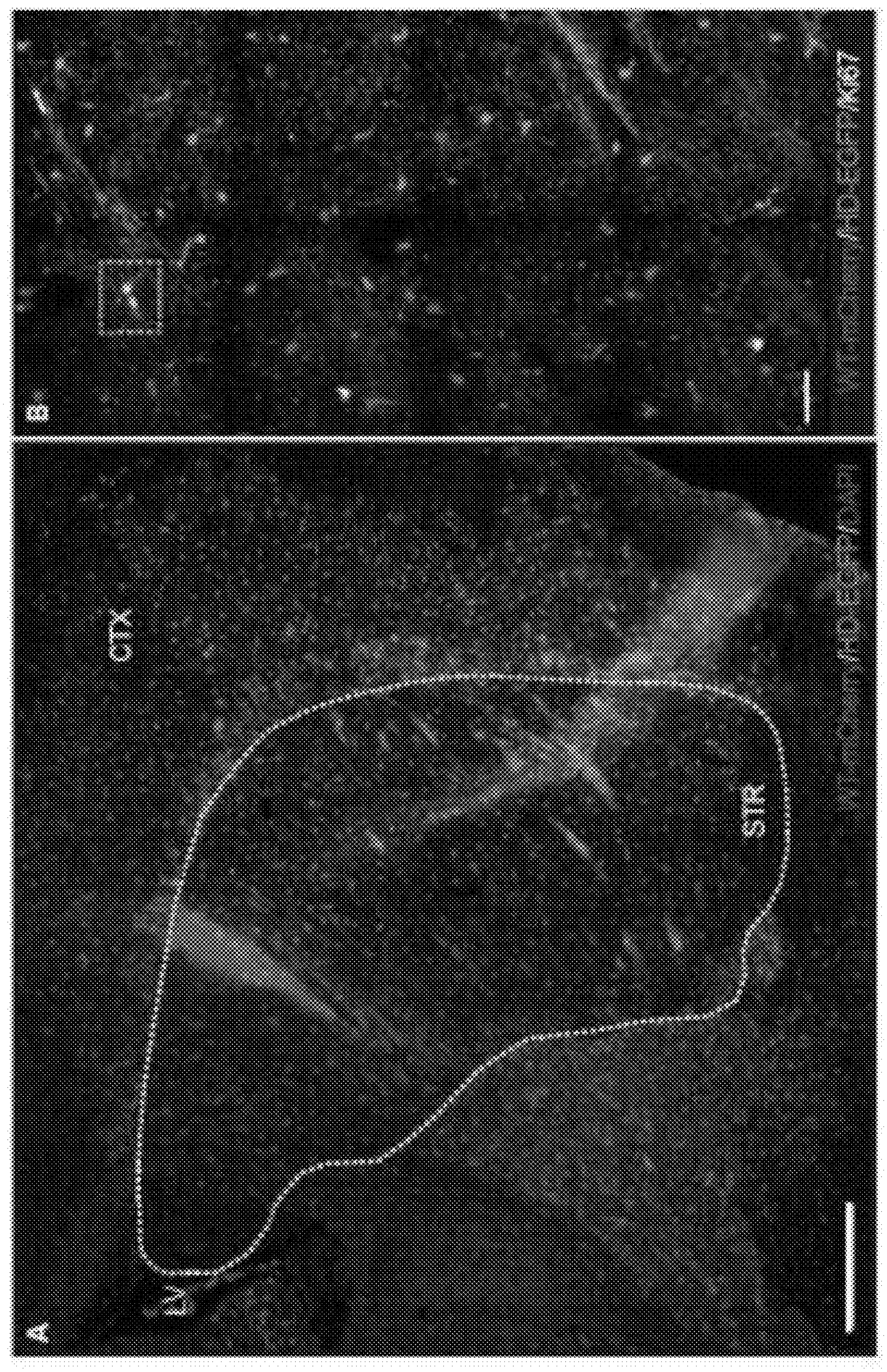
FIG. 16, Panels A-B show proliferative advantage drives WT glia to advance through the humanized HD striatum.

Murine chimeras with striata substantially humanized by HD glia (HD chimeras, FIG. 5) were generated to provide an in vivo model by which to assess the replacement of diseased human glia by their healthy counterparts. hGPCs derived from mHTT-expressing hESCs engineered to express EGFP (FIG. 1 and FIG. 5; henceforth designated as HD) were implanted into the neostriatum of immunocompromised Rag1(−/−) mice and their expansion histologically was monitored (FIG. 15, Panel A).

Following implantation, HD glia rapidly infiltrated the murine striatum, migrating and expanding firstly within the striatal white matter tracts (FIG. 15, Panel B). Gradually, these cells expanded outwards, progressively displacing their murine counterparts from the striatal neuropil, so that by 36 weeks, the murine striatum was substantially humanized by HD glia (FIG. 15, Panel B, 15, Panel F, and 15, Panel G). The advance of HD glia was driven by their mitotic expansion, with their total number doubling between 12 and 36 weeks (FIG. 15, Panel C; P=0.0032). Inversely, as they expanded and matured within their newly established domains, their proliferative cell pool (Ki67+) was progressively depleted (FIG. 15, Panel D, and I; P=0.0036), slowing their expansion rate over time.

Most of the HD glia expanded as Olig2+ GPCs (72.7±1.9%), which persisted as the new resident pool after replacing their murine counterparts. A fraction of these (4.8±0.9%) further differentiated into GFAP+ astrocytes (FIG. 15, Panel I and 15, Panel J). Astrocytic differentiation was mostly observed within striatal white matter tracts. These sick astrocytes lacked the structural complexity typically observed in healthy counterparts and displayed abnormal fiber architecture, as previously reported (FIG. 15, Panel J; Osipovitch, M. et al., "Human ESC-Derived Chimeric Mouse Models of Huntington's Disease Reveal Cell-Intrinsic Defects in Glial Progenitor Cell Differentiation," Cell Stem Cell 24:107-122 (2019), which is hereby incorporated by reference in its entirety).

Figure 5:
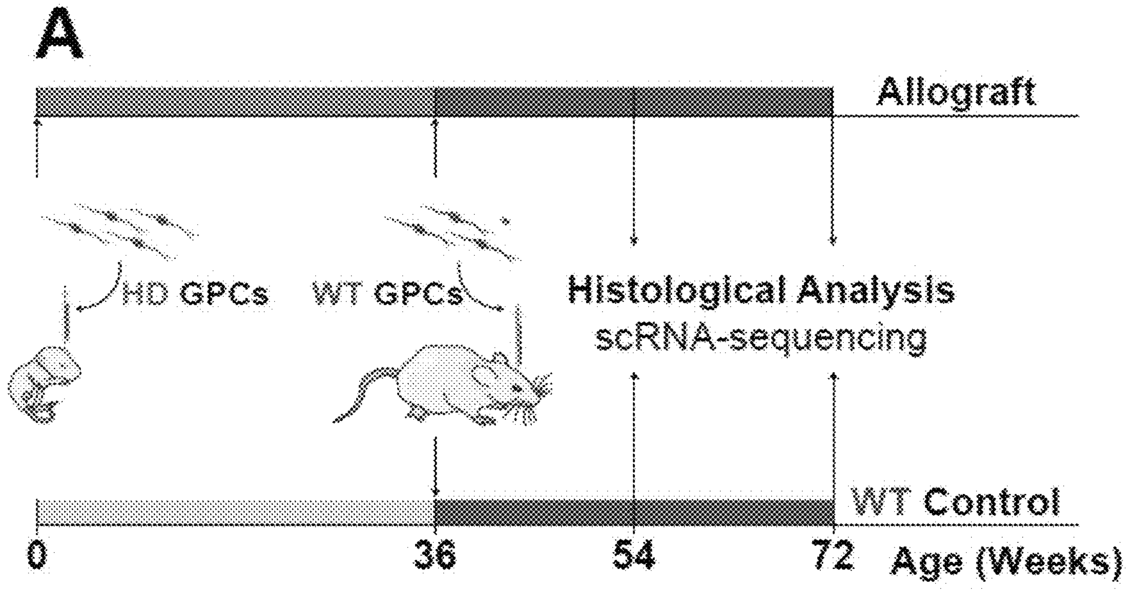
FIG. 5 illustrates the experimental design of the HD vs WT mouse and the HD control mouse.
Figure 6:
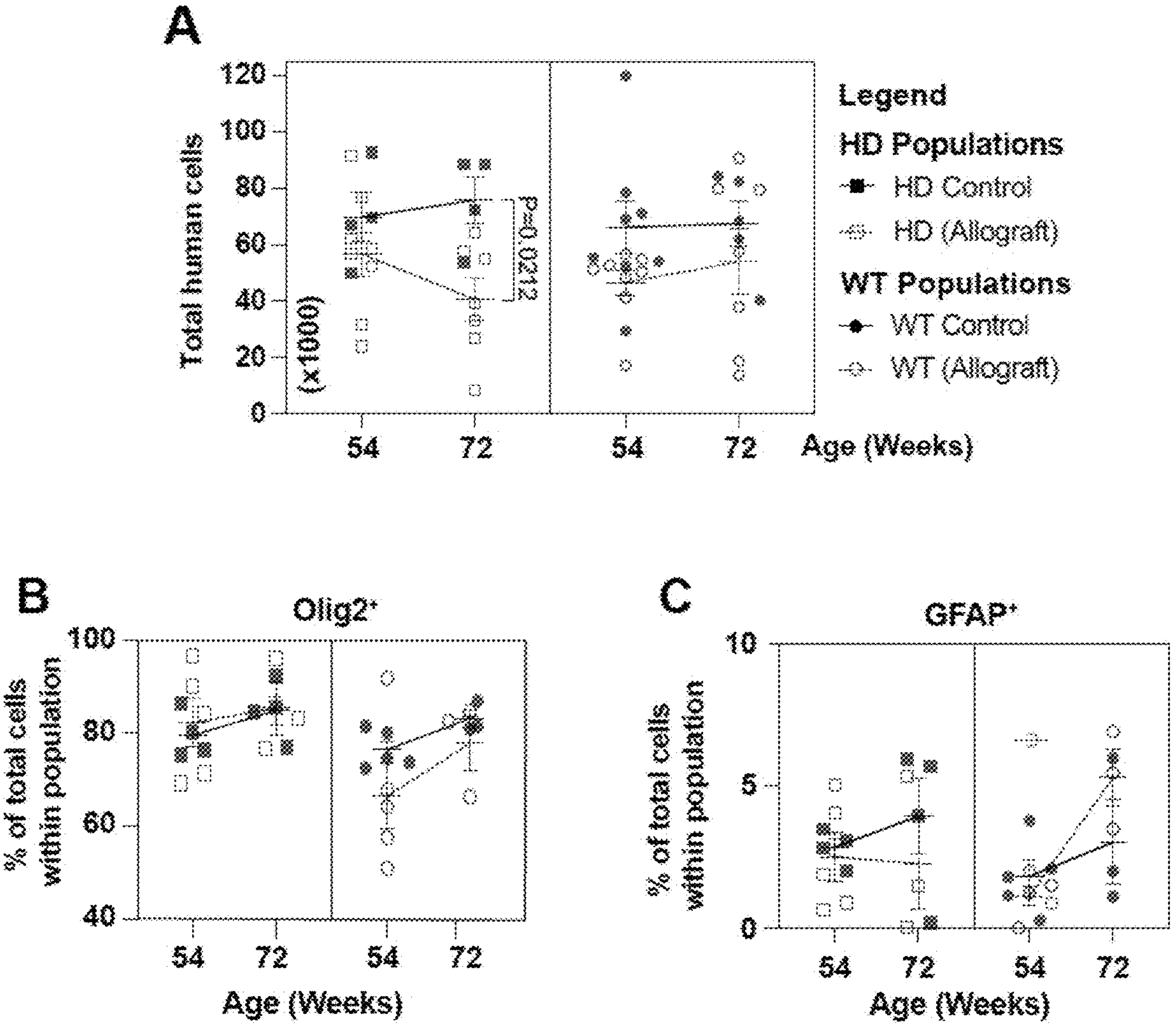
FIG. 6, Panels A-C show human wildtype glia outcompete previously integrated human HD glia. Panel A provides stereological estimations demonstrate that the total number of HD glia progressively decreases relatively to HD chimera controls as WT glia expands within the humanized striatum; Two-way ANOVA with Šidák's multiple comparisons test. Panel B and Panel C show the proportion of GPCs (Olig2+, Panel B) and astrocytes (GFAP+, Panel C) in both populations was maintained as they competed for striatal dominance; HD Control-n=4 for both timepoints; WT Control-n=4 for 54 weeks, n=3 for 72 weeks; HD vs WT-n=5 for 54 weeks, n=3 for 72 weeks; Orange arrows point to co-labelled cells. Data shown as means±s.e.m with individual data points. Panels D-E shows representative images of HD glia (Panel D) and WT glia (Panel E) of WT glia expanded as Olig2+ (white) GPCs displacing their HD counterparts. Within areas where they became dominant, they further differentiated into hGFAP+ (white) astrocytes.
Figure 6:
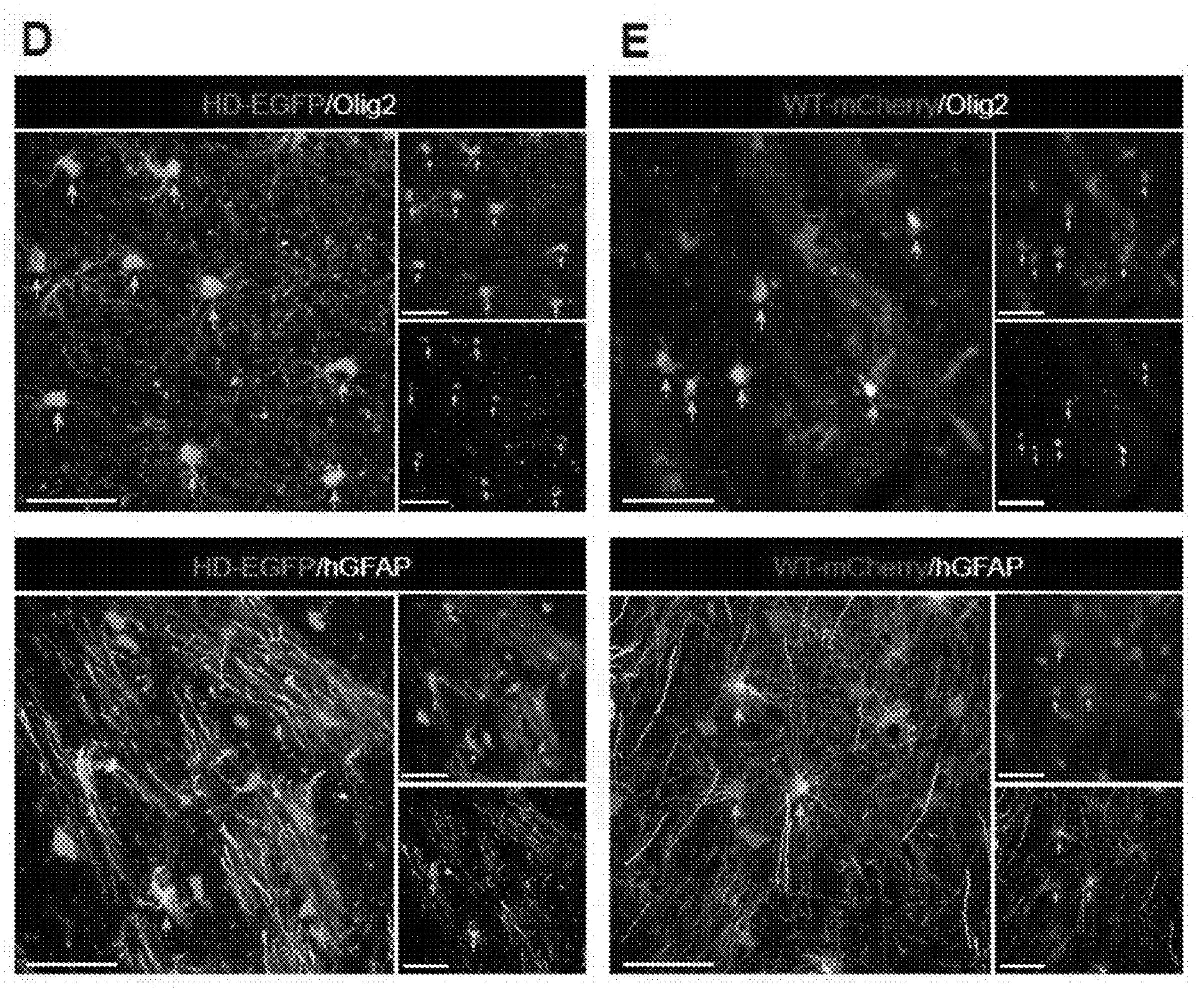

Example 4: Healthy WT hGPCs Infiltrate the HD Chimeric Adult Striatum and Outcompete Resident Glia The established chimeras whose striatal glia are largely mHTT-expressing and human were used to determine how the resident HD human glia might respond to the introduction of healthy hGPCs and whether the resident glial populations might to some extent be replaced. hGPCs derived from WT hESCs engineered to express mCherry (FIG. 1, FIG. 2, and FIG. 3; henceforth designated as WT) were engrafted into the striatum of 36 weeks old HD chimeras and monitored for expansion using histology as they competed for striatal domination (FIG. 5).

Following engraftment, WT glia pervaded the previously humanized striatum, gradually displacing their HD counterparts as they expanded from their implantation site (FIG. 4). This process was slow but sustained, over time yielding substantial repopulation of the HD striatum (FIG. 4; 54 weeks, p<0.0001; 72 weeks, p<0.0001). Remarkably, the expansion of WT glia was paralleled by a concurrent elimination of HD glia from the tissue (as opposed to their spatial relocation) (FIG. 4; 54 weeks-P<0.0001, 72 weeks-P<0.0001), and was typically characterized by a discrete advancing front behind which almost no HD glia could be found (FIG. 4).

Mutually exclusive domains formed in the wake of competition between Olig2+ GPCs (FIG. 4). These comprised most of the WT glial population (80.1±4.7% at 72 weeks), which persisted as the new resident GPC pool after replacing their HD counterparts. Their potential to generate astroglia was maintained, as a fraction of these (4.0±1.5% at 72 weeks) further differentiated into GFAP+ astrocytes (FIG. 6) within their newly established domains. Curiously, within regions dominated by WT glia, HD astrocytes (GFAP+) lingered, primarily within white matter tracts (FIG. 4). Nonetheless, the overall ratio between Olig2+ and GFAP+ glia remained stable throughout the experiment in both populations (FIG. 6) indicating that while GPC replacement precedes astrocytic replacement, proportional phenotypic repopulation is achieved over time.

Figure 7:
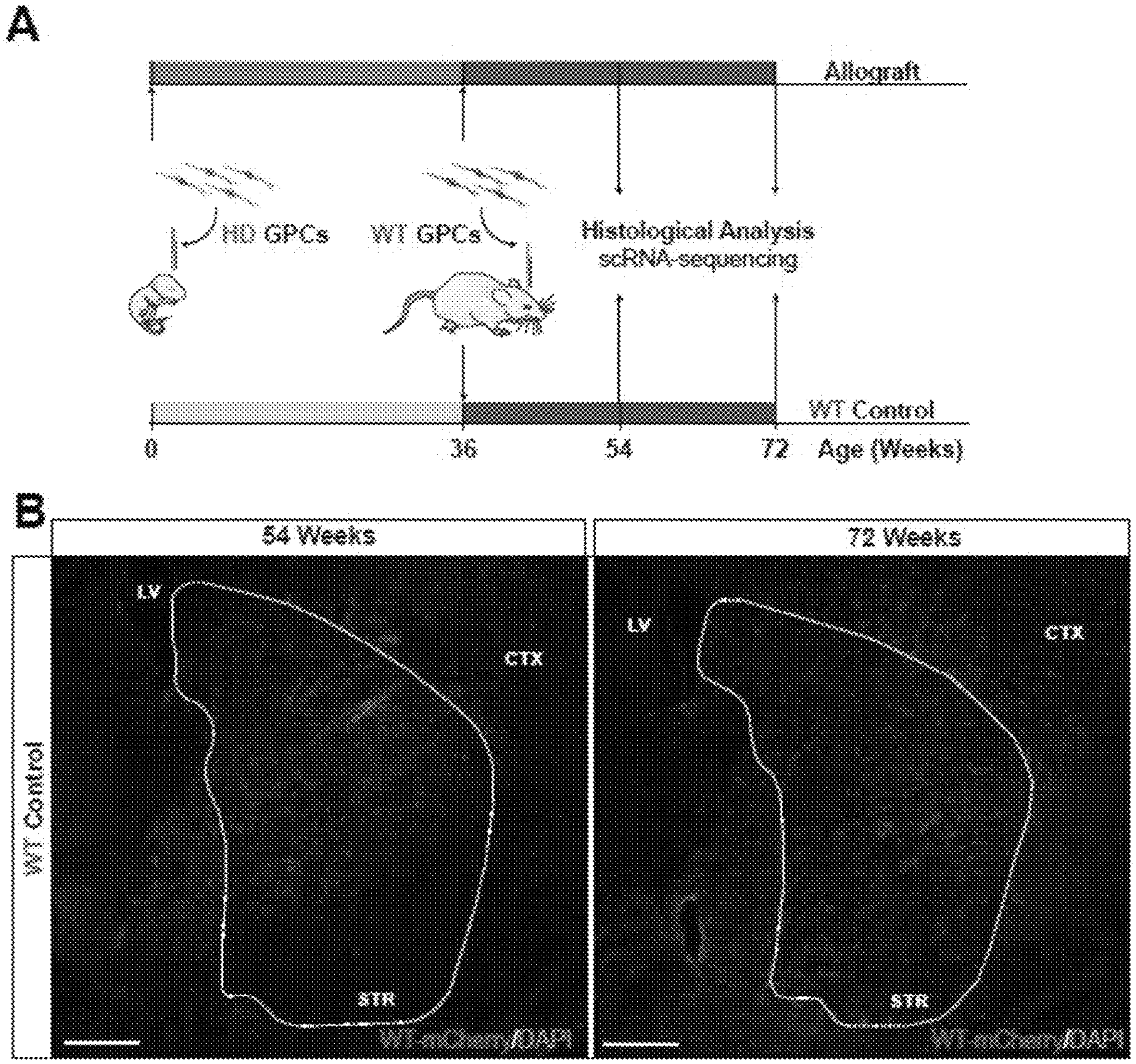
FIG. 7, Panels A-B illustrates the experimental design and analytic timepoints of the WT Control group (Panel A). Panel B shows representative images of engraftment of WT glia (mCherry+, red) into the adult striatum of Rag1(−/−) mice yields substantial humanization of the murine striatum over time. Panels C-D show volumetric quantifications show that WT glia infiltrate and disperse throughout the murine striatum over time, and they do so more broadly than those grafted onto HD chimeras; WT (HD vs WT Group)—n=8 for 54 weeks, n=7 for 72 weeks vs WT Control—n=7 for 54 weeks, n=5 for 72 weeks; Two-way ANOVA with Šidák's multiple comparisons test; Main effects are shown as numerical P values; Data is presented as means±s.e.m.
Figure 7:
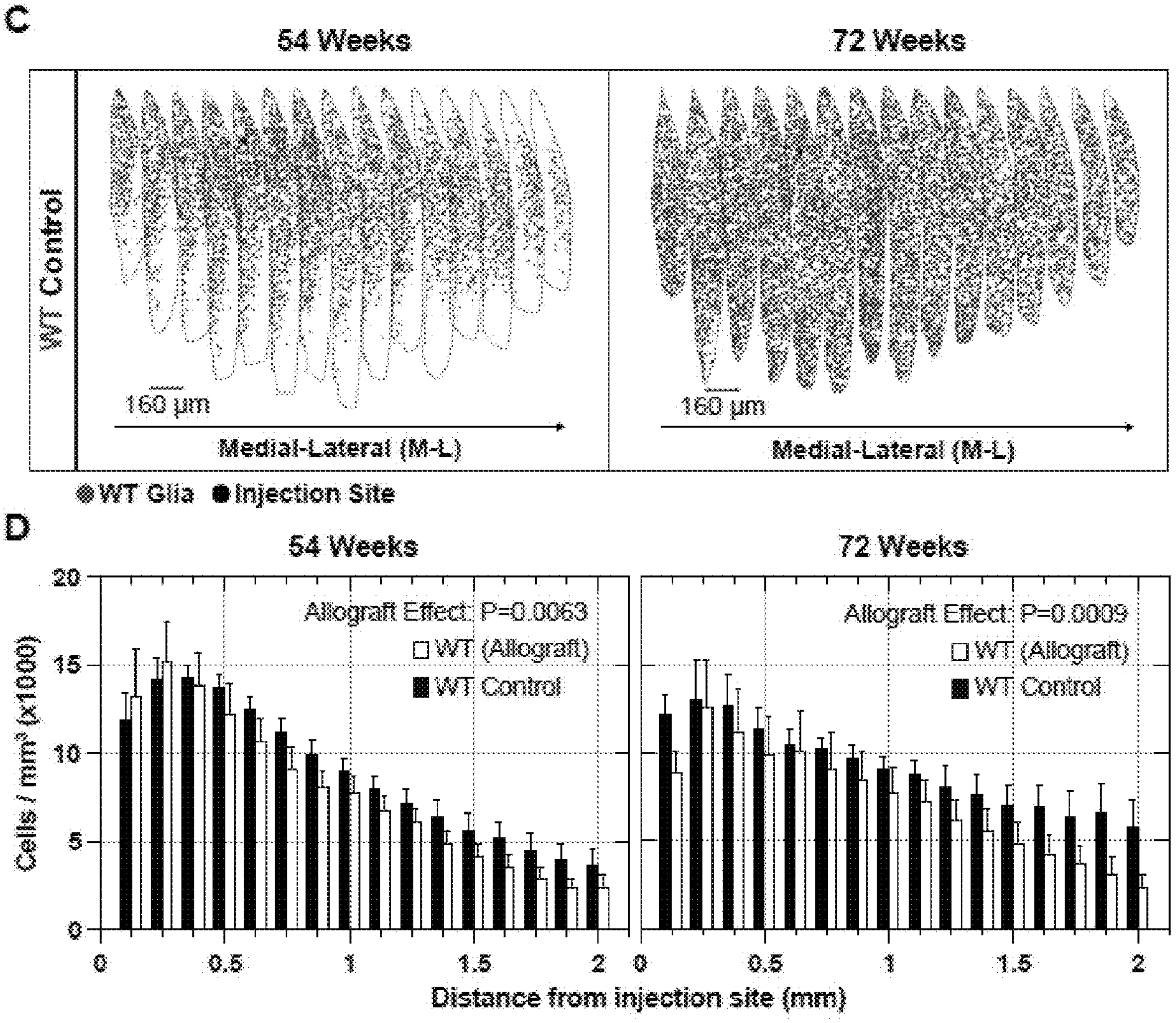

Interestingly, human-human glial replacement developed at a slower rate than human-murine glial replacement, as WT hGPCs implanted into naïve adult Rag1(−/−) mice expanded throughout the host striatum more broadly than those grafted into neonatally-chimerized adult Rag1(−/−) mice (FIG. 7; 54 weeks: P=0.14, 72 weeks: P=0.0009). These results indicate that competitive glial replacement develops with species-specific kinetics that differ between xenogeneic and allogeneic grafts.

Figure 8:
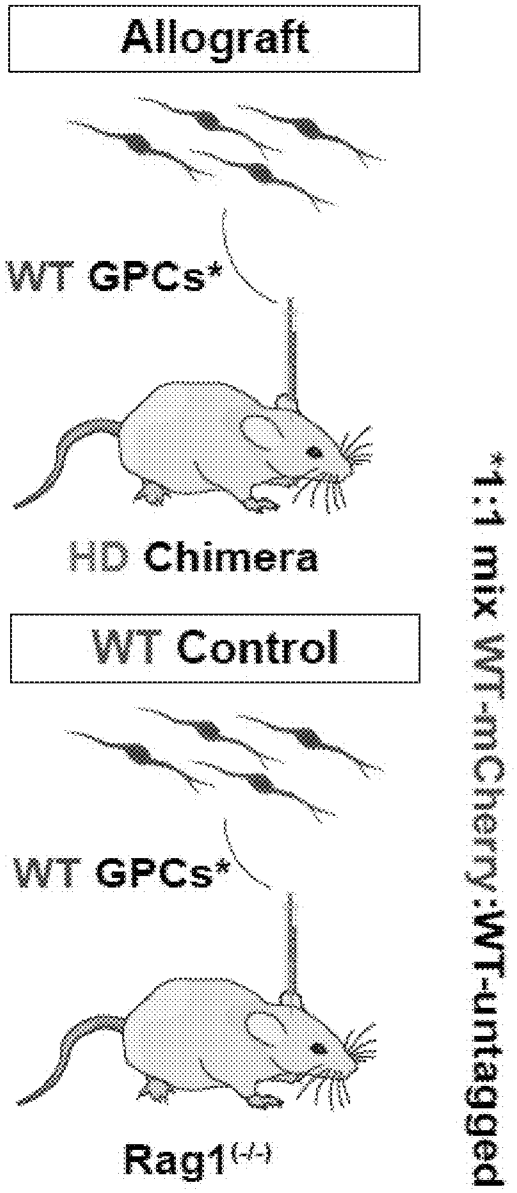
FIG. 8 illustrates the experimental design for mice that received a 1:1 mixture of mCherry-tagged (WT-mCherry) and untagged (WT-untagged) WT glia.
Figure 9:
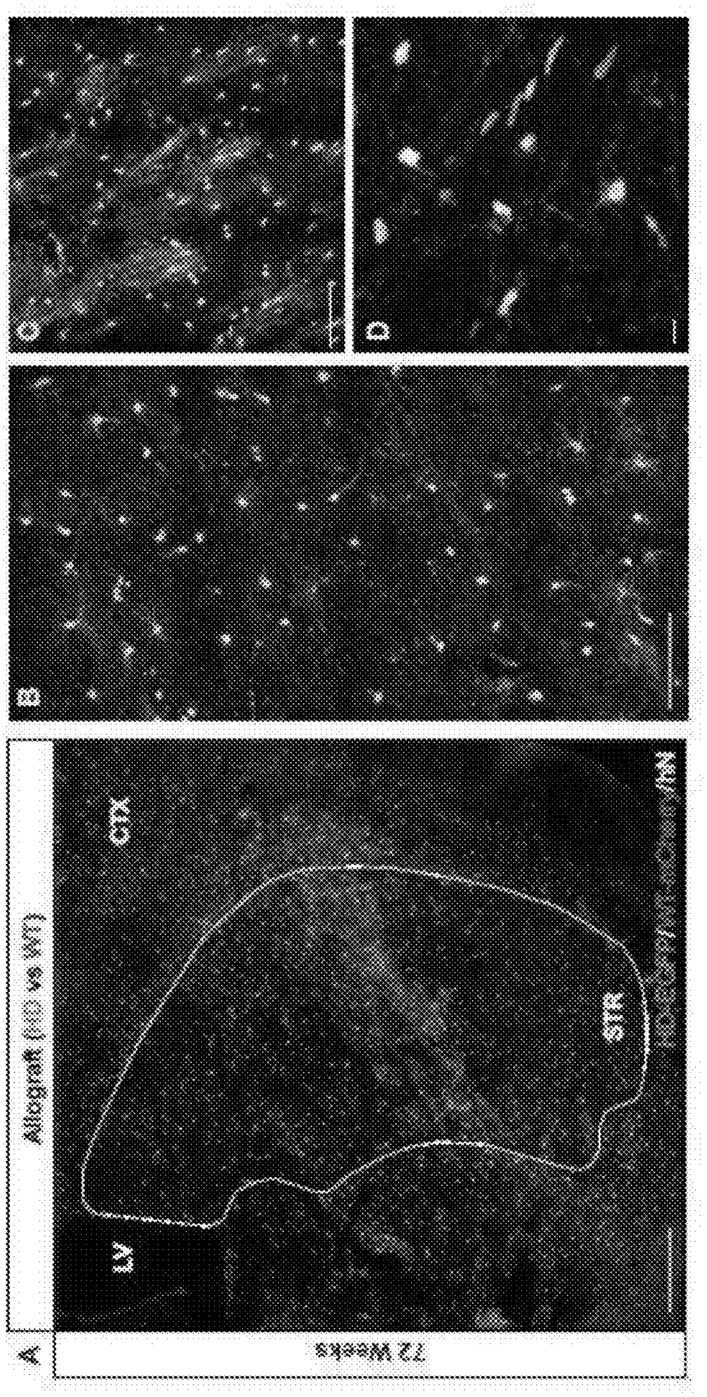
FIG. 9, Panels A-D show co-engrafted isogenic clones of wildtype glia thrive and admix while displacing HD glia. Panel A shows immunolabeling against human nuclear antigen (hN) shows that both WT-mCherry (mCherry+hN+, red, white) and WT-untagged (mCherry-EGFP-hN+, white) glia expanded within the previously humanized striatum, progressively displacing HD glia (EGFP+hN+, green, white). Scale bar 500 μm. Panel B shows vast homotypic domains were formed as mixed WT glia expanded and displaced resident HD glia. Scale bar 100 μm. Panel C shows isogenic WT-mCherry and WT-untagged were found admixing. Scale bar 100 μm. Panel D shows that within WT glia dominated domains, only more complex astrocyte-like HD glia could be found, typically within white matter tracts. Scale bar: 10 μm.
Figure 10:
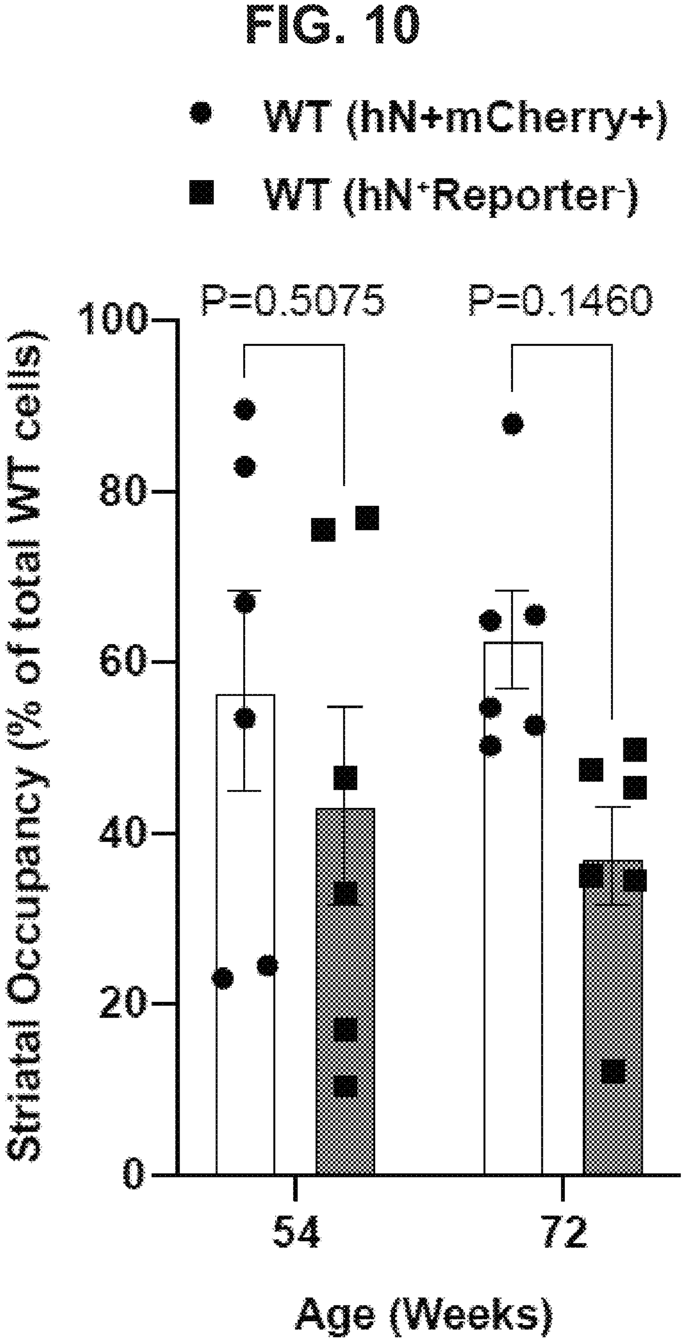
FIG. 10 shows quantification of the proportion of WT-mCherry and WT-untagged glia within the striatum showed no significant difference between the two populations at either quantified timepoint (n=6 for each timepoint); Two-way ANOVA with Šidák's multiple comparisons test; means±s.e.m.
Figure 11:
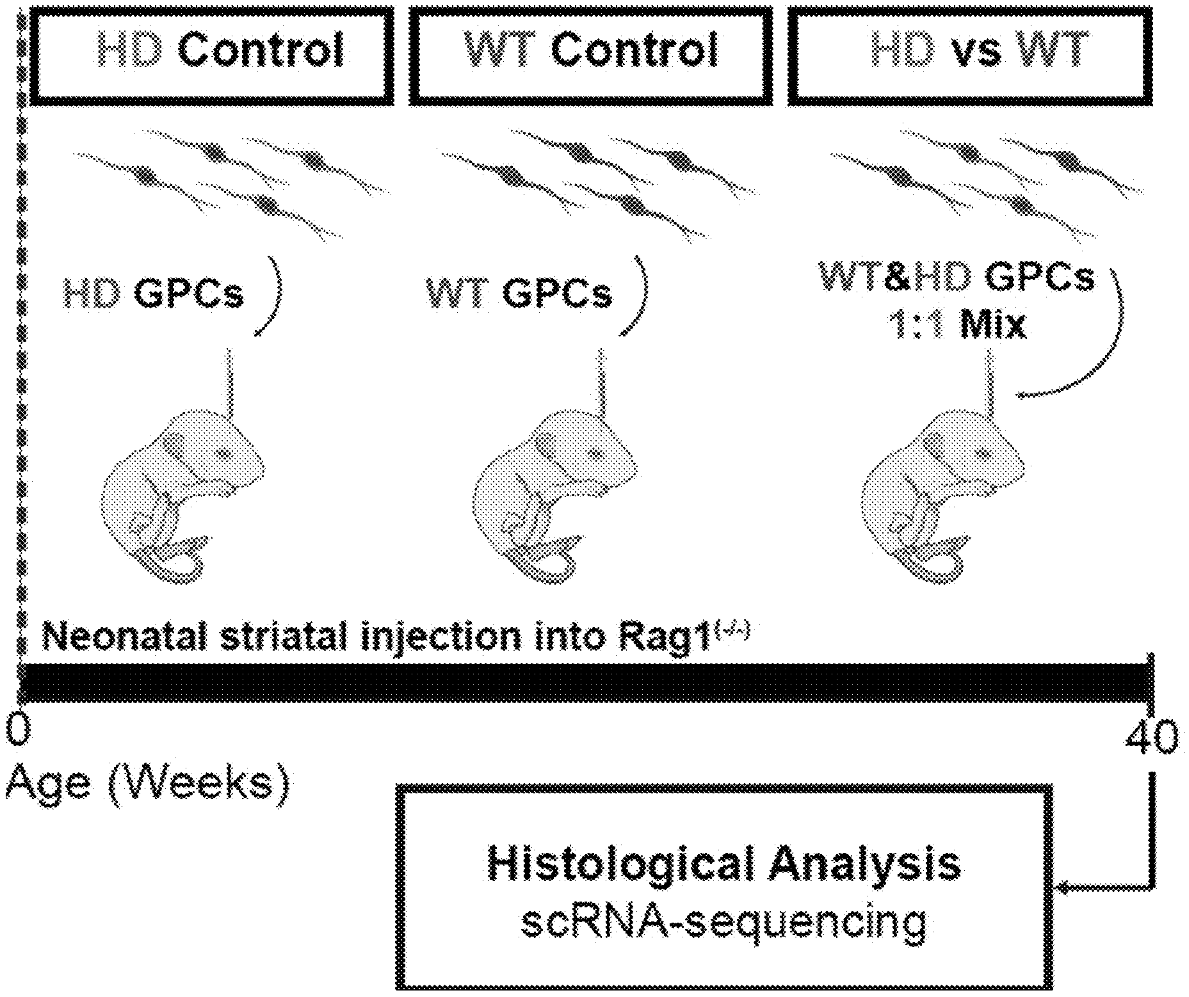
FIG. 11 illustrates the experimental design for co-engrafting WT and HT glia in neonatal mice.
Figure 12:
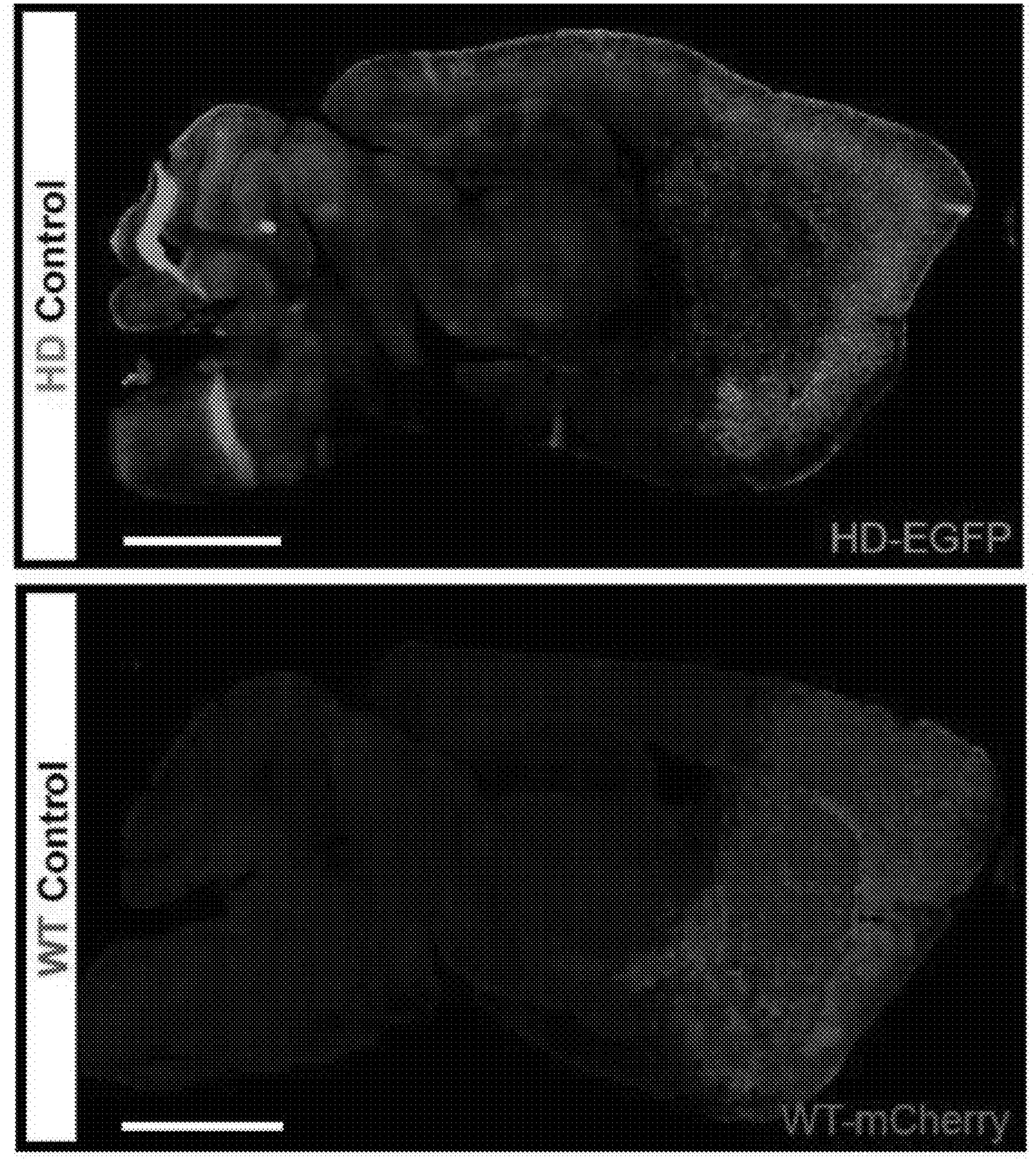
FIG. 12, Panels A-C show representative images of the proportion of WT and HD glia within the striatum in mice co-engrafted with WT and HT glia. The images show no significant growth advantage to either cell population; n=5; two-tailed paired t-test.
Figure 12:
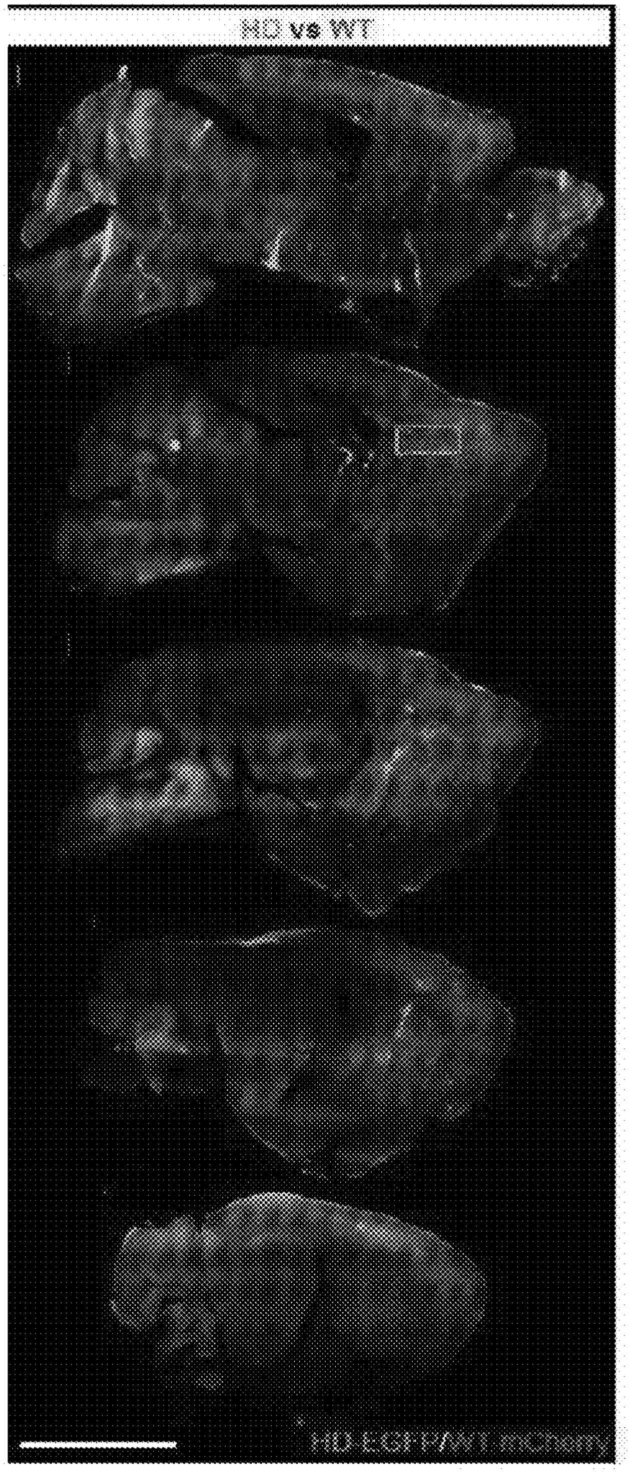
Figure 12:
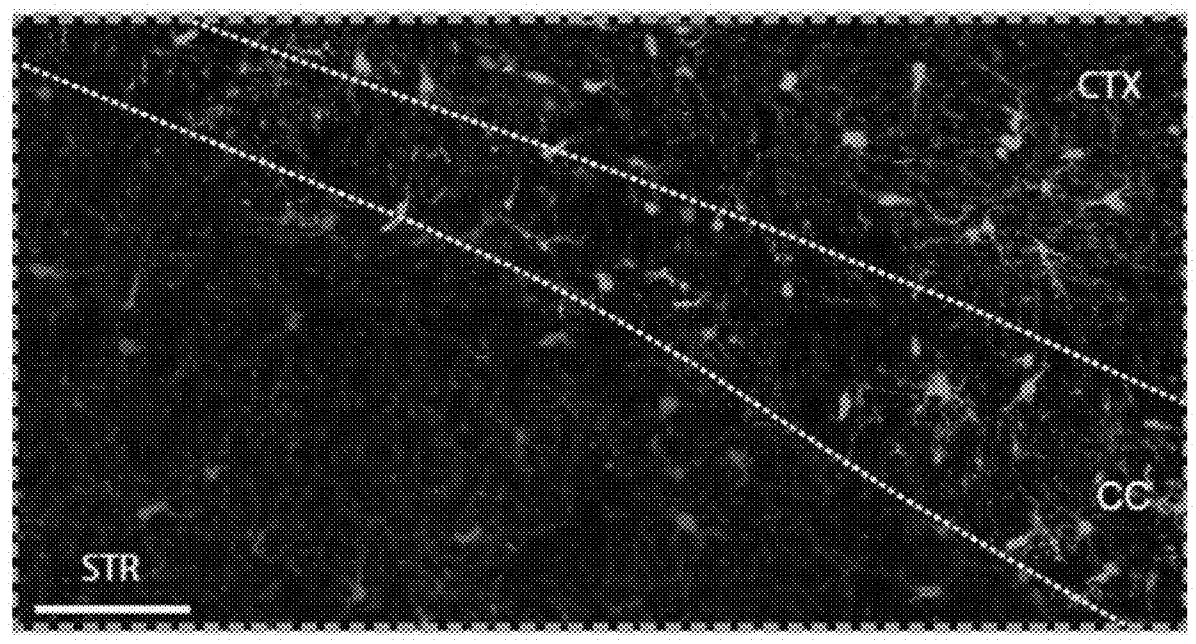
Figure 12:
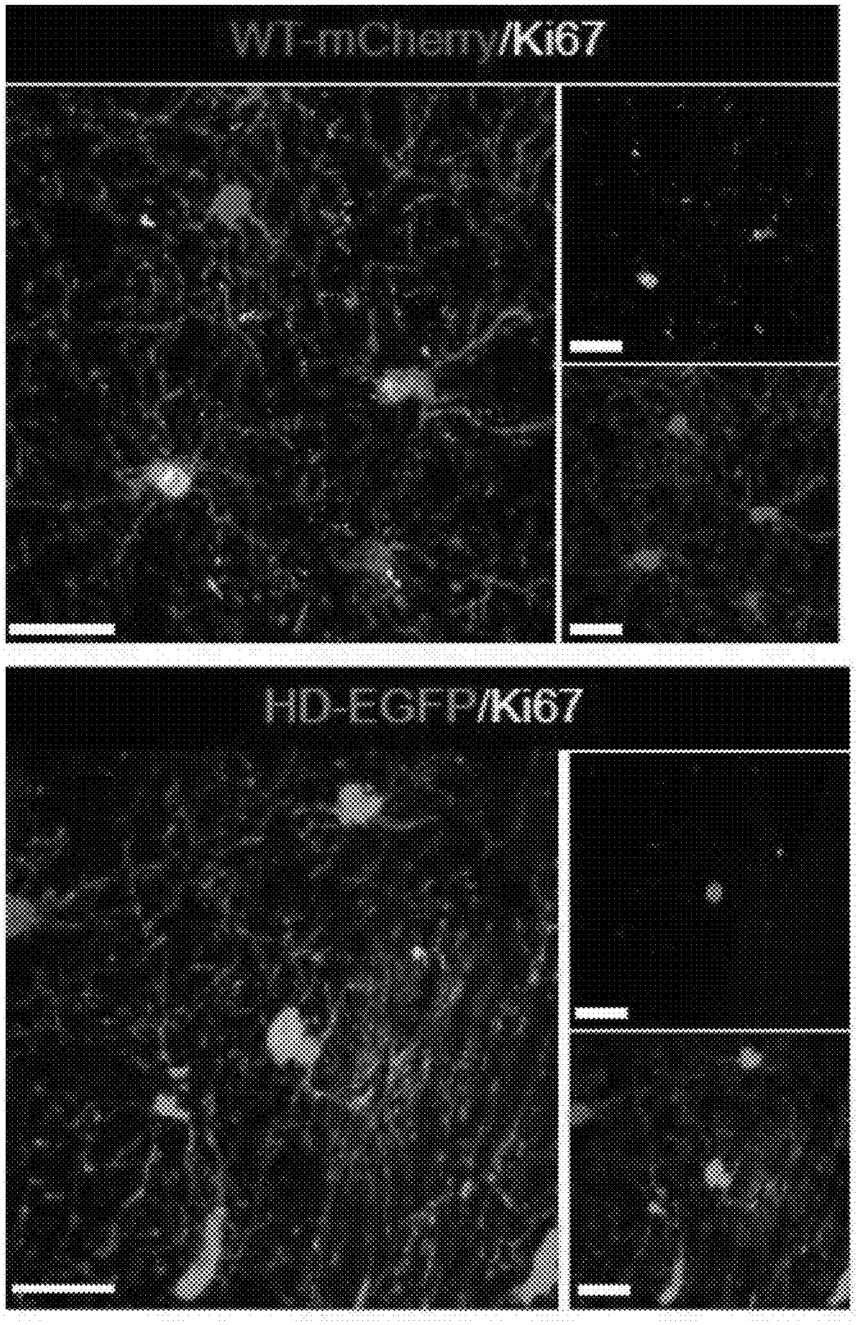
Figure 13:
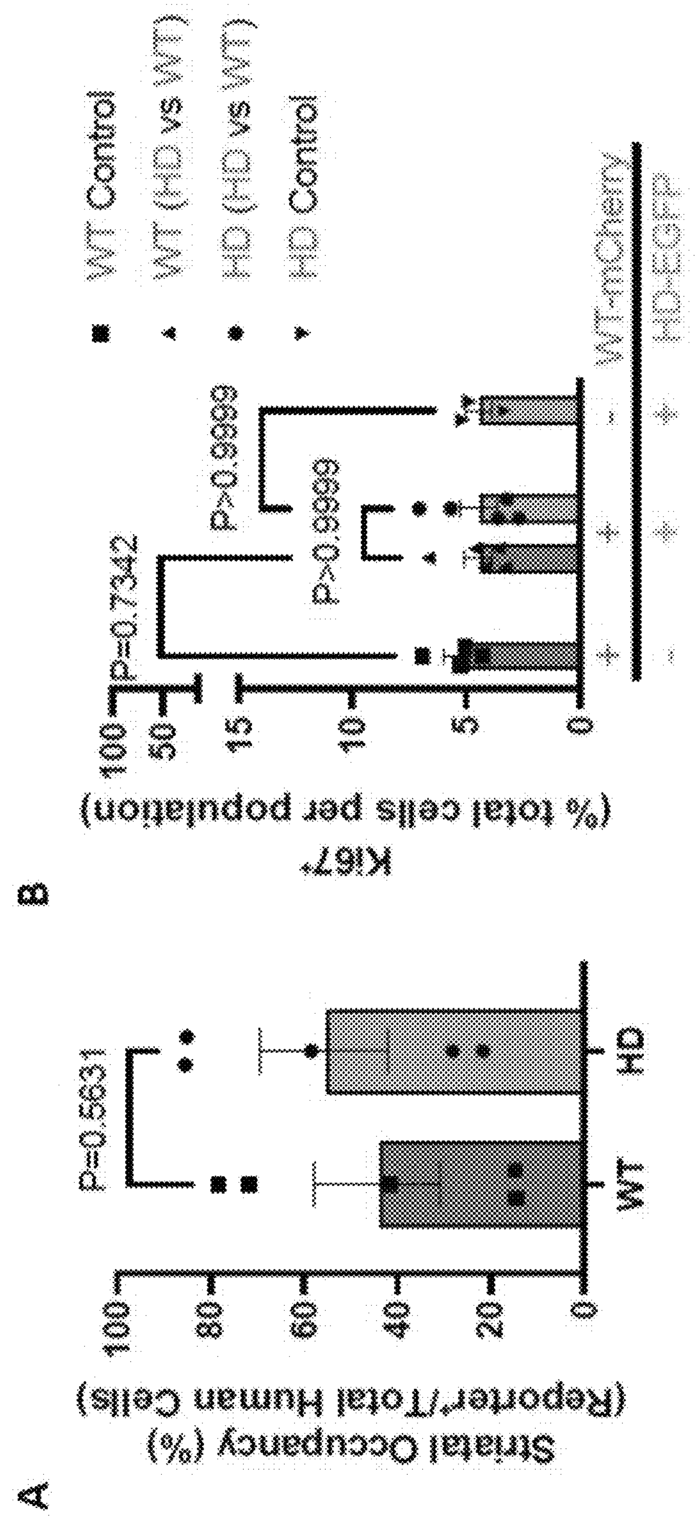
FIG. 13, Panels A-B demonstrates equal growth of neonatally engrafted WT and HD glia is sustained by equally proliferative Ki67+ (white) glial pools; HD Control-n=3; WT Control-n=4; HD vs WT-n=5; One-way ANOVA with Tukey's multiple comparisons test.
Figure 14:
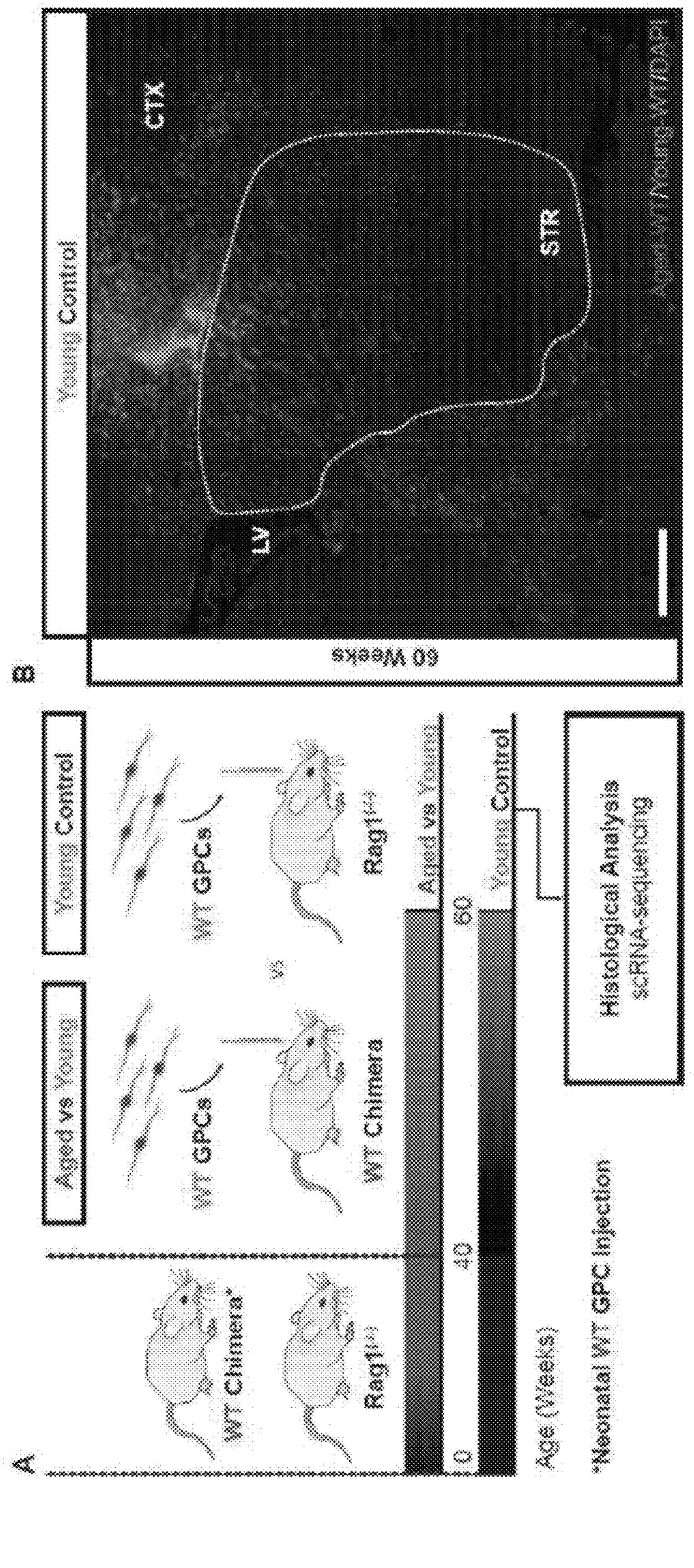
FIG. 14, Panels A-B demonstrate differences in cellular age are sufficient to drive human glial repopulation.

These results were not an artifact of off-target effects derived from gene editing nor fluorescent reporter expression toxicity, as co-engrafted hGPCs derived from WT-mCherry and their unmodified counterparts (WT-untagged) (FIG. 8), expanded equally within the striatum of HD chimeras and yielded analogous glial repopulation (FIG. 9 and FIG. 10; 54 Weeks—P=0.5075—72 Weeks—P=0.1460). As such, analysis done in (FIG. 4) and (FIG. 6 and FIG. 7) reports samples from both experimental paradigms. Remarkably, while WT and HD glia strongly segregated from each other, the two isogenic clones of WT glia could be found admixing (FIG. 9), indicating that active recognition precedes competitive elimination of HD glia from the tissue.

Example 5: Human WT Glia Enjoy a Proliferative Advantage Relative to Resident HD Glia Striatal humanization by HD glia progressed with a gradual exhaustion of their proliferative cell pool as they expanded and matured within the tissue (FIG. 1, Panel D). Therefore, whether the selective expansion of younger WT glia within the HD striatum was sustained by a difference in proliferative capacity between the two populations was tested. The temporal expression of Ki67 in both WT and HD glial populations was assessed as competitive striatal repopulation unfolded.

At both 54 and 72 weeks of age, the mitotic fraction of implanted WT glia was significantly larger than that of resident HD glia (FIG. 4, Panels I and J, 54 weeks-P<0.0001, 72 weeks-P=0.009). These data indicate that the repopulation of the HD striatum by WT glia was fueled by a relatively enriched proliferative cell pool. It's important to note that while this proliferative advantage became less pronounced as the cells aged, it was maintained throughout the experiment. With this in mind, the sustained proliferative advantage of implanted WT glia over their HD counterparts, should provide a driving force for continuous striatal repopulation beyond the observed experimental timepoints.

Figure 19:
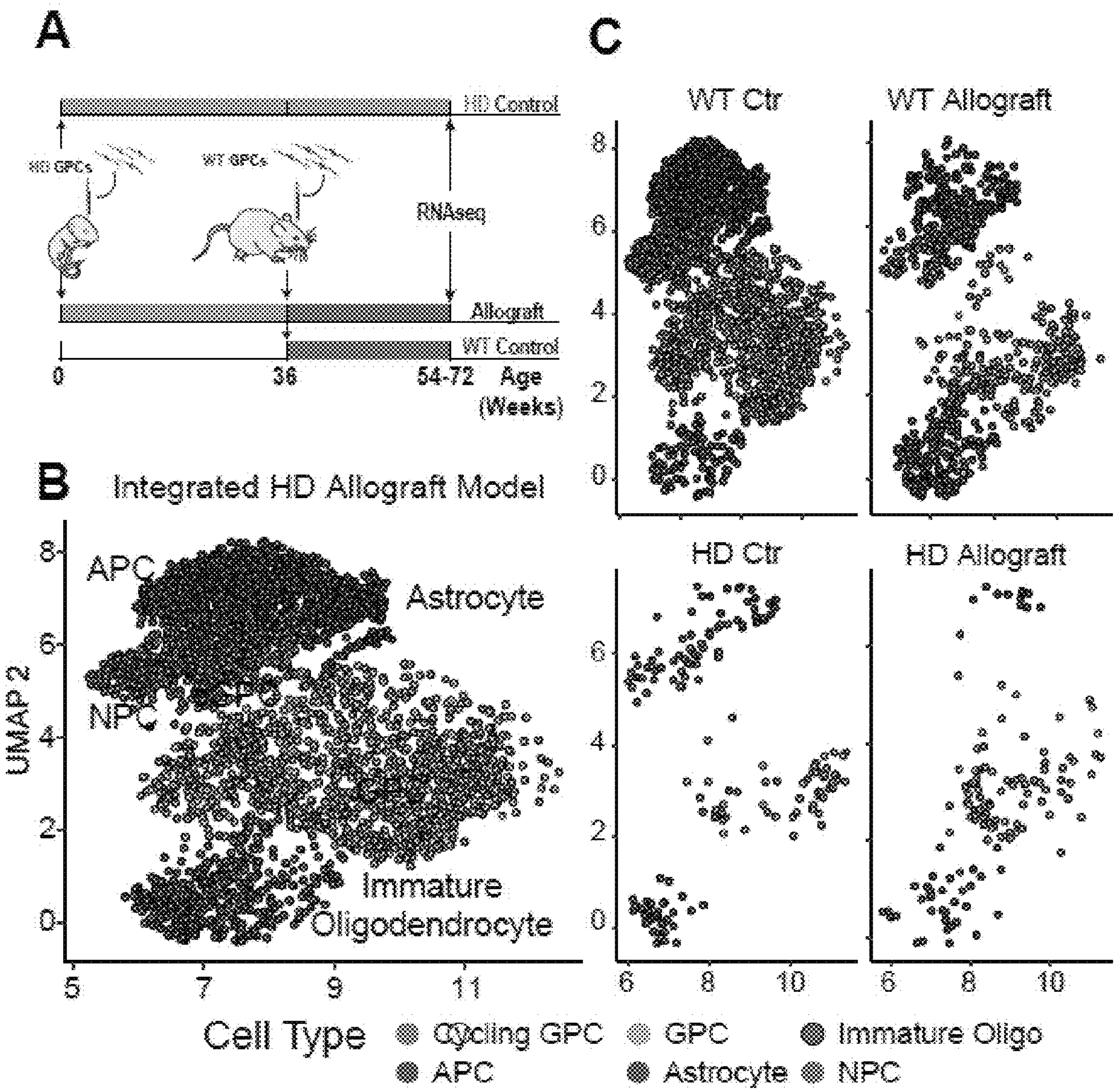
FIG. 19 shows WT glia acquire a dominant competitor transcriptional profile in the face of resident HD glia. Panel A. Experimental design. Panels B and C. Uniform manifold approximation projection (UMAP) visualization of the integrated (Panel B) and split by group (Panel C) scRNA-seq data identifies six major cell populations. Panel D. Stacked bar plot proportions of cell types in each group. Panel E. Cell cycle analysis notched box plots of cycling GPCs and GPCs in the G2/M phase. The box indicates the interquartile range, the notch indicates the 95% confidence interval with the median at the center of the notch, and the error bars represent the minimum and maximum non-outlier values. Panel F. Venn diagram of pairwise differentially expressed GPC genes (Log2 fold change>0.15, adjusted p-value<0.05). Panel G. Curated ingenuity pathway analysis of genes differentially expressed between GPC groups. The size of circles represent p-value while the shading indicates activation Z-Score with red being more active in the upper group and green being more active in the lower group. Panel H. Heatmap of curated pairwise differentially expressed GPC genes. Panel I-Violin plots of pairwise differentially expressed GPC ribosomal gene log 2 fold changes. Comparisons between groups in Panel E utilized Dunn tests following a Kruskal-Wallis test with multiple comparisons adjusted via the Benjamini-Hochberg method. *=<0.05, <0.01, *=<0.001, ****=<0.0001 adjusted p-value.
Figure 19:
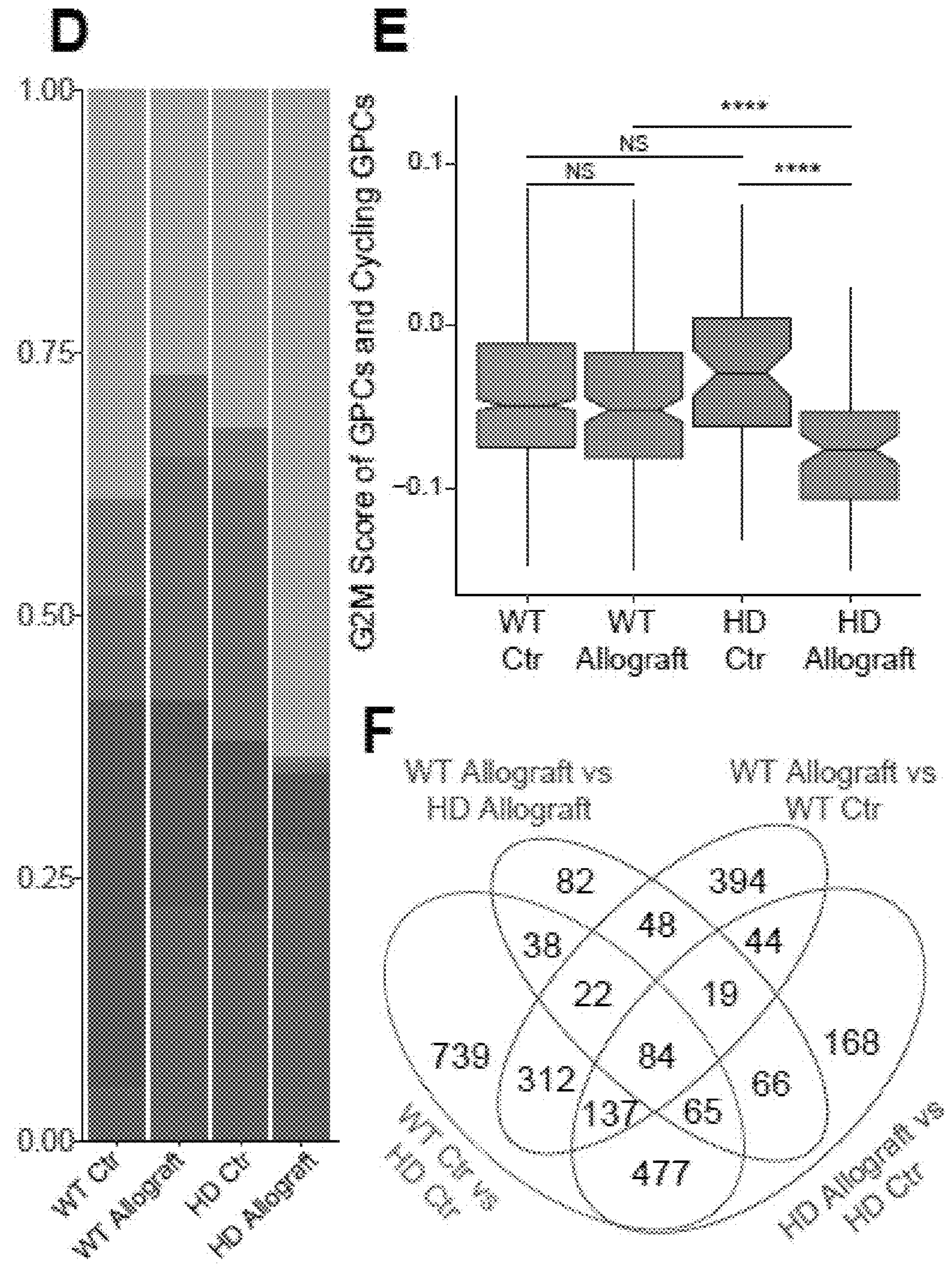
Figure 19:
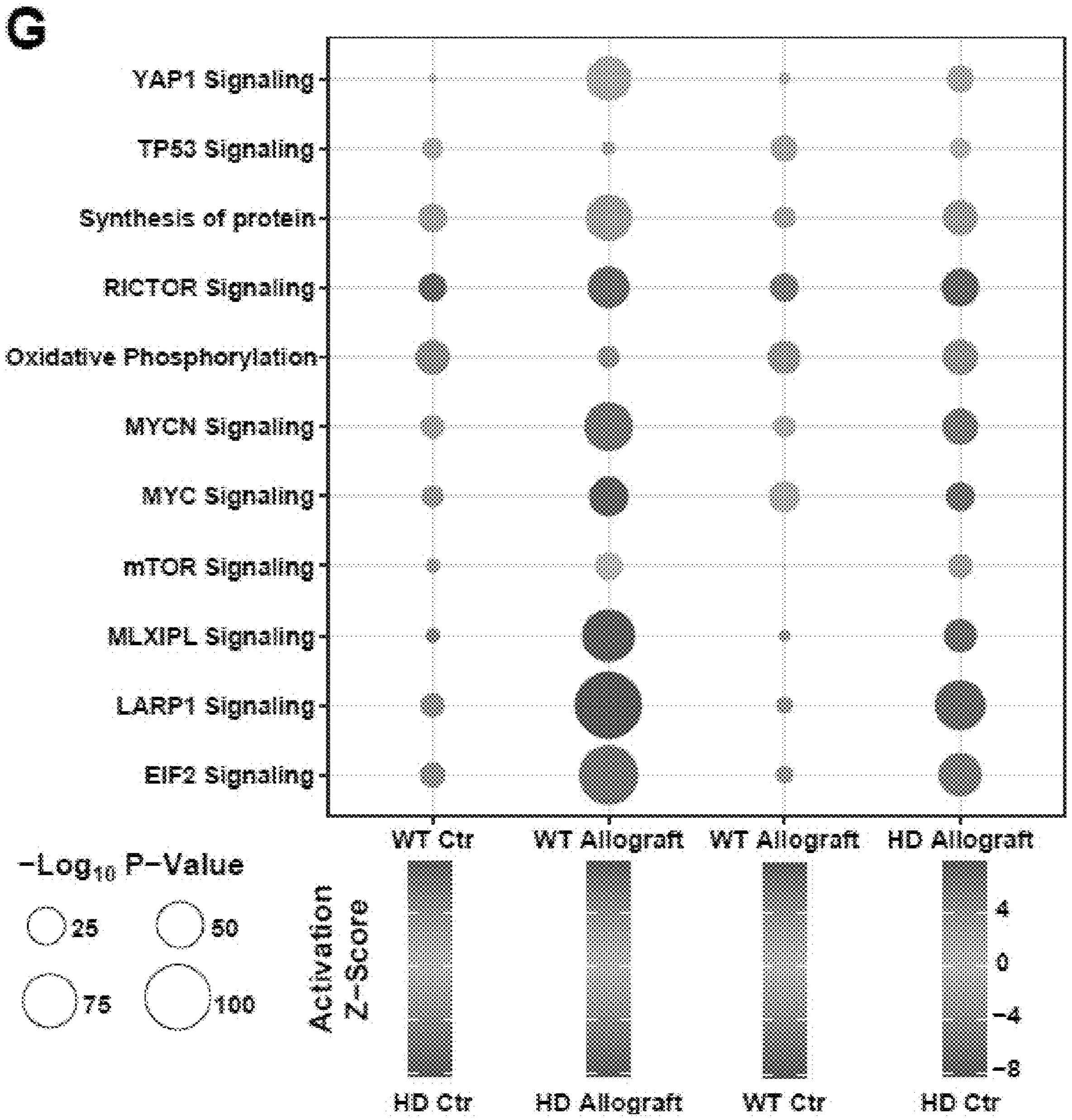
Figure 19:
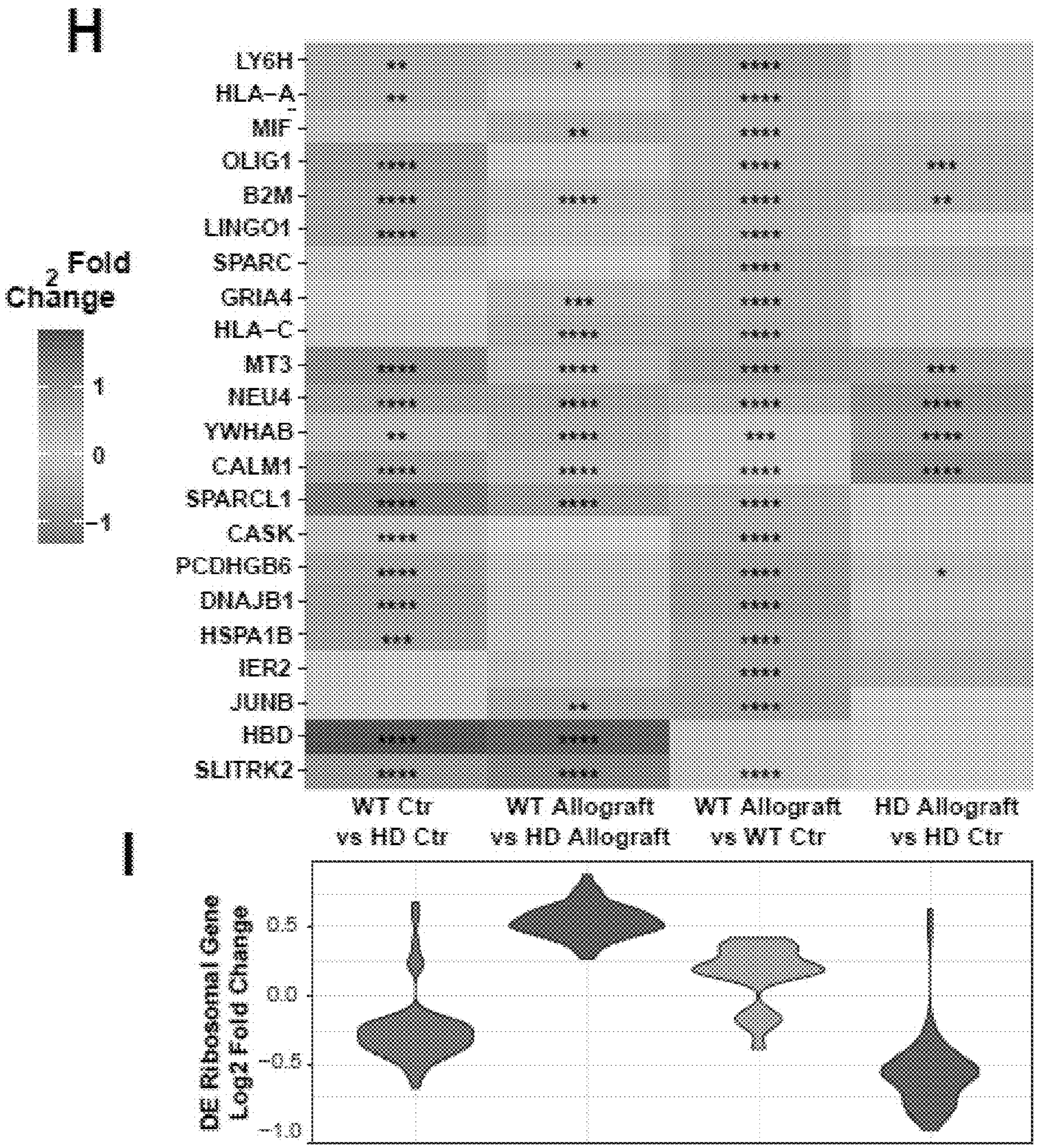

Example 6: Human WT glia assume a dominant competitor profile when encountering HD glia Having established that implanted WT hGPCs effectively colonize the HD glial chimeric striata at the expense of the resident mHTT-expressing glia, it was next sought to define the molecular signals underlying their competitive dominance. To that end, the transcriptional profiles of WT and HD human glia isolated from the striata of chimeras in which the two cell populations were co-resident and competing were analyzed, as well as from their respective controls in which one or the other was transplanted without the other, using single cell RNA-sequencing (scRNA-seq;

10X Genomics, v3.1 chemistry) (FIG. 19, Panel A). Following integration of all captures and aligning against human sequence, Louvain community detection revealed six major populations of human glia; these included hGPCs, cycling hGPCs, immature oligodendrocytes (iOL), neural progenitor cells (NPCs), astrocytes, and their intermediate progenitors (astrocyte progenitor cells, APCs) (FIG. 19, Panels B-D). Within these populations, cell cycle analysis predicted a higher fraction of actively proliferating G2/M phase cells in competing WT cells compared to their HD counterparts (FIG. 19, Panel E), aligning with the histological observations (FIG. 4, Panel J). To proceed, study focused on hGPCs as the primary competing population in the model. Pairwise differential expression revealed discrete sets of differentially expressed genes across groups (FIG. 19, Panel F), and subsequent functional analysis with Ingenuity pathway analysis (IPA) within the hGPC population revealed numerous salient terms pertaining to their competition (FIG. 19, Panel G).

During competition, it was found WT GPCs activate pathways driving protein synthesis, whereas HD GPCs were predicted to downregulate them. Predicted upstream transcription factor activation identified YAP1, MYC, and MYCN—conserved master regulators of cell growth and proliferation—as significantly modulated across experimental groups. Importantly, YAP1 and MYC targets were found to be selectively down-regulated in competing HD GPCs relatively to their controls (FIG. 19, Panel G). Notably, this down-regulation was attended by a marked repression of ribosomal encoding genes (FIG. 19, Panel I). Conversely, competing WT hGPCs showed an upregulation of both YAP1 and MYC targets, as well as in the expression of ribosomal encoding genes, relative to controls (FIG. 19, Panels G-H). As such, these data suggest that the implanted WT hGPCs actively assumed a competitively dominant phenotype upon contact with their HD counterparts, to drive the latter's local elimination while promoting their own expansion and colonization.

Example 7: Age Differences Drive Competitive Human Glial Repopulation

Figure 17:
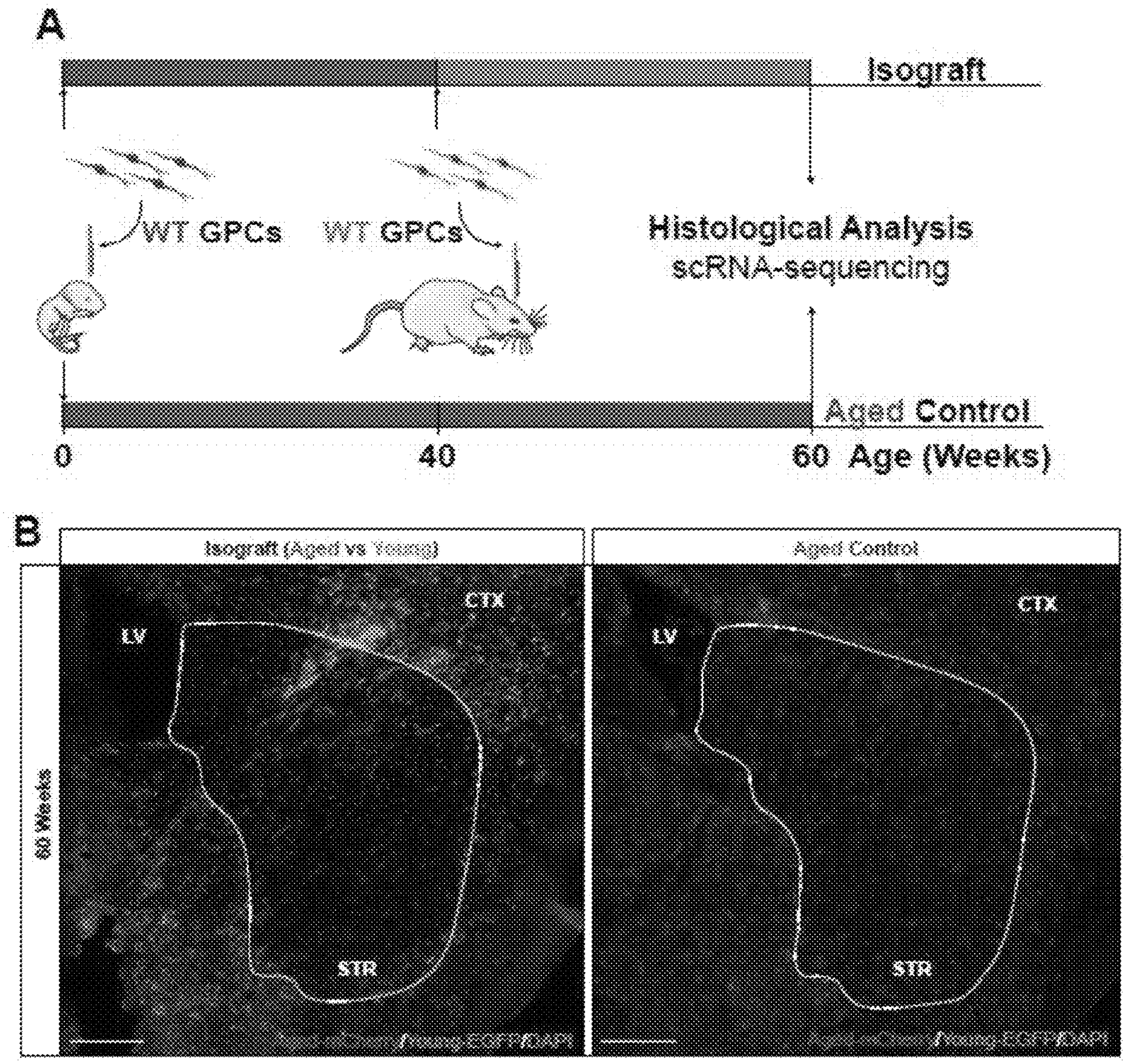
FIG. 17, Panels A-E show differences in cellular age are sufficient to drive competitive glial repopulation. shows differences in cell age are sufficient to drive competitive repopulation of humanized striata. Panel A. Experimental design and analytical endpoints. Panel B. Engraftment of younger WT glia (EGFP+, green) into the striatum of WT chimeras yielded selective replacement of their aged counterparts (mCherry+, red). Dashed outlines demarcate the striatal regions within which human cells were mapped and quantified. Panel C. WT chimeric control, engrafted only at birth. Panel D. Rendered examples of mapped striata. Volumetric quantification shows that the younger WT glia replace their older isogenic counterparts as they expand from their injection site; Panel E. Aged vs. Young (Isograft), n=3. Their advance tracked the progressive elimination of aged WT glia from the tissue, relative to control WT chimeras (Aged control); Panel F. Aged (Isograft) vs. Aged (Control) n=3 each; 2-way ANOVA with Šidák's multiple comparisons test; Interactions or main effects are shown as numerical P values, while post-hoc comparisons are shown as: ** P<0.0001, * P<0.001, ** P<0.01, *P<0.05; data presented as means±SEM. Panel G. At the interface between young and aged WT glia, a higher incidence of Ki67+ (white) cells can be seen within the younger population. Dashed square represents inset color split (H). Panel I. Quantification of Ki67+ cells shows that younger WT glia are significantly more proliferative than their aged counterparts; n=3 for all experimental groups; One-way ANOVA with Šidák's multiple comparisons test; data are shown as means±SEM with individual data points. Panels B-C. STR, striatum (caudate-putamen); LV, lateral ventricle; CTX, cortex.). Scale: Panel B, 500 μm; Panel C, 100 μm; Panel E-100 μm; Panel G-50 μm.
Figure 17:
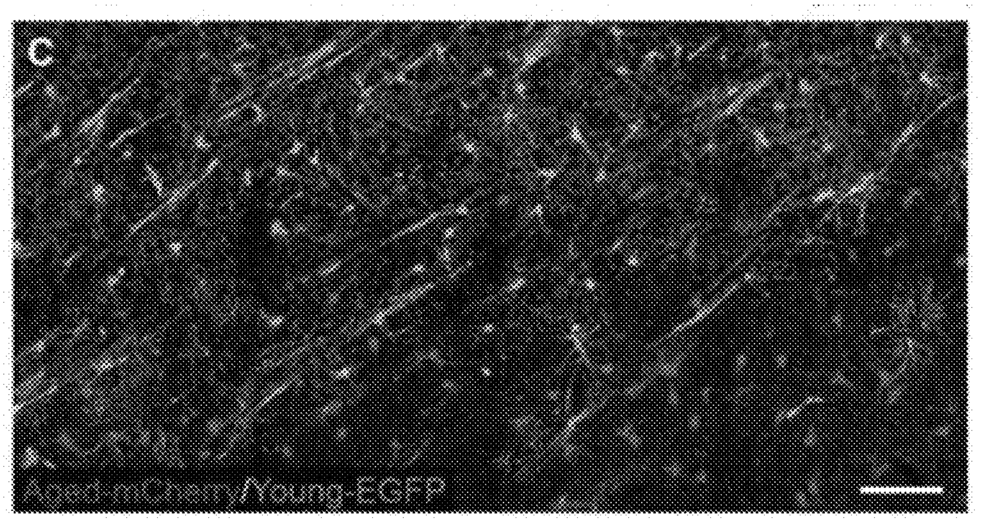
Figure 17:
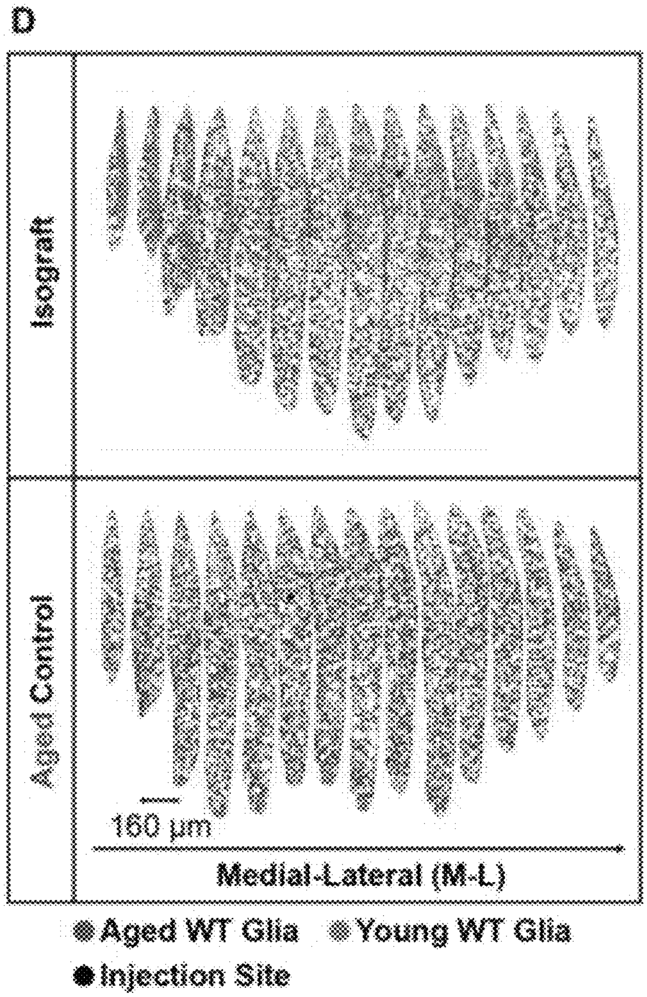
Figure 17:
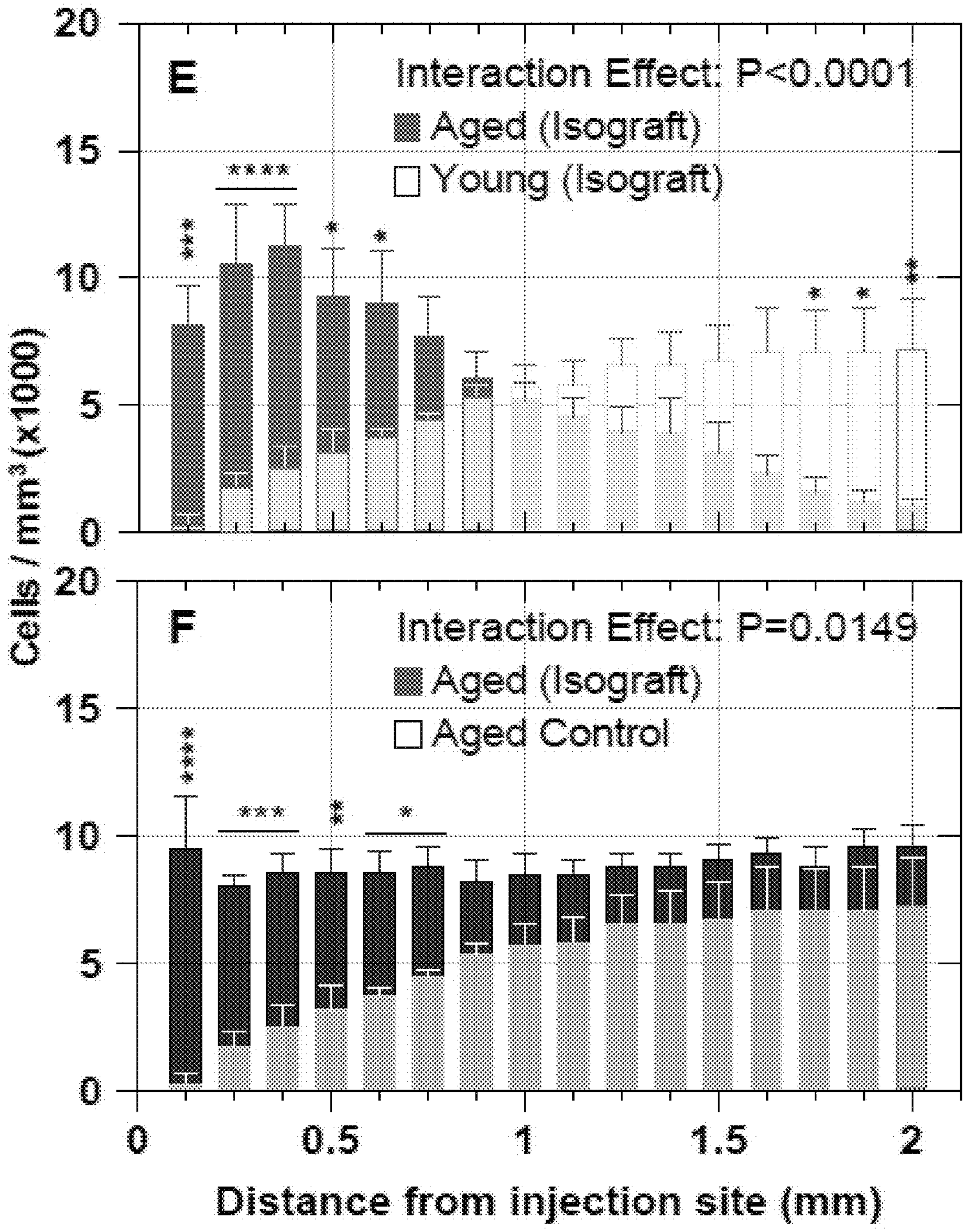
Figure 17:
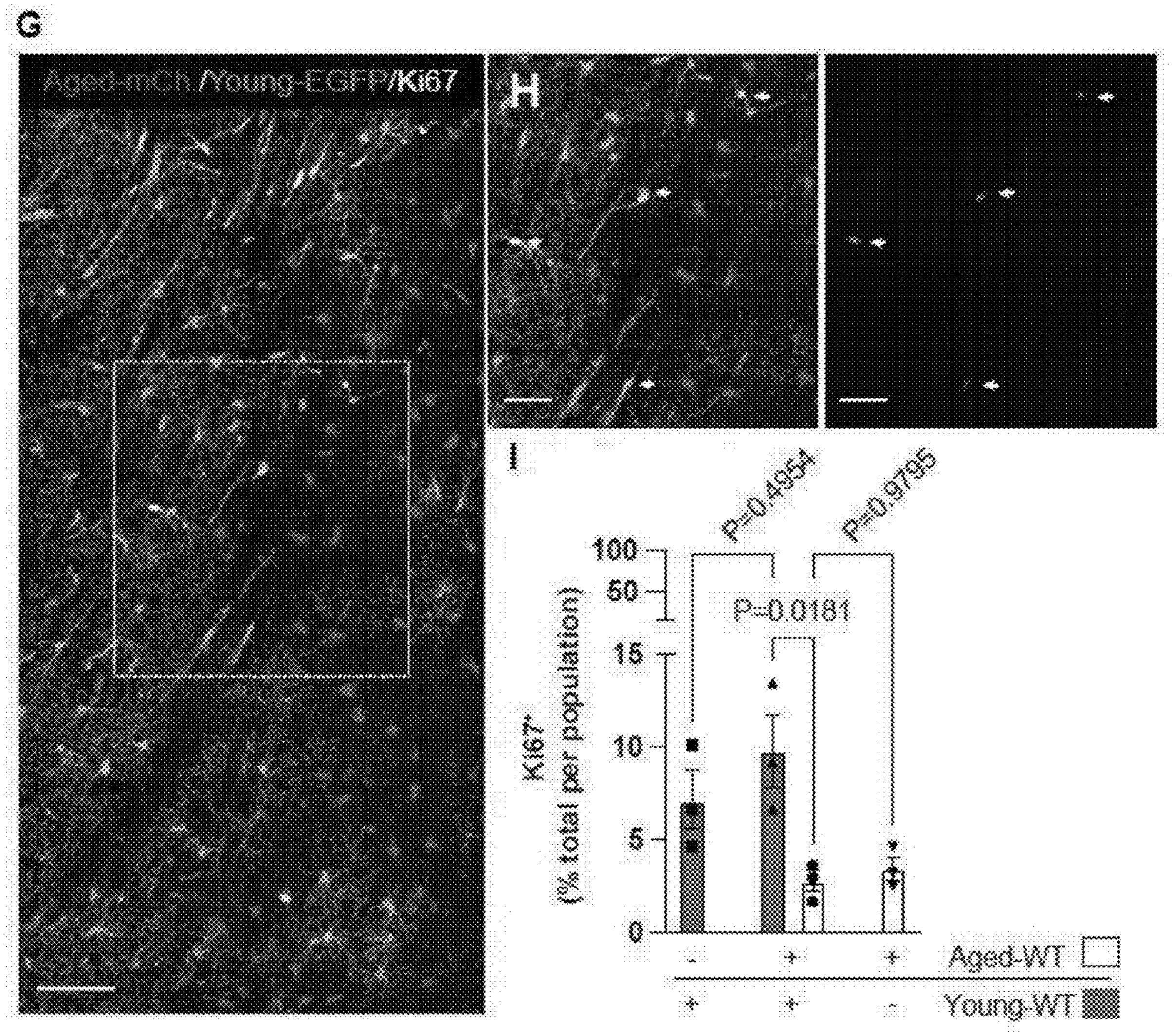

Since WT cells transplanted into adult hosts were fundamentally younger than the resident host cells that they displaced and replaced, it was next asked if differences in cell age, besides disease status, might have contributed to the competitive success of the late donor cells. To that end, engrafted hGPCs newly produced from WT hESCs were engineered to express EGFP into the striata of 40 week-old adult glial chimeras, which had been perinatally engrafted with hGPCs derived from mCherry-tagged, otherwise isogenic WT hESCs (FIG. 17, Panel A). The expansion of the transplanted cells histologically was monitored, so as to map the relative fitness and competitive performance of these isogenic, but otherwise distinctly aged pools of hGPCs.

The expansion of implanted WT glia within the striatum of WT chimeras was strikingly similar to their expansion in the striata of HD chimeras (FIG. 4). Following engraftment, the younger WT glia rapidly infiltrated the previously humanized striatum, progressively displacing their aged counterparts as they expanded from their implantation site, ultimately yielding substantial recolonization of the tissue (FIG. 17, Panels B-D and E; $P<0.0001$). Their expansion was paralleled by the local elimination of aged WT glia (FIG. 17, Panels B-D and F; $P<0.0001$), which was also marked by a discrete advancing front, behind which few already-resident WT glia could be found (FIG. 17, Panel C). Accordingly, it was also noted that the mitotic fraction of implanted WT glia was significantly larger than that of their resident aged counterparts (FIG. 17, Panels G-I; $P=0.018$). Together, these data indicated that the repopulation of the human WT glial chimeric striatum by younger isogenic hGPCs was attended by the replacement of the older cells by their younger counterparts, fueled in part by the relative expansion of the younger, more mitotically active cell population.

Figure 20:
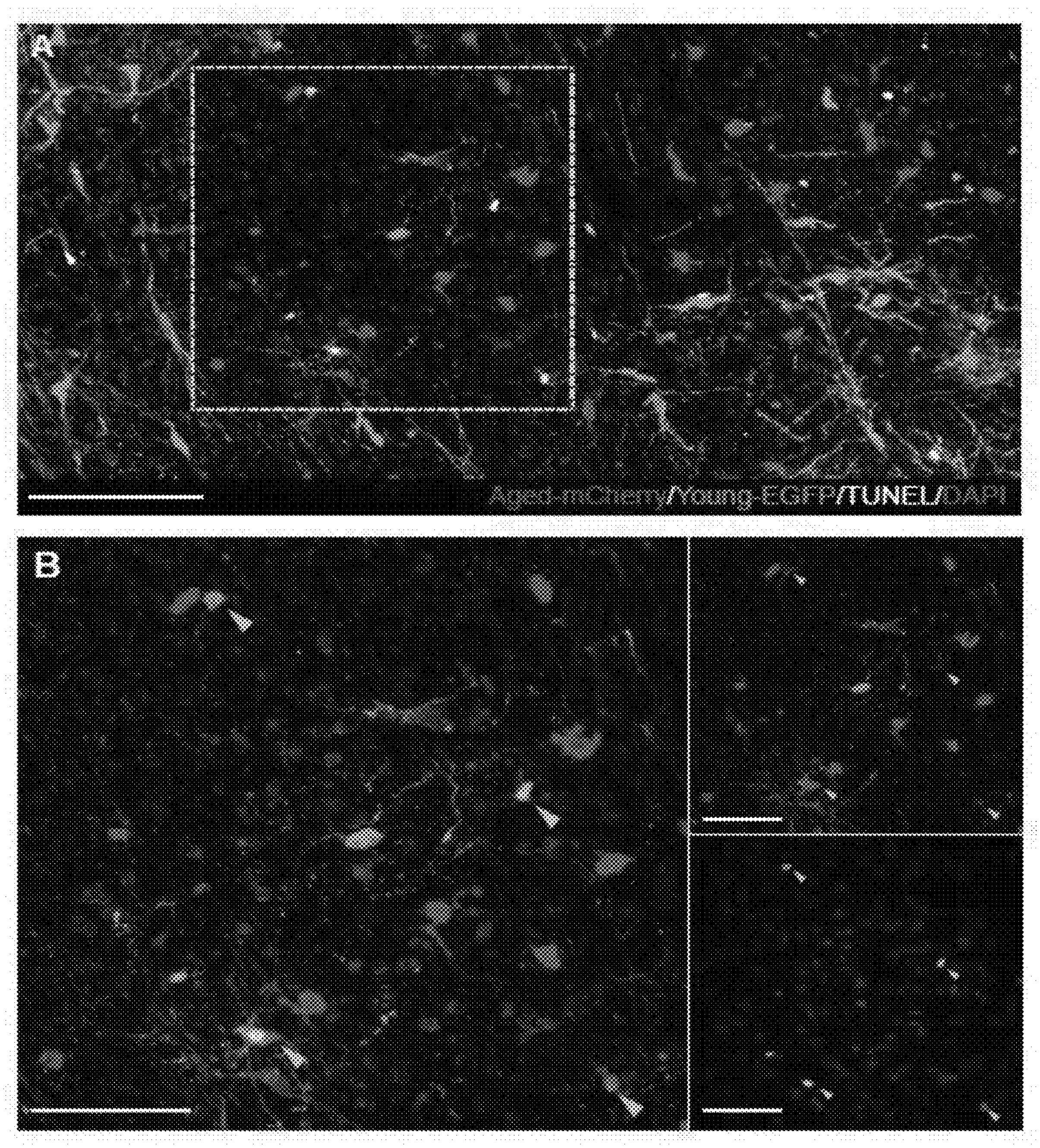
FIG. 20 shows aged human glia are eliminated by their younger counterparts through induced apoptosis. Panel A. At the border between young (EGFP+, green) and aged WT glia (mCherry+, red), a higher incidence of apoptotic TUNEL+ (white) cells are apparent in the aged population. Panel B. Higher magnification of a competitive interface between these distinct populations shows resident glia selectively undergoing apoptosis. Panel C. Quantification of TUNEL+ cells shows significantly higher incidence of TUNEL+ cells among aged resident WT glia, relative to both their younger isogenic counterparts, and to aged WT chimeric controls not challenged with younger cells. Quantification was performed on pooled samples from 60 and 80 weeks timepoints (n=5 for all experimental groups). One-way ANOVA with Šidák's multiple comparisons test; data are shown as means±SEM with individual data points. Scale: Panel A, 100 μm; Panel B, 50 μm.
Figure 20:
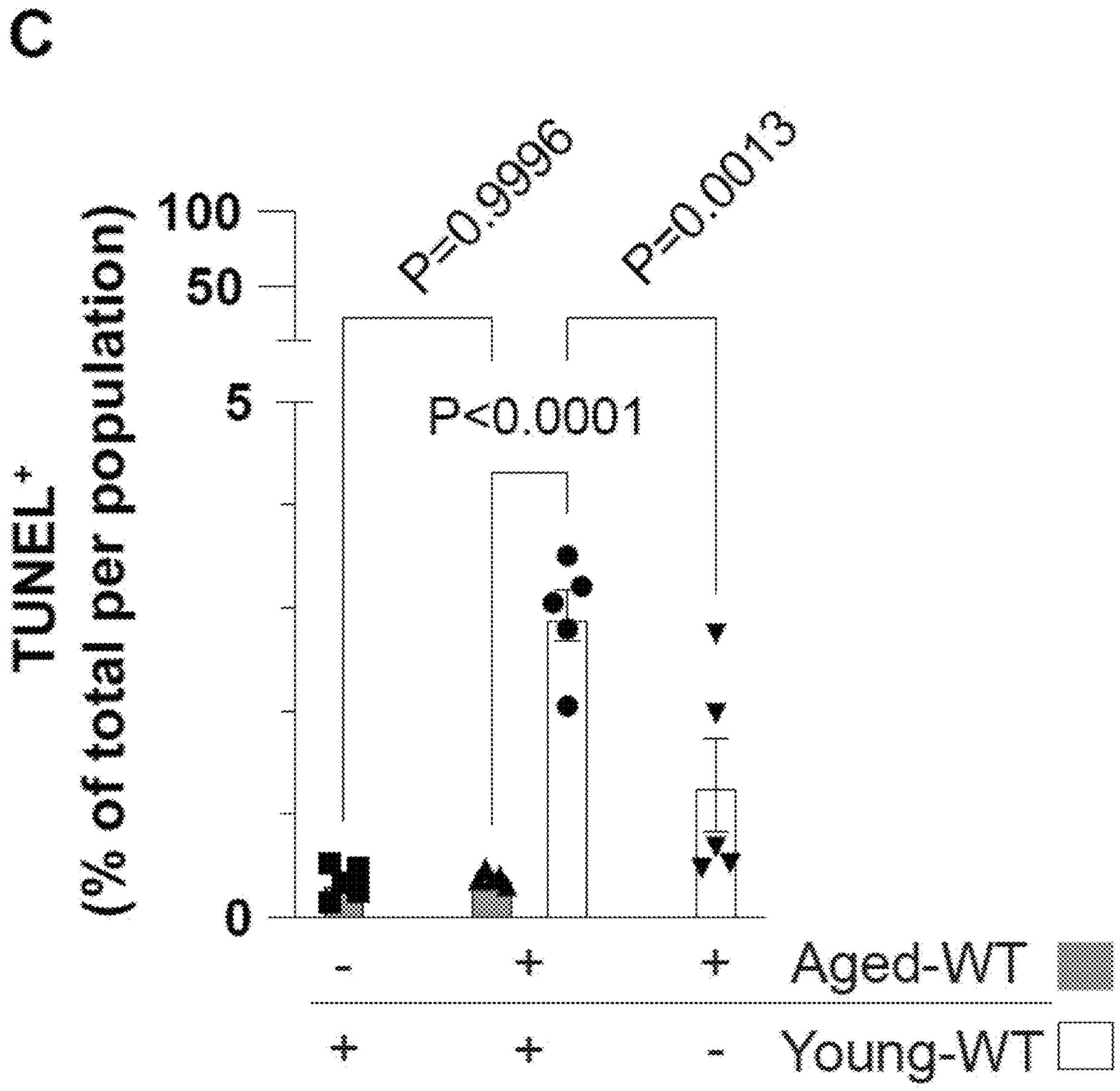

Example 8: Young Cells Replace their Older Counterparts Via the Induction of Apoptosis Since younger glia appeared to exert clear competitive dominance over their older counterparts, it was next asked whether the elimination of the older glia by younger cells occurred passively, as a result of the higher proliferation rate of the younger cells leading to the relative attrition of the older residents during normal turnover, or whether replacement was actively driven by the induction of programmed cell death in the older cells by the more fit younger cells. To address this question, the TUNEL assay was used to compare the rates of apoptosis in aged and young WT glial populations as they competed in the host striatum, as well as at their respective baselines in singly-transplanted controls. It was found that as competitive repopulation unfolded, that aged WT glia underwent apoptosis at a markedly higher rate than their younger counterparts (FIG. 20, Panels A-C; $P<0.0001$). Critically, the increased apoptosis of older, resident glia appeared to be driven by their interaction with younger cells, since a significantly higher proportion of aged glia was found to be apoptotic in chimeras transplanted as adults with younger cells, than in controls that did not receive the later adult injection (FIG. 30, Panel C; $P=0.0013$). These data suggest that aged resident glia confronted by their younger counterparts are actively eliminated, at least in part via apoptosis triggered by their encounter with the younger hGPCs, whose greater relative fitness permitted their repopulation of the chimeric host striatum.

Figure 21:
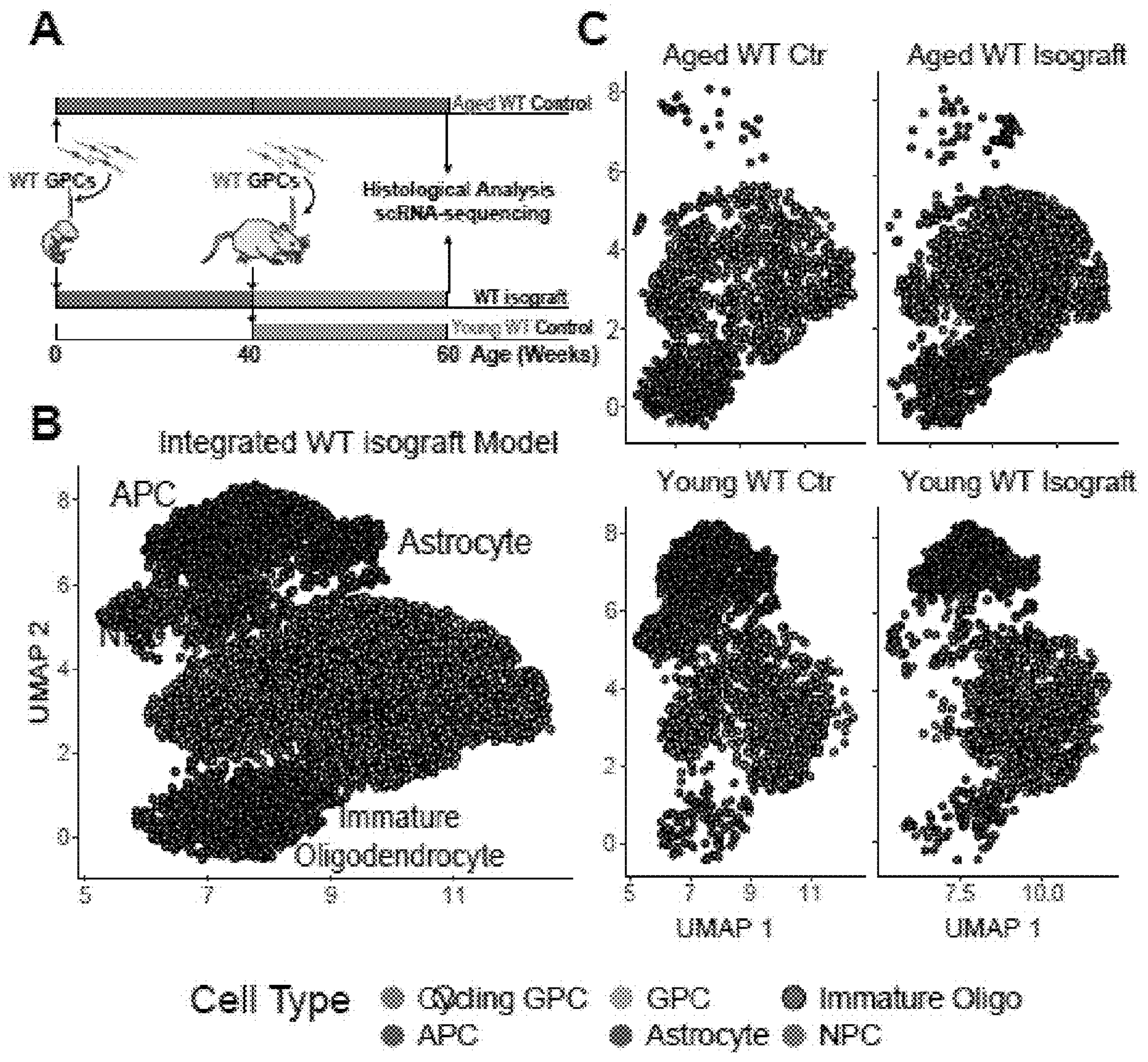
FIG. 21 shows WT glia acquire a dominant transcriptional profile when confronting their aged counterparts. Panel A. Experimental design. Panel B-C. Uniform manifold approximation projection (UMAP) visualization of the integrated (Panel B) and split by group (Panel C) scRNA-seq data identifies six major cell populations. Panel D. Stacked bar plot proportions of cell types in each group. Panel E. Cell cycle analysis notched box plots of cycling GPCs and GPCs in the G2/M phase. The box indicates the interquartile range, the notch indicates the 95% confidence interval with the median at the center of the notch, and the error bars represent the minimum and maximum non-outlier values. Panel F. Venn diagram of pairwise differentially expressed GPC genes (Log2 fold change>0.15, adjusted p-value<0.05). Panel G. Curated Ingenuity Pathway analysis of genes differentially expressed between GPC groups. The size of circles represents p-value while the shading indicates activation Z-Score with red being more active in the upper group and green being more active in the lower group. Panel H. Heatmap of curated pairwise differentially expressed GPC genes. Panel I. Violin plots of pairwise differentially expressed GPC ribosomal gene log 2 fold changes. Comparisons between groups in E utilized Dunn tests, following a Kruskal-Wallis test with multiple comparisons adjusted via the Benjamini-Hochberg method. *=<0.05, <0.01, *=<0.001, ****=<0.0001 adjusted p-value.
Figure 21:
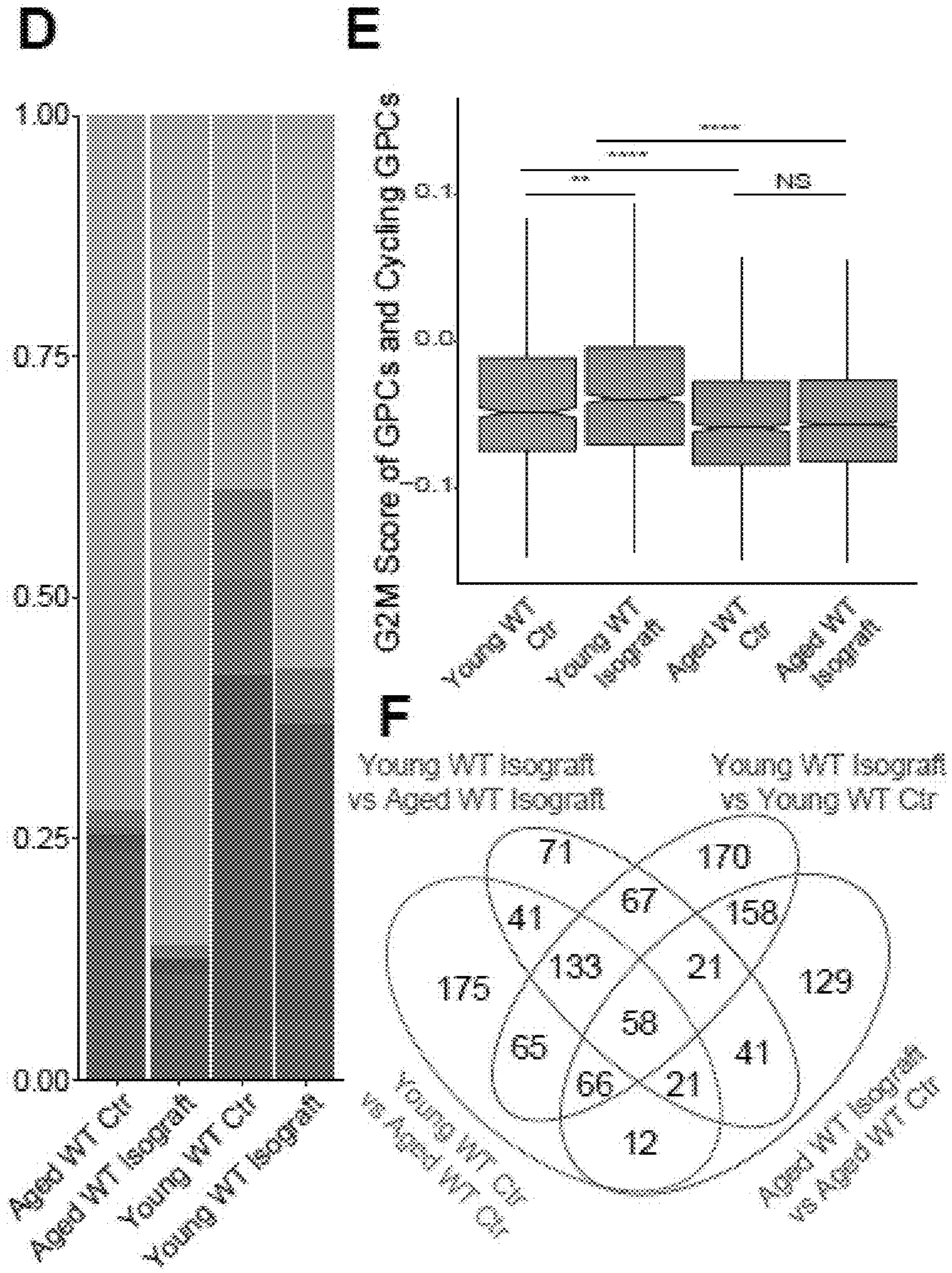
Figure 21:
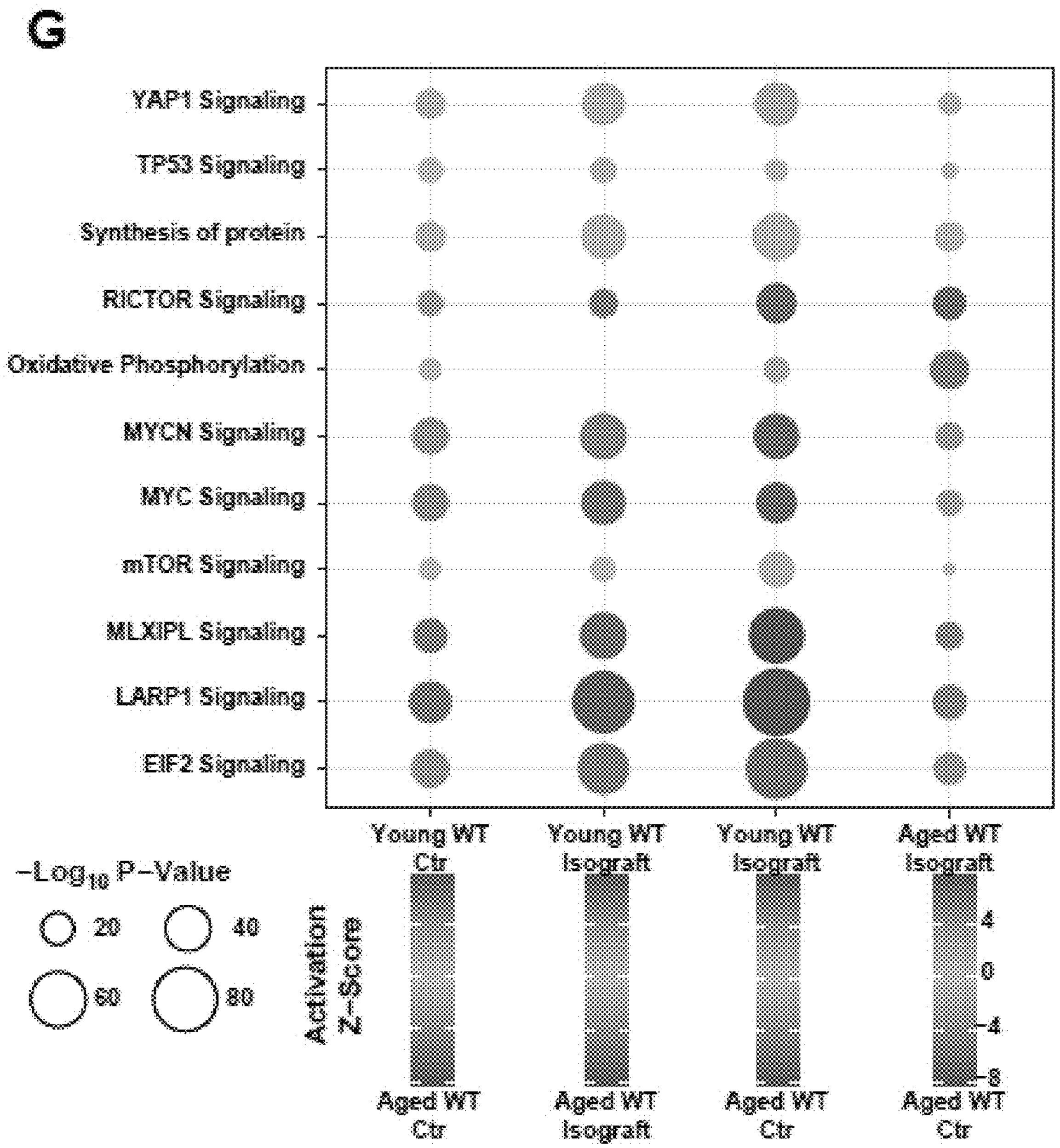
Figure 21:
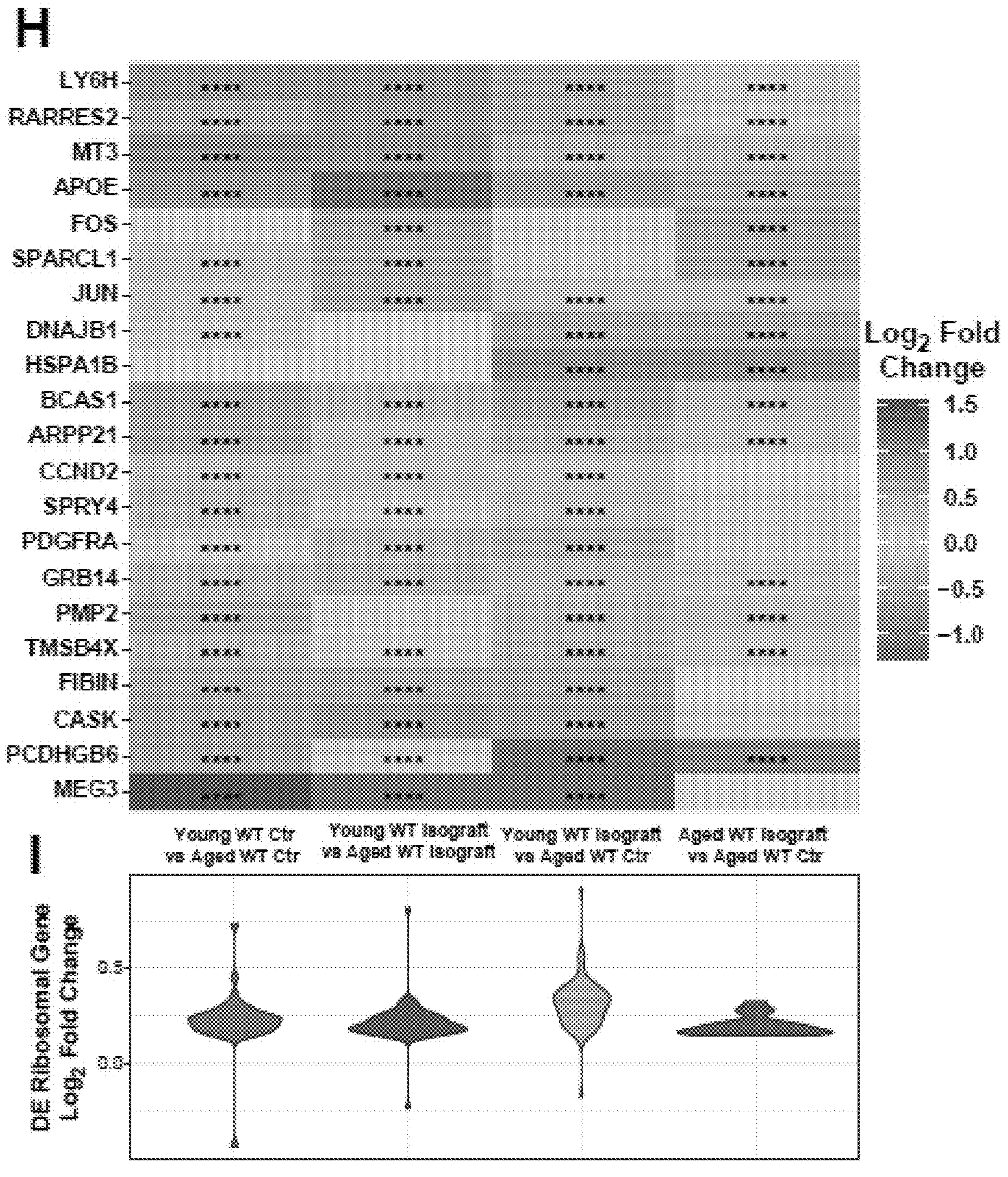

Example 9: Young hGPCs Acquire a Signature of Dominance when Challenged with Older Isogenic Cells To ascertain if the molecular signals underlying the competitive dominance of younger WT glia over aged WT glia are similar to those underlying their dominance over HD glia, the transcriptional signatures of competing young and aged WT glia and their respective controls were analyzed, using scRNA-seq (FIG. 21, Panel A). Within the sequenced populations (FIG. 21, Panel B-D), it was noted that the fraction of competing aged WT cells in the G2/M phase of the cell cycle to be markedly lower than their younger counterparts (FIG. 21, Panel E), in accord with the histological data (FIG. 17, Panel I). Differential expression analysis revealed discrete sets of genes differentially expressed between competing young and aged WT GPCs (FIG. 21, Panel F and H), and subsequent IPA analysis of those gene sets revealed a signature similar to that observed between donor (young) WT and already-resident (aged) HD GPCs in our competitive allograft model (FIG. 21, Panel G). In particular, genes functionally associated with protein synthesis, including ribosomal genes as well as upstream YAP1, MYC and MYCN signaling, were all activated in competing young WT GPCs relative to their aged counterparts (FIG. 21, Panel G). Yet despite these similarities, in other respects aged WT GPCs responded differently than did HD GPCs to newly implanted WT GPCs. In contrast to HD GPCs, aged WT cells confronted with younger isogenic competitors upregulated both YAP1 and MYC targets relative to their non-competing controls (FIG. 21, Panel G) with a concomitant upregulation of ribosomal genes (FIG. 21, Panel I). This difference in their profiles may represent an intrinsic capacity to respond competitively when challenged, which mHTT-expressing HD hGPCs lack. Nonetheless, this upregulation was insufficient to match the greater fitness of their younger counterparts, which similarly—but to a relatively greater degree-manifested the selective upregulation of YAP1 and MYC targets, as well as ribosomal genes, relative to their non-competing controls (FIG. 21, Panels G-H). Together, these data indicate that the determinants of relative cell fitness may be conserved across different scenarios of challenge, and that the outcomes of the resultant competition are heavily influenced by the relative ages of the competing populations.

Figure 22:
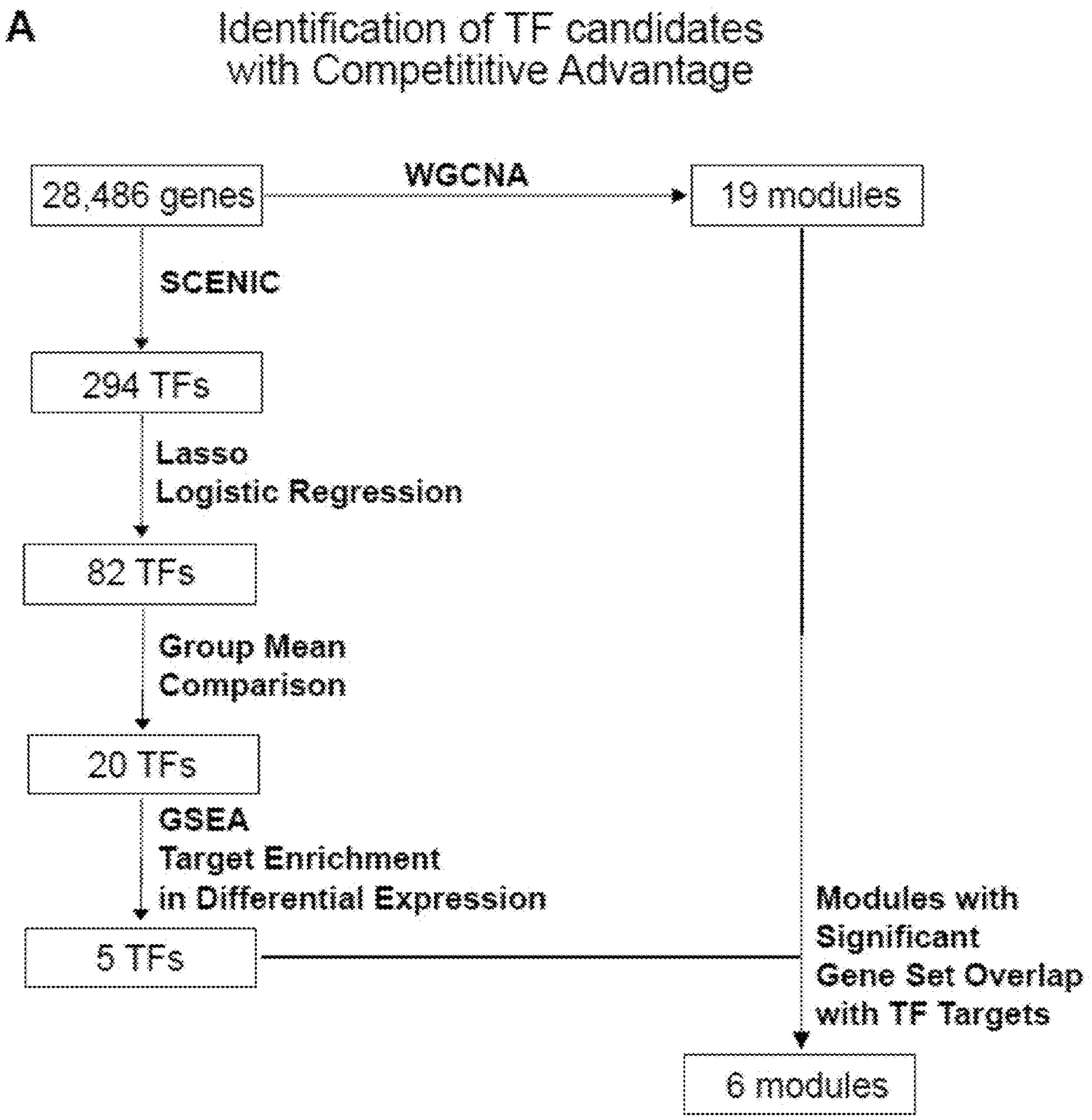
FIG. 22 shows transcriptional signature of competitive advantage. Panel A. Schematic of transcription factor candidate identification. Panel B. Violin plots of identified WGCNA module eigengenes per condition. Represented are significant modules (black, green, blue, brown, red, cyan), whose members are enriched for the downstream targets of the five transcription factors in Panel E. Panel C. Relative importance analysis to estimate the differential contribution of each biological factor (age vs genotype) to each module eigengene. Panel D. Gene set enrichment analysis (GSEA) highlighted those prioritized transcription factors whose regulons were enriched for upregulated genes in dominant young WT cells. Panel E. Important transcription factors predicted via SCENIC to establish competitive advantage and their relative activities across groups. Panel F. Regulatory network with represented downstream targets and their functional signaling pathways. Targets belong to highlighted modules in Panel B, and their expressions are controlled by at least one other important transcription factors in Panel E. NES: Network enrichment score.
Figure 22:
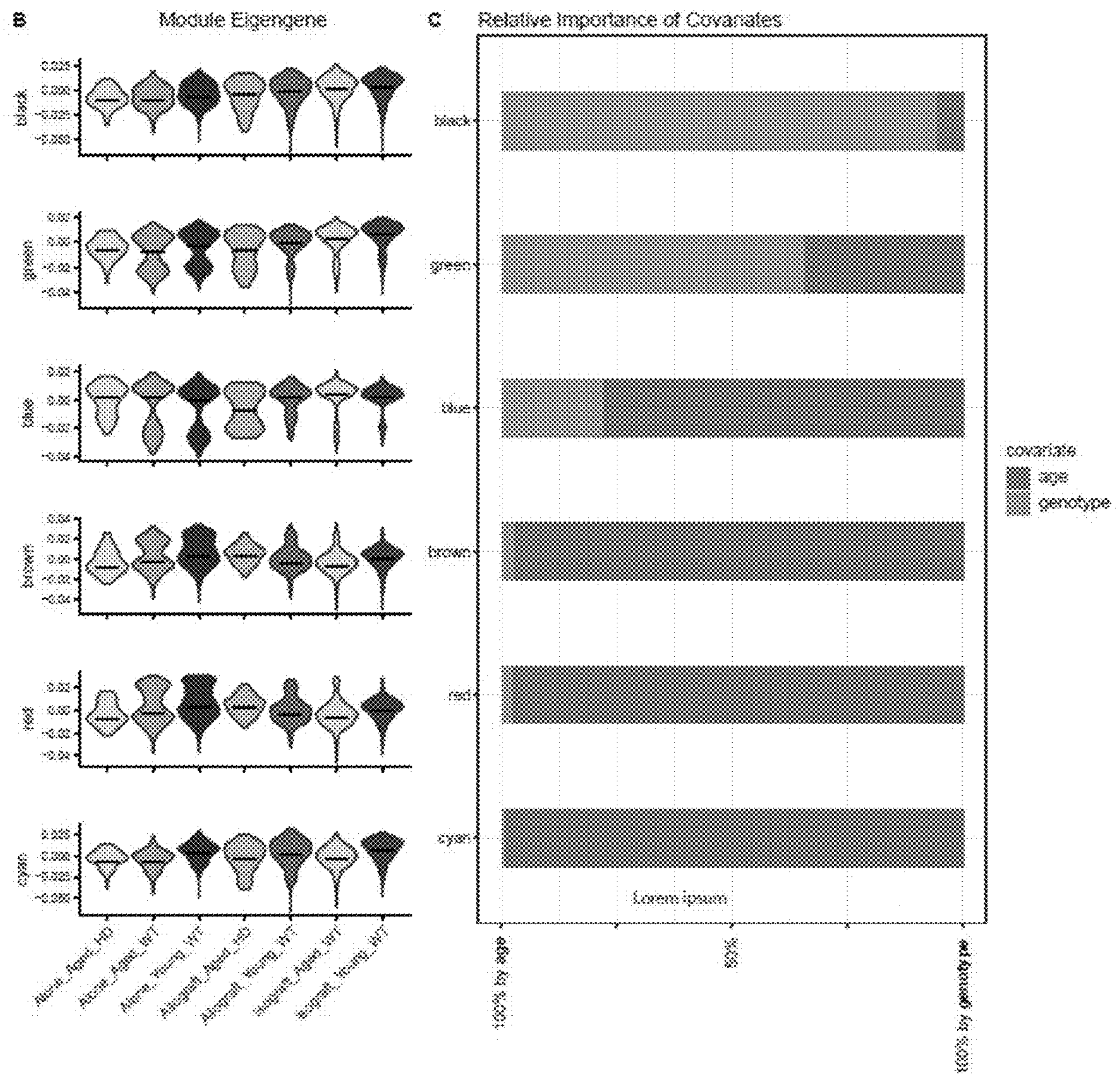
Figure 22:
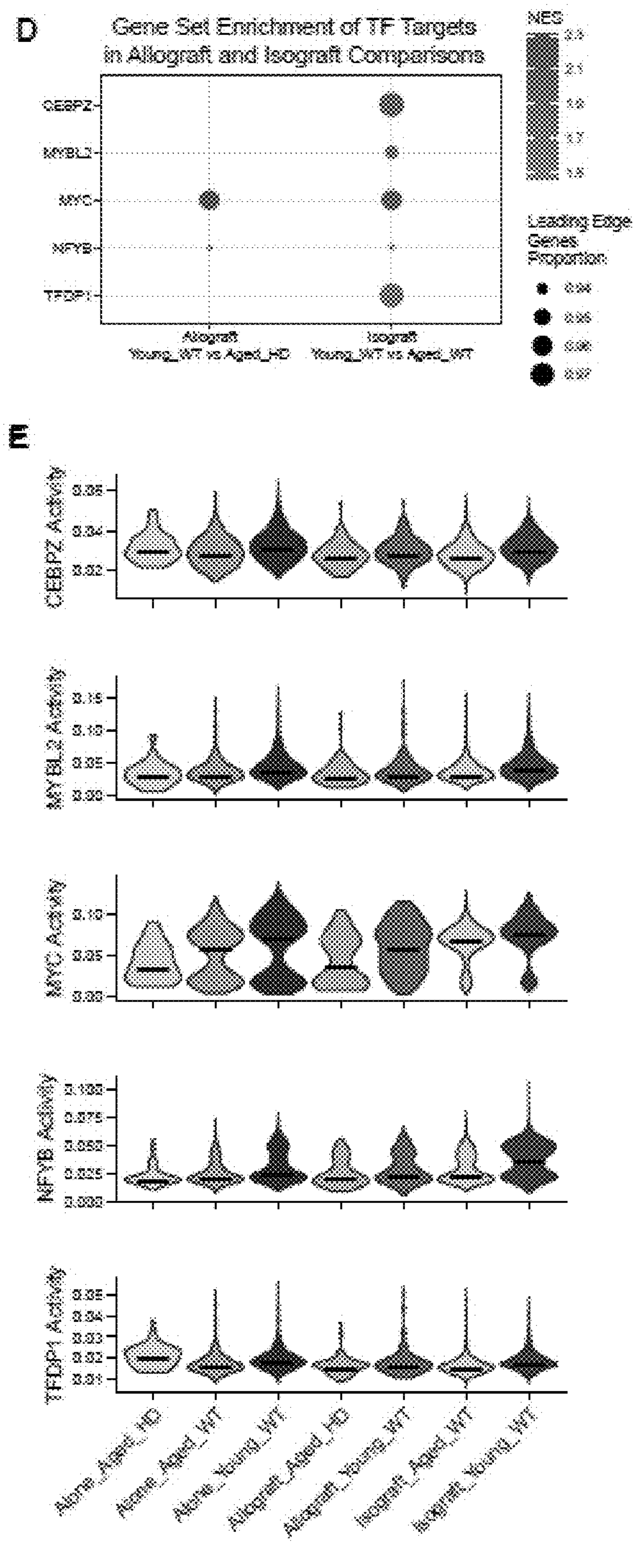
Figure 22:
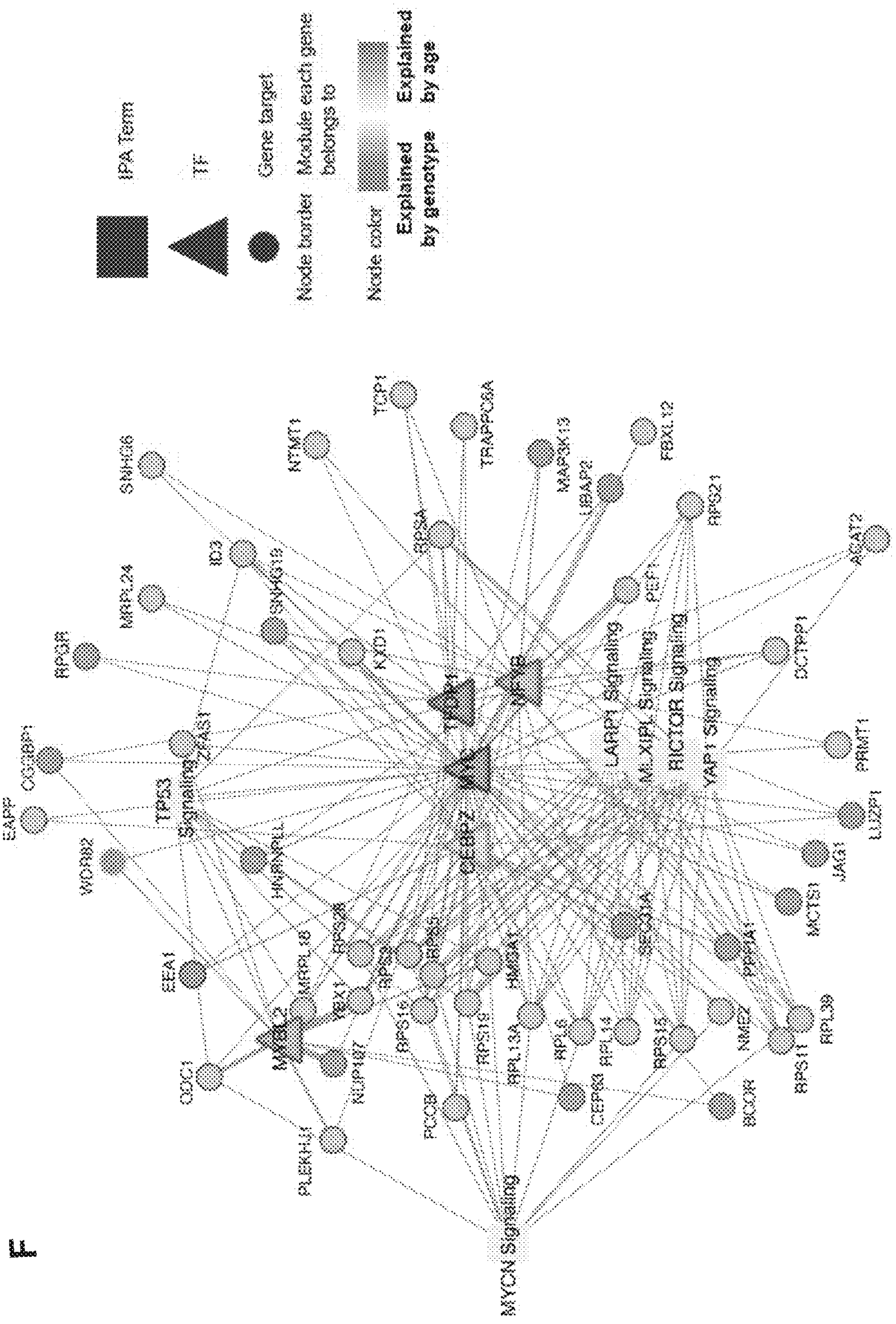

Example 10: Competitive Advantage is Linked to a Discrete Set of Transcription Factors It was next asked what gene signatures would define the competitive advantage of newly-transplanted human GPCs over resident cells. To that end, a multi-stepped analysis using lasso-regulated logistic regression was applied (FIG. 22, Panel A), that pinpointed 5 TFs (CEBPZ, MYBL2, MYC, NFYB, TFDP1) whose activities could significantly explain the dominance of young WT GPCs over both aged HD and aged WT GPCs. These 5 TFs and their putative targets established gene sets (regulons) which were upregulated (normalized enrichment score [NES]>0, adjusted p<10-2) in the young WT cells, in both the allograft and isograft models (FIG. 22, Panel D). It was also noticed that while their activities varied when not in a competitive environment (aged HD, aged WT, young WT alone), their mean activities were higher in the dominant young WT cells in both allograft (vs HD) and isograft (vs older isogenic self) paradigms, especially so for MYC (FIG. 22, Panel E).

Next, it was set out to identify cohorts of genes with defined expression patterns, as well as significant overlaps to the five prioritized regulons above. Weighted gene co-expression network analysis (WGCNA) was first employed to detect a total of 19 modules in the GPC dataset (FIG. 22, Panel A). Six modules harbored genes with significant overlap to the targets of CEBPZ, MYBL2, MYC, NFYB, and TFDP1 (FIG. 22, Panel B). It was then asked if the expression pattern of prioritized modules could be explained by the age of cells (young vs. old), by their genotype (HD vs. WT), or both. WGCNA defines module eigengene as the first principal component of a gene cohort, representing thereby the general expression pattern of all genes within that module. As such, linear models were built where module eigengene was a response that was described by both age and genotype. It was observed that modules brown, red, and cyan were mostly influenced by age, while modules black, blue, and green were influenced by both age and genotype (FIG. 22, Panel C).

MYC, whose regulated pathway activation had already been inferred as conferring competitive advantage was also one of the five prioritized TFs. The MYC regulon and its downstream targets were further characterized, and it was noticed how these downstream targets were also regulated by the other prioritized TFs (FIG. 22, Panel F). Interestingly, while MYC localized to module brown, a large proportion of its targets belonged to module blue. The blue module genes were similarly expressed in the non-competing control paradigms, but their expression levels were higher in the young WT compared to the aged HD in the WT vs HD allograft paradigm (FIG. 22, Panel B), a pattern suggesting that the blue signature was not activated unless cells were in a competing environment. Furthermore, lower expression of these genes was noted in the aged HD relative to the aged WT hGPCs (FIG. 22, Panel E-F), which may highlight the intrinsically greater capacity of WT cells to compete, congruent with the earlier observation that aged WT hGPCs respond differently than HD hGPCs when challenged with newly-engrafted WT GPCs. Importantly, the blue module eigengene could be described by both genotype and age, demonstrating that the competitive advantage associated with MYC signaling was driven by both of these variables. Accordingly, the targets in this network were enriched for pathways regulating cell proliferation (TP53, RICTOR, YAP), gene transcription (MYCN, MLXIPL), and protein synthesis (LARP1), each of which had been previously noted as differentially-expressed in each competitive scenario (FIGS. 19 and 21). As such, the output of this competition-triggered regulatory network appeared to confer competitive advantage upon young WT hGPCs when introduced into the adult brain, whether confronted by older HD-derived or isogenic hGPCs.

Example 11: CD140a Selection Enriches for Human Fetal Glial Progenitors More Efficiently than does A2B5

Figure 23:
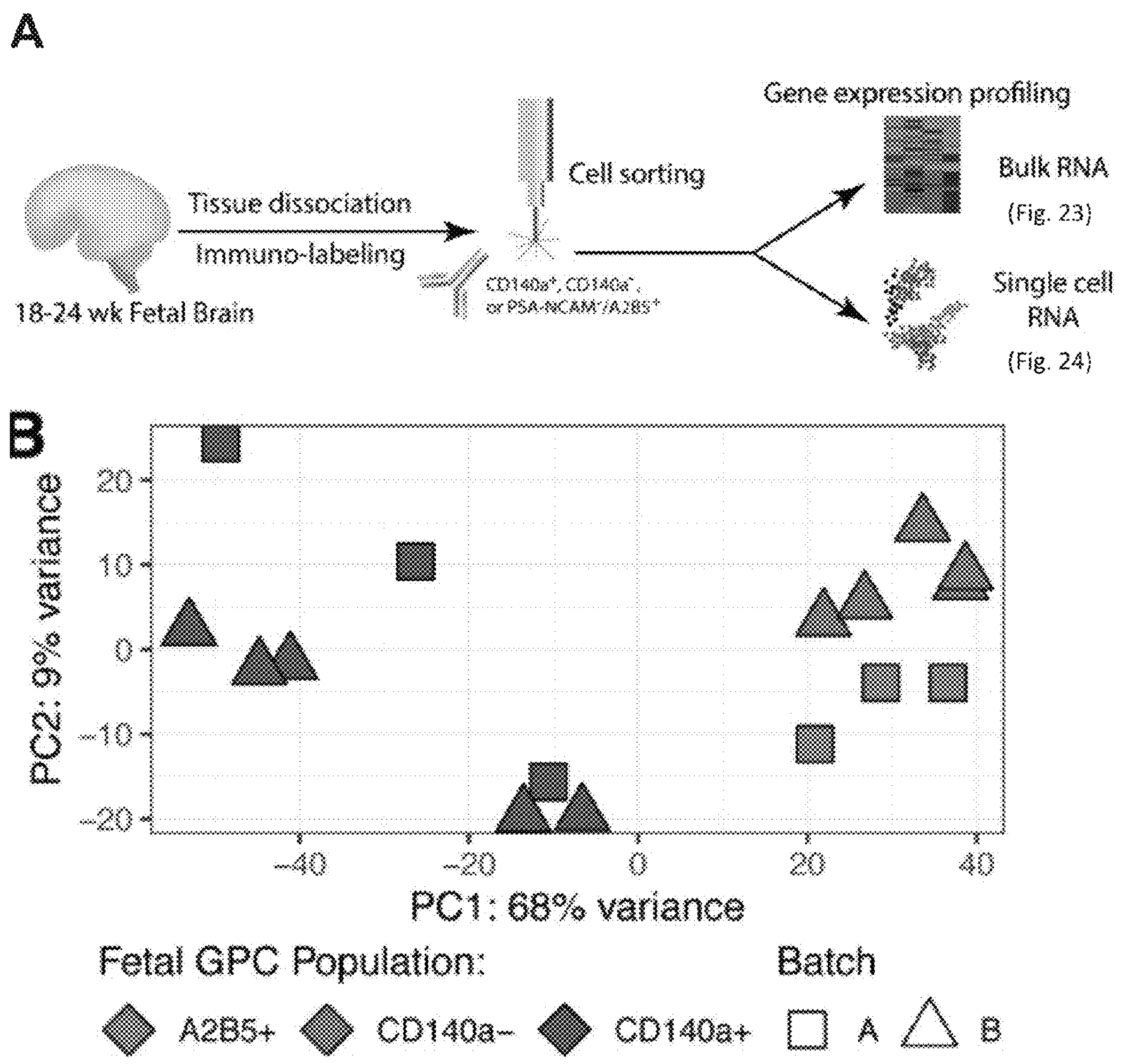
FIG. 23 shows Bulk RNA-Seq Characterization of human fetal GPCs. Panel A. Workflow of bulk and scRNA-Sequencing of CD140a+, CD140a−, and A2B5+/PSA-NCAM— selected 2nd trimester human fetal brain isolates. Panel B. Principal component analysis of all samples across two batches. Panel C. Venn diagram of CD140a+vs CD140a— and CD140+vs A2B5+/PSA-NCAM-differentially-expressed gene sets (p<0.01 and absolute log 2-fold change >1). Panel D. Significant Ingenuity Pathway Analysis terms for both genesets. Size represents—log 10 p-value and color represents activation Z-Score (Blue, CD140a+; Red, A2B5+ or CD140a−). Panel E. Log2-fold changes of significant genes for both genesets. Missing bars were not significant. Panel F. Heatmap of transformed transcripts per million (TPM) of selected genes in Panel E.
Figure 23:
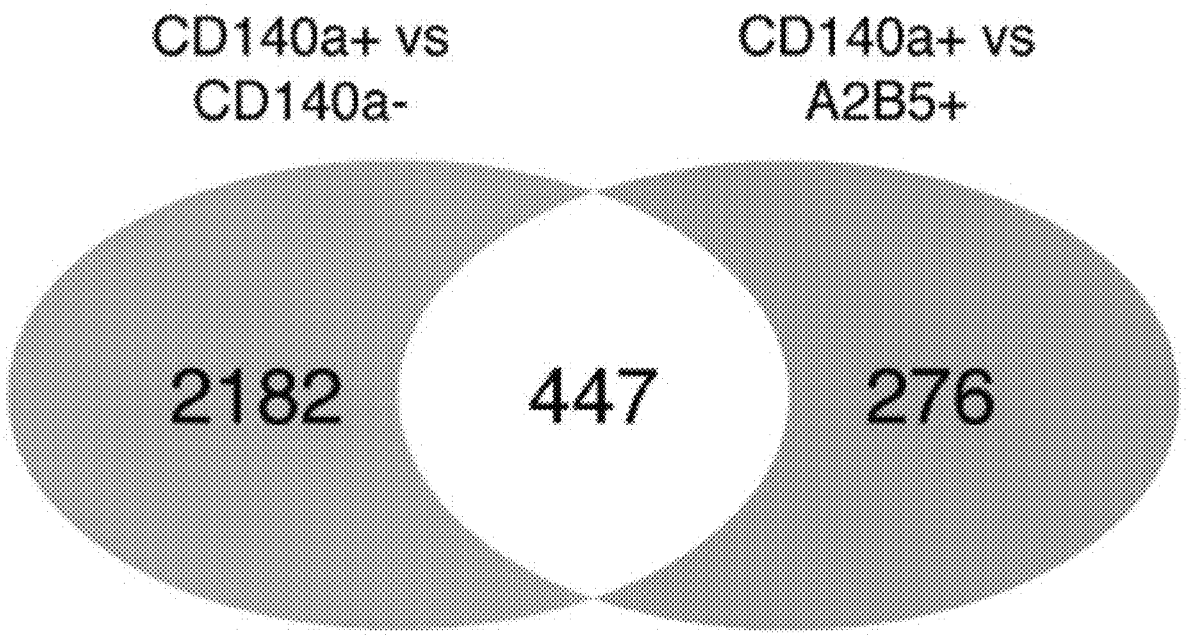
Figure 23:
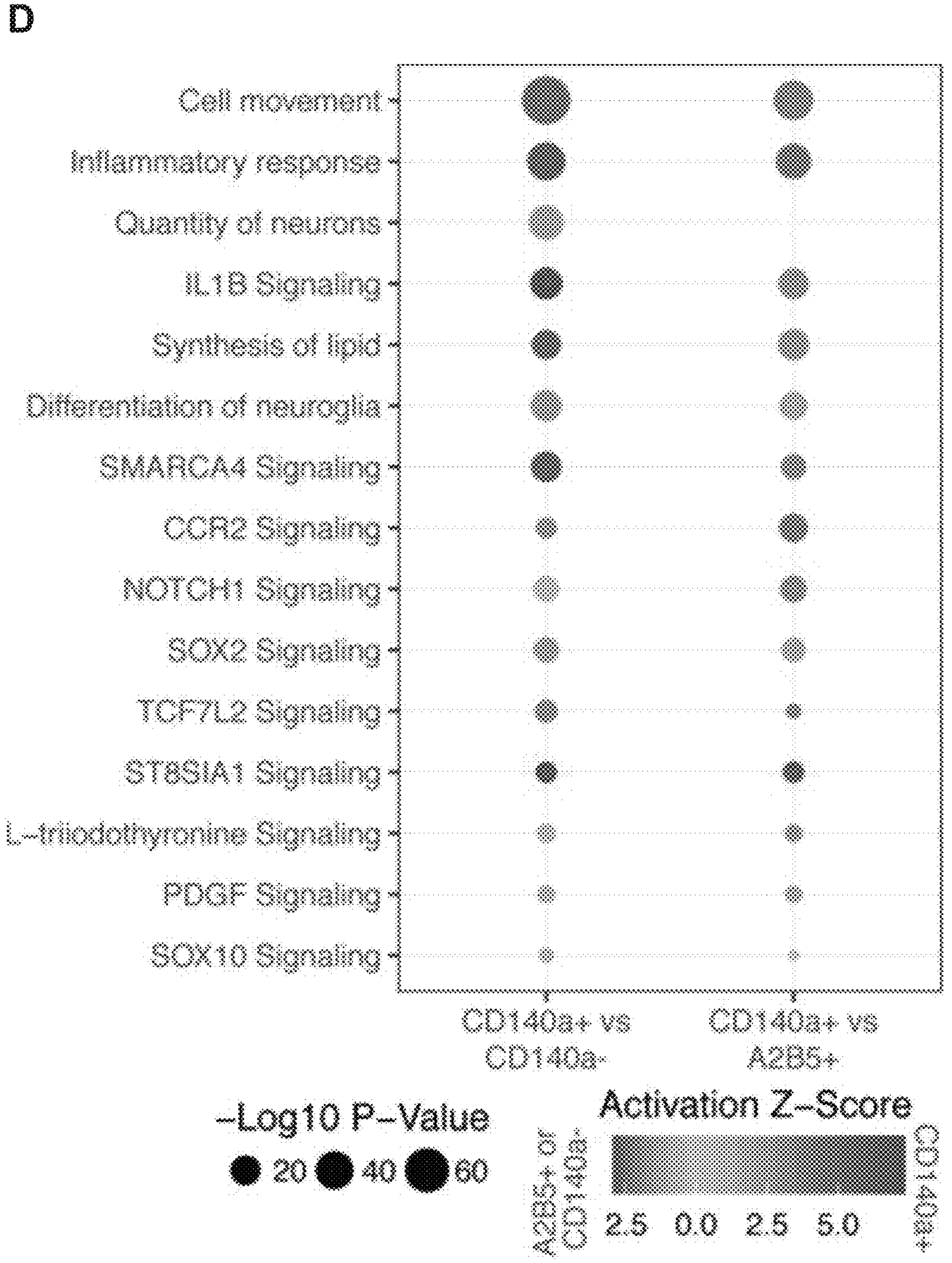
Figure 23:
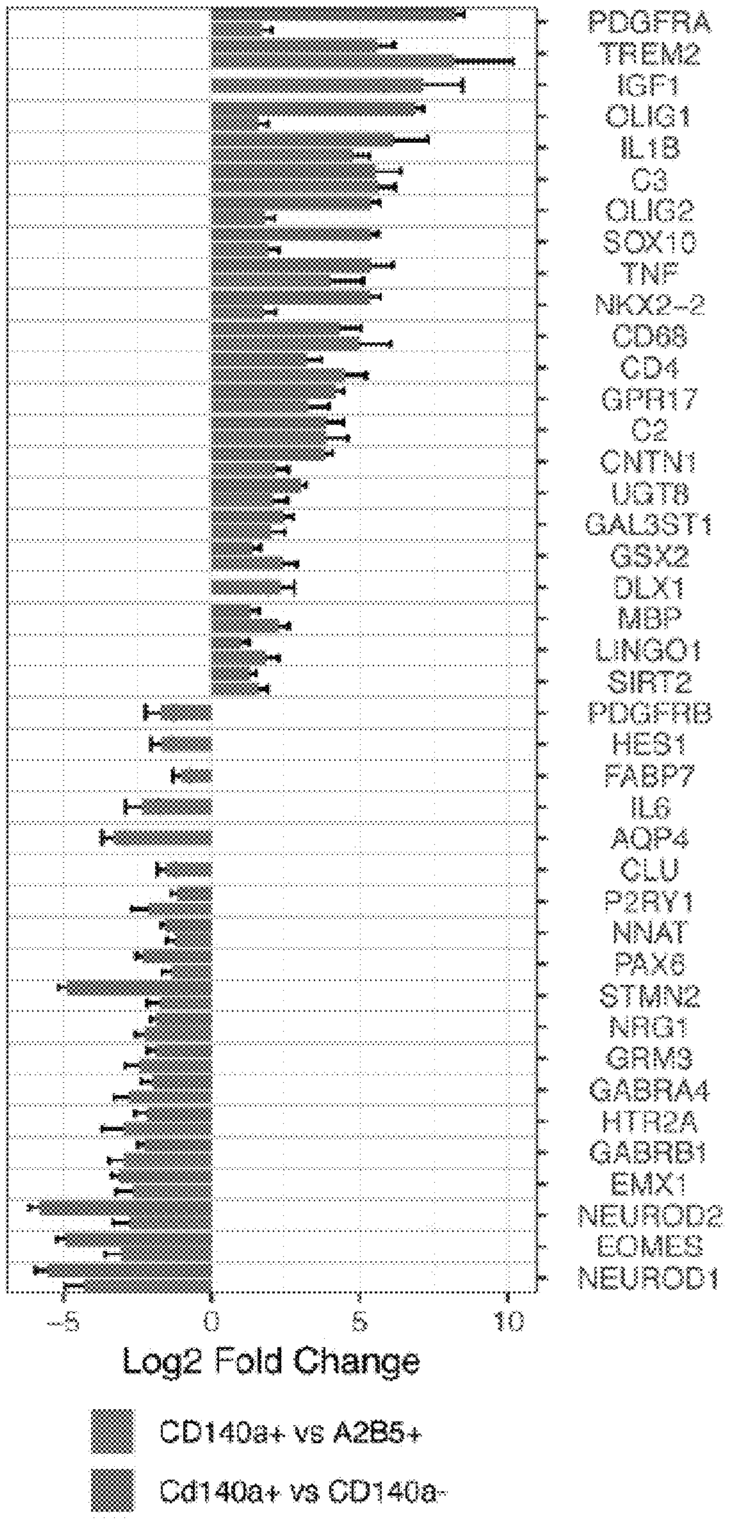
Figure 23:
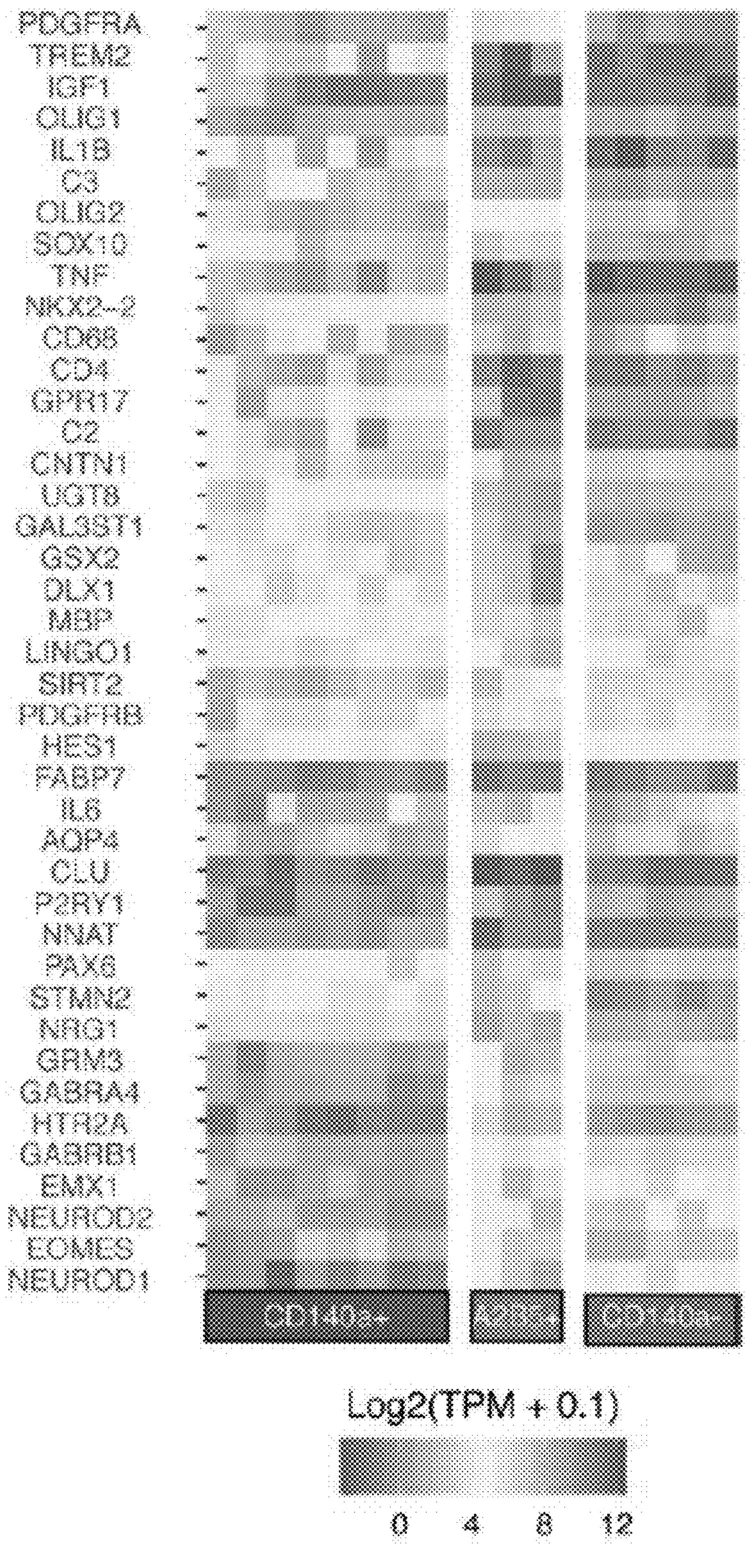

To identify the transcriptional concomitants to GPC aging, the study first used bulk and single cell RNA-Seq to characterize hGPCs derived from second trimester fetal human tissue, whether isolated by targeting the CD140a epitope of PDGFRα (Sim et al. (2011a). Nature Biotechnology 29, 934-941), or the glial gangliosides recognized by monoclonal antibody A2B5 (e.g. Windrem, et al. (2004). Nat Med 10, 93-974). To that end, two sample-matched experiments were carried out whereby the ventricular/subventricular zones (VZ/SVZ) of 18-22 week gestational age (g.a.) fetal brains were dissociated and sorted via fluorescence activated cell sorting (FACS), for either CD140α+ and A2B5+/PSA-NCAM-(A2B5+) GPCs isolated from the same fetal brain (n=3), or for CD140α+ GPCs as well as the CD140α-depleted remainder (n=5; FIG. 23, Panel A). Bulk RNA-Seq libraries were then generated and deeply sequenced for both experiments. Principal component analysis (PCA) showed segregation of the CD140α+ and A2B5+ cells, and further segregation of both from the CD140α-depleted samples (FIG. 23, Panel B). Differential expression in both paired cohorts (p<0.01, absolute log 2 fold change >1) identified 723 genes as differentially-expressed between CD140α+ and A2B5+ GPCs (435 in CD140α, 288 in A2B5). In contrast, 2,629 genes distinguished CD140α+ GPCs from CD140α— cells (FIG. 23, Panel C). Differential gene expression directionality was highly consistent when comparing CD140+ to either A2B5+ or CD140— cells, with all but 4 genes being concordant.

Pathway enrichment analysis using Ingenuity Pathway Analysis (IPA) of both of these gene sets identified similar pathways as relatively active in CD140+ GPCs; these pathways included cell movement, oligodendroglial differentiation, lipid synthesis, and downstream PDGF, SOX10, and TCF7L2 signaling (FIG. 23, Panel D). As expected, stronger activation Z-scores were typically observed when comparing CD140α+ GPCs to CD140α-cells rather than to A2B5+ GPCs. Interestingly, CD140α+ cells also differentially expressed a number of pathways related to the immune system, likely due to small amounts of microglial contamination as a result of re-expression of PDGFaR epitopes on the microglial surface. A2B5+ samples additionally displayed upregulated ST8SIA1, the enzyme responsible for A2B5 synthesis (Sim et al. (2009). Neuron Glia Biol 5, 45-55), as well as pro-neural pathways.

Among the genes differentially upregulated in CD140α+ isolates were PDGFRA itself, and a number of early oligodendroglial genes including OLIG1, OLIG2, NKX2-2, SOX10, and GPR17 (FIGS. 23, Panel E-F). Furthermore, the CD140α+ fraction also exhibited increased expression of later myelinogenesis-associated genes, including MBP, GAL3ST1, and UGT8. Beyond enrichment of the oligodendroglial lineage, many genes typically associated with microglia were also enriched in the CD140a isolates, including CD68, C2, C3, C4, and TREM2. In contrast, A2B5+ isolates exhibited enrichment of astrocytic (AQ4, CLU) and early neuronal (NEUROD1, NEUROD2, GABRG1, GABRA4, EOMES, HTR2A) genes, suggesting the expression of A2B5 by immature astrocytes and neurons as well as by GPCs and oligodendroglial lineage cells. Overall then, oligodendroglial enrichment was significantly greater in CD140α+ GPCs than A2B5-defined GPCs, when each was compared to depleted fractions, suggesting the CD140a isolates as being the more enriched in hGPCs, and thus CD140a as the more appropriate phenotype for head-to-head comparison with adult hGPCs.

Figure 24:
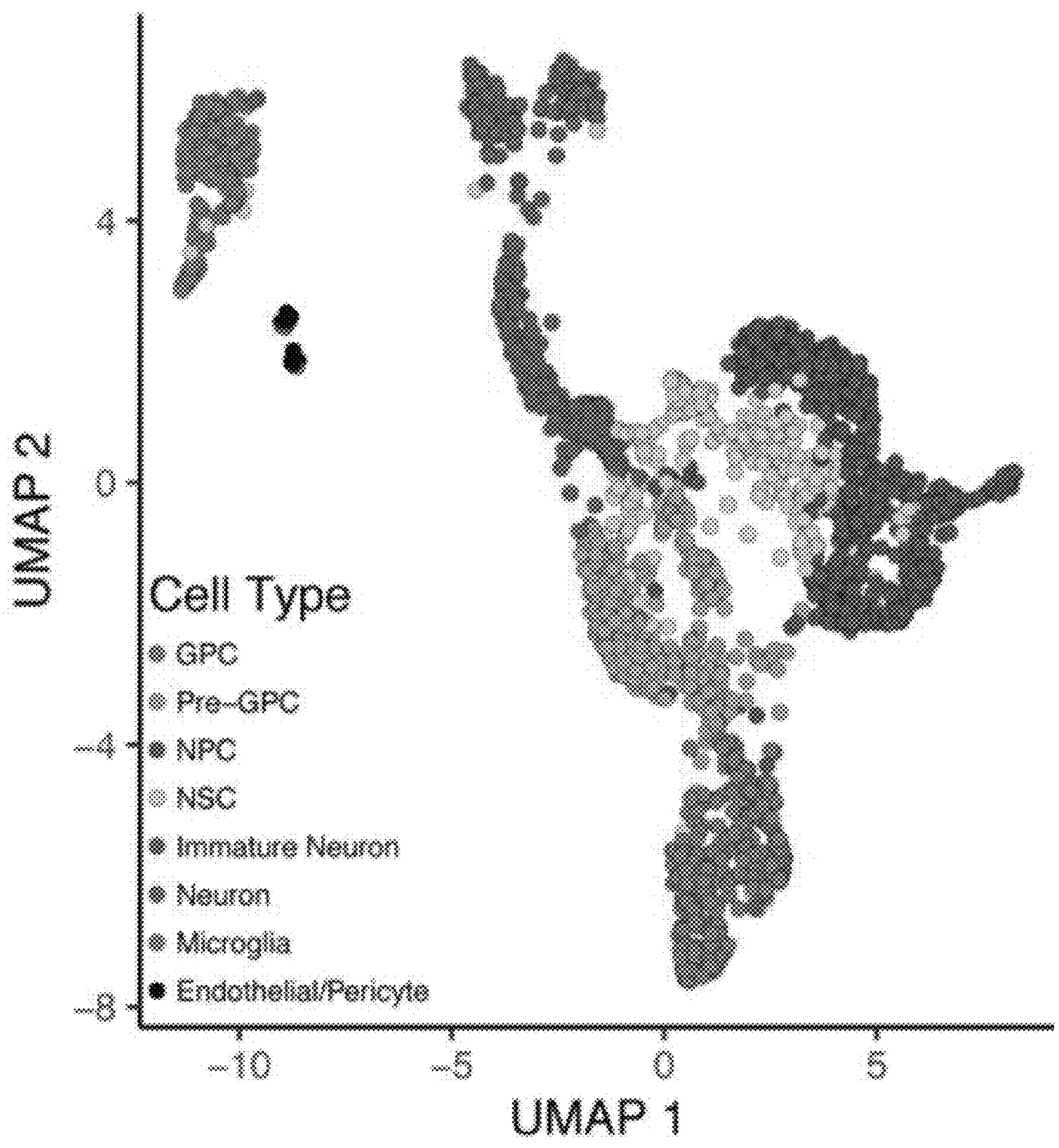
FIG. 24 shows single cell RNA-sequencing of CD140a and A2B5 selected human fetal GPCs. Panel A. UMAP plot of the primary cell types identified during scRNA-Seq analysis of FACS isolated hGPCs derived from 20 week gestational age human fetal VZ/SVZ. Panel B-Panel C. UMAP of only PSA-NCAM−/A2B5+ (B) or CD140a+ (C) human fetal cells. Panel D. Violin plots of cell type-selective marker genes. Panel E. Volcano plot of GPC vs pre-GPC populations. Panel F. Feature plots of select differentially expressed genes between GPCs and pre-GPCs. Panel G. Select significantly-enriched GPC and pre-GPC IPA terms, indicating their -log 10 p-value and activation Z-Score. Panel H. Select feature plots of transcription factors predicted to be significantly activated in fetal hGPCs. Relative transcription factor regulon activation is displayed as calculated using the SCENIC package.
Figure 24:
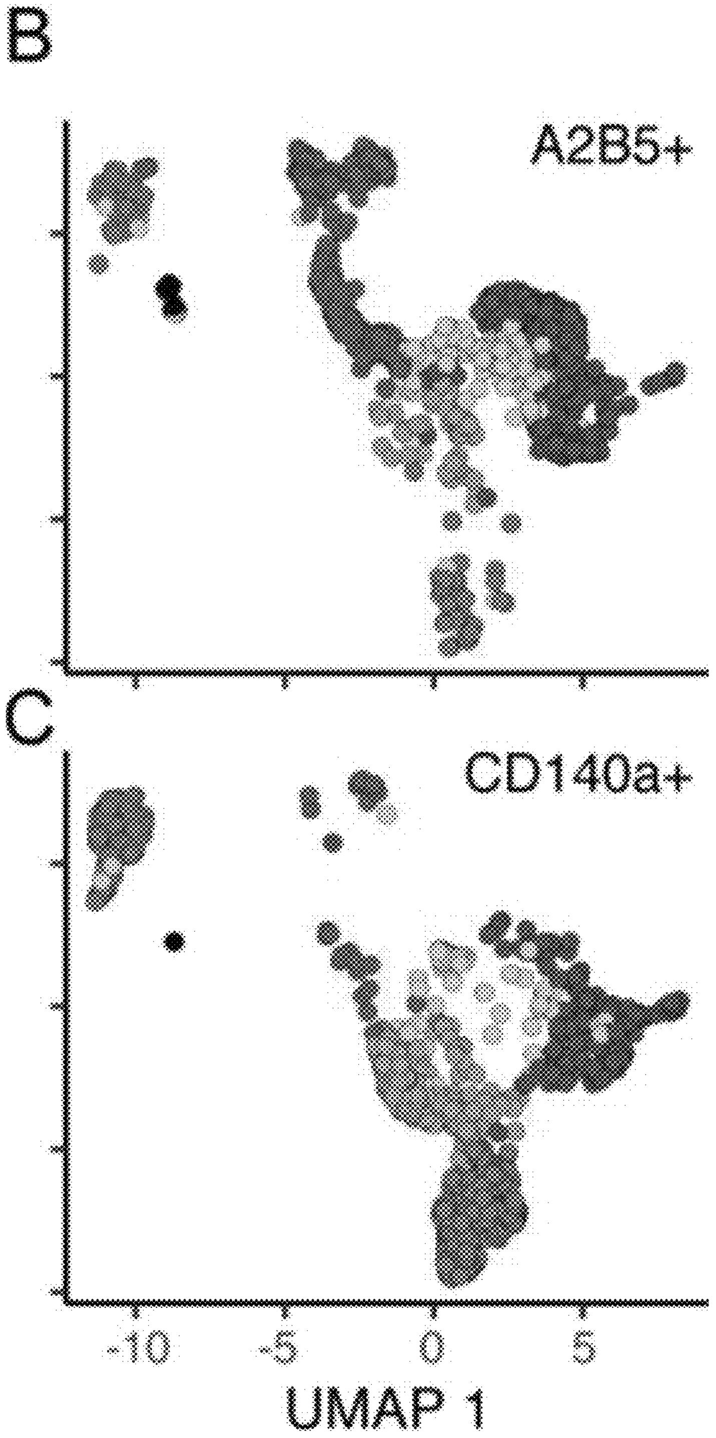
Figure 24:
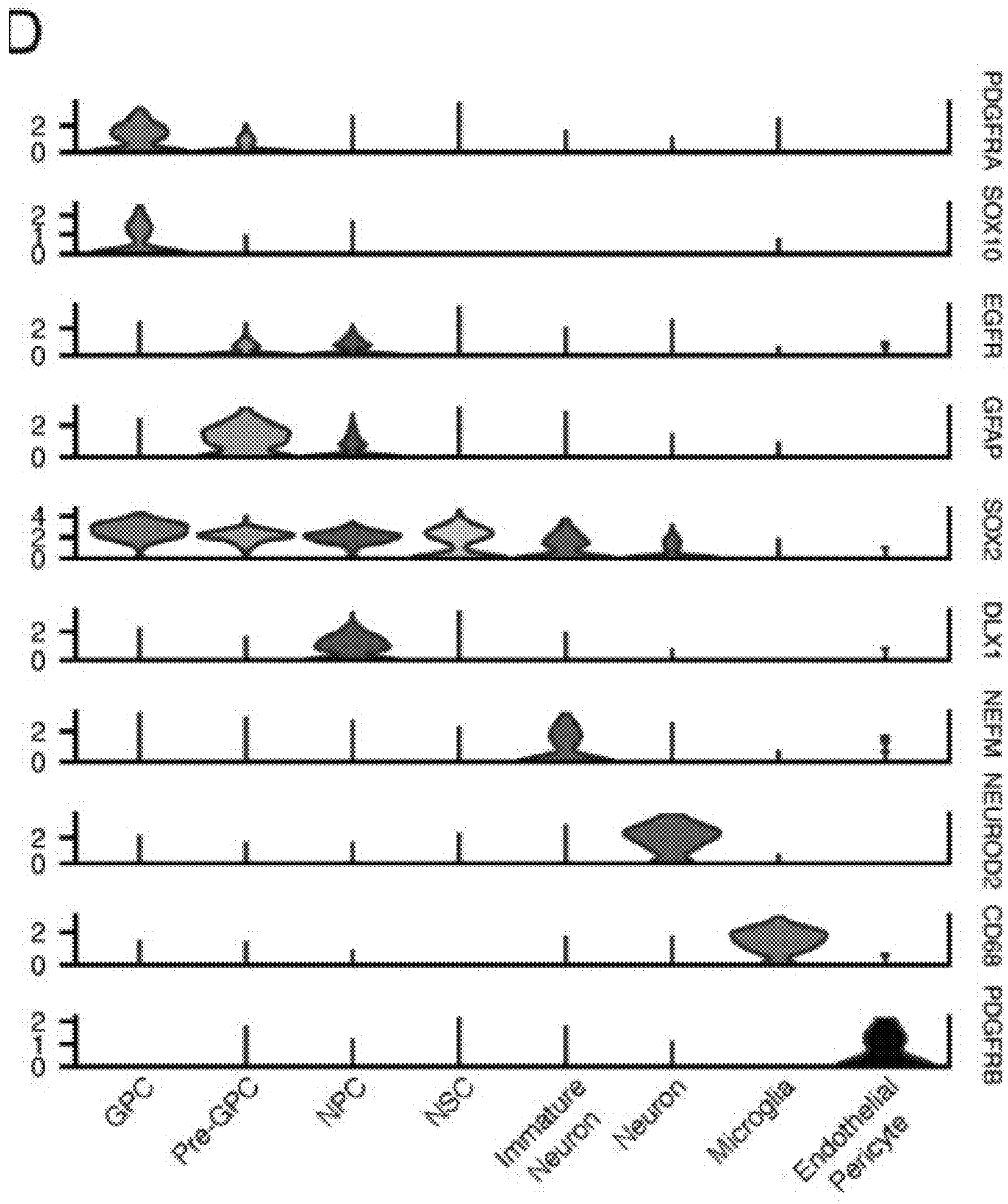
Figure 24:
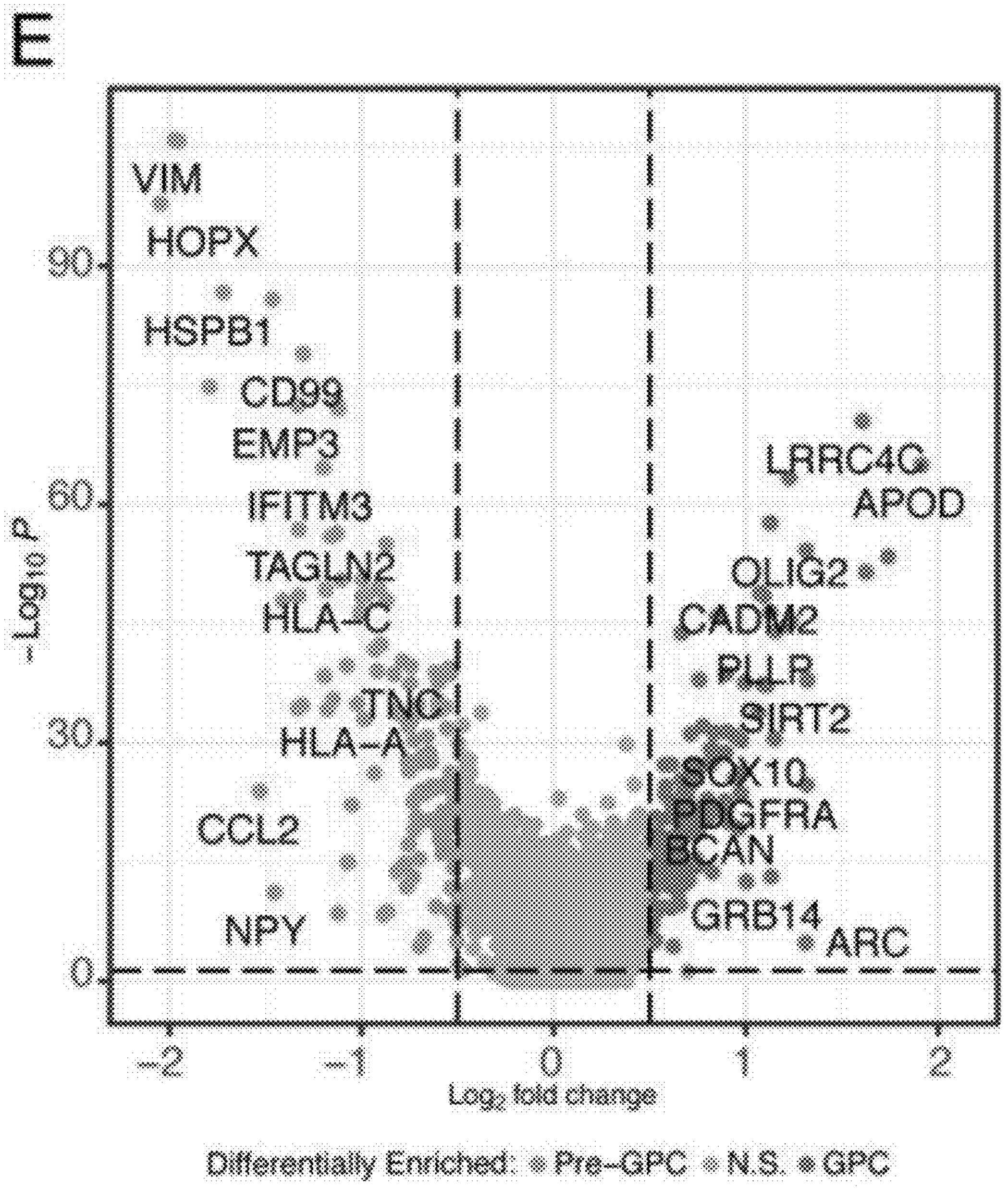
Figure 24:
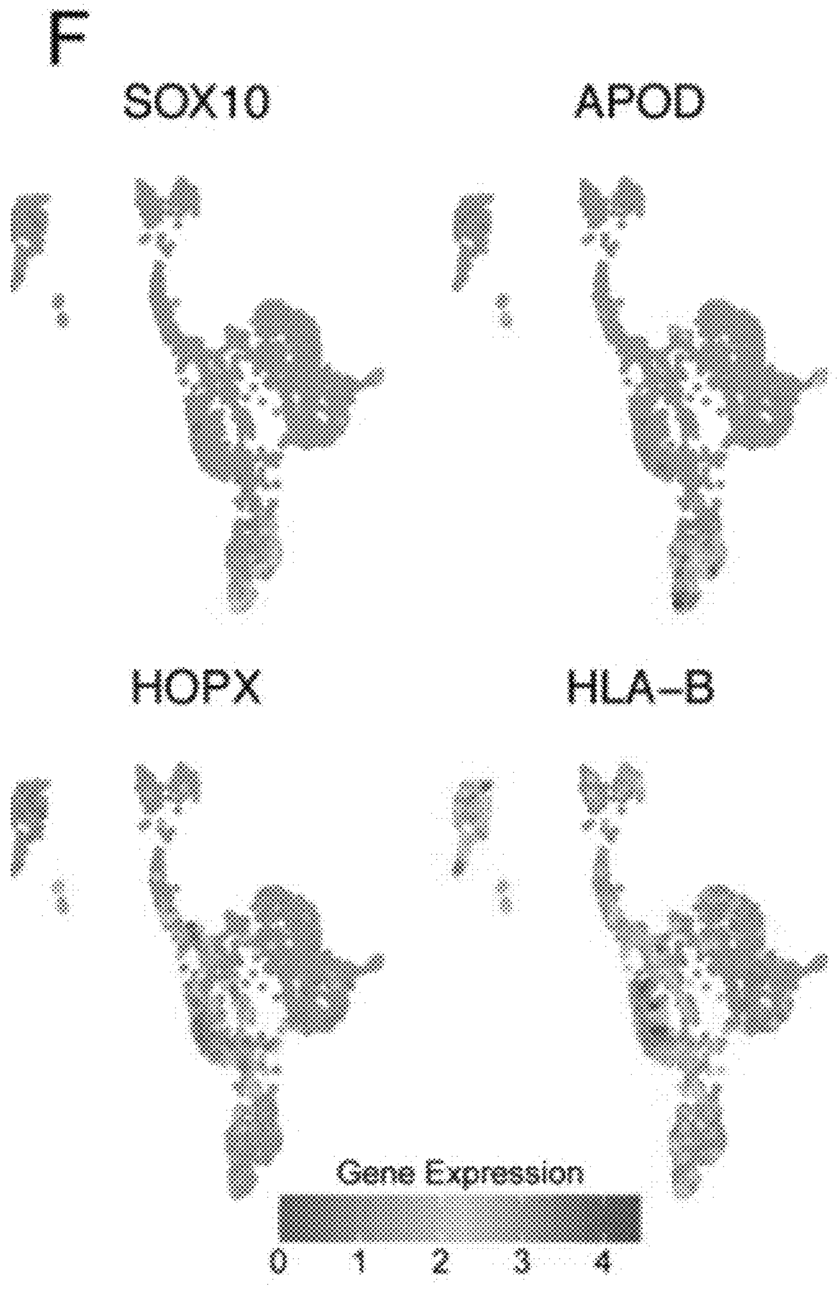
Figure 24:
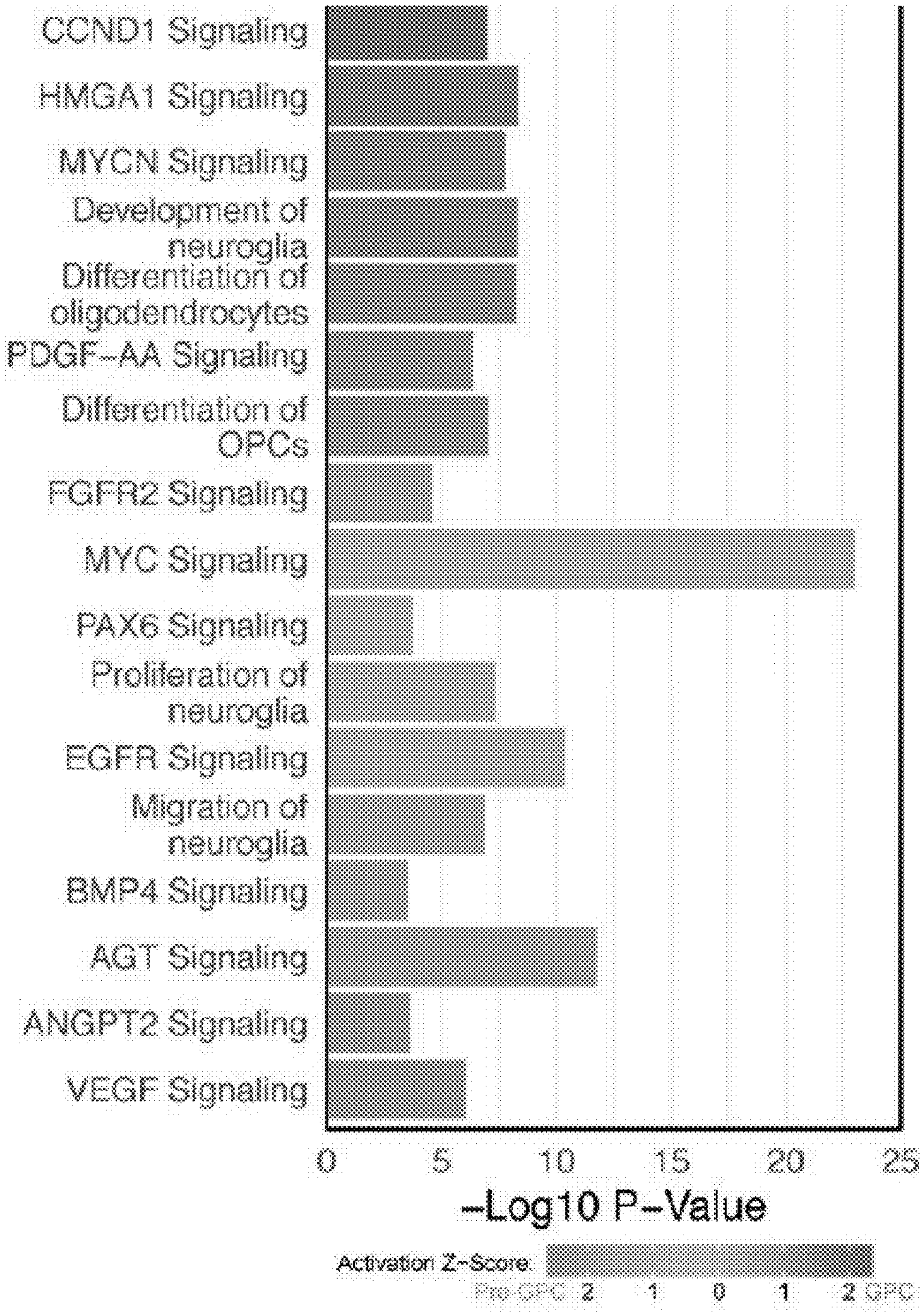
Figure 24:
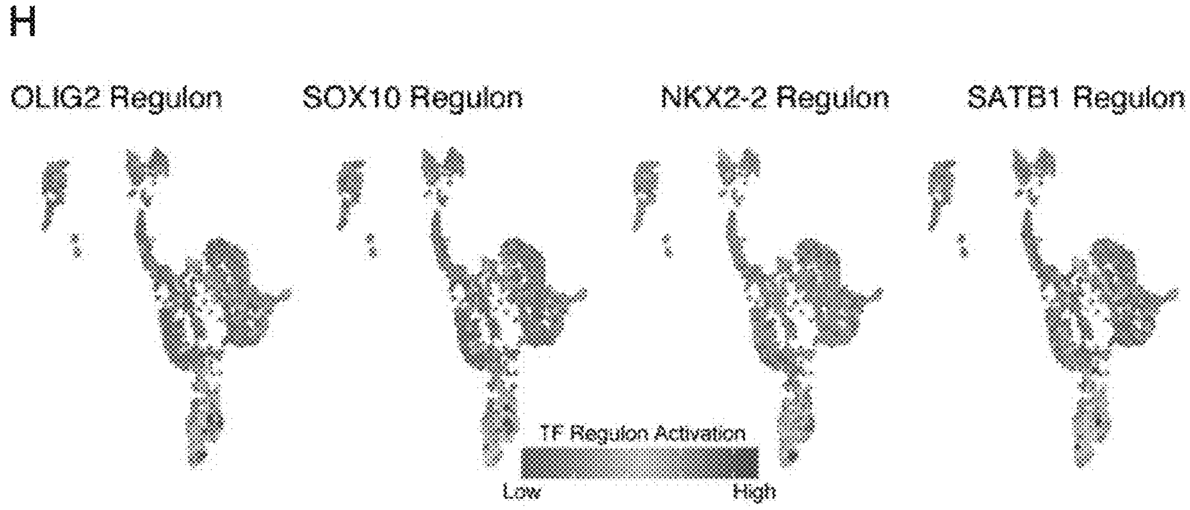

Example 12: Single Cell RNA-Sequencing Reveals Cellular Heterogeneity within Human Fetal GPC Isolates To further delineate the composition of fetal hGPC isolates at single cell resolution, the study isolated both CD140α+ and A2B5+ hGPCs from 20-week g.a. fetal VZ/SVZ via FACS, and then assayed the transcriptomes of each by single cell RNA-Seq. The study sought to capture >1,000 cells of each; following filtration of low-quality cells (unique genes <500, mitochondrial gene percentage >15%), the study was left with 1,053 PSA-NCAM−/A2B5+ and 957 CD140α+ high quality cells (median 6,845 unique molecular identifiers and 2,336 unique genes per cell). Dimensional reduction via uniform manifold approximation and projection (UMAP), followed by shared nearest neighbor modularity-based clustering of all cells using Seurat (Butler et al. (2018). Nat Biotechnol 36, 411-420), revealed 11 clusters with 8 primary cell types, as defined by their differential enrichment of marker genes. These primary cell types included: GPCs, pre-GPCs, neural progenitor cells (NPCs), immature neurons, neurons, microglia, and a cluster consisting of endothelial cells and pericytes. The study found that the CD140α+ FACS isolates were more enriched for GPC and pre-GPC populations than were the fetal A2B5+/PSA-NCAM-cells (FIG. 24, Panel A-D). Furthermore, whereas the CD140α-sorted cells were largely limited to GPCs and pre-GPCs, with only scattered microglial contamination, the A2B5+/PSA-NCAM-isolates also included astrocytes and neuronal lineage cells, the latter despite the upfront depletion of neuronal PSA-NCAM. These data supported the more selective and phenotypically-restricted nature of CD140a rather than A2B5-based GPC isolation.

On that basis, the study next explored the gene expression profiles of the predominant cell populations in the CD140α+ fetal isolates, GPCs and pre-GPCs. Differential expression between these two pools yielded 269 (143 upregulated, 126 down-regulated; p<0.01, log 2 fold change >0.5; FIG. 24, Panel E). During the pre-GPC to GPC transition, early oligodendroglial lineage genes were rapidly upregulated (OLIG2, SOX10, NKX2-2, PLLP, APOD), whereas those expressed in pre-GPCs effectively disappeared (VIM, HOPX, TAGLN2, TNC). Interestingly, genes involved in the human leukocyte antigen system, including HLA-A, HLA-B, HLA-C and B2M, were all downregulated as the cells transitioned to GPC stage (FIG. 24, Panel F). IPA analysis indicated that pre-GPCs were relatively enriched for terms related to migration, proliferation, and those presaging astrocytic identity (BMP4, AGT, and VEGF signaling), whereas GPCs displayed enrichment for terms associated with acquisition of an oligodendroglial identity (PDGF-AA, FGFR2, CCND1), in addition to activation of the MYC and MYCN pathways (FIG. 24, Panel G). Using single cell co-expression data together with promoter motif enrichment using the SCENIC package (Aibar et al. (2017). Nat Methods 14, 1083-1086), the study then identified 262 transcription factors that were predicted to be relatively activated in GPCs vs pre-GPCs (Wilcoxon rank sum test, p<0.01). These included SATB1, as well as the early GPC specification factors OLIG2, SOX10, and NKX2-2 (FIG. 24, Panel H).

Example 13: Human Adult and Fetal GPCs are Transcriptionally Distinct

Figure 25:
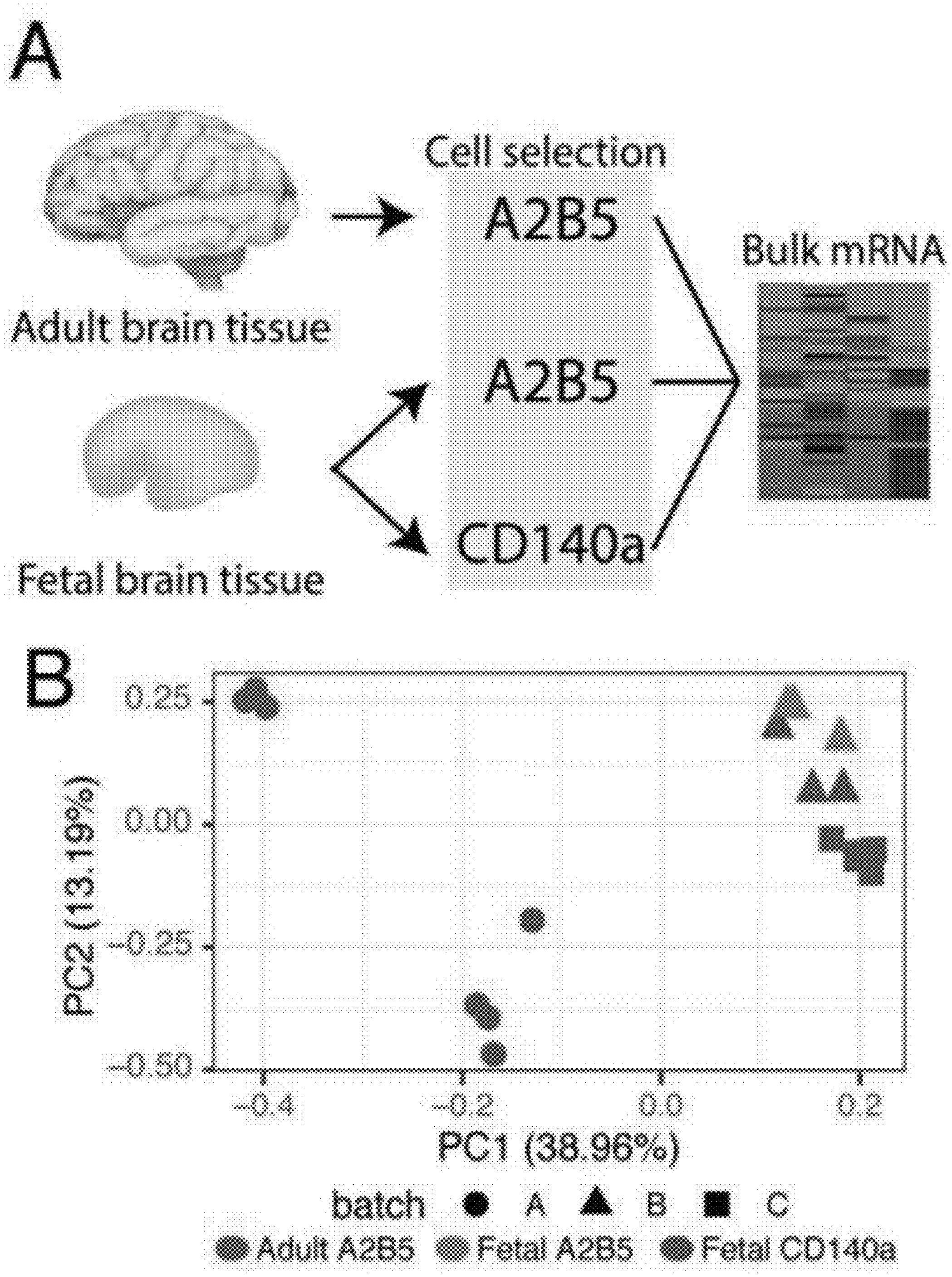
FIG. 25 shows adult human GPCs are transcriptionally and functionally distinct from fetal GPCs. Panel A. Workflow of bulk RNA-Seq analysis of human adult and fetal GPCs. Panel B. Principal component analysis of all samples across three batches. Panel C. Venn Diagram of both Adult vs Fetal differential expression gene sets. Panel D. IPA network of curated terms and genes. Node size is proportionate to node degree. Label color corresponds to enrichment in either adult (red) or fetal (blue) populations. Panel E. Bar plots of significant IPA terms by module. Z-Scores indicate predicted activation in fetal (blue) or adult (red) hGPCs. Panel F. Bar plot of log 2-fold changes and heatmap of network genes' TPM.
Figure 25:
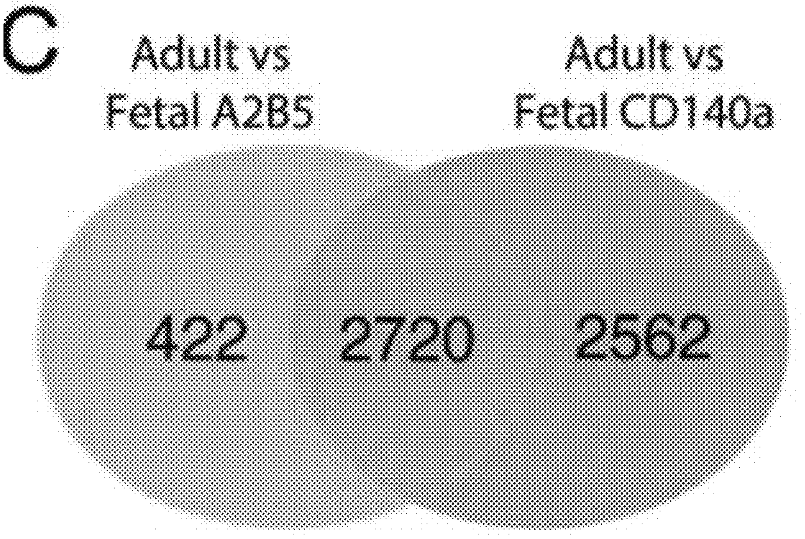
Figure 25:
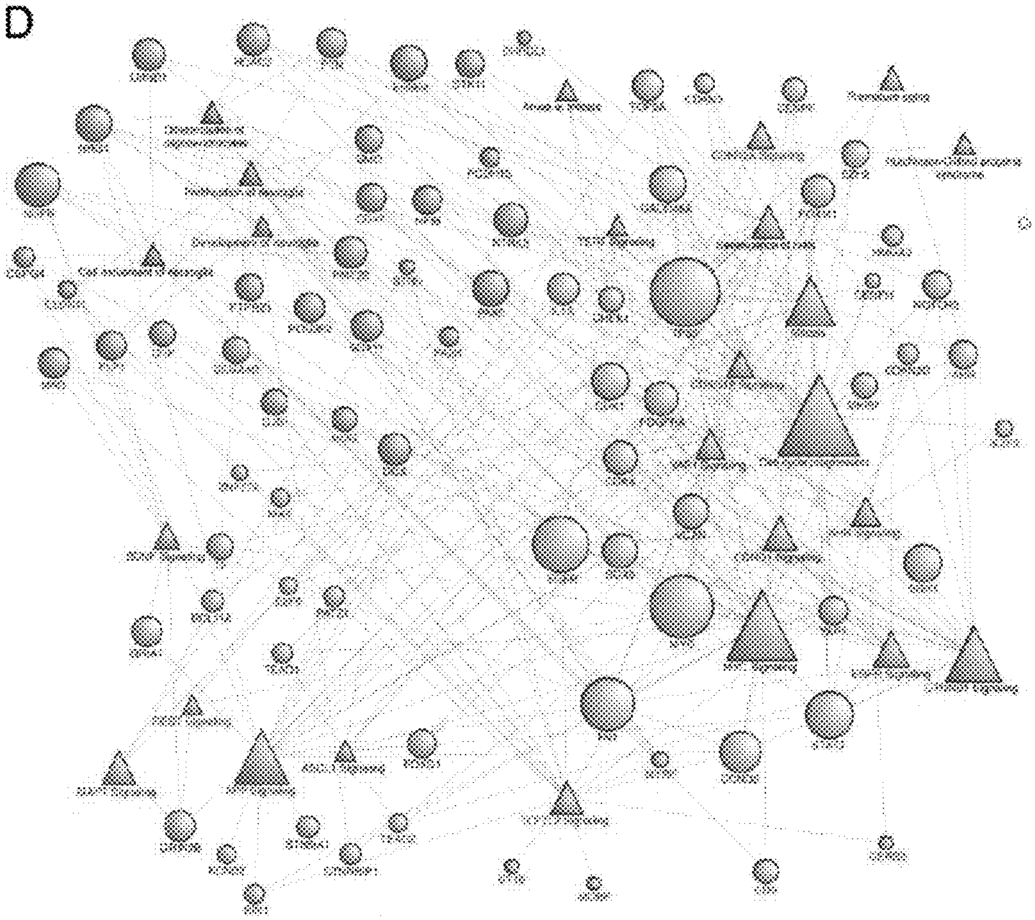
Figure 25:
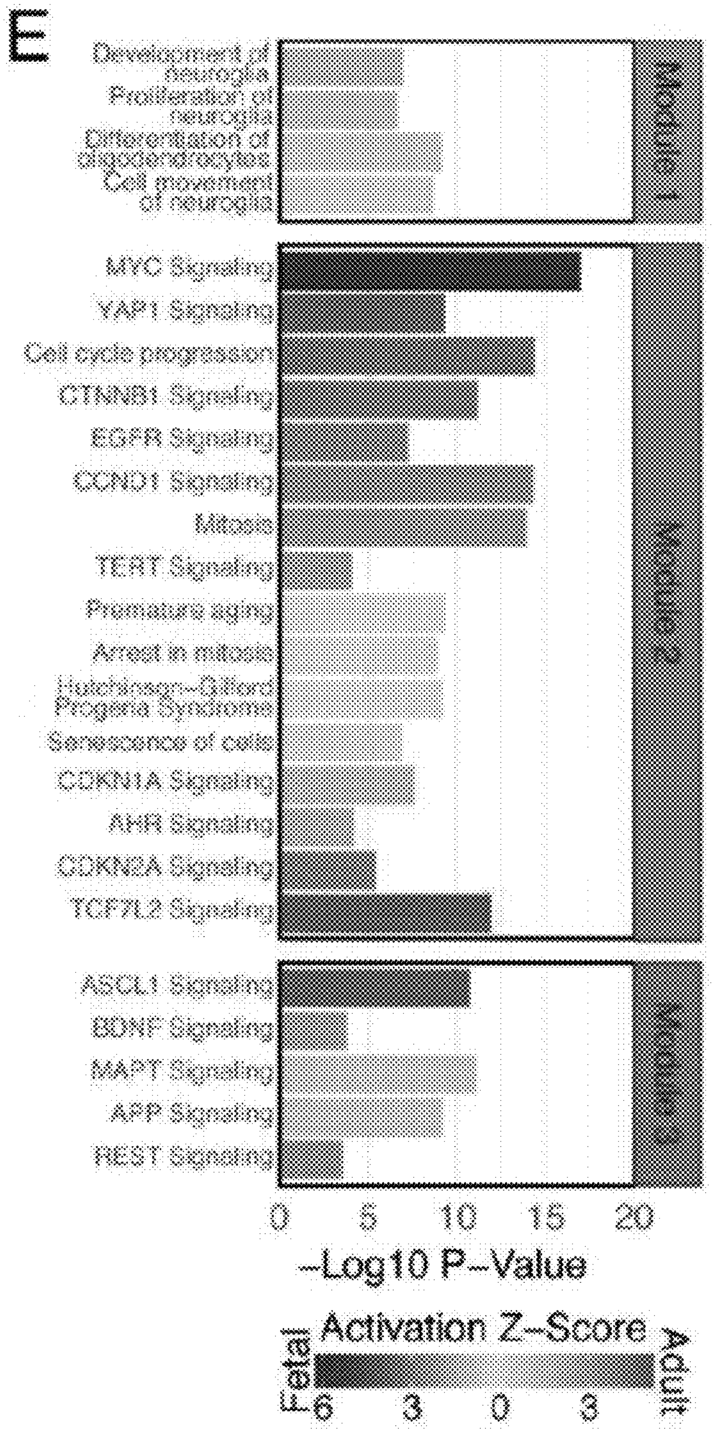
Figure 25:
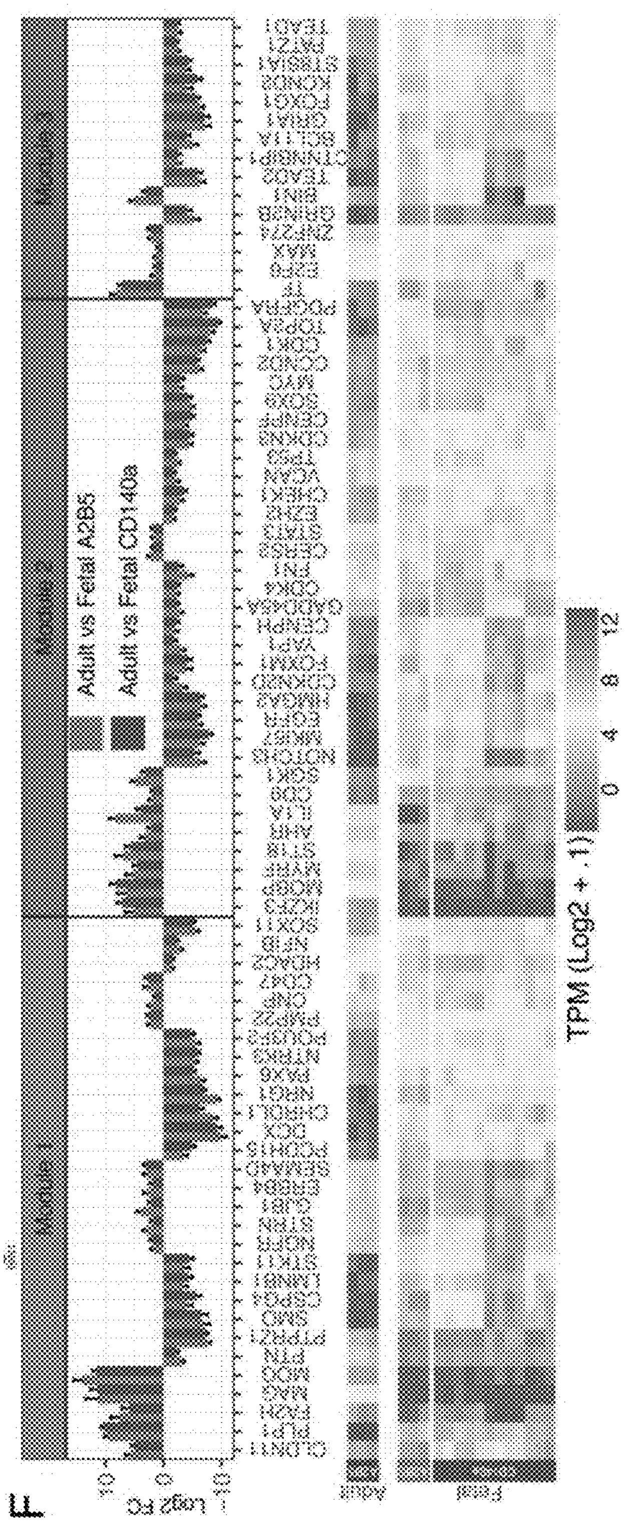

The study next asked how adult hGPCs might differ in their transcription from fetal hGPCs. To this end, A2B5+ hGPCs were isolated from surgically-resected adult human temporal neocortex (19-21 years old, n=3) and their bulk RNA expression assessed, as paired together with four additional fetal CD140α+ samples. Previously it has been noted that A2B5 selection is sufficient to isolate GPCs from adult human brain, and is more sensitive than CD140a in that regard, given the maturation-associated down-regulation of PDGFRA expression in adult hGPCs (e.g. Sim, et al. (2006). Ann Neurol 59, 763-779). Confirming that prior observation, the study found here that PDGFRA in A2B5+ adult GPCs was expressed with a median TPM of 0.55, compared to a median TPM of 47.56 for fetal A2B5+ cells. By pairing our sequencing and analysis with fetal CD140α-selected cells, we enabled regression of sequencing batch effects while simultaneously increasing power (FIG. 25, Panel A). Depletion of PSA-NCAM+ cells was not necessary for adult hGPC samples, as the expression of PSA-NCAM ceases in the adult cortex and white matter (Seki and Arai (1993). Neurosci Res 17, 265-290). As a result, PCA of human adult and fetal GPCs illustrated tight clustering of adult GPCs, sharply segregated from both sorted fetal hGPC pools (FIG. 25, Panel B). Differential expression of adult GPCs compared to either A2B5+ or CD140α+ fetal GPC populations yielded 3,142 and 5,282 significant genes, respectively (p<0.01; absolute log 2 fold-change >1) (FIG. 25, Panel C). To increase the accuracy of defining differential expression, downstream analyses were carried out on the intersecting 2,720 genes (FIG. 25, Panel D, 1,060 up-regulated and 1,660 down-regulated in adult GPCs, compared to fetal hGPCs). Remarkably, within these two differentially-expressed gene sets, 100% of genes were directionally concordant.

To better understand the differences between adult and fetal GPCs, we next constructed a gene ontology network of non-redundant significant IPA terms and their contributing differentially-expressed genes (FIG. 25, Panel D-E). Spin glass community detection of this network (Reichardt and Bornholdt (2006). Phys Rev E Stat Nonlin Soft Matter Phys 74, 016110) uncovered three modules (Modules M1-M3) of highly connected functional terms (FIG. 25, Panel E) and genes (FIG. 25, Panel F). MI included terms and genes linked to glial development, proliferation, and movement. Notably, a number of genes associated with GPC ontogeny were downregulated in adult GPCs; these included CSPG4/NG2, PCDH15, CHRDL1, LMNB1, PTPRZ1, and ST8SIA1 (e.g. Yattah, et al. (2020). Neurochem Res 45, 606-619). In contrast, numerous genes whose appearance precedes and continues through oligodendrocyte differentiation and myelination were upregulated in adult GPCs, including MAG, MOG, MYRF, PLP1, CD9, CLDN11, CNP, ERBB4, GJB1, PMP22, and SEMA4D.

Module 2 harbored numerous terms associated with cellular aging and the modulation of proliferation and senescence. Cell cycle progression and mitosis were predicted to be activated in fetal GPCs due to strong enrichment of proliferative factors including MKI67, TOP2A, CENPF, CENPH, CHEK1, EZH2 and numerous cyclins, including CDK 1 and CDK4. Furthermore, proliferation-inducing pathways were also inferred to be activated; these included MYC, CCND1, and YAPI signaling, of which both YAP1 and MYC transcripts were similarly upregulated (e.g. Bretones, et al. (2015). Biochim Biophys Acta 1849, 506-516). In that regard, transient overexpression of MYC in aged rodent GPCs has recently been shown to restore their capacity to both proliferate and differentiate (Neumann et al. (2021a). Nature Aging 1, 826-837). Conversely, adult GPCs exhibited an upregulation of senescence-associated transcripts, including E2F6, MAP3K7, DMTF1/DMP1, OGT, AHR, RUNX1, and RUNX2 (Lee and Zhang (2016). Proceedings of the National Academy of Sciences 113, E3213-E3220). At the same time, adult hGPCs exhibited a down-regulation of fetal transcripts that included LMNB1, PATZ1, BCL11A, HDAC2, FN1, EZH2, and YAP1 and its cofactor TEAD1 (e.g. Sundar, et al. (2018). FASEB journal: official publication of the Federation of American Societies for Experimental Biology 32, 4955-4971). As a result, functional terms predicted to be active in adult hGPCs included senescence, the rapid onset of aging observed in Hutchinson-Gilford progeria, and cyclin-dependent kinase inhibitory pathways downstream of CDKN1A/p21 and CDKN2A/p16. Furthermore, AHR and its signaling pathway, which has been implicated in driving senescence via the inhibition of MYC (Yang, et al. (2005). Oncogene 24, 7869-7881), was similarly upregulated in adult GPCs.

Module 3 consisted primarily of developmental and disease linked signaling pathways that have also been associated with aging. This included the predicted activation of ASCL1 and BDNF signaling in fetal hGPCs and MAPT/Tau, APP, and REST signaling in adult GPCs (e.g. Harris, et al. (2021). Cell Stem Cell). Overall, the transcriptional and functional profiling of adult GPCs revealed a reduction in transcripts associated with proliferative capacity, and a shift toward senescence and more mature phenotype.

Example 14: Inference of Transcription Factor Activity Implicates Adult GPC Transcriptional Repressors Given the significant transcriptional disparity between adult and fetal GPCs, the study next asked whether it could infer which transcription factors direct their identities. To accomplish this, the study first scanned two promoter windows (500 bp up/100 bp down, 10 kb up/10 kb down) of adult or fetal enriched GPC gene sets to infer significantly enriched TF motifs (Aibar, et al. (2017). Nat Methods 14, 1083-1086). This identified 48 TFs that were also differentially-expressed in the scanned intersecting dataset. Among these, the study focused on TFs whose primary means of DNA interaction were exclusively either repressive or stimulatory, while also considering the enrichment of their known cofactors. This analysis yielded 12 potential upstream regulators to explore (FIG. 26, Panel A-C): 4 adult repressors, E2F6, ZNF274, MAX, and IKZF3; 1 adult activator, STAT3; 3 fetal repressors, BCL11A HDAC2, and EZH2; and 4 fetal activators, MYC, HMGA2, NFIB, and TEAD2. Interestingly, of these predicted TFs, 3 groups shared a high concordance of motif similarity within their targeted promoters: 1) E2F6, ZNF274, MAX, and MYC; 2) STAT3 and BCL11A; and 3) EZH2 and HDAC2, suggesting that they may cooperate or compete for DNA binding at shared loci (FIG. 26, Panel A).

Figure 26:
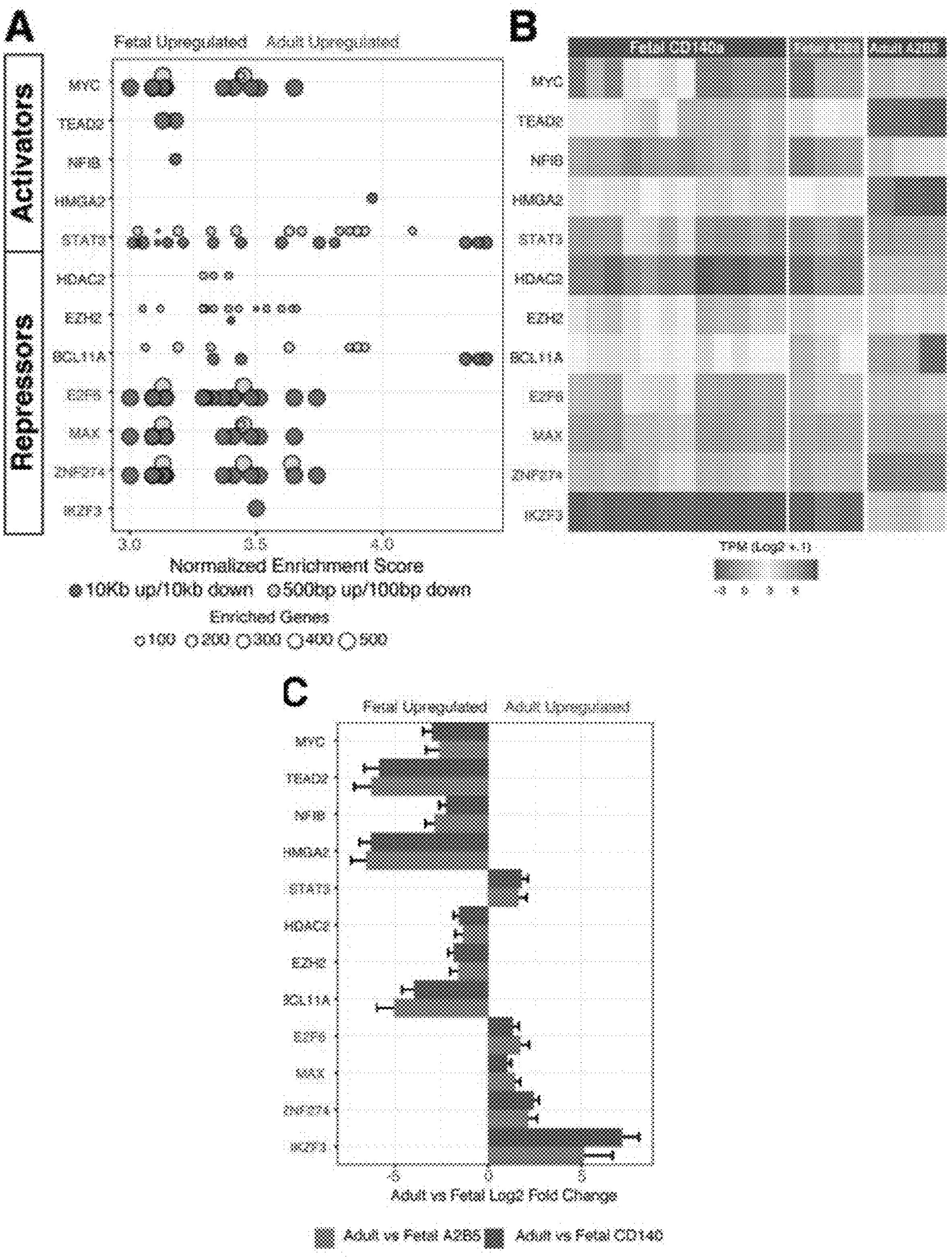
FIG. 26 shows inference of transcription factor activity implicates a set of transcriptional repressors in the establishment of adult hGPC identity. Panel A. Normalized enrichment score plots of significantly enriched transcription factors predicted to be active in fetal and adult GPCs. Each dot is a motif whose size indicates how many genes in which that motif is predicted to be active, and the color represents the window around the promoter at which that motif was found enriched. Panel B. Heatmap of enriched TF TPMs, and Panel C, log-fold changes vs adult GPCs, for both fetal hGPC isolates. Panels D-G. Predicted direct transcription factor activity of curated genes split into Panel D, fetal activators; Panel E, fetal repressors; Panel F, adult activators; and Panel G, adult repressors. Color indicates differential expression in either adult (red) or fetal (blue) hGPCs; shape dictates type of node (octagon, repressor; rectangle, activator; oval, other target gene). Boxed and circled genes indicate functionally-related genes contributing to either glial progenitor/oligodendrocyte identity, senescence/proliferation targets, or upstream or downstream TFs that were also deemed activated.
Figure 26:
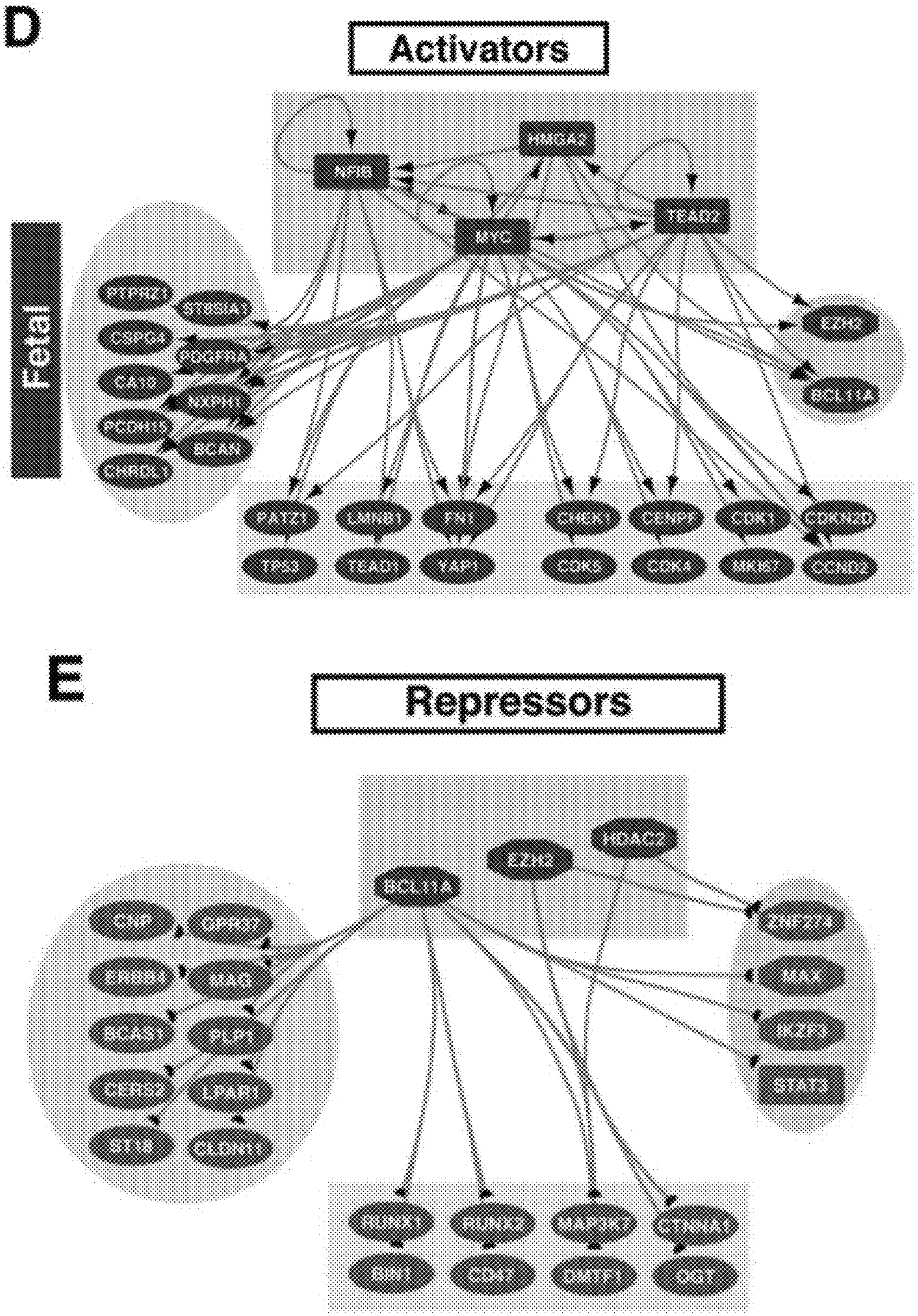
Figure 26:
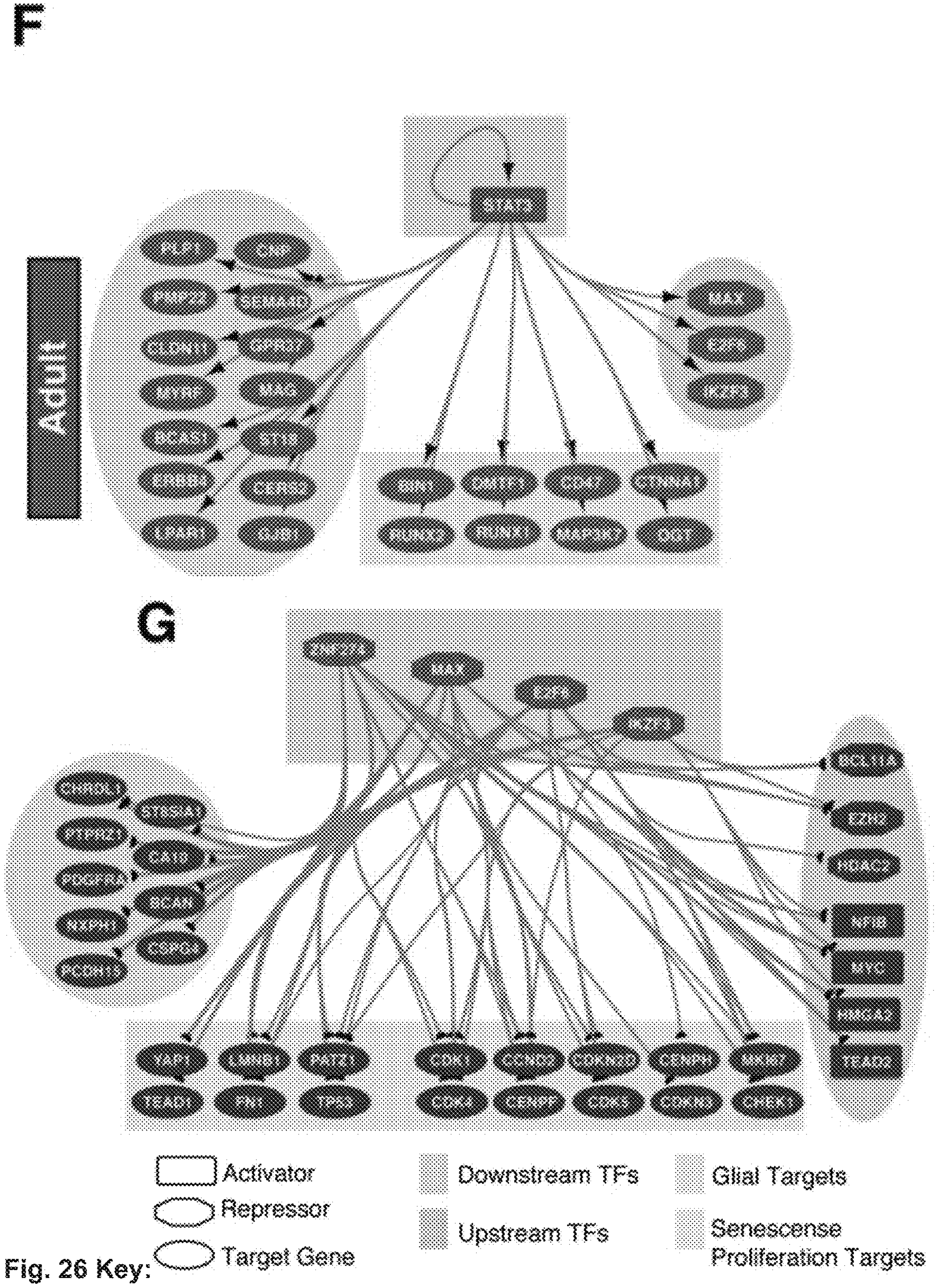

The study next constructed four potential signaling pathways based on curated transcriptional interactions, to predict those genes targeted by our set of TFs (FIG. 26, Panel D-G). Among activators enriched in fetal GPCs (FIG. 26, Panel D), MYC, a proliferative factor (Dang (1999). Molecular and Cellular Biology 19, 1.), NFIB, a key determinant of gliogenesis (Deneen, et al. (2006). Neuron 52, 953-968), TEAD2, a YAP/TAZ effector, and HMGA2, another proliferative factor, were each predicted to activate cohorts of progenitor stage genes, including both mitogenesis-associated transcripts and those demonstrated to inhibit the onset of senescence (e.g. Diepenbruck, et al. (2014). Journal of cell science 127, 1523-1536). Direct positive regulation was also predicted between these four fetal activators, with NFIB being driven by HMGA2 and TEAD2, MYC being driven by TEAD2 and NFIB, HMGA2 being driven by MYC and TEAD2, and TEAD2 being reciprocally driven by MYC (FIG. 26, Panel D). In contrast to these fetal activators, fetal stage repressors, including the C2H2 type zinc finger BCL11A, the polycomb repressive complex subunit EZH2, and histone deacetylase HDAC2, were each predicted to repress more mature oligodendrocytic gene expression at this stage (FIG. 26, Panel E) (Nakamura, et al. (2000). Mol Cell Biol 20, 3178-3186). Furthermore, all three of these TFs were predicted to inhibit targets implicated in senescence. As such, these factors appear to directly orchestrate downstream transcriptional events leading to maintenance of the cycling progenitor state.

The study next assessed these predicted adult GPC signaling networks for a potential mechanism responsible for their age-related gene expression changes. STAT3 was predicted to shift GPC identity towards glial maturation via the upregulation of a large cohort of early differentiation- and myelination-associated oligodendrocytic genes (FIG. 26, Panel F). In addition, STAT3 was also inferred to activate a set of senescence-associated genes including BIN1, RUNX1, RUNX2, DMTF1, CD47, MAP3K7, CTNNA1, and OGT. At the same time, repression in adult GPCs was predicted to be effected through the Ikaros family zinc finger IKZF3/Aiolos, the KRAB (kruppel associated box) zinc finger ZNF274, the MYC-associated factor MAX, and cell cycle regulator E2F6 (FIG. 26, Panel G) (e.g. Frietze, et al. (2010). PLOS One 5, e15082). Targeting by this set of transcription factors predicted repression of those gene sets contributing to the fetal GPC signature, and this was indeed observed in the down-regulation of the early progenitor genes PDGFRA and CSPG4, as well as of the cell cyclicity genes CDK1, CDK4, and MKI67. Repression of YAP1, LMNB1, and TEAD1, whose expression slows or prevents the onset of senescence, was also predicted. Interestingly, this set of four adult repressors predicted the down-regulated expression of each of the fetal enriched activators NFIB, MYC, TEAD2, and HMGA2, in addition to the fetal enriched repressors BCL11A, EZH2, and HDAC2.

Figure 27:
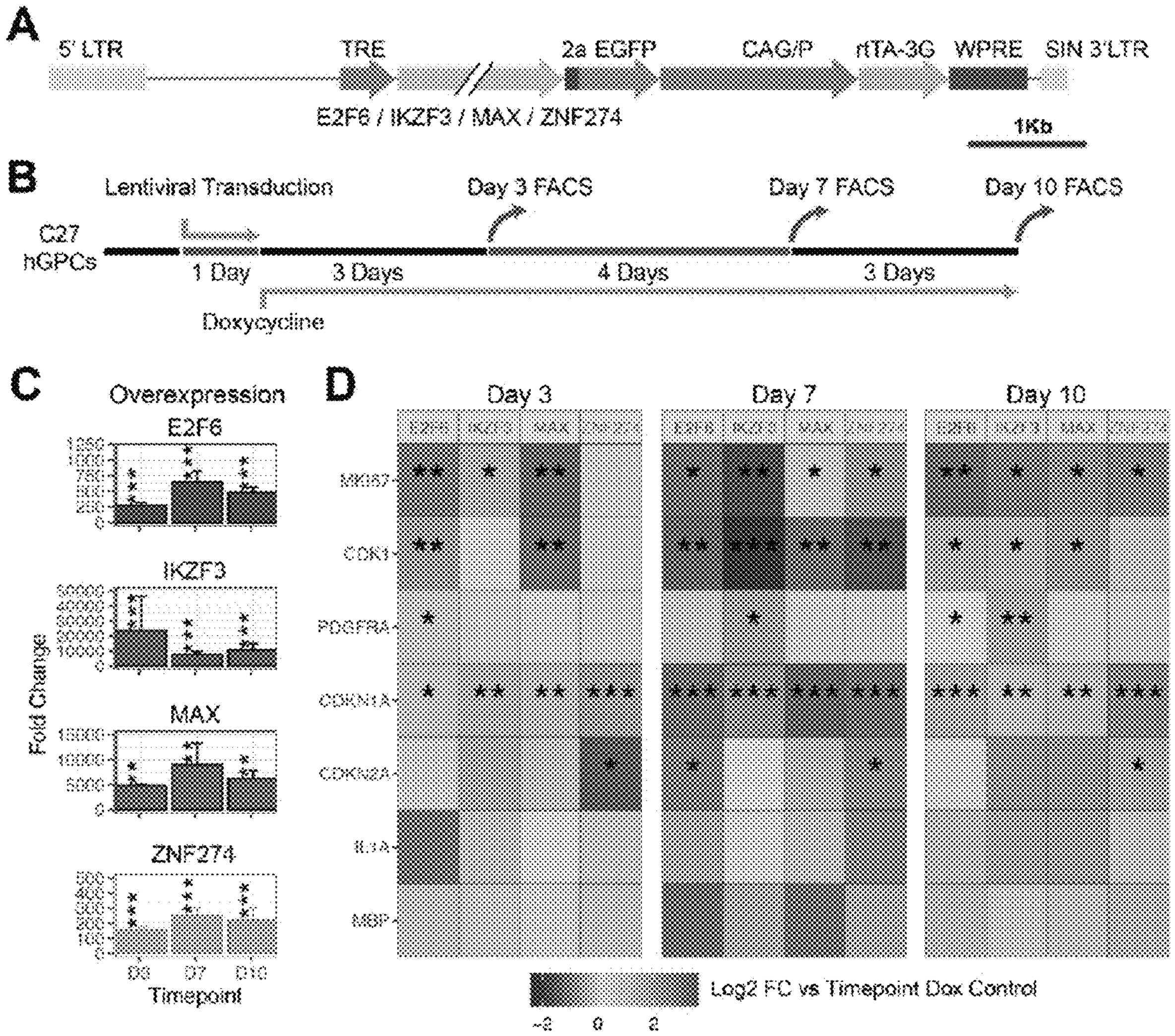
FIG. 27 shows induction of an aged GPC transcriptome via adult hGPC-enriched repressors. Panel A. Schematic outlining the structure of four distinct doxycycline (Dox)-inducible EGFP lentiviral expression vectors, each encoding one of the transcriptional repressors: E2F6, IKZF3, MAX, or ZNF274. Panel B. Induced pluripotent stem cell (iPSC)-derived hGPC cultures (line C27 (Chambers et al., 2009; Wang et al., 2013)) were transduced with a single lentivirus or vehicle for one day, and then treated with Dox for the remainder of the experiment. At 3, 7, and 10 days following initiation of Dox-induced transgene expression, hGPCs were isolated via FACS for qPCR. Panel C. qPCRs of Dox-treated cells showing expression of each transcription factor, vs matched timepoint controls. Panel D. qPCR fold-change heatmap of select aging related genes. Within timepoint comparisons to controls were calculated via post hoc least-squares means tests of linear models following regression of a cell batch effect. FDR adjusted p-values: *<0.05, <0.01, *<0.001 . . .

Example 15: Expression of Adult-Enriched Repressors Induces Age-Associated Transcriptional Changes in GPCs The next asked whether the four adult-enriched transcriptional repressors that were identified, E2F6, IKZF3, MAX, and ZNF274, were individually sufficient to induce aspects of the age-associated changes in gene expression by otherwise young GPCs. To accomplish this, the study designed doxycycline (Dox) inducible overexpression lentiviruses for each transcription factor (FIG. 27, Panel A). Briefly, the study first identified which protein-coding isoform was most abundant in adult GPCs for each repressor, so as to best mimic endogenous age-associated upregulation; these candidates were E2F6-202, IKZF3-217, MAX-201, and ZNF274-201. These cDNAs were cloned downstream of a tetracycline response element promoter, and upstream of a T2A self-cleaving EGFP reporter (FIG. 27, Panel A). Human induced pluripotent stem cell (iPSC)-derived hGPC cultures, prepared from the C27 line as previously described (Wang, et al. (2013). Cell Stem Cell 12, 252-264), were then infected for 24 hrs, and then treated with Dox to induce transgene overexpression. C27 iPSC-derived GPCs were chosen as their transcriptome resembles that of fetal GPCs, and they are similarly capable of engrafting and myelinating dysmyelinated mice upon transplantation (e.g. Windrem, et al. (2017). Cell Stem Cell 21, 195-208.e196). Over-expressing cells were selected via FACS for EGFP expression, at 3, 7, and 10 days following Dox addition (FIG. 27, Panel B, n=3-5). Uninfected cultures given Dox were used as controls.

Figure 28:
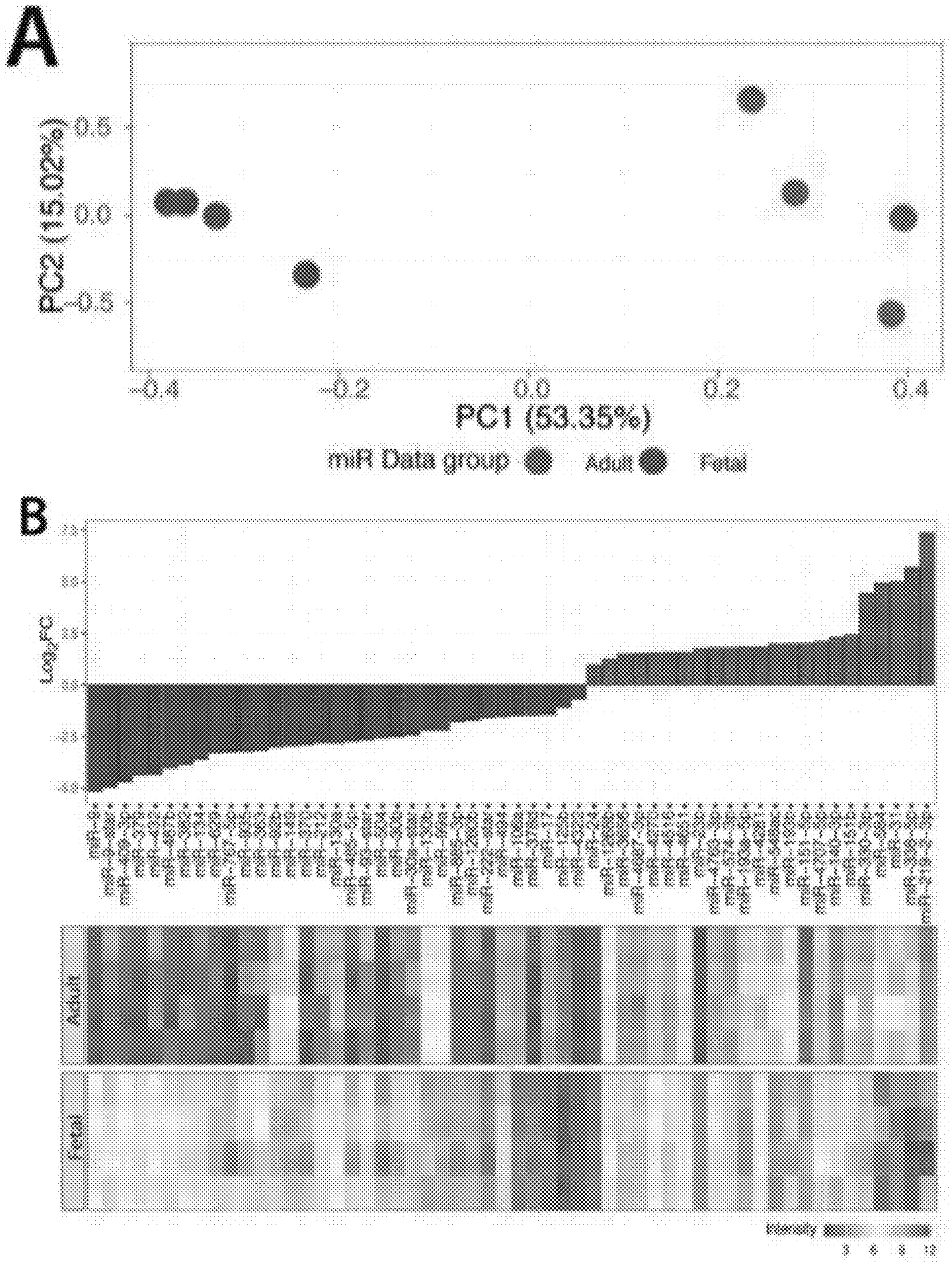
FIG. 28 shows miRNAs drive adult GPC transcriptional divergence in parallel to transcription factor activity. Panel A. Principal component analysis of miRNA microarray samples from human A2B5+ adult and CD140a+ fetal GPCs. Panel B. Log2 fold change bar plots and heatmap of differentially expressed miRNAs. Panel C. Characterization bubble plot of enrichment of miRNAs, versus the average log 2 FC of its predicted gene targets. Panel D-Panel E.
Figure 28:
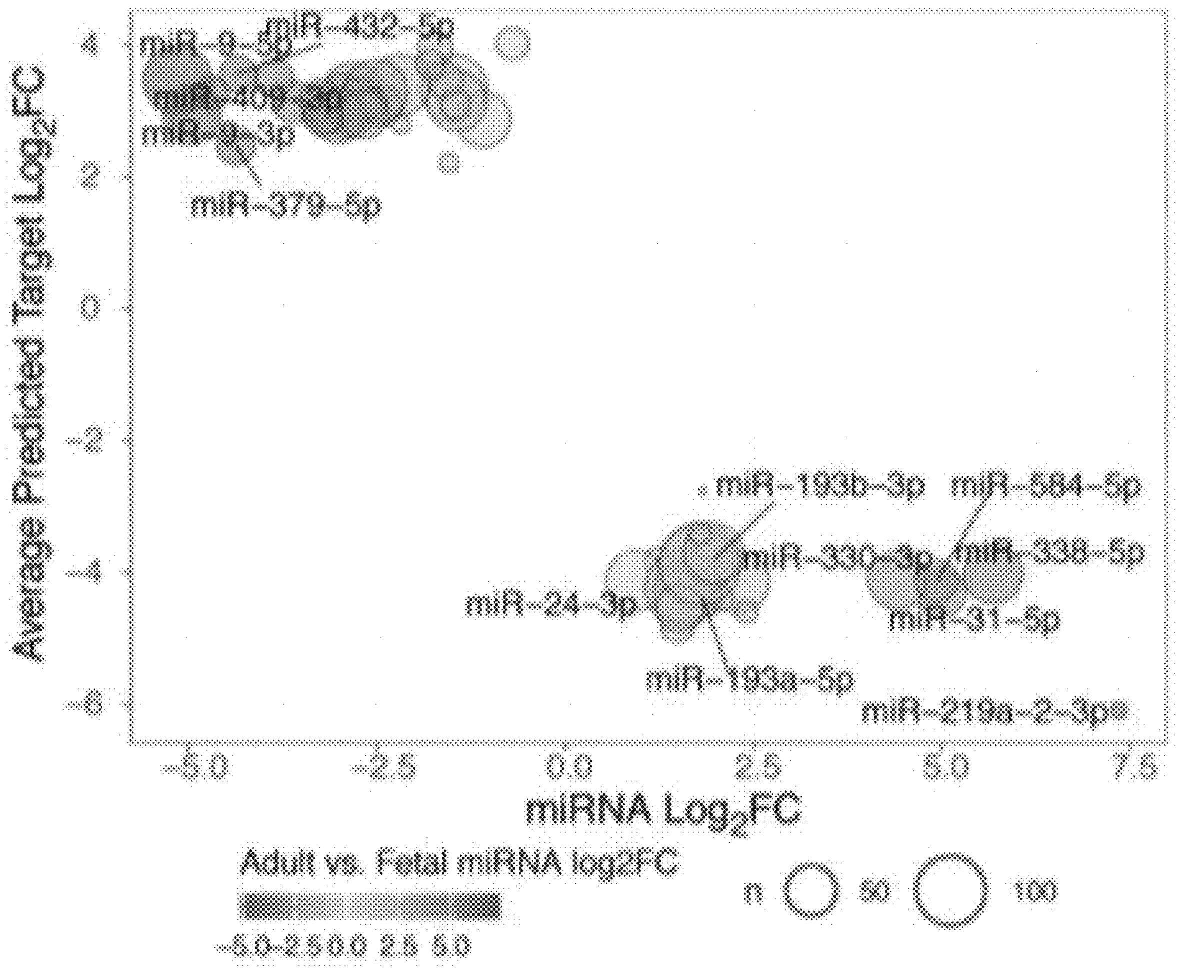
Figure 28:
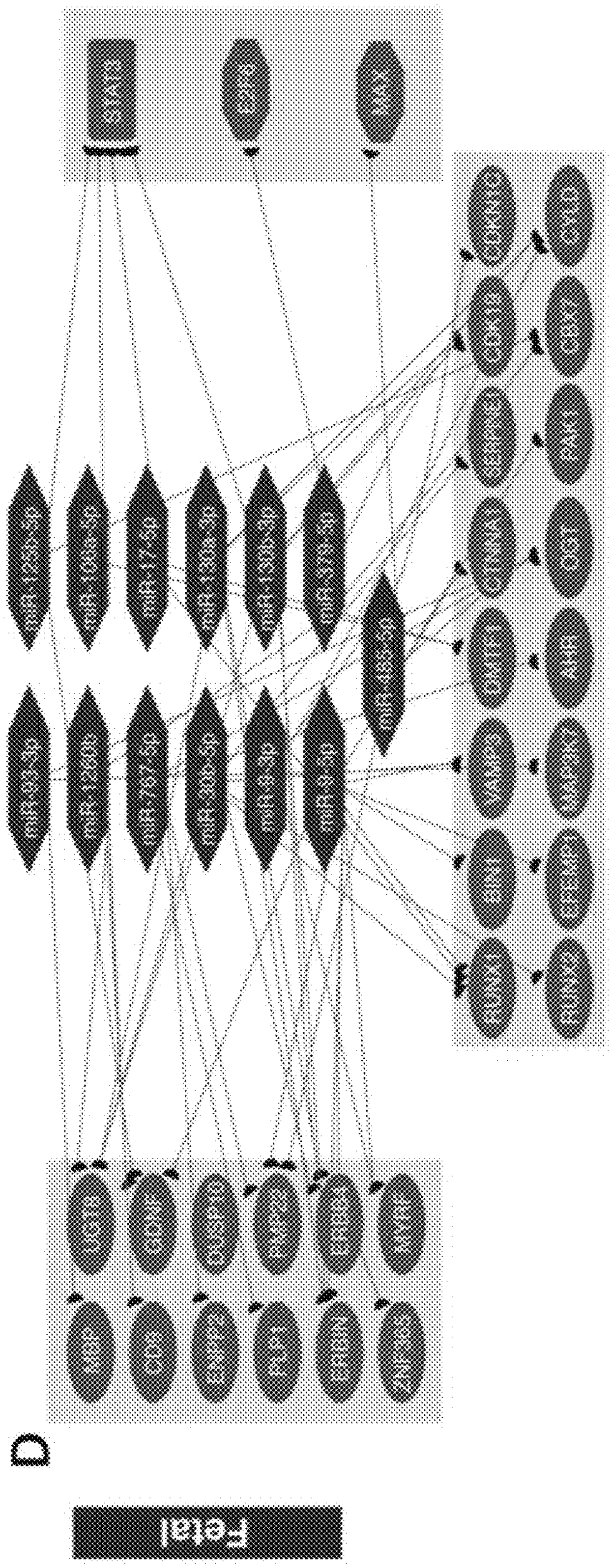
Figure 28:
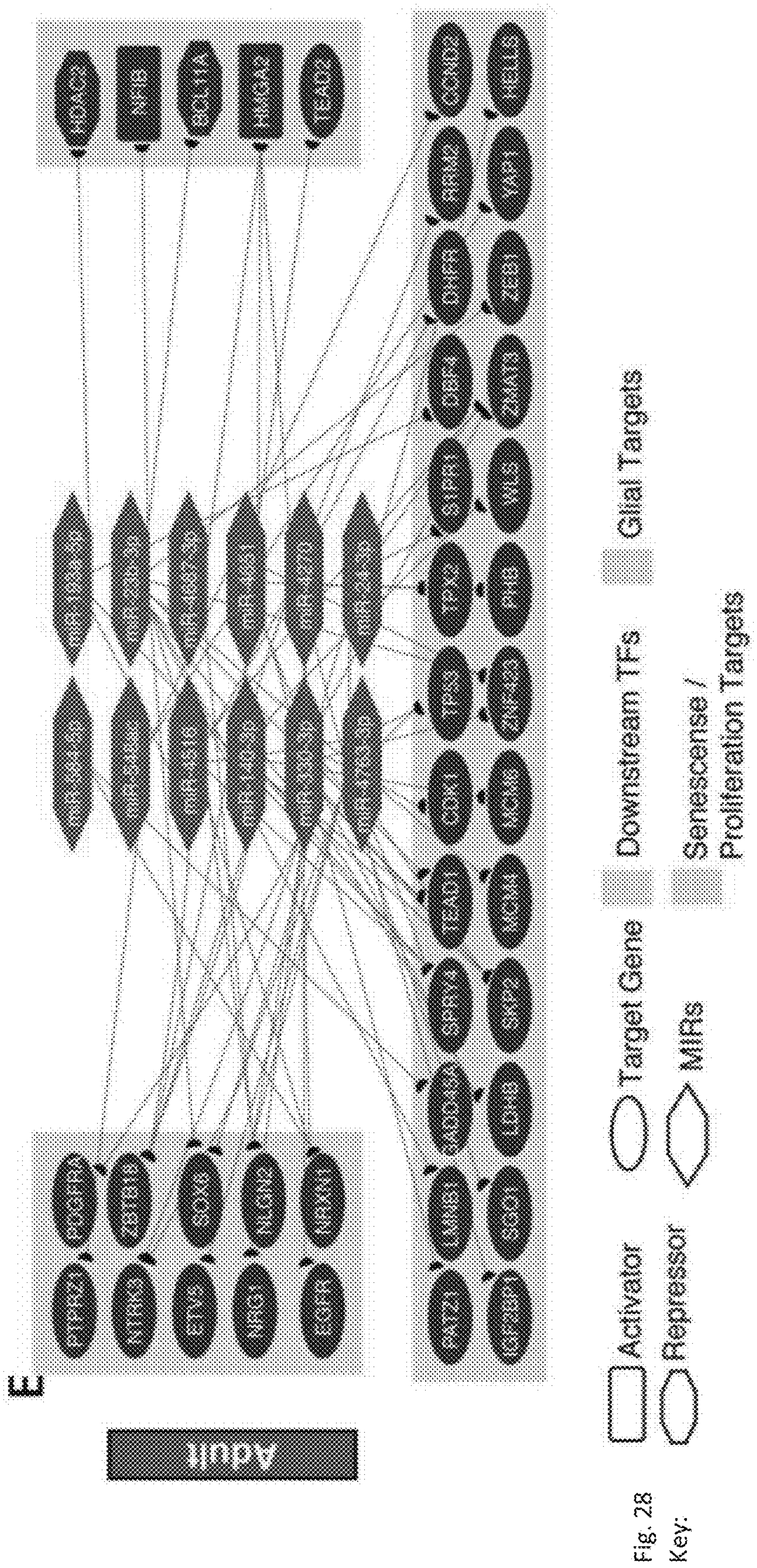

RNA was extracted and aging-associated genes of interest were analyzed by qPCR. Significant induction of each adult-enriched repressor was observed at each timepoint following Dox supplementation (FIG. 27, Panel C). MKI67 and CDK1, genes whose upregulation are associated with active cell division, were significantly repressed at two or more timepoints in each over-expression paradigm (FIG. 27, Panel D). This was consistent with their diminished expression in adult GPCs, and suggested their direct repression by E2F6, MAX, and ZNF274 (MKI67), or by all four (CDK1). The GPC stage marker PDGFRA, the cognate receptor for PDGF-AA, was also significantly repressed at two timepoints in the IKZF3-transduced GPCs, as well as in the E2F6-transduced GPCs at day 3, consistent with its repression in normal adult GPCs. Interestingly, the senescence-associated cyclin-dependent kinase inhibitor CDKN1A/p21 was upregulated in response to each of the tested repressors at all timepoints, while CDKN2A/p16 was similarly upregulated in at all timepoints in ZNF274-transduced hGPCs, as well as in the E2F6-over-expressing GPCs at day 7 (FIG. 27, Panel D). In addition, MBP and IL1A, both of which are strongly upregulated in adult hGPCs relative to fetal, both exhibited sharp trends towards upregulated expression in response to repressor transduction, although timepoint-associated variability prevented their increments from achieving statistical significance. Together, these data supported the prediction that forced, premature expression of the adult-enriched GPC repressors, E2F6, IKZF3, MAX, and ZNF274, are individually sufficient to induce multiple features of the aged GPC transcriptome in young, iPSC-derived GPCs Example 16: The miRNA Expression Pattern of Fetal hGPCs Predicts their Suppression of Senescence To identify potential post-transcriptional regulators of gene expression, we assessed differences in miRNA expression between adult and fetal GPCs (n=4) utilizing Affymetrix® GeneChip™ miRNA 3.0 arrays. PCA displayed segregation of both GPC populations as defined by their miRNA expression profiles (FIG. 28, Panel A). Differential expression between both ages (adjusted p-value <0.01) yielded 56 genes (23 enriched in adult GPCs, 33 enriched in fetal GPCs, FIG. 28, Panel B-C). Notably among these differentially expressed miRNAs were the adult oligodendrocyte regulators miR-219a-3p and miR-338-5p (e.g. Wang, et al. (2017). Dev Cell 40, 566-582.e565) in addition to fetal progenitor stage miRNAs miR-9-3p, miR-9-5p (Lau, et al. (2008). J Neurosci 28, 11720-11730), and miR-17-5p (Budde, et al. (2010). Development 137, 2127).

The study next utilized this cohort of miRNAs to predict genes whose expression might be expected to be repressed via miRNA upregulation, separately analyzing both the adult and fetal GPC pools. To accomplish this, the study used miRNAtap to query five miRNA gene target databases: DIANA (Maragkakis, et al. (2011). Nucleic Acids Res 39, W145-148), Miranda (Enright, et al. (2003). MicroRNA targets in Drosophila. Genome biology 5, R1), PicTar (Lall, et al. (2006). Current biology: CB 16, 460-471.), TargetScan (Friedman, et al. (2009). Genome Res 19, 92-105), and miRDB (Wong and Wang (2015). Nucleic Acids Res 43, D146-152). To maximize precision, genes were only considered a target if they appeared in at least two databases. Among fetal-enriched miRs, this approach predicted an average of 36.3 (SD=24.5) repressed genes per miRNA. In contrast, among adult hGPC-enriched miRNAs, an average of 46.4 (SD=37.8) genes were predicted as targets per miRNA (FIG. 28, Panel C). Altogether, this identified the potential repression of 48.8% of adult GPC-enriched genes via fetal miRNAs, and repression of 39.9% of fetal GPC-enriched genes by adult miRNAs.

To assess the functional importance of these miRNA-dependent post-transcriptional regulatory mechanisms, we curated fetal and adult networks according to miRNA targeting of functionally-relevant, differentially expressed genes (FIG. 28, Panel D-E). Our proposed upstream adult transcriptional regulators STAT3, E2F6, and MAX were predicted to be inhibited via 7 miRNAs in fetal GPCs (FIG. 28, Panel D); these included the already-validated repression of STAT3 in other cell types by miR-126b-5p, miR-106a-5p, miR-17-5p, miR-130a-3p, and miR-130b-3p (e.g. Du, et al. (2014a). Cellular Physiology and Biochemistry 34, 955-965). In parallel, a number of early and mature oligodendrocytic genes were concurrently targeted for inhibition, all consistent with maintenance of the progenitor state; these included MBP, UGT8, CD9, PLP1, MYRF, and PMP22 (Goldman and Kuypers, (2015). Development 142, 3983-3995). Importantly, a cohort of genes linked to either the induction of senescence or inhibition of proliferation, or both, were also predicted to be actively repressed in fetal GPCs. These included RUNX1, RUNX2, BIN1, DMTF1/DMP1, CTNNA1, SERPINE1, CDKNIC, PAK1, IFI16, EFEMP1, MAP3K7, AHR, OGT, CBX7, and CYLD (e.g. Eckers, et al. (2016). Sci Rep 6, 19618). Inhibition of senescence or activation of proliferation have also been noted by several of the miRNAs identified here, including miR-17-5p, miR-93-3p, miR-1260b, miR-106a-5p, miR-767-5p, miR-130a-3p, miR-9-3p, miR-9-5p, and miR-130b-

3p (e.g, Borgdorff, et al. (2010). Oncogene 29, 2262-2271). Together, these data provide a complementary mechanism by which fetal hGPCs may maintain their characteristic progenitor transcriptional state and signature.

Example 17: Adult miRNA Signaling May Repress the Proliferative Progenitor State and Augur Senescence The study next inspected the potential miRNA regulatory network within adult hGPCs (FIG. 28, Panel E). This implicated five miRNAs controlling five identified active fetal transcriptional regulators including HDAC2, NFIB, BCLLIA, TEAD2, and HMGA2, whose silencing via miR-4651 has previously been shown to inhibit proliferation (Han, et al. (2020). Int J Oral Sci 12, 10.). This cohort of miRNAs were predicted to operate in parallel to adult transcriptional repressors in inhibiting expression of genes involved in maintaining the GPC progenitor state including PDGFRA, PTPRZ1, ZBTB18, SOX6, EGFR, and NRXN1. Furthermore, the adult miRNA environment was predicted to repress numerous genes known to induce a proliferative state or to delay senescence, including LMNB1 (Freund, et al. (2012). Mol Biol Cell 23, 2066-2075), PATZ1 (Cho, et al. (2012). Cell Death Differ 19, 703-712), GADD45A (Hollander, et al. (1999). Nat Genet 23, 176-184.), YAP1 and TEADI (Xie et al., 2013), CDK1 (Diril, et al. (2012). Proc Natl Acad Sci USA 109, 3826-3831.), TPX2 (Rohrberg, et al. (2020). Cell Rep 30, 3368-3382 e3367), SIPRI (Liu, et al. (2019). Journal of Experimental & Clinical Cancer Research 38, 369), RRM2 (Aird, et al. (2013). Cell Rep 3, 1252-1265), CCND2 (Bunt, et al. (2010). Mol Cancer Res 8, 1344-1357), SGO1 (Murakami-Tonami, et al. (2016). Scientific Reports 6, 31615), MCM4 and MCM6 (Mason, et al. (2004). Oncogene 23, 9238-9246), ZNF423 (Hernandez-Segura, et al. (2017). Current biology: CB 27, 2652-2660 e2654), PHB (Piper, et al. (2002). Aging cell 1, 149-157), WLS (Poudel, et al. (2020). Stem Cells.), and ZMAT3 (Kim, et al. (2012). EMBO J 31, 4289-4303). More directly, induction of senescence or inhibition of proliferation has been linked to the upregulation of miR-584-5p (Li, et al. (2017). J Exp Clin Cancer Res 36, 59), miR-193a-5p (Chen, et al. (2016). J Exp Clin Cancer Res 35, 173), miR-548ac (Song, et al. (2020). Oncol Lett 20, 69), miR-23b-3p (Campos-Viguri, et al. (2020). Sci Rep 10, 3256), miR-140-3p and miR-330-3p (Wang, Yet al. (2020b). Aging 12, 20366-20379). Taken together, these data implicate these miRs as active participants in maintenance of the progenitor state in fetal hGPCs, and their modulation as a likely mechanism by which adult hGPCs assume their signatory gene expression profile.

Example 18: Transcription Factor Regulation of miRNAs Establishes and Consolidates GPC Identity The study next sought to predict the upstream regulation of differentially expressed miRNAs in fetal and adult GPCs by querying the TransmiR transcription factor miRNA regulation database (Tong, et al. (2019). TransmiR v2.0: an updated transcription factor-microRNA regulation database. Nucleic Acids Res 47, D253-D258). This approach predicted regulation of 54 of 56 of age-specific GPC miRNAs via 66 transcription factors that were similarly determined to be significantly differentially expressed between fetal and adult GPCs. Interestingly, the top four predicted miRNA-regulating TFs were all MYC-associated factors including MAX, MYC itself, E2F6, and the fetal enriched MYC associated zinc finger protein, MAZ, targeting 36, 33, 30, and 28 unique differentially expressed miRNAs respectively.

Inspection of proposed relationships in the context of the 12 TF candidates indicated a large number of fetal hGPC-enriched miRNAs that were predicted to be targeted by both fetal activators and adult repressors, whereas those miRNAs enriched in adult GPCs were more uniquely targeted. MYC was predicted to drive the expression of numerous miRNAs in fetal GPCs, many of which were predicted to be repressed in adulthood via E2F6, MAX or both. miR-130a-3p in particular was predicted to be targeted by MYC, MAX, and E2F6, in addition to activation via TEAD2. Notably among validated TF-miRNA interactions in other cell types, the upregulation of the rejuvenating miR-17-5p by MYC, and its repression by MAX (Du, et al. (2014b). miR-17 extends mouse lifespan by inhibiting senescence signaling mediated by MKP7. Cell Death Dis 5, e1355), has been reported. Similarly, the parallel activation of the proliferative miR-130-3p by MYC or TEAD2 and YAP1 (Shen, et al. (2015). A miR-130a-YAP positive feedback loop promotes organ size and tumorigenesis. Cell Res 25, 997-1012), has been reported, as has the activation of both arms of miR-9 by MYC (Ma, L., et al. (2010a). miR-9, a MYC/MYCN-activated microRNA, regulates E-cadherin and cancer metastasis. Nat Cell Biol 12, 247-256), which decreases with oligodendrocytic maturity (Lau, P., et al. (2008). Identification of dynamically regulated microRNA and mRNA networks in developing oligodendrocytes. J Neurosci 28, 11720-11730).

In adult GPCs, enriched miRNAs predicted to be regulated by our significantly enriched TF cohort were more likely to be only targeted by an adult activator of fetal repressor with only miR-151a-5p and miR-4687-3p, a predicted inhibitor of HMGA2, being targeted in opposition by STAT3 versus BCL11A and EZH2 respectively. Beyond this, miR-1268b was predicted to be inhibited by both EZH2 and HDAC2 in parallel. Notably, key oligodendrocytic microRNA, miR-219a-2-3p was predicted to remain inhibited in fetal GPCs via EZH2, whereas STAT3 likely drives the expression of 7 other miRs independently. Interestingly, STAT3, whose increased activity has been linked to senescence (Kojima, et al. (2013). IL-6-STAT3 signaling and premature senescence. JAKSTAT 2, e25763), was also predicted to drive the expression of a cohort of miRNAs independently associated with the induction of senescence, including miR-584-5p, miR-330-3p, miR-23b-3p, and miR-140-3p.

Through integration of transcriptional and miRNA profiling, pathway enrichment analyses, and target predictions, we propose a model of human GPC aging whereby fetal hGPCs maintain progenitor gene expression, activate proliferative programs, and prevent senescence, while repressing oligodendrocytic and senescent gene programs both transcriptionally, and post-transcriptionally via microRNA. With adult maturation and the passage of time as well as of population doublings, hGPCs begin to upregulate repressors of these fetal progenitor-linked networks, while also activating programs to further a progressively more differentiated and ultimately senescent phenotype.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A method of rejuvenating glial cells of the brain and/or brain stem in a subject, said method comprising:
   introducing a population of genetically modified glial progenitor cells into the brain and/or brain stem of the subject,
   wherein the genetically modified glial progenitor cells have increased expression of CEBPZ, MYBL2, NFYB, and TFDP1 genes compared to the same type of glial progenitor cells that have not been genetically modified, and
   wherein said increased expression of the CEBPZ, MYBL2, NFYB, and TFDP1 genes in the genetically modified glial progenitor cells confer a competitive advantage over a population of native or already resident glial progenitor cells in the subject.

2. The method of claim 1, wherein the CEBPZ gene encodes a protein product having the amino acid sequence of SEQ ID NO:4, the MYBL2 gene encodes a protein product having the amino acid sequence of SEQ ID NO:5 or 6, the NFYB gene encodes a protein product having the amino acid sequence of SEQ ID NO:9, and the TFDP1 gene encodes a protein product having the amino acid sequence of SEQ ID NO:10.

3. The method of claim 1, wherein expression of the genes CEBPZ, MYBL2, NFYB, and TFDP1 genes is increased by at least 100% at the mRNA level in the genetically modified glial progenitor cells compared to the same type of glial progenitor cells that have not been genetically modified.

4. The method of claim 1, wherein the subject is a human and wherein the genetically modified glial progenitor cells are derived from human glial progenitor cells.

5. The method of claim 4, wherein the human glial progenitor cells are derived from fetal tissue, embryonic stem cells, or induced pluripotent stem cells.

6. The method of claim 1, wherein said introducing results in replacement of the native or already resident glial cells in the forebrain, striatum, and/or cerebellum of the subject with the genetically modified glial progenitor cells.

7. The method of claim 1, wherein the genetically modified glial progenitor cells are derived from human glial progenitor cells.

8. The method of claim 7, wherein the human glial progenitor cells are derived from fetal tissue, embryonic stem cells, or induced pluripotent stem cells.

* * * * *